(12) United States Patent
Lancaster et al.

(10) Patent No.: US 11,773,151 B2
(45) Date of Patent: *Oct. 3, 2023

(54) ULTRA-LONG ACTING INSULIN-FC FUSION PROTEINS AND METHODS OF USE

(71) Applicant: Akston Biosciences Corporation, Beverly, MA (US)

(72) Inventors: Thomas M. Lancaster, Wenham, MA (US); Todd C. Zion, Marblehead, MA (US)

(73) Assignee: Akston Biosciences Corporation, Beverly, MA (US)

( * ) Notice: Subject to any disclaimer, the term of this patent is extended or adjusted under 35 U.S.C. 154(b) by 87 days.

This patent is subject to a terminal disclaimer.

(21) Appl. No.: 17/488,852

(22) Filed: Sep. 29, 2021

(65) Prior Publication Data
US 2022/0017590 A1    Jan. 20, 2022

Related U.S. Application Data

(63) Continuation of application No. 17/019,059, filed on Sep. 11, 2020, now Pat. No. 11,261,229, which is a
(Continued)

(51) Int. Cl.
*C07K 14/62* (2006.01)
*A61P 3/10* (2006.01)
(Continued)

(52) U.S. Cl.
CPC .......... *C07K 14/62* (2013.01); *A61K 9/0019* (2013.01); *A61K 47/65* (2017.08); *A61P 3/10* (2018.01);
(Continued)

(58) Field of Classification Search
CPC ...... C07K 14/62; C07K 1/22; C07K 16/2869; C07K 2317/94; C07K 2319/30;
(Continued)

(56) References Cited

U.S. PATENT DOCUMENTS

| 8,188,231 B2 | 5/2012 | Lazar et al. |
| 8,933,207 B2 | 1/2015 | Chen et al. |

(Continued)

FOREIGN PATENT DOCUMENTS

| CN | 101891823 | 11/2010 |
| CN | 103509118 | 1/2014 |

(Continued)

OTHER PUBLICATIONS

Kumar, P., et al (2014) Current practices and research updates on diabetes mellitus in canine Veterinary World 7(11); 952-959 (Year: 2014).*

(Continued)

*Primary Examiner* — Scarlett Y Goon
*Assistant Examiner* — Audrey L Buttice
(74) *Attorney, Agent, or Firm* — Hovey Williams LLP

(57) ABSTRACT

The present disclosure provides recombinantly manufactured ultra-long acting insulin-Fc fusion proteins for use in treating canine and feline diabetes. The insulin-Fc fusion proteins comprise an insulin polypeptide linked via a peptide linker to an Fc-fragment of canine or feline origin. Based on the results obtained, creating a treatment that is amenable to low cost manufacturing, exhibits sufficient in vivo bioactivity, displays extended duration of bioactivity, does not induce anti-drug antibodies, and substantially retains is potency over multiple administrations, requires a non-obvious combination of insulin polypeptide, peptide linkers, and species-specific Fc fragment, in addition to selective mutations on one or more of these components. Exemplary ultra-long acting insulin-Fc fusion proteins, polynucleotides encoding these insulin-Fc fusion proteins, and pharmaceutical formulations of exemplary insulin-Fc fusion proteins are provided, in addition to methods of use and preparation.

15 Claims, 29 Drawing Sheets

Specification includes a Sequence Listing.

Related U.S. Application Data continuation of application No. 16/776,065, filed on Jan. 29, 2020, now Pat. No. 10,870,686, which is a continuation of application No. 16/775,979, filed on Jan. 29, 2020, now Pat. No. 10,961,294, which is a continuation of application No. PCT/US2019/040010, filed on Jun. 28, 2019.

(60) Provisional application No. 62/837,188, filed on Apr. 22, 2019, provisional application No. 62/827,809, filed on Apr. 1, 2019, provisional application No. 62/824,176, filed on Mar. 26, 2019, provisional application No. 62/781,378, filed on Dec. 18, 2018, provisional application No. 62/781,368, filed on Dec. 18, 2018, provisional application No. 62/774,682, filed on Dec. 3, 2018, provisional application No. 62/743,358, filed on Oct. 9, 2018, provisional application No. 62/740,735, filed on Oct. 3, 2018, provisional application No. 62/719,347, filed on Aug. 17, 2018, provisional application No. 62/702,167, filed on Jul. 23, 2018, provisional application No. 62/698,648, filed on Jul. 16, 2018, provisional application No. 62/696,645, filed on Jul. 11, 2018, provisional application No. 62/693,814, filed on Jul. 3, 2018, provisional application No. 62/692,507, filed on Jun. 29, 2018, provisional application No. 62/692,498, filed on Jun. 29, 2018.

(51) Int. Cl.

| | | |
|---|---|---|
| *A61K 9/00* | (2006.01) | |
| *C07K 16/28* | (2006.01) | |
| *C12N 15/62* | (2006.01) | |
| *A61K 47/65* | (2017.01) | |
| *C07K 1/22* | (2006.01) | |
| *C07H 21/04* | (2006.01) | |
| *A61K 38/00* | (2006.01) | |

(52) U.S. Cl.
CPC ............. *C07H 21/04* (2013.01); *C07K 1/22* (2013.01); *C07K 16/2869* (2013.01); *C12N 15/62* (2013.01); *A61K 38/00* (2013.01); *C07K 2317/94* (2013.01); *C07K 2319/30* (2013.01)

(58) Field of Classification Search
CPC .... A61K 9/0019; A61K 9/0021; A61K 47/65; A61K 47/6811; A61K 38/00; A61P 3/10; C07H 21/04; C12N 15/62
See application file for complete search history.

(56) References Cited

U.S. PATENT DOCUMENTS

| | | | |
|---|---|---|---|
| 9,074,015 | B2 | 7/2015 | Lancaster et al. |
| 9,855,318 | B2 | 1/2018 | Baldwin et al. |
| 10,597,435 | B2 | 3/2020 | Lancaster et al. |
| 10,709,766 | B2 | 7/2020 | Baldwin et al. |
| 10,822,386 | B2 | 11/2020 | Weiss |
| 10,851,147 | B2 | 12/2020 | Lancaster et al. |
| 10,870,686 | B2 | 12/2020 | Lancaster et al. |
| 10,894,089 | B2 | 1/2021 | Heo et al. |
| 10,947,292 | B2 | 3/2021 | Lancaster et al. |
| 10,961,294 | B2 | 3/2021 | Lancaster et al. |
| 2003/0040601 | A1 | 2/2003 | Diers et al. |
| 2012/0093814 | A1 | 4/2012 | Canada et al. |
| 2013/0142795 | A1 | 6/2013 | Bai et al. |
| 2013/0190475 | A1 | 7/2013 | Chen et al. |
| 2013/0190476 | A1 | 7/2013 | Lancaster et al. |
| 2014/0037699 | A1 | 2/2014 | Zion et al. |
| 2014/0302028 | A1 | 10/2014 | Zha |
| 2016/0289290 | A1 | 10/2016 | Meehl et al. |
| 2016/0324932 | A1 | 11/2016 | Baldwin et al. |
| 2018/0009869 | A1 | 1/2018 | Lu et al. |
| 2018/0161448 | A1 | 6/2018 | Heo et al. |
| 2018/0177851 | A1 | 6/2018 | Baldwin et al. |
| 2019/0315828 | A1 | 10/2019 | Lancaster et al. |
| 2019/0382439 | A1 | 12/2019 | Kim et al. |
| 2020/0131243 | A1 | 4/2020 | Lancaster et al. |
| 2020/0140516 | A1 | 5/2020 | Weiss |
| 2020/0140517 | A1 | 5/2020 | Weiss |
| 2020/0157169 | A1 | 5/2020 | Lancaster et al. |
| 2020/0157170 | A1 | 5/2020 | Lancaster et al. |
| 2020/0157171 | A1 | 5/2020 | Lancaster et al. |
| 2020/0231646 | A1 | 7/2020 | Lancaster et al. |
| 2020/0299343 | A1 | 9/2020 | Doerner et al. |
| 2020/0407413 | A1 | 12/2020 | Lancaster et al. |
| 2020/0407414 | A1 | 12/2020 | Lancaster et al. |
| 2021/0300983 | A1 | 9/2021 | Lancaster et al. |
| 2021/0309709 | A1 | 10/2021 | Lancaster et al. |
| 2021/0324033 | A1 | 10/2021 | Lancaster et al. |
| 2021/0340212 | A1 | 11/2021 | Zion et al. |

FOREIGN PATENT DOCUMENTS

| | | | | |
|---|---|---|---|---|
| EP | 3303380 | | 4/2018 | |
| EP | 3517544 | | 7/2019 | |
| EP | 2963056 | | 11/2019 | |
| EP | 3656792 | | 5/2020 | |
| WO | 2010117760 | | 10/2010 | |
| WO | WO-2014093387 | A1 * | 6/2014 | ........... A61K 38/179 |
| WO | 2016044676 | | 3/2016 | |
| WO | 2016119023 | | 8/2016 | |
| WO | 2016177771 | | 11/2016 | |
| WO | 2016178905 | | 11/2016 | |
| WO | 2018009921 | | 1/2018 | |
| WO | 2018073185 | | 4/2018 | |
| WO | 2018107117 | | 6/2018 | |
| WO | 2019035010 | | 2/2019 | |
| WO | 2019204206 | | 10/2019 | |
| WO | 2020006529 | | 1/2020 | |
| WO | 2020070276 | | 4/2020 | |
| WO | 2020106748 | | 5/2020 | |
| WO | 2020236762 | | 11/2020 | |
| WO | 2021011827 | | 1/2021 | |
| WO | 2021022149 | | 2/2021 | |
| WO | 2021126584 | | 6/2021 | |

OTHER PUBLICATIONS

Zhang, Z., et al (2003) Protein engineering of insulin: Two novel fast-acting insulins [B16Ala] insulin and [B26Ala] insulin Science in China (series C) 46(5); 474-480 (Year: 2003).*

Alleva, et al., "Immunological characterization and therapeutic activity of an altered-peptide ligand, NBI-6024, based on the immunodominant type 1 diabetes autoantigen insulin B-chain (9-23) peptide", Diabetes, 2002, 51(7) pp. 2126-2134.

Baeshen, et al., "Cell factories for insulin production", Microbial Cell Factories, 2014,13(141).

Brüggemann, et al., "The immunogenicity of chimeric antibodies", Journal of Experimental Medicine, 1989, 170(6) pp. 2153-2157.

Hua, et al., "Design of an Active Ultrastable Single-chain Insulin Analog", Journal of Biological Chemistry, 2008, 283(21) pp. 14703-14716.

Strietzel, et al., "In Vitro functional characterization of feline IgGs", Veterinary Immunology and Immunopathology, 2014, 158(3-4) pp. 214-223 (abstract attached).

Tang, et al., "Cloning and characterization of cDNAs encoding four different canine immunoglobulin γ chains", Veterinary Immunology and Immunopathology, 2001, 80(3-4) pp. 259-270 (abstract attached).

Terada, et al., "A chimeric human-cat Fcγ-Fel d1 fusion protein inhibits systemic, pulmonary, and cutaneous allergic reactivity to intratracheal challenge in mice sensitized to Fel d1, the major cat allergen", Clinical Immunology, 2006, 120(1) pp. 45-56 (abstract attached).

Wang, et al., "Proinsulin-Transferrin Fusion Protein as a Novel Long-Acting Insulin Analog for the Inhibition of Hepatic Glucose Production", Diabetes, 2014, 63 pp. 1779-1788.

(56) References Cited

OTHER PUBLICATIONS yourgenome.org, "What does DNA do?", 2016, https://www.yourgenome.org/facts/what-does-dna-do.

Wang, et al., "IgG Fc engineering to modulate antibody effector functions", Protein Cell, Jan. 2018, 9(1), pp. 63-73.

Kim, et al., "Mammalian cell transfection: the present and the future", Analytical and Bioanalytical Chemistry, 2010, 397(8), pp. 3173-3178.

Fan, et al., "Improving the efficiency of CHO cell line generation using glutamine synthetase gene knockout cells", Biotechnology and Bioengineering, 2012, 109(4), pp. 1007-1015 (abstract attached).

Lodish, et al., Molecular Cell Biology, Molecular Cell Biology, 4th edition, 2000, www.ncbi.nlm.gov/books/NBK21654 (abstract attached).

Horvath, et al., "An automated DNA synthesizer employing deoxynucleoside 3'-phosphoramidites", Methods in Enzymology, Academic Press, 1987, 154, pp. 314-326 (abstract attached).

Dumont, et al., "Human cell lines for biopharmaceutical manufacturing: history, status, and future perspectives", Critical Reviews in Biotechnology, 2016, 36(6), pp. 1110-1122.

Singh, et al., "Combined blockade of HER2 and VEGF exerts greater growth inhibition of HER2-overexpressing gastric cancer xenografts than individual blockade", Experimental and Molecular Medicine, 2013, 45, 11 pages.

Huang, et al., "Production of recombinant murine-human chimeric IgM and IgG anti-Jsb for use in the clinical laboratory", Transfusion, 2003, 43(6), pp. 758-764 (abstract attached).

International Search Report and Written Opinion in corresponding PCT/US2019/040010, dated Nov. 12, 2019.

Walter, et al., "No effect of the altered peptide ligand NBI-6024 on beta-cell residual function and insulin needs in new-onset type 1 diabetes", Diabetes Care, 2009, 32(11), pp. 2036-2040.

Office Action in co-pending U.S. Appl. No. 17/019,059, dated Apr. 2, 2021.

\* cited by examiner

```
SEQ ID NO: 44    FVNQHLCGSDLVEALALVCGERGFFYTDPTGGGPRRGIVEQCCHSICSLYQLENYCNGGG    60
SEQ ID NO: 46    FVNQHLCGSDLVEALALVCGERGFFYTDPTGGGPRRGIVEQCCHSICSLYQLENYCNGGG    60
SEQ ID NO: 48    FVNQHLCGSDLVEALALVCGERGFFYTDPTGGGPRRGIVEQCCHSICSLYQLENYCNGGG    60
SEQ ID NO: 42    FVNQHLCGSDLVEALALVCGERGFFYTDPTGGGPRRGIVEQCCHSICSLYQLENYCNGGG    60
SEQ ID NO: 50    FVNQHLCGSDLVEALALVCGERGFFYTDPTGGGPRRGIVEQCCHSICSLYQLENYCNGGG    60
                 ************************************************************

SEQ ID NO: 44    GAGGGGRCTDTPPCPVPEPLGGPSVLIFPPKPKDILRITRTPEVTCVVLDLGREDPEVQI    120
SEQ ID NO: 46    GAGGGGRCTDTPPCPVPEPLGGPSVLIFPPKPKDILRITRTPEVTCVVLDLGREDPEVQI    120
SEQ ID NO: 48    GAGGGGRCTDTPPCPVPEPLGGPSVLIFPPKPKDILRITRTPEVTCVVLDLGREDPEVQI    120
SEQ ID NO: 42    GAGGGGRCTDTPPCPVPEPLGGPSVLIFPPKPKDILRITRTPEVTCVVLDLGREDPEVQI    120
SEQ ID NO: 50    GAGGGGRCTDTPPCPVPEPLGGPSVLIFPPKPKDILRITRTPEVTCVVLDLGREDPEVQI    120
                 ************************************************************

SEQ ID NO: 44    SWFVDGKEVHTAKTQSREQQFNGTYRVVSVLPIEHQDWLTGKEFKCRVNHIDLPSPIERT    180
SEQ ID NO: 46    SWFVDGKEVHTAKTQSREQQFNGTYRVVSVLPIEHQDWLTGKEFKCRVNHIDLPSPIERT    180
SEQ ID NO: 48    SWFVDGKEVHTAKTQSREQQFNGTYRVVSVLPIEHQDWLTGKEFKCRVNHIDLPSPIERT    180
SEQ ID NO: 42    SWFVDGKEVHTAKTQSREQQFNGTYRVVSVLPIEHQDWLTGKEFKCRVNHIDLPSPIERT    180
SEQ ID NO: 50    SWFVDGKEVHTAKTQSREQQFNGTYRVVSVLPIEHQDWLTGKEFKCRVNHIDLPSPIERT    180
                 ************************************************************

SEQ ID NO: 44    ISKARGRAHKPSVYVLPPSPKELSSSDTVSITCLIKDFYPPDIDVEWQSNGQQEPERKHR    240
SEQ ID NO: 46    ISKARGRAHKPSVYVLPPSPKELSSSDTVSITCLIKDFYPPDIDVEWQSNGQQEPERKHR    240
SEQ ID NO: 48    ISKARGRAHKPSVYVLPPSPKELSSSDTVSITCLIKDFYPPDIDVEWQSNGQQEPERKHR    240
SEQ ID NO: 42    ISKARGRAHKPSVYVLPPSPKELSSSDTVSITCLIKDFYPPDIDVEWQSNGQQEPERKHR    240
SEQ ID NO: 50    ISKARGRAHKPSVYVLPPSPKELSSSDTVSITCLIKDFYPPDIDVEWQSNGQQEPERKHR    240
                 ************************************************************

SEQ ID NO: 44    MTPPQLDEDGSYFLYSKLSVDKSRWQQGDPFTCAVLHEALHSHYTQKSLSLSPG    294
SEQ ID NO: 46    MTPPQLDEDGSYFLYSKLSVDKSRWQQGDPFTCAVLHETLQSHYTDLSLSHSPG    294
SEQ ID NO: 48    MTPPQLDEDGSYFLYSKLSVDKSRWQQGDPFTCAVMHETLQSHYTDLSLSHSPG    294
SEQ ID NO: 42    MTPPQLDEDGSYFLYSKLSVDKSRWQQGDPFTCAVMHETLQNHYTDLSLSHSPG    294
SEQ ID NO: 50    MTPPQLDEDGSYFLYSKLSVDKSRWQQGDPFTCAVLHETLQNHYTDLSLSHSPG    294
                 ***********************************:**:*:.***: *** ***
```

FIG. 3

```
SEQ ID NO: 42    FVNQHLCGSDLVEALALVCGERGFFYTDPTGGGPRRGIVEQCCHSICSLYQLENYCNGGG    60
SEQ ID NO: 56    FVNQHLCGSDLVEALALVCGERGFFYTDPTGGGPRRGIVEQCCHSICSLYQLENYCNGGG    60
SEQ ID NO: 52    FVNQHLCGSDLVEALALVCGERGFFYTDPTGGGPRRGIVEQCCHSICSLYQLENYCNGGG    60
SEQ ID NO: 54    FVNQHLCGSDLVEALALVCGERGFFYTDPTGGGPRRGIVEQCCHSICSLYQLENYCNGGG    60
                 ************************************************************

SEQ ID NO: 42    GAGGGGRCTDTPPCPVPEPLGGPSVLIFPPKPKDILRITRTPEVTCVVLDLGREDPEVQI   120
SEQ ID NO: 56    GAGGGGC---ISPCPVPESLGGPSVFIFPPKPKDILRITRTPEITCVVLDLGREDPEVQI   117
SEQ ID NO: 52    GAGGGGDCPK---CPAPEMLGGPSVFIFPPKPKDTLLIARTPEVTCVVVDLDPEDPEVQI   117
SEQ ID NO: 54    GAGGGG-CNN-CPCPGCGLLGGPSVFIFPPKPKDILVTARTPTVTCVVVDLDPENPEVQI   118
                 ******     **    ******:******** *  :*** :****:**  *:*****

SEQ ID NO: 42    SWFVDGKEVHTAKTQSREQQFNGTYRVVSVLPIEHQDWLTGKEFKCRVNHIDLPSPIERT   180
SEQ ID NO: 56    SWFVDGKEVHTAKTQPREQQFNSTYRVVSVLPIEHQDWLTGKEFKCRVNHIGLPSPIERT   177
SEQ ID NO: 52    SWFVDGKQMQTAKTQPREEQFNGTYRVVSVLPIGHQDWLKGKQFTCKVNNKALPSPIERT   177
SEQ ID NO: 54    SWFVDSKQVQTANTQPREEQSNGTYRVVSVLPIGHQDWLSGKQFKCKVNNKALPSPIEEI   178
                 *****.*:::**:** **:* *.**********.*****.**:*.*:**:  ******.

SEQ ID NO: 42    ISKARGRAHKPSVYVLPPSPKELSSSDTVSITCLIKDFYPPDIDVEWQSNGQQEPERKHR   240
SEQ ID NO: 56    ISKARGQAHQPSVYVLPPSPKELSSSDTVTLTCLIKDFFPPEIDVEWQSNGQPEPESKYH   237
SEQ ID NO: 52    ISKARGQAHQPSVYVLPPSREELS-KNTVSLTCLIKDFFPPDIDVEWQSNGQQEPESKYR   236
SEQ ID NO: 54    ISKTPGQAHQPNVYVLPPSRDEMS-KNTVTLTCLVKDFFPPEIDVEWQSNGQQEPESKYR   237
                 ***: *:**:*.****** .:*    :**::***:***:***:** ********** *::

SEQ ID NO: 42    MTPPQLDEDGSYFLYSKLSVDKSRWQQGDPFTCAVMHETLQNHYTDLSLSHSPG        294
SEQ ID NO: 56    TTAPQLDEDGSYFLYSKLSVDKSRWQQGDTFTCAVMHEALQNHYTDLSLSHSPG        291
SEQ ID NO: 52    TTPPQLDEDGSYFLYSKLSVDKSRWQRGDTFICAVMHEALHNHYTQESLSHSPG        290
SEQ ID NO: 54    MTPPQLDEDGSYFLYSKLSVDKSRWQRGDTFICAVMHEALHNHYTQISLSHSPG        291
                 * ***********************:**.* ******:*:****:  *******
```

FIG. 4

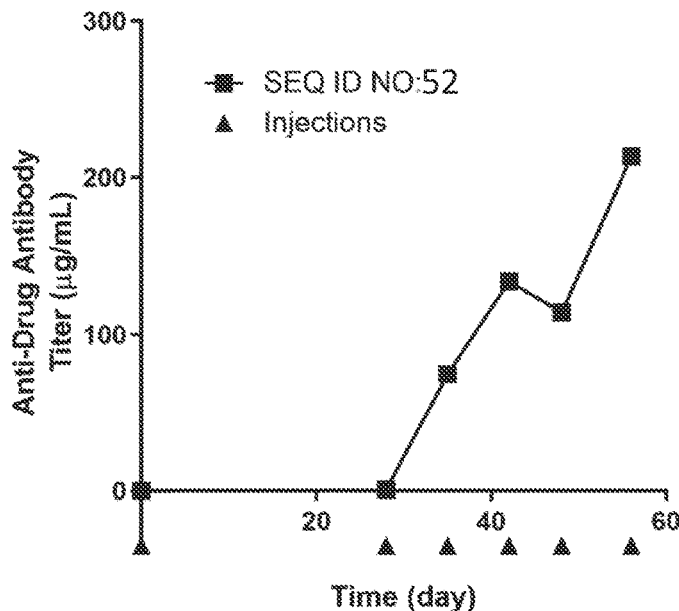

FIG. 7

| | | |
|---|---|---|
| SEQ ID NO: 58 | FVNQHLCGSDLVEALALVCGERGFFYTDPTGGGPRRGIVEQCCHSICSLYQLENYCNGGG | 60 |
| SEQ ID NO: 60 | FVNQHLCGSDLVEALALVCGERGFFYTDPTGGGPRRGIVEQCCHSICSLYQLENYCNGGG | 60 |
| SEQ ID NO: 62 | FVNQHLCGSDLVEALALVCGERGFFYTDPTGGGPRRGIVEQCCHSICSLYQLENYCNGGG | 60 |
| SEQ ID NO: 64 | FVNQHLCGSDLVEALALVCGERGFFYTDPTGGGPRRGIVEQCCHSICSLYQLENYCNGGG | 60 |
| | ************************************************************ | |
| SEQ ID NO: 58 | GAGGGGDCPKCPAPEMLGGPSVFIFPPKPKDTLLIARTPEVTCVVVDLDPEDPEVQISWF | 120 |
| SEQ ID NO: 60 | GAGGGGDCPKCPAPEMLGGPSVFIFPPKPKDTLLIARTPEVTCVVVDLDPEDPEVQISWF | 120 |
| SEQ ID NO: 62 | GAGGGGDCPKCPAPEMLGGPSVFIFPPKPKDTLLIARTPEVTCVVVDLDPEDPEVQISWF | 120 |
| SEQ ID NO: 64 | GAGGGGDCPKCPAPEMLGGPSVFIFPPKPKDTLLIARTPEVTCVVVDLDPEDPEVQISWF | 120 |
| | ************************************************************ | |
| SEQ ID NO: 58 | VDGKQMQTAKTQPREEQFQGTYRVVSVLPIGHQDWLKGKQFTCKVNNKALPSPIERTISK | 180 |
| SEQ ID NO: 60 | VDGKQMQTAKTQPREEQFSGTYRVVSVLPIGHQDWLKGKQFTCKVNNKALPSPIERTISK | 180 |
| SEQ ID NO: 62 | VDGKQMQTAKTQPREEQFDGTYRVVSVLPIGHQDWLKGKQFTCKVNNKALPSPIERTISK | 180 |
| SEQ ID NO: 64 | VDGKQMQTAKTQPREEQFKGTYRVVSVLPIGHQDWLKGKQFTCKVNNKALPSPIERTISK | 180 |
| | ****************.*************************************** | |
| SEQ ID NO: 58 | ARGQAHQPSVYVLPPSREELSKNTVSLTCLIKDFFPPDIDVEWQSNGQQEPESKYRTTPP | 240 |
| SEQ ID NO: 60 | ARGQAHQPSVYVLPPSREELSKNTVSLTCLIKDFFPPDIDVEWQSNGQQEPESKYRTTPP | 240 |
| SEQ ID NO: 62 | ARGQAHQPSVYVLPPSREELSKNTVSLTCLIKDFFPPDIDVEWQSNGQQEPESKYRTTPP | 240 |
| SEQ ID NO: 64 | ARGQAHQPSVYVLPPSREELSKNTVSLTCLIKDFFPPDIDVEWQSNGQQEPESKYRTTPP | 240 |
| | ************************************************************ | |
| SEQ ID NO: 58 | QLDEDGSYFLYSKLSVDKSRWQRGDTFICAVMHEALHNHYTQESLSHSPG | 290 |
| SEQ ID NO: 60 | QLDEDGSYFLYSKLSVDKSRWQRGDTFICAVMHEALHNHYTQESLSHSPG | 290 |
| SEQ ID NO: 62 | QLDEDGSYFLYSKLSVDKSRWQRGDTFICAVMHEALHNHYTQESLSHSPG | 290 |
| SEQ ID NO: 64 | QLDEDGSYFLYSKLSVDKSRWQRGDTFICAVMHEALHNHYTQESLSHSPG | 290 |
| | ************************************************* | |

FIG. 8

```
SEQ ID NO: 66    FVNQHLCGSHLVEALALVCGERGFFYTDPTGGGPRRGIVEQCCTSICSLYQLENYCNGGG    60
SEQ ID NO: 68    FVNQHLCGSHLVQALYLVCGERGFFYTDPTGGGPRRGIVEQCCTSICSLYQLENYCGG-G    59
SEQ ID NO: 70    FVNQHLCGSELVEALALVCGERGFFYTDPTGGGPRRGIVEQCCTSICSLYQLENYCGG-G    59
SEQ ID NO: 72    FVNQHLCGSHLVEALALVCGEAGFFYTDPTGGGPRRGIVEQCCTSICSLYQLENYCGG-G    59
SEQ ID NO: 74    FVNQHLCGSHLVEALALVCGERGFYYTDPTGGGPRRGIVEQCCTSICSLYQLENYCGG-G    59
SEQ ID NO: 76    FVNQHLCGSHLVEALALVCGERGFFYTDPTGGGPRRGIVEQCCTSICSLYQLENYCGG-G    59
                 *********.**:** ***** **:*********************************.* *

SEQ ID NO: 66    GAGGGGDCPKCPAPEMLGGPSVFIFPPKPKDTLLIARTPEVTCVVVDLDPEDPEVQISWF    120
SEQ ID NO: 68    GAGGGGDCPKCPAPEMLGGPSVFIFPPKPKDTLLIARTPEVTCVVVDLDPEDPEVQISWF    119
SEQ ID NO: 70    GAGGGGDCPKCPAPEMLGGPSVFIFPPKPKDTLLIARTPEVTCVVVDLDPEDPEVQISWF    119
SEQ ID NO: 72    GAGGGGDCPKCPAPEMLGGPSVFIFPPKPKDTLLIARTPEVTCVVVDLDPEDPEVQISWF    119
SEQ ID NO: 74    GAGGGGDCPKCPAPEMLGGPSVFIFPPKPKDTLLIARTPEVTCVVVDLDPEDPEVQISWF    119
SEQ ID NO: 76    GAGGGGDCPKCPAPEMLGGPSVFIFPPKPKDTLLIARTPEVTCVVVDLDPEDPEVQISWF    119
                 ************************************************************

SEQ ID NO: 66    VDGKQMQTAKTQPREEQFQGTYRVVSVLPIGHQDWLKGKQFTCKVNNKALPSPIERTISK    180
SEQ ID NO: 68    VDGKQMQTAKTQPREEQFSGTYRVVSVLPIGHQDWLKGKQFTCKVNNKALPSPIERTISK    179
SEQ ID NO: 70    VDGKQMQTAKTQPREEQFSGTYRVVSVLPIGHQDWLKGKQFTCKVNNKALPSPIERTISK    179
SEQ ID NO: 72    VDGKQMQTAKTQPREEQFSGTYRVVSVLPIGHQDWLKGKQFTCKVNNKALPSPIERTISK    179
SEQ ID NO: 74    VDGKQMQTAKTQPREEQFSGTYRVVSVLPIGHQDWLKGKQFTCKVNNKALPSPIERTISK    179
SEQ ID NO: 76    VDGKQMQTAKTQPREEQFSGTYRVVSVLPIGHQDWLKGKQFTCKVNNKALPSPIERTISK    179
                 ******************.*****************************************

SEQ ID NO: 66    ARGQAHQPSVYVLPPSREELSKNTVSLTCLIKDFFPPDIDVEWQSNGQQEPESKYRTTPP    240
SEQ ID NO: 68    ARGQAHQPSVYVLPPSREELSKNTVSLTCLIKDFFPPDIDVEWQSNGQQEPESKYRTTPP    239
SEQ ID NO: 70    ARGQAHQPSVYVLPPSREELSKNTVSLTCLIKDFFPPDIDVEWQSNGQQEPESKYRTTPP    239
SEQ ID NO: 72    ARGQAHQPSVYVLPPSREELSKNTVSLTCLIKDFFPPDIDVEWQSNGQQEPESKYRTTPP    239
SEQ ID NO: 74    ARGQAHQPSVYVLPPSREELSKNTVSLTCLIKDFFPPDIDVEWQSNGQQEPESKYRTTPP    239
SEQ ID NO: 76    ARGQAHQPSVYVLPPSREELSKNTVSLTCLIKDFFPPDIDVEWQSNGQQEPESKYRTTPP    239
                 ************************************************************

SEQ ID NO: 66    QLDEDGSYFLYSKLSVDKSRWQRGDTFICAVMHEALHNHYTQESLSHSPG    290
SEQ ID NO: 68    QLDEDGSYFLYSKLSVDKSRWQRGDTFICAVMHEALHNHYTQESLSHSPG    289
SEQ ID NO: 70    QLDEDGSYFLYSKLSVDKSRWQRGDTFICAVMHEALHNHYTQESLSHSPG    289
SEQ ID NO: 72    QLDEDGSYFLYSKLSVDKSRWQRGDTFICAVMHEALHNHYTQESLSHSPG    289
SEQ ID NO: 74    QLDEDGSYFLYSKLSVDKSRWQRGDTFICAVMHEALHNHYTQESLSHSPG    289
SEQ ID NO: 76    QLDEDGSYFLYSKLSVDKSRWQRGDTFICAVMHEALHNHYTQESLSHSPG    289
                 *************************************************
```

FIG. 12

```
SEQ ID NO: 66   FVNQHLCGSHLVEALALVCGERGFFYTDPTGG------GPRRGIVEQCCTSICSLYQLENY   55
SEQ ID NO: 78   FVNQHLCGSHLVQALYLVCGERGFFYTDPTQRGGG---GGQRGIVEQCCTSICSLYQLENY   58
SEQ ID NO: 80   FVNQHLCGSHLVEALALVCGERGFFYTDPTGGGGGSGGGGGIVEQCCTSICSLYQLENY    60
SEQ ID NO: 82   FVNQHLCGSHLVEALALVCGERGFFYTDPGGGG------GGGGGIVEQCCTSICSLYQLENY 56
SEQ ID NO: 84   FVNQHLCGSHLVEALALVCGERGFFYT-PGGGG------GGGGGIVEQCCTSICSLYQLENY 55
                ************:** *********** *         *   ********************

SEQ ID NO: 66   CNGGGGAGGGGDCPKCPAPEMLGGPSVFIFPPKPKDTLLIARTPEVTCVVVDLDPEDPEV   115
SEQ ID NO: 78   CGG-GGAGGGGDCPKCPAPEMLGGPSVFIFPPKPKDTLLIARTPEVTCVVVDLDPEDPEV   117
SEQ ID NO: 80   CGG-GGAGGGGDCPKCPAPEMLGGPSVFIFPPKPKDTLLIARTPEVTCVVVDLDPEDPEV   119
SEQ ID NO: 82   CGG-GGAGGGGDCPKCPAPEMLGGPSVFIFPPKPKDTLLIARTPEVTCVVVDLDPEDPEV   115
SEQ ID NO: 84   CGG-GGAGGGGDCPKCPAPEMLGGPSVFIFPPKPKDTLLIARTPEVTCVVVDLDPEDPEV   114
                *.* ********************************************************

SEQ ID NO: 66   QISWFVDGKQMQTAKTQPREEQFQGTYRVVSVLPIGHQDWLKGKQFTCKVNNKALPSPIE   175
SEQ ID NO: 78   QISWFVDGKQMQTAKTQPREEQFSGTYRVVSVLPIGHQDWLKGKQFTCKVNNKALPSPIE   177
SEQ ID NO: 80   QISWFVDGKQMQTAKTQPREEQFSGTYRVVSVLPIGHQDWLKGKQFTCKVNNKALPSPIE   179
SEQ ID NO: 82   QISWFVDGKQMQTAKTQPREEQFSGTYRVVSVLPIGHQDWLKGKQFTCKVNNKALPSPIE   175
SEQ ID NO: 84   QISWFVDGKQMQTAKTQPREEQFSGTYRVVSVLPIGHQDWLKGKQFTCKVNNKALPSPIE   174
                ***********************.************************************

SEQ ID NO: 66   RTISKARGQAHQPSVYVLPPSREELSKNTVSLTCLIKDFFPPDIDVEWQSNGQQEPESKY   235
SEQ ID NO: 78   RTISKARGQAHQPSVYVLPPSREELSKNTVSLTCLIKDFFPPDIDVEWQSNGQQEPESKY   237
SEQ ID NO: 80   RTISKARGQAHQPSVYVLPPSREELSKNTVSLTCLIKDFFPPDIDVEWQSNGQQEPESKY   239
SEQ ID NO: 82   RTISKARGQAHQPSVYVLPPSREELSKNTVSLTCLIKDFFPPDIDVEWQSNGQQEPESKY   235
SEQ ID NO: 84   RTISKARGQAHQPSVYVLPPSREELSKNTVSLTCLIKDFFPPDIDVEWQSNGQQEPESKY   234
                ************************************************************

SEQ ID NO: 66   RTTPPQLDEDGSYFLYSKLSVDKSRWQRGDTFICAVMHEALHNHYTQESLSHSPG   290
SEQ ID NO: 78   RTTPPQLDEDGSYFLYSKLSVDKSRWQRGDTFICAVMHEALHNHYTQESLSHSPG   292
SEQ ID NO: 80   RTTPPQLDEDGSYFLYSKLSVDKSRWQRGDTFICAVMHEALHNHYTQESLSHSPG   294
SEQ ID NO: 82   RTTPPQLDEDGSYFLYSKLSVDKSRWQRGDTFICAVMHEALHNHYTQESLSHSPG   290
SEQ ID NO: 84   RTTPPQLDEDGSYFLYSKLSVDKSRWQRGDTFICAVMHEALHNHYTQESLSHSPG   289
                *******************************************************
```

FIG. 13

```
SEQ ID NO: 86    FVNQHLCGSHLVEALALVCGERGFFYTDPTGGGPRRGIVEQCCTSICSLYQLENYCGGGG    60
SEQ ID NO: 66    FVNQHLCGSHLVEALALVCGERGFFYTDPTGGGPRRGIVEQCCTSICSLYQLENYCNGGG    60
SEQ ID NO: 76    FVNQHLCGSHLVEALALVCGERGFFYTDPTGGGPRRGIVEQCCTSICSLYQLENYCGGGG    60
                 ************************************************████████.███

SEQ ID NO: 86    GQGGGGQGGGGQGGGGGDCPKCPAPEMLGGPSVFIFPPKPKDTLLIARTPEVTCVVVDLD   120
SEQ ID NO: 66    GA-------------GGGGDCPKCPAPEMLGGPSVFIFPPKPKDTLLIARTPEVTCVVVDLD   109
SEQ ID NO: 76    A--------------GGGGDCPKCPAPEMLGGPSVFIFPPKPKDTLLIARTPEVTCVVVDLD   108
                  .             ************************************************

SEQ ID NO: 86    PEDPEVQISWFVDGKQMQTAKTQPREEQFSGTYRVVSVLPIGHQDWLKGKQFTCKVNNKA   180
SEQ ID NO: 66    PEDPEVQISWFVDGKQMQTAKTQPREEQFQGTYRVVSVLPIGHQDWLKGKQFTCKVNNKA   169
SEQ ID NO: 76    PEDPEVQISWFVDGKQMQTAKTQPREEQFSGTYRVVSVLPIGHQDWLKGKQFTCKVNNKA   168
                 *****************************.*****************************

SEQ ID NO: 86    LPSPIERTISKARGQAHQPSVYVLPPSREELSKNTVSLTCLIKDFFPPDIDVEWQSNGQQ   240
SEQ ID NO: 66    LPSPIERTISKARGQAHQPSVYVLPPSREELSKNTVSLTCLIKDFFPPDIDVEWQSNGQQ   229
SEQ ID NO: 76    LPSPIERTISKARGQAHQPSVYVLPPSREELSKNTVSLTCLIKDFFPPDIDVEWQSNGQQ   228
                 ************************************************************

SEQ ID NO: 86    EPESKYRTTPPQLDEDGSYFLYSKLSVDKSRWQRGDTFICAVMHEALHNHYTQESLSHSP   300
SEQ ID NO: 66    EPESKYRTTPPQLDEDGSYFLYSKLSVDKSRWQRGDTFICAVMHEALHNHYTQESLSHSP   289
SEQ ID NO: 76    EPESKYRTTPPQLDEDGSYFLYSKLSVDKSRWQRGDTFICAVMHEALHNHYTQESLSHSP   288
                 ************************************************************

SEQ ID NO: 86    G    301
SEQ ID NO: 66    G    290
SEQ ID NO: 76    G    289
                 *
```

FIG. 14

```
SEQ ID NO: 66    FVNQHLCGSHLVEALALVCGERGFFYTDPTGGG-PRRGIVEQCCTSICSLYQLENYCNGG    59
SEQ ID NO: 82    FVNQHLCGSHLVEALALVCGERGFFYTDPGGGGGGGGGIVEQCCTSICSLYQLENYCGG-    59
SEQ ID NO: 88    FVNQHLCGSHLVEALALVCGERGFFYTQG-GGGGGGGGGIVEQCCTSICSLYQLENYCGG-    58
SEQ ID NO: 84    FVNQHLCGSHLVEALALVCGERGFFYTPG-GGGGGGGGGIVEQCCTSICSLYQLENYCGG-    58
                 *************************  ***    ********************.*

SEQ ID NO: 66    GGAGGGGDCPKCPAPEMLGGPSVFIFPPKPKDTLLIARTPEVTCVVVDLDPEDPEVQISW    119
SEQ ID NO: 82    GGAGGGGDCPKCPAPEMLGGPSVFIFPPKPKDTLLIARTPEVTCVVVDLDPEDPEVQISW    119
SEQ ID NO: 88    GGAGGGGDCPKCPAPEMLGGPSVFIFPPKPKDTLLIARTPEVTCVVVDLDPEDPEVQISW    118
SEQ ID NO: 84    GGAGGGGDCPKCPAPEMLGGPSVFIFPPKPKDTLLIARTPEVTCVVVDLDPEDPEVQISW    118
                 ************************************************************

SEQ ID NO: 66    FVDGKQMQTAKTQPREEQFQGTYRVVSVLPIGHQDWLKGKQFTCKVNNKALPSPIERTIS    179
SEQ ID NO: 82    FVDGKQMQTAKTQPREEQFSGTYRVVSVLPIGHQDWLKGKQFTCKVNNKALPSPIERTIS    179
SEQ ID NO: 88    FVDGKQMQTAKTQPREEQFSGTYRVVSVLPIGHQDWLKGKQFTCKVNNKALPSPIERTIS    178
SEQ ID NO: 84    FVDGKQMQTAKTQPREEQFSGTYRVVSVLPIGHQDWLKGKQFTCKVNNKALPSPIERTIS    178
                 *******************.****************************************

SEQ ID NO: 66    KARGQAHQPSVYVLPPSREELSKNTVSLTCLIKDFFPPDIDVEWQSNGQQEPESKYRTTP    239
SEQ ID NO: 82    KARGQAHQPSVYVLPPSREELSKNTVSLTCLIKDFFPPDIDVEWQSNGQQEPESKYRTTP    239
SEQ ID NO: 88    KARGQAHQPSVYVLPPSREELSKNTVSLTCLIKDFFPPDIDVEWQSNGQQEPESKYRTTP    238
SEQ ID NO: 84    KARGQAHQPSVYVLPPSREELSKNTVSLTCLIKDFFPPDIDVEWQSNGQQEPESKYRTTP    238
                 ************************************************************

SEQ ID NO: 66    PQLDEDGSYFLYSKLSVDKSRWQRGDTFICAVMHEALHNHYTQESLSHSPG           290
SEQ ID NO: 82    PQLDEDGSYFLYSKLSVDKSRWQRGDTFICAVMHEALHNHYTQESLSHSPG           290
SEQ ID NO: 88    PQLDEDGSYFLYSKLSVDKSRWQRGDTFICAVMHEALHNHYTQESLSHSPG           289
SEQ ID NO: 84    PQLDEDGSYFLYSKLSVDKSRWQRGDTFICAVMHEALHNHYTQESLSHSPG           289
                 **************************************************
```

FIG. 15

```
SEQ ID NO: 66   FVNQHLCGSHLVEALALVCGERGFFYTDPTGG-GPRRGIVEQCCTSICSLYQLENYCNGG   59
SEQ ID NO: 90   FVNQHLCGSHLVEALELVCGERGFFYTPKTGGSGGGGGIVEQCCTSTCSLDQLENYCGG-   59
SEQ ID NO: 92   FVNQHLCGSHLVEALELVCGERGFHYGGGGGGSGGGGGIVEQCCTSTCSLDQLENYCNHG   60
SEQ ID NO: 34   FVNQHLCGSHLVEALELVCGERGFHYGGGGGGSGGGGGIVEQCCTSTCSLDQLENYCNGG   60
SEQ ID NO: 32   FVNQHLCGSHLVEALELVCGERGFHYGGGGGGSGGGGGIVEQCCTSTCSLDQLENYCGG-   59
SEQ ID NO: 94   FVNQHLCGSHLVEALELVCGERGFFYGGGGGGSGGGGGIVEQCCTSTCSLDQLENYCGG-   59
                *************** *******.*    ** *    ********* *** ******.

SEQ ID NO: 66   GG--------------AGGGGDCPKCPAPEMLGGPSVFIFPPKPKDTLLIARTPEVTCVVVD   107
SEQ ID NO: 90   GGGGQGGGGQGGGGQGGGGGDCPKCPAPEMLGGPSVFIFPPKPKDTLLIARTPEVTCVVVD   119
SEQ ID NO: 92   GGGGQGGGGQGGGGQGGGGGDCPKCPAPEMLGGPSVFIFPPKPKDTLLIARTPEVTCVVVD   120
SEQ ID NO: 34   GGGGQGGGGQGGGGQGGGGGDCPKCPAPEMLGGPSVFIFPPKPKDTLLIARTPEVTCVVVD   120
SEQ ID NO: 32   GGGGQGGGGQGGGGQGGGGGDCPKCPAPEMLGGPSVFIFPPKPKDTLLIARTPEVTCVVVD   119
SEQ ID NO: 94   GGGGQGGGGQGGGGQGGGGGDCPKCPAPEMLGGPSVFIFPPKPKDTLLIARTPEVTCVVVD   119
                **           .***********************************************

SEQ ID NO: 66   LDPEDPEVQISWFVDGKQMQTAKTQPREEQFQGTYRVVSVLPIGHQDWLKGKQFTCKVNN   167
SEQ ID NO: 90   LDPEDPEVQISWFVDGKQMQTAKTQPREEQFNGTYRVVSVLPIGHQDWLKGKQFTCKVNN   179
SEQ ID NO: 92   LDPEDPEVQISWFVDGKQMQTAKTQPREEQFNGTYRVVSVLPIGHQDWLKGKQFTCKVNN   180
SEQ ID NO: 34   LDPEDPEVQISWFVDGKQMQTAKTQPREEQFNGTYRVVSVLPIGHQDWLKGKQFTCKVNN   180
SEQ ID NO: 32   LDPEDPEVQISWFVDGKQMQTAKTQPREEQFNGTYRVVSVLPIGHQDWLKGKQFTCKVNN   179
SEQ ID NO: 94   LDPEDPEVQISWFVDGKQMQTAKTQPREEQFNGTYRVVSVLPIGHQDWLKGKQFTCKVNN   179
                ******************************:*****************************

SEQ ID NO: 66   KALPSPIERTISKARGQAHQPSVYVLPPSREELSKNTVSLTCLIKDFFPPDIDVEWQSNG   227
SEQ ID NO: 90   KALPSPIERTISKARGQAHQPSVYVLPPSREELSKNTVSLTCLIKDFFPPDIDVEWQSNG   239
SEQ ID NO: 92   KALPSPIERTISKARGQAHQPSVYVLPPSREELSKNTVSLTCLIKDFFPPDIDVEWQSNG   240
SEQ ID NO: 34   KALPSPIERTISKARGQAHQPSVYVLPPSREELSKNTVSLTCLIKDFFPPDIDVEWQSNG   240
SEQ ID NO: 32   KALPSPIERTISKARGQAHQPSVYVLPPSREELSKNTVSLTCLIKDFFPPDIDVEWQSNG   239
SEQ ID NO: 94   KALPSPIERTISKARGQAHQPSVYVLPPSREELSKNTVSLTCLIKDFFPPDIDVEWQSNG   239
                ************************************************************

SEQ ID NO: 66   QQEPESKYRTTPPQLDEDGSYFLYSKLSVDKSRWQRGDTFICAVMHEALHNHYTQESLSH   287
SEQ ID NO: 90   QQEPESKYRTTPPQLDEDGSYFLYSKLSVDKSRWQRGDTFICAVMHEALHNHYTQESLSH   299
SEQ ID NO: 92   QQEPESKYRTTPPQLDEDGSYFLYSKLSVDKSRWQRGDTFICAVMHEALHNHYTQESLSH   300
SEQ ID NO: 34   QQEPESKYRTTPPQLDEDGSYFLYSKLSVDKSRWQRGDTFICAVMHEALHNHYTQESLSH   300
SEQ ID NO: 32   QQEPESKYRTTPPQLDEDGSYFLYSKLSVDKSRWQRGDTFICAVMHEALHNHYTQESLSH   299
SEQ ID NO: 94   QQEPESKYRTTPPQLDEDGSYFLYSKLSVDKSRWQRGDTFICAVMHEALHNHYTQESLSH   299
                ************************************************************

SEQ ID NO: 66   SPG   290
SEQ ID NO: 90   SPG   302
SEQ ID NO: 92   SPG   303
SEQ ID NO: 34   SPG   303
SEQ ID NO: 32   SPG   302
SEQ ID NO: 94   SPG   302
                ***
```

FIG. 16

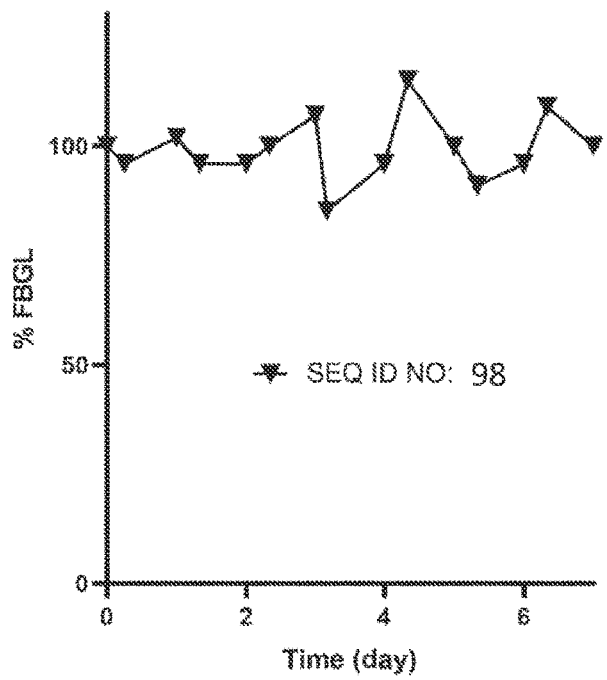

FIG. 23

| SEQ ID NO: 102 | FVNQHLCGSHLVEALELVCGERGFHYGGGGGGSGGGGGIVEQCCTSTCSLDQLENYCGGG | 60 |
| SEQ ID NO: 104 | FVNQHLCGSHLVEALELVCGERGFHYGGGGGGSGGGGGIVEQCCTSTCSLDQLENYCGGG | 60 |
| | ************************************************************ | |

| SEQ ID NO: 102 | GGQGGGGQGGGGQGGGGGDCPKCPAPEMLGGPSVFIFPPKPKDTLLIARTPEVTCVVVAL | 120 |
| SEQ ID NO: 104 | GGQGGGGQGGGGQGGGGGDCPKCPAPEMLGGPSVFIFPPKPKDTLLIARTPEVTCVVVDL | 120 |
| | *********************************************************** * | |

| SEQ ID NO: 102 | DPEDPEVQISWFVDGKQMQTAKTQPREEQFSGTYRVVSVLPIGHQDWLKGKQFTCKVNNK | 180 |
| SEQ ID NO: 104 | DPEDPEVQISWFVDGKQMQTAKTQPREEQFSGTYRVVSVLPIGHQDWLKGKQFTCKVNNK | 180 |
| | ************************************************************ | |

| SEQ ID NO: 102 | ALPSPIERTISKARGQAHQPSVYVLPPSREELSKNTVSLTCLIKDFFPPDIDVEWQSNGQ | 240 |
| SEQ ID NO: 104 | ALPSPIERTISKARGQAHQPSVYVLPPSREELSKNTVSLTCLIKDFFPPDIDVEWQSNGQ | 240 |
| | ************************************************************ | |

| SEQ ID NO: 102 | QEPESKYRTTPPQLDEDGSYFLYSKLSVDKSRWQRGDTFICAVMHEALHNHYTQESLSHS | 300 |
| SEQ ID NO: 104 | QEPESKYRTTPPQLDEDGSYFLYSKLSVDKSRWQRGDTFICAVMHEALHNHYTQESLSHS | 300 |
| | ************************************************************ | |

| SEQ ID NO: 102 | PG | 302 |
| SEQ ID NO: 104 | PG | 302 |
| | ** | |

FIG. 24

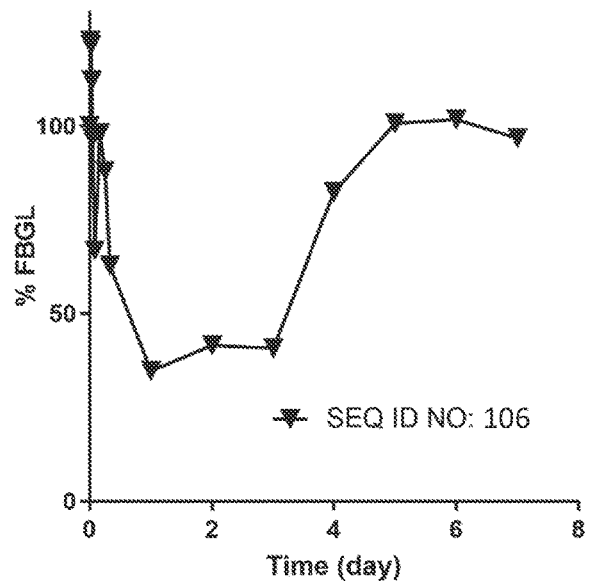

FIG. 27

| | | |
|---|---|---|
| SEQ ID NO: 108 | FVNQHLCGSDLVEALALVCGERGFFYTDPTGGGPRRGIVEQCCHSICSLYQLENYCNGGG | 60 |
| SEQ ID NO: 110 | FVNQHLCGSDLVEALALVCGERGFFYTDPTGGGPRRGIVEQCCHSICSLYQLENYCNGGG | 60 |
| SEQ ID NO: 106 | FVNQHLCGSDLVEALYLVCGERGFFYTDPTGGGPRRGIVEQCCHSICSLYQLENYCNGGG | 60 |
| SEQ ID NO: 112 | FVNQHLCGSDLVEALALVCGERGFFYTDPTGGGPRRGIVEQCCHSICSLYQLENYCNGGG | 60 |
| | ************** ******************************************** | |
| | | |
| SEQ ID NO: 108 | GSGG-GGDCPKCPPPEMLGGPSIFIFPPKPKDTLSISRTPEVTCLVVDLGPDDSDVQITW | 119 |
| SEQ ID NO: 110 | GAGGGGGGEGPKCPVPEIPGAPSVFIFPPKPKDTLSISRTPEVTCLVVDLGPDDSNVQITW | 120 |
| SEQ ID NO: 106 | GSGGGGGGEGPKCPVPEIPGAPSVFIFPPKPKDTLSISRTPEVTCLVVDLGPDDSNVQITW | 120 |
| SEQ ID NO: 112 | GSGGGGGGEGPKCPVPEIPGAPSVFIFPPKPKDTLSISRTPEVTCLVVDLGPDDSNVQITW | 120 |
| | *: : ** : * :****************************:*** | |
| | | |
| SEQ ID NO: 108 | FVDNTQVYTAKTSPREEQFNSTYRVVSVLPILHQDWLKGKEFKCKVNSKSLPSPIERTIS | 179 |
| SEQ ID NO: 110 | FVDNTEMHTAKTRPREEQFNSTYRVVSVLPILHQDWLKGKEFKCKVNSKSLPSAMERTIS | 180 |
| SEQ ID NO: 106 | FVDNTEMHTAKTRPREEQFNSTYRVVSVLPILHQDWLKGKEFKCKVNSKSLPSAMERTIS | 180 |
| SEQ ID NO: 112 | FVDNTEMHTAKTRPREEQFNSTYRVVSVLPILHQDWLKGKEFKCKVNSKSLPSAMERTIS | 180 |
| | ***::: *************************************** :*** | |
| | | |
| SEQ ID NO: 108 | KDKGQPHEPQVYVLPPAQEELSRNKVSVTCLIEGFYPSDIAVEWEITGQPEPENNYRTTP | 239 |
| SEQ ID NO: 110 | KAKGQPHEPQVYVLPPTQEELSENKVSVTCLIKGFHPPDIAVEWEITGQPEPENNYQTTP | 240 |
| SEQ ID NO: 106 | KAKGQPHEPQVYVLPPTQEELSENKVSVTCLIKGFHPPDIAVEWEITGQPEPENNYQTTP | 240 |
| SEQ ID NO: 112 | KAKGQPHEPQVYVLPPTQEELSENKVSVTCLIKGFHPPDIAVEWEITGQPEPENNYQTTP | 240 |
| | * ***********:*.****::* ****************:* | |
| | | |
| SEQ ID NO: 108 | PQLDSDGTYFLYSRLSVDRSRWQRGNTYTCSVSHEALHSHHTQKSLTQSPG | 290 |
| SEQ ID NO: 110 | PQLDSDGTYFLYSRLSVDRSHWQRGNTYTCSVSHEALHSHHTQKSLTQSPG | 291 |
| SEQ ID NO: 106 | PQLDSDGTYFLYSRLSVDRSHWQRGNTYTCSVSHEALHSHHTQKSLTQSPG | 291 |
| SEQ ID NO: 112 | PQLDSDGTYFLYSRLSVDRSHWQRGNTYTCSVSHEALHSHHTQKSLTQSPG | 291 |
| | ******************:**************************** | |

FIG. 28

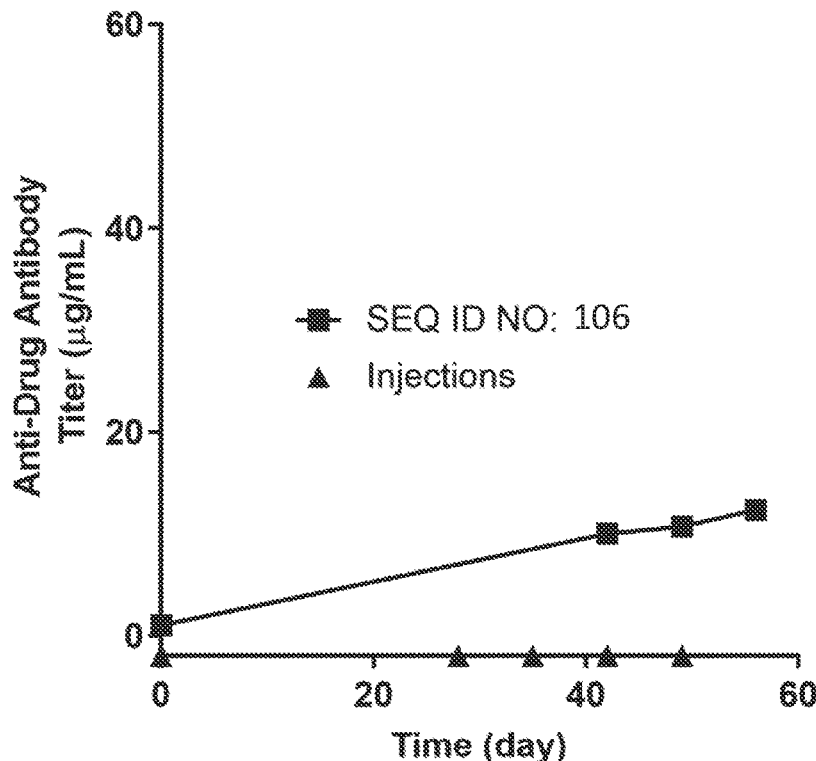

FIG. 29

```
SEQ ID NO: 114    FVNQHLCGSHLVEALALVCGERGFFYTDPAGGGPRRGIVEQCCASVCSLYQLEHYCGGGG  60
SEQ ID NO: 116    FVNQHLCGSHLVEALALVCGERGFFYTDPAGGGPRRGIVEQCCASVCSLYQLEHYCGGGG  60
SEQ ID NO: 108    FVNQHLCGSDLVEALALVCGERGFFYTDPTGGGPRRGIVEQCCHSICSLYQLENYCNGGG  60
SEQ ID NO: 118    FVNQHLCGSHLVEALALVCGERGFFYTDPAGGGPRRGIVEQCCASVCSLYQLEHYCGG-G  59
                  *********.*******************:************** *:*******:**.* *

SEQ ID NO: 114    AGGGGGEGPKCPVPEIPGAPSVFIFPPKPKDTLSISRTPEVTCLVVDLGPDDSNVQITWF  120
SEQ ID NO: 116    AGGGGGEGPKCPVPEIPGAPSVFIFPPKPKDTLSISRTPEVTCLVVDLGPDDSNVQITWF  120
SEQ ID NO: 108    GSGGGGDCPKCPPPEMLGGPSIFIFPPKPKDTLSISRTPEVTCLVVDLGPDDSDVQITWF  120
SEQ ID NO: 118    GAGGGGDCPKCPPPEMLGGPSIFIFPPKPKDTLSISRTPEVTCLVVALGPDDSDVQITWF  119
                  ..****: ****.**:.*.**:*********************** ******.******

SEQ ID NO: 114    VDNTEMHTAKTRPREEQFNSTYRVVSVLPILHQDWLKGKEFKCKVNSKSLPSAMERTISK  180
SEQ ID NO: 116    VDNTEMHTAKTRPREEQFSSTYRVVSVLPILHQDWLKGKEFKCKVNSKSLPSAMERTISK  180
SEQ ID NO: 108    VDNTQVYTAKTSPREEQFNSTYRVVSVLPILHQDWLKGKEFKCKVNSKSLPSPIERTISK  180
SEQ ID NO: 118    VDNTQVYTAKTSPREEQFSSTYRVVSVLPILHQDWLKGKEFKCKVNSKSLPSPIERTISK  179
                  ****:::.**** ******.***********************************.******

SEQ ID NO: 114    AKGQPHEPQVYVLPPTQEELSENKVSVTCLIKGFHPPDIAVEWEITGQPEPENNYQTTPP  240
SEQ ID NO: 116    AKGQPHEPQVYVLPPTQEELSENKVSVTCLIKGFHPPDIAVEWEITGQPEPENNYQTTPP  240
SEQ ID NO: 108    DKGQPHEPQVYVLPPAQEELSRNKVSVTCLIEGFYPSDIAVEWEITGQPEPENNYRTTPP  240
SEQ ID NO: 118    DKGQPHEPQVYVLPPAQEELSRNKVSVTCLIEGFYPSDIAVEWEITGQPEPENNYRTTPP  239
                  ****************:*****.********:**:*.******************:****

SEQ ID NO: 114    QLDSDGTYFLYSRLSVDRSHWQRGNTYTCSVSHEALHSHHTQKSLTQSP-    289
SEQ ID NO: 116    QLDSDGTYFLYSRLSVDRSHWQRGNTYTCSVSHEALHSHHTQKSLTQSPG    290
SEQ ID NO: 108    QLDSDGTYFLYSRLSVDRSRWQRGNTYTCSVSHEALHSHHTQKSLTQSPG    290
SEQ ID NO: 118    QLDSDGTYFLYSRLSVDRSRWQRGNTYTCSVSHEALHSHHTQKSLTQSPG    289
                  *******************:******************************
```

FIG. 30

```
SEQ ID NO: 106    FVNQHLCGSDLVEALYLVCGERGFFYTDPTGG-GPRRGIVEQCCHSICSLYQLENYCNGG    59
SEQ ID NO: 112    FVNQHLCGSDLVEALALVCGERGFFYTDPTGG-GPRRGIVEQCCHSICSLYQLENYCNGG    59
SEQ ID NO: 122    FVNQHLCGSHLVEALELVCGERGFHYGGGGGGSGGGGGIVEQCCTSTCSLDQLENYCGGG    60
                  *********.***** ********.*  ** *  ******* * *** ******.**

SEQ ID NO: 106    GGSG-----------GGGGEGPKCPVPEIPGAPSVFIFPPKPKDTLSISRTPEVTCLVVD    108
SEQ ID NO: 112    GGSG-----------GGGGEGPKCPVPEIPGAPSVFIFPPKPKDTLSISRTPEVTCLVVD    108
SEQ ID NO: 122    GGQGGGGQGGGGQGGGGGGEGPKCPVPEIPGAPSVFIFPPKPKDTLSISRTPEVTCLVVD    120
                  **.*               *****************************************

SEQ ID NO: 106    LGPDDSNVQITWFVDNTEMHTAKTRPREEQFNSTYRVVSVLPILHQDWLKGKEFKCKVNS    168
SEQ ID NO: 112    LGPDDSNVQITWFVDNTEMHTAKTRPREEQFNSTYRVVSVLPILHQDWLKGKEFKCKVNS    168
SEQ ID NO: 122    LGPDDSNVQITWFVDNTEMHTAKTRPREEQFNSTYRVVSVLPILHQDWLKGKEFKCKVNS    180
                  ************************************************************

SEQ ID NO: 106    KSLPSAMERTISKAKGQPHEPQVYVLPPTQEELSENKVSVTCLIKGFHPPDIAVEWEITG    228
SEQ ID NO: 112    KSLPSAMERTISKAKGQPHEPQVYVLPPTQEELSENKVSVTCLIKGFHPPDIAVEWEITG    228
SEQ ID NO: 122    KSLPSAMERTISKAKGQPHEPQVYVLPPTQEELSENKVSVTCLIKGFHPPDIAVEWEITG    240
                  ************************************************************

SEQ ID NO: 106    QPEPENNYQTTPPQLDSDGTYFLYSRLSVDRSHWQRGNTYTCSVSHEALHSHHTQKSLTQ    288
SEQ ID NO: 112    QPEPENNYQTTPPQLDSDGTYFLYSRLSVDRSHWQRGNTYTCSVSHEALHSHHTQKSLTQ    288
SEQ ID NO: 122    QPEPENNYQTTPPQLDSDGTYFLYSRLSVDRSHWQRGNTYTCSVSHEALHSHHTQKSLTQ    300
                  ************************************************************

SEQ ID NO: 106    SPG    291
SEQ ID NO: 112    SPG    291
SEQ ID NO: 122    SPG    303
                  ***
```

FIG. 31

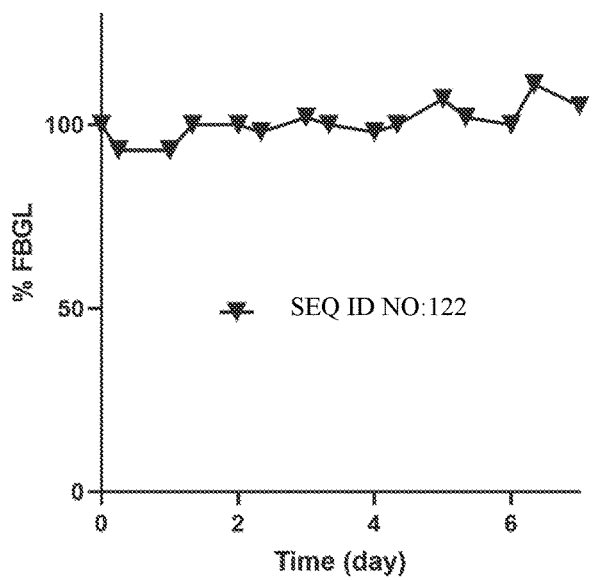

FIG. 32

```
SEQ ID NO: 31  atggaatggagctgggtctttctcttcttcctgtcagtaacgactggtgtccactccttc
SEQ ID NO: 32   M  E  W  S  W  V  F  L  F  F  L  S  V  T  T  G  V  H  S  F
               gtgaaccagcacctgtgcggctcccacctggtggaagctctggaactcgtgtgcggcgag
                V  N  Q  H  L  C  G  S  H  L  V  E  A  L  E  L  V  C  G  E
               cggggcttccactacggggtggcggaggaggttctggtggcggcggaggcatcgtggaa
                R  G  F  H  Y  G  G  G  G  S  G  G  G  G  I  V  E
               cagtgctgcacctccacctgctcctggaccagctggaaaactactgcggtggcggaggt
                Q  C  C  T  S  T  C  S  L  D  Q  L  E  N  Y  C  G  G  G
               ggtcaaggaggcggtggacagggtggaggtgggcagggaggaggcgggggagactgcccc
                G  Q  G  G  G  Q  G  G  G  Q  G  G  G  D  C  P
               aagtgccccgctcccgagatgctgggcggacccagcgtgttcatcttccctcccaagccc
                K  C  P  A  P  E  M  L  G  G  P  S  V  F  I  F  P  P  K  P
               aaggacacactgctgatcgccaggaccccggaggtgacctgcgtggtggtggacctggat
                K  D  T  L  L  I  A  R  T  P  E  V  T  C  V  V  V  D  L  D
               cccgaagaccccgaggtgcagatcagctggttcgtggatggaaagcagatgcagaccgcc
                P  E  D  P  E  V  Q  I  S  W  F  V  D  G  K  Q  M  Q  T  A
               aagacccaaccccgggaagagcagttcaacggcacctacagggtggtgagtgtgttgccc
                K  T  Q  P  R  E  E  Q  F  N  G  T  Y  R  V  V  S  V  L  P
               atcggccaccaggactggctgaaggggaagcaattcacatgcaaggttaataacaaggcc
                I  G  H  Q  D  W  L  K  G  K  Q  F  T  C  K  V  N  N  K  A
               ctgcccagccccatcgagaggaccatcagcaaggccaggggccaggcccaccagccatct
                L  P  S  P  I  E  R  T  I  S  K  A  R  G  Q  A  H  Q  P  S
               gtgtacgtgctgcccccatctagggaggaactgagcaagaacacagtcagccttacttgc
                V  Y  V  L  P  P  S  R  E  E  L  S  K  N  T  V  S  L  T  C
               ctgatcaaggacttcttcccaccggacatagacgtggagtggcagagtaacggccagcag
                L  I  K  D  F  F  P  P  D  I  D  V  E  W  Q  S  N  G  Q  Q
               gagcccgagagcaagtataggaccacaccgccccaactggacgaggacggaagctacttc
                E  P  E  S  K  Y  R  T  T  P  P  Q  L  D  E  D  G  S  Y  F
               ctctacagcaaattgagcgttgacaaaagcaggtggcagcgaggcgacaccttcatctgc
                L  Y  S  K  L  S  V  D  K  S  R  W  Q  R  G  D  T  F  I  C
               gccgtgatgcacgaggctttgcataaccactacacccaggagagcctgtcccacagcccc
                A  V  M  H  E  A  L  H  N  H  Y  T  Q  E  S  L  S  H  S  P
               ggatag
                G  -
```

FIG. 38

```
SEQ ID NO: 33    Q  C  C  T  S  T  C  S  L  D  Q  L  E  N  Y  C  N  G  G  G
SEQ ID NO: 34    ggtggtcaaggaggcggtggacagggtggaggtgggcagggaggaggcggggagactgc
                  G  G  Q  G  G  G  Q  G  G  G  Q  G  G  G  G  D  C
                 cccaagtgccccgctcccgagatgctgggcggacccagcgtgttcatcttccctcccaag
                  P  K  C  P  A  P  E  M  L  G  G  P  S  V  F  I  F  P  P  K
                 cccaaggacacactgctgatcgccaggacccCggaggtgacctgcgtggtggtggacctg
                  P  K  D  T  L  L  I  A  R  T  P  E  V  T  C  V  V  V  D  L
                 gatcccgaagaccccgaggtgcagatcagctggttcgtggatggaaagcagatgcagacc
                  D  P  E  D  P  E  V  Q  I  S  W  F  V  D  G  K  Q  M  Q  T
                 gccaagacccaaccccgggaagagcagttcaacggcacctacagggtggtgagtgtgttg
                  A  K  T  Q  P  R  E  E  Q  F  N  G  T  Y  R  V  V  S  V  L
                 cccatcggccaccaggactggctgaaggggaagcaattcacatgcaaggttaataacaag
                  P  I  G  H  Q  D  W  L  K  G  K  Q  F  T  C  K  V  N  N  K
                 gccctgcccagccccatcgagaggaccatcagcaaggccaggggccaggcccaccagcca
                  A  L  P  S  P  I  E  R  T  I  S  K  A  R  G  Q  A  H  Q  P
                 tctgtgtacgtgctgccccccatctagggaggaactgagcaagaacacagtcagccttact
                  S  V  Y  V  L  P  P  S  R  E  E  L  S  K  N  T  V  S  L  T
                 tgcctgatcaaggacttcttcccaccggacatagacgtggagtggcagagtaacggccag
                  C  L  I  K  D  F  F  P  P  D  I  D  V  E  W  Q  S  N  G  Q
                 caggagcccgagagcaagtataggaccacaccgccccaactggacgaggacggaagctac
                  Q  E  P  E  S  K  Y  R  T  T  P  Q  L  D  E  D  G  S  Y
                 ttcctctacagcaaattgagcgttgacaaaagcaggtggcagcgaggcgacaccttcatc
                  F  L  Y  S  K  L  S  V  D  K  S  R  W  Q  R  G  D  T  F  I
                 tgcgccgtgatgcacgaggctttgcataaccactacacccaggagagcctgtcccacagc
                  C  A  V  M  H  E  A  L  H  N  H  Y  T  Q  E  S  L  S  H  S
                 cccggatag
                  P  G  -
```

FIG. 39

```
SEQ ID NO: 35  atggaatggagctgggtctttctcttcttcctgtcagtaacgactggtgtccactccttc
SEQ ID NO: 36   M  E  W  S  W  V  F  L  F  F  L  S  V  T  T  G  V  H  S  F
               gtgaaccagcacctgtgcggctcccacctggtggaagctctggcactcgtgtgcggcgag
                V  N  Q  H  L  C  G  S  H  L  V  E  A  L  V  C  G  E
               cggggcttccactacggggtggcggaggaggttctggtggcggcggaggcatcgtggaa
                R  G  F  H  Y  G  G  G  G  S  G  G  G  G  I  V  E
               cagtgctgcacctccacctgctccctggaccagctggaaaactactgcggtggcggaggt
                Q  C  C  T  S  T  C  S  L  D  Q  L  E  N  Y  C  G  G  G  G
               ggtcaaggaggcggtggacagggtggaggtgggcagggaggaggcggggagactgcccc
                G  Q  G  G  G  Q  G  G  G  Q  G  G  G  D  C  P
               aagtgccccgctcccgagatgctgggcggacccagcgtgttcatcttccctcccaagccc
                K  C  P  A  P  E  M  L  G  G  P  S  V  F  I  F  P  P  K  P
               aaggacacactgctgatcgccaggaccccggaggtgacctgcgtggtggtggacctggat
                K  D  T  L  L  I  A  R  T  P  E  V  T  C  V  V  V  D  L  D
               cccgaagaccccgaggtgcagatcagctggttcgtggatggaaagcagatgcagaccgcc
                P  E  D  P  E  V  Q  I  S  W  F  V  D  G  K  Q  M  Q  T  A
               aagacccaaccccgggaagagcagttctcaggcacctacagggtggtgagtgtgttgccc
                K  T  Q  P  R  E  E  Q  F  S  G  T  Y  R  V  V  S  V  L  P
               atcggccaccaggactggctgaaggggaagcaattcacatgcaaggttaataacaaggcc
                I  G  H  Q  D  W  L  K  G  K  Q  F  T  C  K  V  N  N  K  A
               ctgcccagccccatcgagaggaccatcagcaaggccaggggccaggcccaccagccatct
                L  P  S  P  I  E  R  T  I  S  K  A  R  G  Q  A  H  Q  P  S
               gtgtacgtgctgcccccatctagggaggaactgagcaagaacacagtcagccttacttgc
                V  Y  V  L  P  P  S  R  E  E  L  S  K  N  T  V  S  L  T  C
               ctgatcaaggacttcttcccaccggacatagacgtggagtggcagagtaacggccagcag
                L  I  K  D  F  F  P  P  D  I  D  V  E  W  Q  S  N  G  Q  Q
               gagcccgagagcaagtataggaccacaccgccccaactggacgaggacggaagctacttc
                E  P  E  S  K  Y  R  T  T  P  P  Q  L  D  E  D  G  S  Y  F
               ctctacagcaaattgagcgttgacaaaagcaggtggcagcgaggcgacaccttcatctgc
                L  Y  S  K  L  S  V  D  K  S  R  W  Q  R  G  D  T  F  I  C
               gccgtgatgcacgaggctttgcataaccactacacccaggagagcctgtcccacagcccc
                A  V  M  H  E  A  L  H  N  H  Y  T  Q  E  S  L  S  H  S  P
               ggatag
                G  -
```

FIG. 40

```
SEQ ID NO: 37  atggaatggagctgggtctttctcttcttcctgtcagtaacgactggtgtccactccttc
SEQ ID NO: 38   M  E  W  S  W  V  F  L  F  F  L  S  V  T  T  G  V  H  S  F
               gtgaaccagcacctgtgcggctcccacctggtggaagctctggaactcgtgtgcggcgag
                V  N  Q  H  L  C  G  S  H  L  V  E  A  L  E  L  V  C  G  E
               cggggcttccactacggggtggcggaggaggttctggtggcggcggaggcatcgtggaa
                R  G  F  H  Y  G  G  G  G  G  S  G  G  G  G  I  V  E
               cagtgctgcacctccacctgctccctggaccagctggaaaactactgcggtggcggaggt
                Q  C  C  T  S  T  C  S  L  D  Q  L  E  N  Y  C  G  G  G  G
               ggtcaaggaggcggtggacagggtggaggtgggcagggaggaggcggggggagactgcccc
                G  Q  G  G  G  Q  G  G  G  Q  G  G  G  D  C  P
               aaatgtcctccgcctgagatgctgggtggccctagcatcttcatcttcccgcccaagccc
                K  C  P  P  P  E  M  L  G  G  P  S  I  F  I  F  P  P  K  P
               aaggatactctgtccattagcaggaccccgaggtgacctgcctggtggtggacctgggg
                K  D  T  L  S  I  S  R  T  P  E  V  T  C  L  V  V  D  L  G
               ccagacgactctgacgtgcagatcacctggttcgtagacaacacccaggtttacactgcc
                P  D  D  S  D  V  Q  I  T  W  F  V  D  N  T  Q  V  Y  T  A
               aagaccagtcccagggaggagcagttcaacagcacatacagggtggtgagcgttctgccc
                K  T  S  P  R  E  E  Q  F  N  S  T  Y  R  V  V  S  V  L  P
               atcctgcaccaggactggctgaaaggcaaagagttcaagtgtaaggtgaacagcaagagc
                I  L  H  Q  D  W  L  K  G  K  E  F  K  C  K  V  N  S  K  S
               ctgccagcccattgaaaggaccatcagcaaggacaagggccagccgcacgagccccaa
                L  P  S  P  I  E  R  T  I  S  K  D  K  G  Q  P  H  E  P  Q
               gtctacgtgctgccccagcacaggaagagctgagcaggaacaaggttagcgtgacatgc
                V  Y  V  L  P  P  A  Q  E  E  L  S  R  N  K  V  S  V  T  C
               ctgatcgagggtttctaccccagcgacatcgccgtggagtgggaaatcaccggccaaccc
                L  I  E  G  F  Y  P  S  D  I  A  V  E  W  E  I  T  G  Q  P
               gagcccgagaacaactacaggaccactccgccgcaactggacagcgacgggacctacttc
                E  P  E  N  N  Y  R  T  T  P  Q  L  D  S  D  G  T  Y  F
               ttgtatagcaggctgagcgtggaccggagcaggtggcagaggggcaacacctacacttgc
                L  Y  S  R  L  S  V  D  R  S  R  W  Q  R  G  N  T  Y  T  C
               agcgtgagccacgaggccttgcacagccaccacactcagaagagtctgacccagagcccg
                S  V  S  H  E  A  L  H  S  H  H  T  Q  K  S  L  T  Q  S  P
               ggatag
                G  -
```

FIG. 41

```
SEQ ID NO: 39   atggaatggagctgggtctttctcttcttcctgtcagtaacgactggtgtccactccttc
SEQ ID NO: 40    M  E  W  S  W  V  F  L  F  F  L  S  V  T  T  G  V  H  S  F
                gtgaaccagcacctgtgcggctcccacctggtggaagctctggcactcgtgtgcggcgag
                 V  N  Q  H  L  C  G  S  H  L  V  E  A  L  A  L  V  C  G  E
                cggggcttccactacggggtggcggaggaggttctggtggcggcggaggcatcgtggaa
                 R  G  F  H  Y  G  G  G  G  S  G  G  G  G  I  V  E
                cagtgctgcacctccacctgctccctggaccagctggaaaactactgcggtggcggaggt
                 Q  C  C  T  S  T  C  S  L  D  Q  L  E  N  Y  C  G  G  G
                ggtcaaggaggcggtggacagggtggaggtgggcaggaggaggcggggagactgcccc
                 G  Q  G  G  G  Q  G  G  G  Q  G  G  G  D  C  P
                aaatgtcctccgcctgagatgctgggtggccctagcatcttcatcttcccgcccaagccc
                 K  C  P  P  P  E  M  L  G  G  P  S  I  F  I  F  P  P  K  P
                aaggatactctgtccattagcaggaccccgaggtgacctgcctggtggtggacctgggg
                 K  D  T  L  S  I  S  R  T  P  E  V  T  C  L  V  V  D  L  G
                ccagacgactctgacgtgcagatcacctggttcgtagacaacacccaggtttacactgcc
                 P  D  D  S  D  V  Q  I  T  W  F  V  D  N  T  Q  V  Y  T  A
                aagaccagtcccagggaggagcagttcagcagcacatacagggtggtgagcgttctgccc
                 K  T  S  P  R  E  E  Q  F  S  S  T  Y  R  V  V  S  V  L  P
                atcctgcaccaggactggctgaaaggcaaagagttcaagtgtaaggtgaacagcaagagc
                 I  L  H  Q  D  W  L  K  G  K  E  F  K  C  K  V  N  S  K  S
                ctgcccagccccattgaaaggaccatcagcaaggacaagggccagccgcacgagccccaa
                 L  P  S  P  I  E  R  T  I  S  K  D  K  G  Q  P  H  E  P  Q
                gtctacgtgctgccccagcacaggaagagctgagcaggaacaaggttagcgtgacatgc
                 V  Y  V  L  P  P  A  Q  E  E  L  S  R  N  K  V  S  V  T  C
                ctgatcgagggtttctaccccagcgacatcgccgtggagtgggaaatcaccggccaaccc
                 L  I  E  G  F  Y  P  S  D  I  A  V  E  W  E  I  T  G  Q  P
                gagcccgagaacaactacaggaccactccgccgcaactggacagcgacgggacctacttc
                 E  P  E  N  N  Y  R  T  T  P  P  Q  L  D  S  D  G  T  Y  F
                ttgtatagcaggctgagcgtggaccggagcaggtggcagagggggcaacacctacacttgc
                 L  Y  S  R  L  S  V  D  R  S  R  W  Q  R  G  N  T  Y  T  C
                agcgtgagccacgaggccttgcacagccaccacactcagaagagtctgacccagagcccg
                 S  V  S  H  E  A  L  H  S  H  H  T  Q  K  S  L  T  Q  S  P
                ggatag
                 G  -
```

FIG. 42

ULTRA-LONG ACTING INSULIN-FC FUSION PROTEINS AND METHODS OF USE

PRIORITY AND RELATED APPLICATIONS

The present application is a continuation of U.S. patent application Ser. No. 17/019,059, filed Sep. 11, 2021, which is a continuation of U.S. patent application Ser. No. 16/776,065, filed Jan. 29, 2020, which is a continuation of U.S. patent application Ser. No. 16/775,979, filed Jan. 29, 2020, which claims priority to and is a U.S. bypass continuation of PCT Patent Application Serial No. PCT/US2019/040010, filed Jun. 28, 2019, which claims the priority benefit of each of the following U.S. Provisional Patent Applications: Ser. No. 62/837,188, filed Apr. 22, 2019, Ser. No. 62/827,809, filed Apr. 1, 2019, Ser. No. 62/824,176, filed Mar. 26, 2019, Ser. No. 62/781,378, filed Dec. 18, 2018, Ser. No. 62/781,368, filed Dec. 18, 2018, Ser. No. 62/774,682, filed Dec. 3, 2018, Ser. No. 62/743,358, filed Oct. 9, 2018, Ser. No. 62/740,735, filed Oct. 3, 2018, Ser. No. 62/719,347, filed Aug. 17, 2018, Ser. No. 62/702,167, filed Jul. 23, 2018, Ser. No. 62/698,648, filed Jul. 16, 2018, Ser. No. 62/696,645, filed Jul. 11, 2018, Ser. No. 62/693,814, filed Jul. 3, 2018, Ser. No. 62/692,507, filed Jun. 29, 2018, and Ser. No. 62/692,498, filed Jun. 29, 2018. The contents of each of the aforementioned patent applications are hereby incorporated herein by reference in their entirety.

SEQUENCE LISTING

The following application contains a sequence listing presented in accordance with 37 C.F.R. 1.822. The sequence listing entitled "SequenceListing_ABC-3PCUS-2CN2.txt" is submitted as an ASCII computer readable text file ("CRF") created on Sep. 28, 2021 as 228,702 bytes, which is incorporated by reference herein.

TECHNICAL FIELD

The present technology relates to compositions of insulin-Fc fusion proteins and their use to treat diabetes in companion animals, e.g., dogs or cats.

BACKGROUND

The following description of the background of the present technology is provided simply as an aid in understanding the present technology and is not admitted to describe or constitute prior art to the present technology.

Diabetes is a chronic condition characterized by an insulin deficiency and/or ineffective use of insulin. Diabetics that have an absolute deficiency of insulin are categorized as having type 1 or insulin-dependent diabetes mellitus (IDDM). Type 1 diabetics are thought to have a genetic predisposition combined with immunologic destruction of the insulin-producing p-cells of the pancreas. In comparison, diabetics that can still produce some insulin but have a relative deficiency due to insulin resistance or other dysfunction, are classified as having type 2 or non-insulin-dependent diabetes mellitus (NIDDM). Type 2 diabetes is linked to genetic predisposition, obesity, and certain medications.

When a dog or a cat does not produce insulin or cannot use it normally, blood sugar levels elevate, resulting in hyperglycemia. Dogs generally exhibit an atypical glycemia phenotype with strong similarities to human type 1 diabetes. Dogs also occasionally exhibit atypical glycemia with strong similarities to type 2 diabetes in humans. Female dogs can also develop temporary insulin resistance while in heat or pregnant. In all cases, the dogs are treated with chronic insulin injection therapy. Cats generally exhibit an atypical glycemia phenotype with strong similarities to human type 2 diabetes (i.e., insulin resistance), but by the time the disease is diagnosed by a veterinarian, it has progressed to resemble a type 1 diabetes condition (inflammatory disease in pancreas with significant loss of beta cell mass), and the cat is dependent on exogenous insulin. Some diabetic cats can be managed with dietary changes and oral medication, but the majority of diabetic cats receive chronic insulin injection therapy to maintain adequate regulation. Left untreated, diabetes in dogs and cats can lead to weight loss, loss of appetite, vomiting, dehydration, problems with motor function, coma, and even death.

Approximately 0.24% of dogs and approximately 0.68% of cats in the United States are affected by diabetes. Current diabetes therapies for dogs and cats include the use of insulin, such as Vetsulin® for dogs (Intervet Inc., d.b.a. MERCK Animal Health, Summit, N.J.) and ProZinc® for cats (Boehringer Ingelheim Vetmedica, Duluth, Ga.) which are administered once or twice daily. The burden of frequent injections on owners often results in a lack of treatment regimen compliance and under-dosing, leading to poor long-term health outcomes. In fact, the cost of insulin therapy and the practicality of dosing their pets up to 14 times per week leads a significant percentage of owners to select euthanasia for their pets as an alternative to intensive management of diabetes. Therefore, there is a need for cost effective and less burdensome treatment options for this disease.

SUMMARY OF THE PRESENT TECHNOLOGY

In an aspect, the present disclosure provides a fusion protein comprising an insulin polypeptide and an Fc fragment, wherein the insulin polypeptide and the Fc fragment are connected by a linker, such as a peptide linker, wherein the Fc fragment is of non-human animal origin and comprises the following sequence: DCPKCPAPEMLGGPSVFIFPPKPKDTLLIARTPEVTCVVVDLDPEDPEVQISWFVDGKQMQT AKTQPREEQFNGTYRVVSVLPIGHQDWLKGKQF TCKVNNKALPSPIERTISKARGQAHQPS VYVLPPSREELSKNTVSLTCLIKDFFPPDIDVEWQSNGQQEPESKYRTTPPQLDEDGSYFLYS KLSVDKSRWQRGDTFICAVMHEALHNHYTQESLSHSPG (SEQ ID NO: 16). In some embodiments, the insulin polypeptide of fusion protein comprises the sequence FVNQHLCGSX1LVEALELVCGERGFHYGGGGGGSGGGGGIVEQCCX2STCSLDQLENYCX3 (SEQ ID NO: 6), where X1 is not D, X2 is not H, and X3 is absent or N. In some embodiments, the insulin polypeptide of the fusion protein comprises the sequence FVNQHLCGSX1LVEALELVCGERGFHYGGGGGGSG-GGGGIVEQCCX2STCSLDQLENYCX3 (SEQ ID NO: 6), where X1 is H, X2 is T, and X3 is absent or N. In embodiments, the insulin polypeptide and the Fc fragment of the fusion protein are connected by a linker, such as a peptide linker, comprising the sequence GGGGGQGGGGQGGGGQGGGG (SEQ ID NO: 14).

In embodiments, the fusion protein comprises the sequence FVNQHLCGSHLVEALELVCGERGFHYGGG-GGGSGGGGGIVEQCCTSTCSLDQLENYCGGG GGQ-GGGGQGGGGQGGGGGDCPKCPAPEMLGGPSVFIF-PPKPKDTLLIARTPEVTCVVVDL DPEDPEVQISWFV-DGKQMQTAKTQPREEQFNGTYRVVSVLPIGHQDW-LKGKQFTCKVNN KALPSPIERTISKARGQAHQPSV- YVLPPSREELSKNTVSL TCLIKDFFPPDIDVEWQSN-GQQE PESKYRTTPPQLDEDGSYFLYSKLSVDKSRW-QRGDTFICAVMHEALHNHYTQESLSHSPG (SEQ ID NO: 32). In embodiments, the fusion protein comprises the sequence (SEQ ID NO: 34)
FVNQHLCGSHLVEALELVCGERGFHYGGGGGGSGGGGGIVEQCCTSTCS

LDQLENYCNGGGGGQGGGGQGGGGQGGGGDCPKCPAPEMLGGPSVFIF

PPKPKDTLLIARTPEVTCVVVDLDPEDPEVQISWFVDGKQMQTAKTQPR

EEQFNGTYRVVSVLPIGHQDWLKGKQFTCKVNNKALPSPIERTISKARG

QAHQPSVYVLPPSREELSKNTVSLTCLIKDFFPPDIDVEWQSNGQQEPE

SKYRTTPPQLDEDGSYFLYSKLSVDKSRWQRGDTFICAVMHEALHNHYT

QESLSHSPG.

In an aspect, the present disclosure provides a fusion protein comprising an insulin polypeptide and an Fc fragment, wherein the insulin polypeptide and the Fc fragment are connected by a linker, such as a peptide linker, wherein the Fc fragment comprises the sequence DCPKCPA-PEMLGGPSVFIFPPKPKDTLLIARTPEVTCVVVDL-DPEDPEVQISWFVDGKQMQT AKTQPREEQFSG-TYRVVSVLPIGHQDWLKGKQFTCKVNNKALPSPIER-TISKARGQAHQPS VYVLPPSREELSKNTVSLTCLIK-DFFPPDIDVEWQSNGQQEPESKYRTTPPQLDEDGS-YFLYS KLSVDKSRWQRGDTFICAVMHEALHN-HYTQESLSHSPG (SEQ ID NO: 22). In some embodiments, the insulin polypeptide of the fusion protein comprises the sequence FVNQHLCGSX1LVEALAL-VCGERGFHYGGGGGGSGGGGGIVEQCCX2STCSLD-QLENYC (SEQ ID NO: 10), where X1 is not D and X2 is not H. In some embodiments, the insulin polypeptide of the fusion protein comprises the sequence FVNQHLCGS-X1LVEALALVCGERGFHYGGGGGGSGGGGGIVEQC-CX2STCSLDQLENYC (SEQ ID NO: 10), where X1 is H and X2 is T. In embodiments, the insulin polypeptide and the Fc fragment are connected by a linker, such as a peptide linker, comprising the sequence (SEQ ID NO: 14)
GGGGGQGGGGQGGGGQGGGGG.

In embodiments, the fusion protein comprises the sequence (SEQ ID NO: 36)
FVNQHLCGSHLVEALALVCGERGFHYGGGGGGSGGGGGIVEQCCTSTCS

LDQLENYCGGGGGQGGGGQGGGGQGGGGDCPKCPAPEMLGGPSVFIFP

PKPKDTLLIARTPEVTCVVVDLDPEDPEVQISWFVDGKQMQTAKTQPRE

EQFSGTYRVVSVLPIGHQDWLKGKQFTCKVNNKALPSPIERTISKARGQ

AHQPSVYVLPPSREELSKNTVSLTCLIKDFFPPDIDVEWQSNGQQEPES

KYRTTPPQLDEDGSYFLYSKLSVDKSRWQRGDTFICAVMHEALHNHYTQ

ESLSHSPG.

In an aspect, the present disclosure provides a fusion protein comprising an insulin polypeptide and an Fc fragment, wherein the insulin polypeptide and the Fc fragment are connected by a linker, such as a peptide linker, wherein the Fc fragment is of non-human animal origin and comprises the sequence DCPKCPPPEMLGGPSIFIFPPK-PKDTLSISRTPEVTCLVVDLGPDDSDVQITWFVDN-TQVYTA KTSPREEQFNSTYRVVSVLPILHQDWLK-GKEFKCKVNSKSLPSPIERTISKDKGQPHEPQVY VLP-PAQEELSRNKVSVTCLIEGFYPSDIAVEWEITGQPE-PENNYRTTPPQLDSDGTYFLYSRL SVDRSRWQRGN-TYTCSVSHEALHSHHTQKSLTQSPG (SEQ ID NO: 20). In embodiments, the insulin polypeptide of the fusion protein comprises the sequence FVNQHLCGSX1LVEAL-ELVCGERGFHYGGGGGGSGGGGGIVEQCCX2STCS-LDQLENYCX3 (SEQ ID NO: 6), where X1 is not D, X2 is not H, and X3 is absent. In embodiments, the insulin polypeptide of the fusion protein comprises the sequence FVNQHLCGSX1LVEALELVCGERGFHYGGGGGGSG-GGGGIVEQCCX2STCSLDQLENYCX3 (SEQ ID NO: 6), where X1 is H, X2 is T, and X3 is absent. In embodiments, the insulin polypeptide and the Fc fragment are connected by a linker, such as a peptide linker, comprising the following sequence GGGGGQGGGGQGGGGQGGGGG (SEQ ID NO: 14).

In embodiments, the fusion protein comprises the sequence (SEQ ID NO: 38)
FVNQHLCGSHLVEALELVCGERGEHYGGGGGGSGGGGGIVEQCCTSTCS

LDQLENYCGGGGGQGGGGQGGGGQGGGGDCPKCPPPEMLGGPSIFIFP

PKPKDTLSISRTPEVTCLVVDLGPDDSDVQITWFVDNTQVYTAKTSPRE

EQFNSTYRVVSVLPILHQDWLKGKEFKCKVNSKSLPSPIERTISKDKGQ

PHEPQVYVLPPAQEELSRNKVSVTCLIEGFYPSDIAVEWEITGQPEPEN

NYRTTPPQLDSDGTYFLYSRLSVDRSRWQRGNTYTCSVSHEALHSHHTQ

KSLTQSPG.

In an aspect, the present disclosure provides a fusion protein comprising an insulin polypeptide and an Fc fragment, wherein the insulin polypeptide and the Fc fragment are connected by a linker, such as a peptide linker, wherein the Fc fragment comprises the sequence DCPKCPPPEMLGGPSIFIFPPKPKDTLSISRTPEVTCL-VVDLGPDDSDVQITWFVDNTQVYTA KTSPREEQFS-STYRVVSVLPILHQDWLKGKEFKCKVNSKSLPSPIER-TISKDKGQPHEPQVYV LPPAQEELSRNKVSVTCLI-EGFYPSDIAVEWEITGQPEPENNYRTTPPQLDSDG-TYFLYSRLS VDRSRWQRGNTYTCSVSHEALHSH-HTQKSLTQSPG (SEQ ID NO: 23). In embodiments, the insulin polypeptide of the fusion protein comprises the sequence FVNQHLCGSX1LVEALALVCGERGFHYG-GGGGSGGGGIVEQCCX2STCSLDQLENYC (SEQ ID NO: 10), where X1 is not D and X2 is not H. In embodiments, the insulin polypeptide comprises the following sequence FVNQHLCGSX1LVEALALVCGE-RGFHYGGGGGGSGGGGGIVEQCCX2STCSLDQLEN-YC (SEQ ID NO: 10), where X1 is H and X2 is T. In embodiments, the insulin polypeptide and the Fc fragment are connected by a linker, such as a peptide linker, comprising the sequence (SEQ ID NO: 14)
GGGGGQGGGGQGGGGQGGGGG.

In embodiments, the fusion protein comprises the sequence (SEQ ID NO: 40)
FVNQHLCGSHLVEALALVCGERGFHYGGGGGGSGGGGGIVEQCCTSTCS

LDQLENYCGGGGGQGGGGQGGGGQGGGGGDCPKCPPPEMLGGPSIFIFP

PKPKDTLSISRTPEVTCLVVDLGPDDSDVQITWFVDNTQVYTAKTSPRE

EQFSSTYRVVSVLPILHQDWLKGKEFKCKVNSKSLPSPIERTISKDKGQ

PHEPQVYVLPPAQEELSRNKVSVTCLIEGFYPSDIAVEWEITGQPEPEN

NYRTTPPQLDSDGTYFLYSRLSVDRSRWQRGNTYTCSVSHEALHSHHTQ

KSLTQSPG.

In aspects, the fusion proteins described herein comprise a homodimer. In embodiments, the percentage homodimer of the fusion protein is greater than 90%. In embodiments, the fusion proteins described herein are made using HEK293 cells, and the resulting homodimer titer after purification using Protein A beads or a Protein A column is greater than 50 mg/L. In embodiments, the insulin receptor IC50 for the fusion proteins described herein is less than or equal to 5000 nM. In embodiments, the serum half-life of the fusion proteins described herein in the blood or serum of a target animal upon administration is longer than about 3 days. In embodiments, for the fusion proteins described herein, the time during which there is a statistically significant decrease in blood glucose level in a subject relative to a pre-dose level is longer than one of 2 hours, 6 hours, 9 hours, 12 hours, 18 hours, 1 day, 1.5 days, 2 days, 2.5 days, 3 days, 4 days, 5 days, 6 days, 7 days, or longer.

In aspects, for the fusion proteins described herein, the NAOC after the first subcutaneous injection in a target animal is greater than 150% FBGL·days·kg/mg. In embodiments, for the fusion proteins described herein, the ratio of the NAOC after the third weekly subcutaneous injection of the fusion proteins in the target animal to the NAOC after the first subcutaneous injection of the fusion protein in the target animal is greater than 0.50.

In aspects, fusion proteins as described herein are formulated as a pharmaceutical composition. In embodiments, in the pharmaceutical composition the fusion protein is present at a concentration of about 3 mg/mL or greater. In embodiments, the composition is suitable for subcutaneous administration.

In an aspects, a method is described for lowering the blood glucose level of a target animal, the method comprising administering a physiologically effective amount of a fusion protein as described herein or a pharmaceutical composition thereof to the patient. In embodiments, the target animal is diagnosed with diabetes. In embodiments, the target animal is a dog or a cat. In some embodiments, the fusion protein is administered subcutaneously. In some embodiments, the fusion protein is administered daily, twice weekly, or once weekly to the target animal. In examples, the fusion protein is administered once weekly to the target animal at a dose between 0.025 and 0.5 mg/kg/week. In aspects, a cell engineered to express a fusion protein as described here in described. In examples, the cell is transfected with a nucleic acid encoding the fusion protein. In examples, the cell is a HEK293 cell or a CHO cell.

In an aspect, a cDNA encoding a fusion protein as described herein is described. In embodiments, the cDNA comprises the nucleic acid sequence (SEQ ID NO: 31)
atggaatggagctgggtctttctcttcttcctgtcagtaacgactggtg tccactccttcgtgaaccagcacctgtgcggctcccacctggtggaagc tctggaactcgtgtgcggcgagcggggcttccactacggggtggcgga ggaggttctggtggcggcggaggcatcgtggaacagtgctgcacctcca cctgctccctggaccagctggaaaactactgcggtggcggaggtggtca aggaggcggtggacagggtggaggtgggcagggaggaggcggggagac tgccccaagtgccccgctcccgagatgctgggcggacccagcgtgttca tcttccctcccaagcccaaggacacactgctgatcgccaggaccccgga ggtgacctgcgtggtggtggacctggatcccgaagaccccgaggtgcag atcagctggttcgtggatggaaagcagatgcagaccgccaagacccaac cccgggaagagcagttcaacggcacctacagggtggtgagtgtgttgcc catcggccaccaggactggctgaaggggaagcaattcacatgcaaggtt aataacaaggccctgcccagcccatcgagaggaccatcagcaaggcca ggggccaggcccaccagccatctgtgtacgtgctgcccccatctaggga ggaactgagcaagaacacagtcagccttacttgcctgatcaaggacttc ttcccaccggacatagacgtggagtggcagagtaacggccagcaggagc ccgagagcaagtataggaccacaccgccccaactggacgaggacggaag ctacttcctctacagcaaattgagcgttgacaaaagcaggtggcagcga ggcgacaccttcatctgcgccgtgatgcacgaggctttgcataaccact acacccaggagagcctgtcccacagccccggatag.

In embodiments, the cDNA comprises the nucleic acid sequence (SEQ ID NO: 33)
atggaatggagctgggtctttctcttcttcctgtcagtaacgactggtg tccactccttcgtgaaccagcacctgtgcggctcccacctggtggaagc tctggaactcgtgtgcggcgagcggggcttccactacggggtggcgga ggaggttctggtggcggcggaggcatcgtggaacagtgctgcacctcca cctgctccctggaccagctggaaaactactgcaacggtggcggaggtgg tcaaggaggcggtggacagggtggaggtgggcagggaggaggcggggga gactgccccaagtgccccgctcccgagatgctgggcggacccagcgtgt tcatcttccctcccaagcccaaggacacactgctgatcgccaggacccc ggaggtgacctgcgtggtggtggacctggatcccgaagaccccgaggtg cagatcagctggttcgtggatggaaagcagatgcagaccgccaagaccc aaccccgggaagagcagttcaacggcacctacagggtggtgagtgtgtt gcccatcggccaccaggactggctgaaggggaagcaattcacatgcaag gttaataacaaggccctgcccagcccatcgagaggaccatcagcaagg ccaggggccaggcccaccagccatctgtgtacgtgctgcccccatctag ggaggaactgagcaagaacacagtcagccttacttgcctgatcaaggac ttcttcccaccggacatagacgtggagtggcagagtaacggccagcagg agcccgagagcaagtataggaccacaccgccccaactggacgaggacgg -continued
aagctacttcctctacagcaaattgagcgttgacaaaagcaggtggcag cgaggcgacaccttcatctgcgccgtgatgcacgaggctttgcataacc actacacccaggagagcctgtcccacagccccggatag.

In embodiments, the cDNA comprises the nucleic acid sequence (SEQ ID NO: 35)
atggaatggagctgggtctttctcttcttcctgtcagtaacgactggtg tccactccttcgtgaaccagcacctgtgcggctcccacctggtggaagc tctggcactcgtgtgcggcgagcgggcttccactacgggggtggcgga ggaggttctggtggcggcggaggcatcgtggaacagtgctgcacctcca cctgctccctggaccagctggaaaactactgcggtggcggaggtggtca aggaggcggtggacagggtggaggtgggcagggaggaggcggggagac tgccccaagtgccccgctcccgagatgctgggcggacccagcgtgttca tcttccctcccaagcccaaggacacactgctgatcgccaggaccccgga ggtgacctgcgtggtggtggacctggatcccgaagaccccgaggtgcag atcagctggttcgtggatggaaagcagatgcagaccgccaagacccaac cccgggaagagcagttctcaggcacctacaggggtggtgagtgtgttgcc catcggccaccaggactggctgaaggggaagcaattcacatgcaaggtt aataacaaggccctgcccagccccatcgagaggaccatcagcaaggcca ggggccaggcccaccagccatctgtgtacgtgctgcccccatctaggga ggaactgagcaagaacacagtcagccttacttgcctgatcaaggacttc ttcccaccggacatagacgtggagtggcagagtaacggccagcaggagc ccgagagcaagtataggaccacaccgccccaactggacgaggacggaag ctacttcctctacagcaaattgagcgttgacaaaagcaggtggcagcga ggcgacaccttcatctgcgccgtgatgcacgaggctttgcataaccact acacccaggagagcctgtcccacagccccggatag, In embodiments, the cDNA comprises the nucleic acid sequence (SEQ ID NO: 37)
atggaatggagctgggtctttctcttcttcctgtcagtaacgactggtg tccactccttcgtgaaccagcacctgtgcggctcccacctggtggaagc tctggaactcgtgtgcggcgagcgggcttccactacgggggtggcgga ggaggttctggtggcggcggaggcatcgtggaacagtgctgcacctcca cctgctccctggaccagctggaaaactactgcggtggcggaggtggtca aggaggcggtggacagggtggaggtgggcagggaggaggcggggagac tgccccaaatgtcctccgcctgagatgctgggtggccctagcatcttca tcttcccgcccaagcccaaggatactctgtccattagcaggaccccga ggtgacctgcctggtggtggacctggggccagacgactctgacgtgcag atcacctggttcgtagacaacacccaggtttacactgccaagaccagtc ccagggaggagcagttcaacagcacatacaggggtggtgagcgttctgcc catcctgcaccaggactggctgaaaggcaaagagttcaagtgtaaggtg
-continued
aacagcaagagcctgcccagccccattgaaaggaccatcagcaaggaca agggccagccgcacgagccccaagtctacgtgctgcccccagcacagga agagctgagcaggaacaaggttagcgtgacatgcctgatcgagggtttc taccccagcgacatcgccgtggagtgggaaatcaccggccaacccgagc ccgagaacaactacaggaccactccgccgcaactggacagcgacgggac ctacttcttgtatagcaggctgagcgtggaccggagcaggtggcagagg ggcaacacctacacttgcagcgtgagccacgaggccttgcacagccacc acactcagaagagtctgacccagagcccggatag.

In embodiments, the cDNA comprises the nucleic acid sequence (SEQ ID NO: 39)
atggaatggagctgggtctttctcttcttcctgtcagtaacgactggtg tccactccttcgtgaaccagcacctgtgcggctcccacctggtggaagc tctggcactcgtgtgcggcgagcgggcttccactacgggggtggcgga ggaggttctggtggcggcggaggcatcgtggaacagtgctgcacctcca cctgctccctggaccagctggaaaactactgcggtggcggaggtggtca aggaggcggtggacagggtggaggtgggcagggaggaggcggggagac tgccccaaatgtcctccgcctgagatgctgggtggccctagcatcttca tcttcccgcccaagcccaaggatactctgtccattagcaggaccccga ggtgacctgcctggtggtggacctggggccagacgactctgacgtgcag atcacctggttcgtagacaacacccaggtttacactgccaagaccagtc ccagggaggagcagttcagcagcacatacaggggtggtgagcgttctgcc catcctgcaccaggactggctgaaaggcaaagagttcaagtgtaaggtg aacagcaagagcctgcccagccccattgaaaggaccatcagcaaggaca agggccagccgcacgagccccaagtctacgtgctgcccccagcacagga agagctgagcaggaacaaggttagcgtgacatgcctgatcgagggtttc taccccagcgacatcgccgtggagtgggaaatcaccggccaacccgagc ccgagaacaactacaggaccactccgccgcaactggacagcgacgggac ctacttcttgtatagcaggctgagcgtggaccggagcaggtggcagagg ggcaacacctacacttgcagcgtgagccacgaggccttgcacagccacc acactcagaagagtctgacccagagcccggatag.

BRIEF DESCRIPTION OF THE DRAWINGS

FIG. 3 illustrates a side-by-side sequence comparison of SEQ ID NOs: 42, 44, 46, 48, and 50. "*" represents complete homology across all sequences at a given sequence position, while ":", "." or spaces refer to conservative, moderate, or very different amino acid mutations across the sequences at a given sequence position respectively.

FIG. 4 illustrates a side-by-side sequence comparison of SEQ ID NOs: 42, 52, 54, and 56. "*" represents complete homology across all sequences at a given sequence position, while: or spaces refer to conservative, moderate, or very different amino acid mutations across the sequences at a given sequence position respectively.

FIG. 7 shows the average anti-drug antibody titer (µg/mL) for N=3 dogs dosed subcutaneously on Day 0 (0.30 mg/kg), Day 28 (0.33 mg/kg), Day 35 (0.33 mg/kg), Day 42 (0.50 mg/kg), Day 49 (1.00 mg/kg) and Day 56 (1.00 mg/kg) with the homodimer of SEQ ID NO: 52.

FIG. 8 illustrates a side-by-side sequence comparison of SEQ ID NOs: 58, 60, 62, and 64. "*" represents complete homology across all sequences at a given sequence position, while "." or spaces refer to conservative, moderate, or very different amino acid mutations across the sequences at a given sequence position respectively.

FIG. 12 illustrates a side-by-side sequence comparison of SEQ ID NOs: 66, 68, 70, 72, 74 and 76. "*" represents complete homology across all sequences at a given sequence position, while ":", or spaces refer to conservative, moderate, or very different amino acid mutations across the sequences at a given sequence position respectively.

FIG. 13 illustrates a side-by-side sequence comparison of SEQ ID NOs: 66, 78, 80, 82, and 84. "*" represents complete homology across all sequences at a given sequence position, while ":", "." or spaces refer to conservative, moderate, or very different amino acid mutations across the sequences at a given sequence position respectively.

FIG. 14 illustrates a side-by-side sequence comparison of SEQ ID NOs: 66, 76 and 86. "*" represents complete homology across all sequences at a given sequence position, while ":", "." or spaces refer to conservative, moderate, or very different amino acid mutations across the sequences at a given sequence position respectively.

FIG. 15 illustrates a side-by-side sequence comparison of SEQ ID NOs: 66, 82, 84 and 88. "*" represents complete homology across all sequences at a given sequence position, while "." or spaces refer to conservative, moderate, or very different amino acid mutations across the sequences at a given sequence position respectively.

FIG. 16 illustrates a side-by-side sequence comparison of SEQ ID NOs: 32, 34, 66, 90, 92 and 94. "*" represents complete homology across all sequences at a given sequence position, while ":", or spaces refer to conservative, moderate, or very different amino acid mutations across the sequences at a given sequence position respectively.

FIG. 23 shows % fasting blood glucose levels from Day 0 to Day 7 for N=1 dog dosed subcutaneously on Day 0 at 0.16 mg/kg with the homodimer of SEQ ID NO: 98.

FIG. 24 illustrates a side-by-side sequence comparison of SEQ ID NOs: 102 and 104. "*" represents complete homology across all sequences at a given sequence position, while ":", "." or spaces refer to conservative, moderate, or very different amino acid mutations across the sequences at a given sequence position respectively.

FIG. 27 shows average % fasting blood glucose levels from Day 0 to Day 7 for N=3 cats dosed subcutaneously on Day 0 at 0.8 mg/kg with the homodimer of SEQ ID NO: 106.

FIG. 28 illustrates a side-by-side sequence comparison of SEQ ID NOs: 106, 108, 110 and 112. "*" represents complete homology across all sequences at a given sequence position, while ":", "." or spaces refer to conservative, moderate, or very different amino acid mutations across the sequences at a given sequence position respectively.

FIG. 29 shows the average anti-drug antibody titer (µg/mL) for N=3 cats dosed subcutaneously on Day 0 (0.8 mg/kg), Day 28 (0.6 mg/kg), Day 35 (0.6 mg/kg), Day 42 (0.6 mg/kg) and Day 48 (0.8 mg/kg) with the homodimer of SEQ ID NO: 106.

FIG. 30 illustrates a side-by-side sequence comparison of SEQ ID NOs: 108, 114, 116 and 118. "*" represents complete homology across all sequences at a given sequence position, while ":", "." or spaces refer to conservative, moderate, or very different amino acid mutations across the sequences at a given sequence position respectively.

FIG. 31 illustrates a side-by-side sequence comparison of SEQ ID NOs: 106, 112, and 122. "*" represents complete homology across all sequences at a given sequence position, while "." or spaces refer to conservative, moderate, or very different amino acid mutations across the sequences at a given sequence position respectively.

FIG. 32 shows % fasting blood glucose levels from Day 0 to Day 7 for N=1 cat dosed subcutaneously on Day 0 (0.16 mg/kg) with the homodimer of SEQ ID NO: 122.

Figure 34:
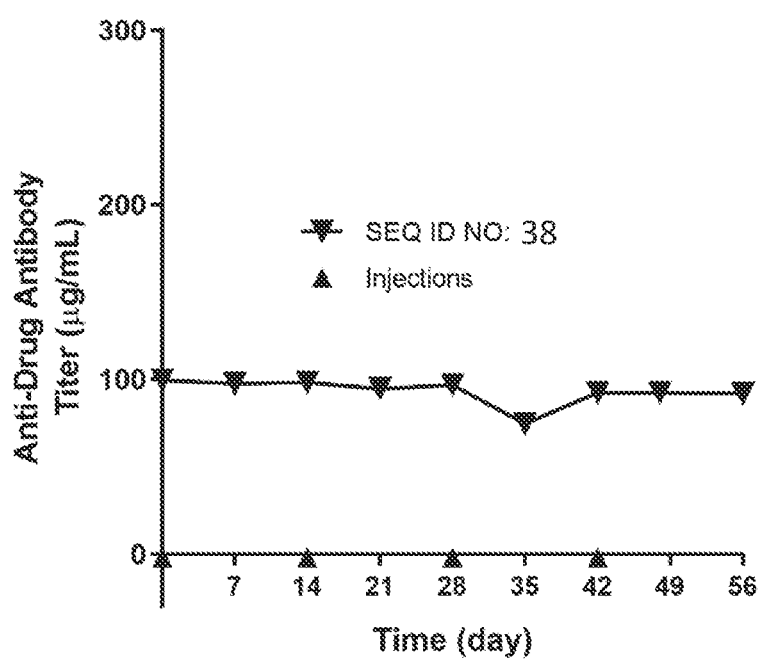

FIG. 34 shows the anti-drug antibody titer (μg/mL) for N=1 cat dosed subcutaneously on Day 0 (0.16 mg/kg), Day 14 (0.16 mg/kg), Day 28 (0.11 mg/kg), and Day 42 (0.09 mg/kg) with the homodimer of SEQ ID NO: 38.

Figure 35:
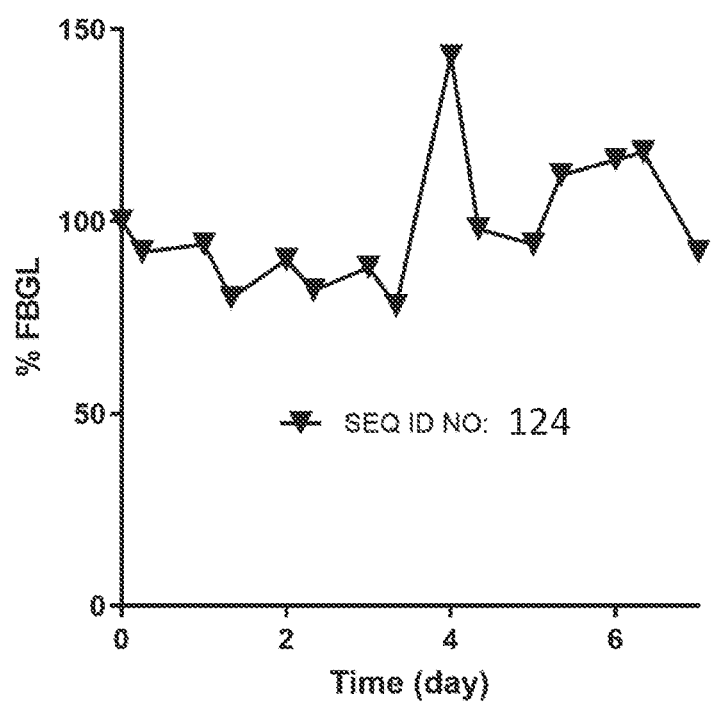

FIG. 35 shows % fasting blood glucose levels from Day 0 to Day 7 for N=1 cat dosed subcutaneously on Day 0 (0.16 mg/kg) with the homodimer of SEQ ID NO: 124.

Figure 36:
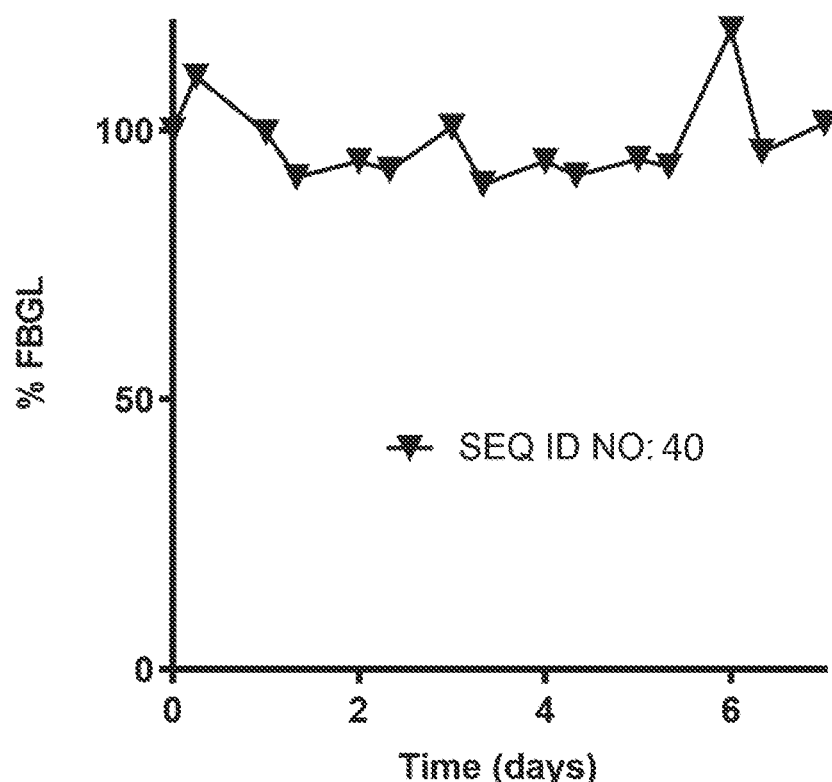

FIG. 36 shows average % fasting blood glucose levels from Day 0 to Day 7 for N=3 cats dosed subcutaneously on Day 0 (0.10 mg/kg) with the homodimer of SEQ ID NO: 40.

Figure 37:
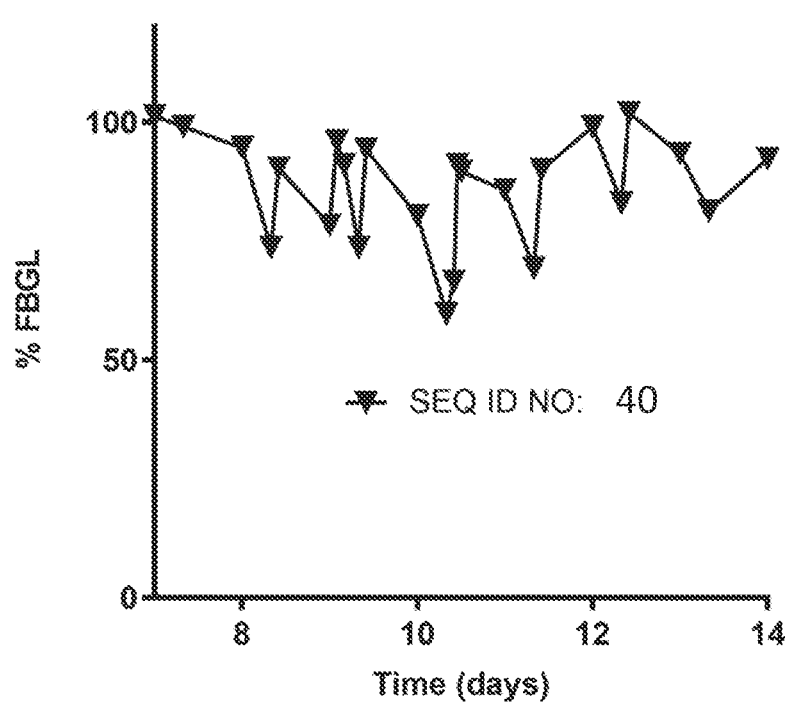

FIG. 37 shows average % fasting blood glucose levels from Day 7 to Day 14 for N=3 cats dosed subcutaneously on Day 7 (0.20 mg/kg) with the homodimer of SEQ ID NO: 40.

FIG. 38 illustrates the "full aa sequence" of a fusion protein (SEQ ID NO: 32) and its corresponding nucleic acid sequence (SEQ ID NO: 31).

FIG. 39 illustrates the "full aa sequence" of a fusion protein (SEQ ID NO: 34) and its corresponding nucleic acid sequence (SEQ ID NO: 33).

FIG. 40 illustrates the "full aa sequence" of a fusion protein (SEQ ID NO: 36) and its corresponding nucleic acid sequence (SEQ ID NO: 35).

FIG. 41 illustrates the "full aa sequence" of a fusion protein (SEQ ID NO: 38) and its corresponding nucleic acid sequence (SEQ ID NO: 37).

FIG. 42 illustrates the "full aa sequence" of a fusion protein (SEQ ID NO: 40) and its corresponding nucleic acid sequence (SEQ ID NO: 39).

DETAILED DESCRIPTION

An insulin treatment that requires less frequent dosing (e.g., once-weekly injections) would be less burdensome on the owners, leading to better compliance, fewer instances of euthanasia, and better outcomes for the pets. For a given species (e.g., dog or cat), a molecule suitable for an ultra-long acting treatment for diabetes should be manufacturable in mammalian cells, for example human embryonic kidney (HEK, e.g., HEK293) cells, with an acceptable titer of the desired homodimer product (e.g., greater than 50 mg/L homodimer titer from transiently transfected HEK cells, greater than 75 mg/L from transiently transfected from HEK cells, greater than 100 mg/L from transiently transfected HEK cells, etc.). Only candidates with a homodimer titer of greater than 50 mg/L are considered useful in the present invention, because experience has demonstrated that homodimer titers less than this level will not likely result in commercial production homodimer titers in Chinese hamster ovary (CHO) cells that meet the stringently low manufacturing cost requirements for veterinary products. In addition, the molecule must bind the insulin receptor with an appreciable affinity (e.g., IC50 less than 5000 nM, IC50 less than 4000 nM, IC50 less than 3000 nM, IC50 less than 2500 nM, etc.) as measured in the 4° C. IM-9 insulin receptor binding assay. Based on experience, only molecules exhibiting insulin receptor activity IC50 values less than 5000 nM are deemed likely to exhibit the requisite bioactivity in the target species. The molecule must also demonstrate sustained bioactivity in vivo (e.g., demonstrate glucose lowering activity greater than about 2 hours, 6 hours, 9 hours, 12 hours, 18 hours, 1 day, 1.5 days, 2 days, 2.5 days, 3 days, 4 days, 5 days, 6 days, 7 days, or longer) to justify less frequent dosing. The molecule must also demonstrate prolonged system residence time in the target animal (e.g., the serum half-life must be greater than 3 days, or longer). The bioactive potency and duration of the bioactivity may be quantitatively represented by calculating the area over the percent fasting blood glucose (% FBGL) curve normalized to a given dose in mg/kg (NAOC) with units of % FBGL·days·kg/mg as described in Example 11. The NAOC increases with a greater drop in % FBGL, which is the case where the molecule demonstrates increased bioactivity, and when the % FBGL takes longer to return to 100%, which is the case where the insulin-Fc fusion protein demonstrates increased duration of action. To be useful as described herein, a molecule must demonstrate a sufficiently high NAOC value (e.g., preferably NAOC greater than 150% FBGL·days·kg/mg, more preferably NAOC greater than 200% FBGL·days·kg/mg, and even more preferably NAOC greater than 250% FBGL·days·kg/mg). Based on experience, at NAOC values greater than 150% FBGL·days·kg/mg, the dose requirements in the target species will be sufficiently low so as to reach an acceptable treatment cost. Lastly, to be useful for treating a chronic disease such as diabetes, the molecule must not induce the production of anti-drug antibodies, especially antibodies that neutralize the bioactivity of the molecule after repeated dosing. Therefore, the molecule must demonstrate similar duration and extent of bioactivity (i.e., NAOC) after multiple repeated doses in the target animal (e.g., the ratio of the NAOC after the third weekly subcutaneous injection to the NAOC after the first weekly subcutaneous injection of the molecule (i.e., the NAOC ratio (NAOCR) after the third dose) is in order of preference greater than 0.50, greater than 0.60, greater than 0.70, greater than 0.80, or greater than 0.90 or more).

Proposed ultra-long acting insulin treatments for human clinical use comprise an insulin-Fc fusion protein making use of a human Fc fragment to prolong their action in vivo. As a human Fc fragment is expected to be immunogenic and therefore capable of inducing the production of anti-drug antibodies in companion animals (e.g., dogs or cats), the human Fc fragment must be replaced with a species-specific (e.g., canine or feline) Fc fragment. However, it was found rather unexpectedly that a simple exchange between the human Fc fragment and the species-specific (e.g., canine or feline) Fc fragment did not yield a product with an acceptable homodimer titer (e.g., a homodimer titer greater than 50 mg/L) or a sufficiently high NAOC value (e.g., a NAOC greater than 150% FBGL·days·kg/mg). For example, in some cases only a specific isotype (e.g., canine IgGB or feline IgG1b) for the Fc fragment resulted in an insulin-Fc fusion protein with a high enough homodimer titer (e.g., a homodimer titer greater than 50 mg/L) and an acceptably high NAOC value (e.g., a NAOC greater than 150% FBGL·days·kg/mg). In other cases, specific amino acids of the insulin polypeptide were found to be immunogenic in the target species thereby requiring site-directed mutations to find the relatively small number of embodiments that were both non-immunogenic and bioactive in the target species with acceptably high NAOC values (e.g., NAOC values greater than 150% FBGL·days·kg/mg) and NAOCR values after the third weekly subcutaneous dose that were greater than 0.5. In further cases, when the Fc fragments were mutated to prevent glycosylation and thereby further reduce the immunogenicity of the insulin-Fc fusion proteins, it was discovered unexpectedly that only specific amino acid mutations in the Fc fragment led to the desired homodimer titers (e.g., homodimer titers greater than 50 mg/L) and NAOC values (e.g., NAOC greater values than 150% FBGL·days·kg/mg). Furthermore, it was discovered that an additional mutation in the insulin component was required to produce these Fc-mutated, non-glycosylated insulin Fc-fusion proteins with the desired homodimer titers (e.g., homodimer titers greater than 50 mg/L) and NAOC values (e.g., NAOC greater values than 150% FBGL·days·kg/mg), while also achieving NAOCR values after the third weekly subcutaneous dose that were greater than 0.5. Provided herein, therefore, are manufacturable, high purity, long-acting, bioactive, non-immunogenic insulin-Fc fusion proteins with acceptably high homodimer titers (e.g., homodimer titers greater than 50 mg/L), NAOC values (e.g., NAOC values greater than 150% FBGL·days·kg/mg), and NAOCR values after the third weekly subcutaneous dose greater than 0.5, suitable for the treatment of diabetes in companion animals (e.g., dogs or cats), each of which comprises an insulin polypeptide, an Fc fragment, and a linker between the insulin polypeptide and the Fc fragment.

Definitions

As used herein, the articles "a" and "an" refer to one or more than one, e.g., to at least one, of the grammatical object of the article. The use of the words "a" or "an" when used in conjunction with the term "comprising" herein may mean "one," but it is also consistent with the meaning of "one or more," "at least one," and "one or more than one."

As used herein, "about" and "approximately" generally mean an acceptable degree of error for the quantity measured given the nature or precision of the measurements. Exemplary degrees of error are within 20 percent (%), typically, within 10%, and more typically, within 5% of a given range of values.

As used herein, an amount of a molecule, compound, conjugate, or substance effective to treat a disorder (e.g., a disorder described herein), "therapeutically effective amount," or "effective amount" refers to an amount of the molecule, compound, conjugate, or substance which is effective, upon single or multiple dose administration(s) to a subject, in treating a subject, or in curing, alleviating, relieving or improving a subject with a disorder (e.g., a disorder described herein) beyond that expected in the absence of such treatment.

As used herein, the term "analog" refers to a compound or conjugate (e.g., a compound or conjugate as described herein, e.g., insulin) having a chemical structure similar to that of another compound or conjugate but differing from it in at least one aspect.

As used herein, the term "antibody" or "antibody molecule" refers to an immunoglobulin molecule (Ig), immunologically active portions of an immunoglobulin (Ig) molecule, i.e., a molecule that contains an antigen binding site that specifically binds, e.g., immunoreacts with, an antigen. As used herein, the term "antibody domain" refers to a variable or constant region of an immunoglobulin. As used herein, the term "antibody domain" refers to a variable or constant region of an immunoglobulin. It is documented in the art that antibodies comprise several classes, for example IgA, IgM, or IgG in the case of mammals (e.g., humans and felines). Classes of immunoglobulins can be further classified into different isotypes, such as IgGA, IgGB, IgGC, and IgGD for canines, or IgG1a, IgG1b, and IgG2 for felines. Those skilled in the art will recognize that immunoglobulin isotypes of a given immunoglobulin class will comprise different amino acid sequences, structures, and functional properties from one another (e.g., different binding affinities to Fc(gamma) receptors). "Specifically binds" or "immunoreacts with" means that the antibody reacts with one or more antigenic determinants of the desired antigen and has a lower affinity for other polypeptides, e.g., does not react with other polypeptides.

As used herein, the term "area-under-the-curve" or "AUC" refers to the integrated area under the % FBGL vs. time curve for a subject after a given dose of an insulin-Fc fusion protein is administered. As used herein, the term "area-over-the curve" or "AOC" is used as a measure of the biological potency of an insulin-Fc fusion protein such that the AOC equals the difference between the total possible area under the % FBGL vs. time curve and the AUC value. As used herein, the "normalized area-over-the curve," "normalized AOC," or "NAOC" is the AOC value divided by the actual dose of insulin-Fc fusion protein administered. As used herein, the term "normalized AOC ratio" or "NAOCR" is the ratio of the NAOC resulting from a particular administration of an insulin-Fc fusion protein to the NAOC resulting from the first administration of an insulin-Fc fusion protein in a series of administrations. The NAOCR thus provides a measure of the change in biological activity of an insulin-Fc fusion protein after repeated administrations.

As used herein, the term "bioactivity," "activity," "biological activity," "potency," "bioactive potency," or "biological potency" refers to the extent to which an insulin-Fc fusion protein activates the insulin receptor and/or exerts a reduction in blood glucose levels in a target subject. As used herein, "in vitro activity" or "insulin receptor activity" refers to the affinity with which an insulin-Fc fusion protein binds to the insulin receptor and is typically measured by the concentration at which an insulin-Fc fusion protein displaces half of an insulin reference standard from the insulin receptor in a competitive binding assay (i.e., IC50). As used herein, "in vivo activity" refers to the extent and duration of reduction in a target subject's fasting blood glucose level after administration of an insulin-Fc fusion protein.

As used herein, the term "biosynthesis," "recombinant synthesis," or "recombinantly made" refers to the process by which an insulin-Fc fusion protein is expressed within a host cell by transfecting the cell with a nucleic acid molecule (e.g., vector) encoding the insulin-Fc fusion protein (e.g., where the entire insulin-Fc fusion protein is encoded by a single nucleic acid molecule). Exemplary host cells include mammalian cells, e.g., HEK293 cells or CHO cells. The cells can be cultured using standard methods in the art and the expressed insulin-Fc fusion protein may be harvested and purified from the cell culture using standard methods in the art.

As used herein, the term "cell surface receptor" refers to a molecule such as a protein, generally found on the external surface of the membrane of a cell and which interacts with soluble molecules, e.g., molecules that circulate in the blood supply. In some embodiments, a cell surface receptor may include a hormone receptor (e.g., an insulin hormone receptor or insulin receptor (IR)) or an Fc receptor which binds to an Fc fragment or the Fc region of an antibody (e.g., an Fc(gamma) receptor, for example Fc(gamma) receptor I, or an Fc neonatal receptor, for example FcRn). As used herein, "in vitro activity" or "Fc(gamma) receptor activity" or "Fc(gamma) receptor binding" or "FcRn receptor activity" or "FcRn binding" refers to the affinity with which an insulin-Fc fusion protein binds to the Fc receptor (e.g. Fc(gamma) receptor or FcRn receptor) and is typically measured by the concentration of an insulin-Fc fusion protein that causes the insulin-Fc fusion protein to reach half of its maximum binding (i.e., EC50 value) as measured on an assay (e.g., an enzyme-linked immunosorbent assay (ELISA) assay) using OD 450 nm values as measured on a microplate reader.

As used herein, the term "fasting blood glucose level" or "FBGL" refers to the average blood glucose level in a target subject at the end of a period during which no food is administered and just prior to the time at which an insulin-Fc fusion protein is administered. As used herein, the term "percent fasting blood glucose level," "% fasting blood glucose level," or "% FBGL" refers to the ratio of a given blood glucose level to the fasting blood glucose level multiplied by 100.

As used herein, the term "immunogenic" or "immunogenicity" refers to the capacity for a given molecule (e.g., an insulin-Fc fusion protein of the present invention) to provoke the immune system of a target subject such that after repeated administrations of the molecule, the subject develops antibodies capable of specifically binding the molecule (i.e., anti-drug antibodies). As used herein, the terms "neutralizing," "neutralizing antibodies", or "neutralizing anti-drug antibodies" refer to the capacity for antibodies to interfere with the compound's biological activity in the target subject. As used herein, the term "immunogenic epitopes," 'immunogenic hot spots," or "hot spots" refers to the mutations or epitopes of a given molecule (e.g., an insulin-Fc fusion protein of the present invention) that are responsible for moderate or strong binding of the anti-drug antibodies.

As used herein, the term "insulin reference standard" is any one of: (i) a naturally occurring insulin from a mammal (e.g., a human, a dog, or a cat); (ii) an insulin polypeptide that does not comprise an Fc fragment; or (iii) a standard of care insulin (e.g., a commercially available insulin).

As used herein, the term "monomer" refers to a protein or a fusion protein comprising a single polypeptide. In embodiments, the "monomer" is a protein or a fusion protein, e.g., a single polypeptide, comprising an insulin polypeptide and an Fc fragment polypeptide, wherein the insulin and Fc fragment polypeptides are joined by peptide bonds to form the single polypeptide. In embodiments, the monomer is encoded by a single nucleic acid molecule.

As used herein, "N-terminus" refers to the start of a protein or polypeptide that is initiated by an amino acid containing a free amine group that is the alpha-amino group of the amino acid (e.g., the free amino that is covalently linked to one carbon atom that is located adjacent to a second carbon atom, wherein the second carbon atom is part of the carbonyl group of the amino acid). As used herein, "C-terminus" refers to the end of a protein or polypeptide that is terminated by an amino acid containing a carboxylic acid group, wherein the carbon atom of the carboxylic acid group is located adjacent to the alpha-amino group of the amino acid.

As used herein, "pharmacodynamics" or "PD" generally refers to the biological effects of an insulin-Fc fusion protein in a subject. Specifically, herein the PD refers to the measure of the reduction in fasting blood glucose level over time in a subject after the administration of an insulin-Fc fusion protein.

As used herein, "pharmacokinetics" or "PK" generally refers to the characteristic interactions of an insulin-Fc fusion protein and the body of the subject in terms of its absorption, distribution, metabolism, and excretion. Specifically, herein the PK refers to the concentration of an insulin-Fc fusion protein in the blood or serum of a subject at a given time after the administration of the insulin-Fc fusion protein. As used herein, "half-life" refers to the time taken for the concentration of insulin-Fc fusion protein in the blood or serum of a subject to reach half of its original value as calculated from a first order exponential decay model for drug elimination. Insulin-Fc fusion proteins with greater "half-life" values demonstrate greater duration of action in the target subject.

The terms "sequence identity" "sequence homology" "homology" or "identical" in amino acid or nucleotide sequences as used herein describes that the same nucleotides or amino acid residues are found within the variant and reference sequences when a specified, contiguous segment of the nucleotide sequence or amino acid sequence of the variant is aligned and compared to the nucleotide sequence or amino acid sequence of the reference sequence. Methods for sequence alignment and for determining identity between sequences are known in the art, including the use of Clustal Omega, which organizes, aligns, and compares sequences for similarity, wherein the software highlights each sequence position and compares across all sequences at that position and assigns one of the following scores: an "*" (asterisk) for sequence positions which have a single, fully conserved residue, a ":" (colon) indicates conservation between groups of strongly similar properties with scoring greater than 0.5 in the Gonnet PAM 250 matrix, and a "." (period) indicates conservation between groups of weakly similar properties with scoring less than or equal to 0.5 in the Gonnet PAM 250 matrix, a "-" (dash) indicates a sequence gap, meaning that no local homology exists within a particular set of comparisons within a certain range of the sequences, and an empty space " " indicates little or no sequence homology for that particular position across the compared sequences. See, for example Ausubel et al., eds. (1995) Current Protocols in Molecular Biology, Chapter 19 (Greene Publishing and Wiley-Interscience, New York); and the ALIGN program (Dayhoff (1978) in Atlas of Polypeptide Sequence and Structure 5: Suppl. 3 (National Biomedical Research Foundation, Washington, D.C.). With respect to optimal alignment of two nucleotide sequences, the contiguous segment of the variant nucleotide sequence may have additional nucleotides or deleted nucleotides with respect to the reference nucleotide sequence. Likewise, for purposes of optimal alignment of two amino acid sequences, the contiguous segment of the variant amino acid sequence may have additional amino acid residues or deleted amino acid residues with respect to the reference amino acid sequence. In some embodiments, the contiguous segment used for comparison to the reference nucleotide sequence or reference amino acid sequence will comprise at least 6, 10, 15, or 20 contiguous nucleotides, or amino acid residues, and may be 30, 40, 50, 100, or more nucleotides or amino acid residues. Corrections for increased sequence identity associated with inclusion of gaps in the variant's nucleotide sequence or amino acid sequence can be made by assigning gap penalties. Methods of sequence alignment are known in the art.

In embodiments, the determination of percent identity or "homology" between two sequences is accomplished using a mathematical algorithm. For example, the percent identity of an amino acid sequence is determined using the Smith-Waterman homology search algorithm using an affine 6 gap search with a gap open penalty of 12 and a gap extension penalty of 2, BLOSUM matrix 62. The Smith-Waterman homology search algorithm is described in Smith and Waterman (1981) Adv. Appl. Math 2:482-489, herein incorporated by reference. In embodiments, the percent identity of a nucleotide sequence is determined using the Smith-Waterman homology search algorithm using a gap open penalty of 25 and a gap extension penalty of 5. Such a determination of sequence identity can be performed using, for example, the DeCypher Hardware Accelerator from TimeLogic.

As used herein, the term "homology" is used to compare two or more proteins by locating common structural characteristics and common spatial distribution of, for instance, beta strands, helices, and folds. Accordingly, homologous protein structures are defined by spatial analyses. Measuring structural homology involves computing the geometric-topological features of a space. One approach used to generate and analyze three-dimensional (3D) protein structures is homology modeling (also called comparative modeling or knowledge-based modeling) which works by finding similar sequences on the basis of the fact that 3D similarity reflects 2D similarity. Homologous structures do not imply sequence similarity as a necessary condition.

As used herein, the terms "subject" and "patient" are intended to include canine and feline animals. Exemplary canine and feline subjects include dogs and cats having a disease or a disorder, e.g., diabetes or another disease or disorder described herein, or normal subjects.

As used herein, the term "titer" or "yield" refers to the amount of a fusion protein product (e.g., an insulin-Fc fusion protein described herein) resulting from the biosynthesis (e.g., in a mammalian cell, e.g., in a HEK293 cell or CHO cell) per volume of the cell culture. The amount of product may be determined at any step of the production process (e.g., before or after purification), but the yield or titer is always stated per volume of the original cell culture. As used herein, the term "product yield" or "total protein yield" refers to the total amount of insulin-Fc fusion protein expressed by cells and purified via at least one affinity chromatography step (e.g., Protein A or Protein G) and includes monomers of insulin-Fc fusion protein, homodimers of insulin-Fc fusion protein, and higher-order molecular aggregates of homodimers of insulin-Fc fusion protein. As used herein, the term "percent homodimer" or "% homodimer" refers to the proportion of a fusion protein product (e.g., an insulin-Fc fusion protein described herein) that is the desired homodimer. As used herein, the term "homodimer titer" refers to the product of the % homodimer and the total protein yield after Protein A purification step reported per volume of the cell culture.

As used herein, the terms "treat" or "treating" a subject having a disease or a disorder refer to subjecting the subject to a regimen, for example the administration of a fusion protein such as a fusion protein described herein, such that at least one symptom of the disease or disorder is cured, healed, alleviated, relieved, altered, remedied, ameliorated, or improved. Treating includes administering an amount effective to alleviate, relieve, alter, remedy, ameliorate, improve or affect the disease or disorder, or the symptoms of the disease or disorder. The treatment may inhibit deterioration or worsening of a symptom of a disease or disorder.

Insulin-Fc Fusion Protein Components and Structure

The present disclosure relates to a composition of a fusion protein (i.e., an insulin-Fc fusion protein) comprising an insulin polypeptide linked via a peptide linker to a species-specific Fc fragment, and its use to treat diabetes in companion animals (e.g., dogs or cats). As used herein, the terms "fusion protein" and "insulin-Fc fusion protein" refer to a protein comprising more than one part, for example from different sources (different proteins, polypeptides, cells, etc.), that are covalently linked through peptide bonds. The insulin-Fc fusion proteins are covalently linked by (i) connecting the genes that encode for each part into a single nucleic acid molecule and (ii) expressing in a host cell (e.g., HEK or CHO) the protein for which the nucleic acid molecule encodes as follows: (N-terminus)-insulin polypeptide-linker-Fc fragment-(C-terminus). The fully recombinant synthesis approach is preferred over methods in which the insulin polypeptide and Fc fragments are synthesized separately and then chemically conjugated. The chemical conjugation step and subsequent purification process increase the manufacturing complexity, reduce product yield, and increase cost.

As used herein, the term "dimer" refers to a protein or a fusion protein comprising two polypeptides linked covalently. In embodiments, two identical polypeptides are linked covalently (e.g., via disulfide bonds) forming a "homodimer" (diagrammatically represented in FIG. 1). Disulfide bonds are shown as dotted lines in FIG. 1.; total number of disulfide bonds in actuality may be greater or less than the number shown in FIG. 1. In embodiments, the homodimer is encoded by a single nucleic acid molecule, wherein the homodimer is made recombinantly inside a cell by first forming insulin-Fc fusion protein monomers and by then assembling two identical insulin-Fc fusion protein monomers into the homodimer upon further processing inside the cell.

As used herein, the terms "multimer," "multimeric," or "multimeric state" refer to non-covalent, associated forms of Fc fusion protein dimers that may be in equilibrium with Fc fusion protein dimers or may act as permanently aggregated versions of Fc fusion protein dimers (e.g., dimers of Fc fusion protein homodimers, trimers of Fc fusion protein homodimers, tetramers of Fc fusion protein homodimers, or higher order aggregates containing five or more Fc fusion protein homodimers). It may be expected that multimeric forms of Fc fusion proteins may have different physical, stability, or pharmacologic activities from that of the insulin-Fc fusion protein homodimers.

Insulin Polypeptide

An insulin polypeptide may be, for example, an insulin or insulin analog produced by β-cells in the islets of Langerhans within the pancreas. Insulin functions by regulating the absorption of glucose from the blood. Upon a stimulus, such as increased protein and glucose levels, insulin is released from β-cells and binds to the insulin receptor (IR), initiating a signal cascade that affects many aspects of mammalian (e.g., human, canine, or feline) metabolism. Disruption of this process is directly related to several diseases, notably diabetes, insulinoma, insulin resistance, metabolic syndromes, and polycystic ovary syndrome. Insulin analogs of the present disclosure may be related to the structure of insulin yet contain one or more modifications. In some embodiments, the insulin analog comprises at least one amino acid substitution, deletion, addition or chemical modification relative to insulin, which may impact a particular feature or characteristic of the insulin-Fc fusion protein. For example, the modifications or alterations described herein may impact the structure, stability, pH sensitivity, bioactivity, or binding affinity of the insulin-Fc fusion protein to a cell surface receptor (e.g., an insulin hormone receptor) relative to a reference standard.

Figure 1:
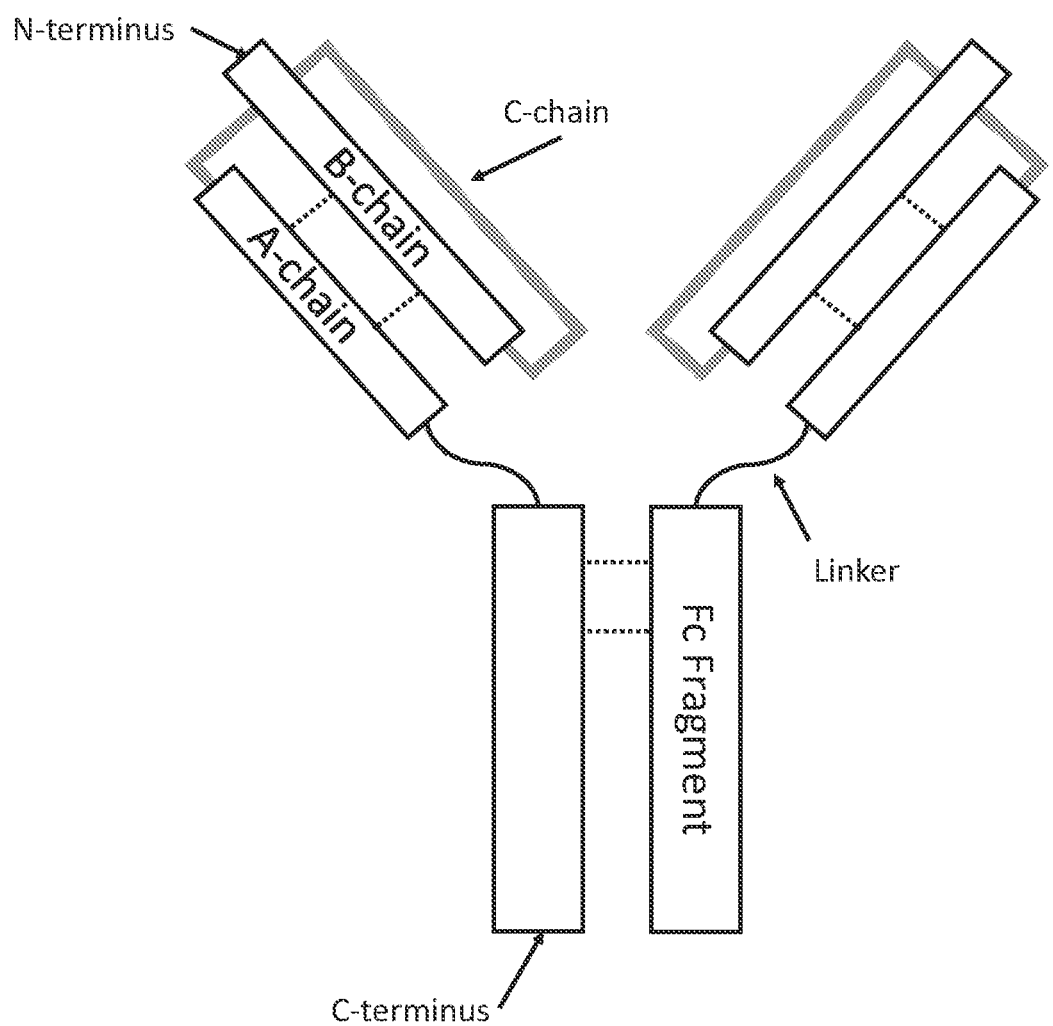
FIG. 1 shows a schematic representation of an exemplary insulin-Fc fusion protein homodimer.

The amino acid sequence of insulin is strongly conserved throughout evolution, particularly in vertebrates. For example, native canine insulin differs by only one amino acid from human insulin, and native feline insulin differs by just four amino acids from human insulin. As used herein, the terms "B-chain", "C-peptide" or "C-chain", and "A-chain" refer to the peptide segments of an insulin polypeptide as illustrated in FIG. 1. Insulin is a 51 amino acid hormone containing two peptide chains (i.e., a B-chain and an A-chain) connected via disulfide bonds (e.g., disulfide bonds formed by one or more B-chain cysteine side chain thiols and one or more A-chain cysteine side chain thiols). The A-chain of insulin is 21 amino acids in length and the B-chain of insulin is 30 amino acids in length. In the native form of insulin, the A-chain contains one intrachain disulfide bond formed by two A-chain cysteine side chain thiols. For reference purposes, the sequences for the human insulin B-chain of SEQ ID NO: 1 and the human insulin A-chain of and SEQ ID NO: 2 are shown below:

(SEQ ID NO: 1)
FVNQHLCGSHLVEALYLVCGERGFFYTPKT (SEQ ID NO: 2)
GIVEQCCTSICSLYQLENYCN

As used herein, the term "insulin" or "insulin polypeptide" encompasses mature insulin, preproinsulin, proinsulin, and naturally occurring insulin, or analogs thereof. In embodiments, an insulin polypeptide can be a full-length insulin polypeptide or a fragment thereof. In embodiments, an insulin polypeptide can comprise one or more fragments from mature insulin, preproinsulin, proinsulin, or naturally occurring insulin.

Insulin is normally constructed as a N-terminus-B-chain:C-chain:A-chain-C-terminus polypeptide, wherein the C-chain is cleaved in order to make it bioactive. For reference purposes, the sequence of the entire human insulin molecule including the C-chain (i.e., human proinsulin) is shown below with the C-chain bolded:

(SEQ ID NO: 3)
FVNQHLCGSHLVEALYLVCGERGFFYTPKTRREAEDLQVGQVELGGGP

GAGSLQPLALEGSLQKRGIVEQCCTSICSLYQLENYCN

The transformation of the single-chain insulin polypeptide into a bioactive two-chain polypeptide is normally accomplished within the β-cells of the islets of Langerhans prior to glucose-stimulated insulin secretion by two endoproteases, Type I endoproteases, PC1 and PC3, that disrupt the C peptide-B chain connection and PC2, and a Type II endoprotease, that cleaves the C peptide-A chain bond at exactly the right sites. However, cell systems used for the biosynthesis of therapeutic molecules such as insulin (e.g., bacteria, yeast, and mammalian (e.g., HEK and CHO) cell systems) do not possess this pathway, and therefore the transformation must take place after expression and harvesting of the single chain polypeptide using chemical or enzymatic methods. All the known techniques for cleaving the C-chain after expression and harvesting rely on first modifying the C-chain such that it terminates in a lysine just before the N-terminus of the A-chain. Then, using an enzyme selected from the trypsin or Lys-C families, which clips peptide bonds specifically at the C-termini of lysine residues, the single chain-insulin polypeptide is cleaved at the C-terminal lysine of the C-chain and at the C-terminal lysine at the $29^{th}$ position from the N-terminus of the B-chain. In some cases, the resulting bioactive two-chain insulin is used without reattaching the clipped amino acid at the $30^{th}$ position from the N-terminus of the B-chain, and in some cases the clipped amino acid at the $30^{th}$ position from the N-terminus of the B-chain is added back to the molecule using an additional enzymatic method. Such a process works well with insulin, because it contains only one lysine in its entire two chain polypeptide form. However, this process cannot be used on the insulin-Fc fusion proteins contained herein, because all known Fc fragments contain multiple lysine residues. The enzymatic cleavage process would, therefore, digest the Fc fragment into non-functional parts, thereby eliminating the ability of the Fc fragment to prolong the action of the insulin polypeptide in vivo. Therefore, an insulin-Fc fusion protein of the present invention must comprise an insulin polypeptide that does not require C-chain cleavage and is therefore bioactive in its single chain form.

A number of bioactive single chain insulin polypeptides have been described in the art. In all cases, the single chain insulin polypeptides contain C-chains of specific length and composition as well as A-chains and B-chains mutated at specific amino acid sites in order to achieve electrostatic balance, prevent aggregation, and enhance insulin receptor (IR) binding and/or downstream signaling to achieve bioactivity at levels comparable to that of the native two-chain insulin. Herein, the location of mutations on peptide segments are notated using the name of the segment (e.g., B-chain, C-chain, A-chain) and the number of the amino acid counting from the N-terminus of the segment. For example, the notation "B16" refers to the 16$^{th}$ amino acid from the N-terminus of the amino acid sequence of the B-chain. The notation "A8" refers to the 8$^{th}$ amino acid from the N-terminus of the A-chain. Furthermore, if an amino acid is mutated from its native form to a new amino acid at a particular location, the location is appended with the one letter amino acid code for the new amino acid. For example, B16A refers to an alanine mutation at the 16$^{th}$ amino acid from the N-terminus of the amino acid sequence of the B-chain and A8H refers to a histidine mutation at the 8$^{th}$ amino acid from the N-terminus of the amino acid sequence of the A-chain.

In one example, a single chain insulin analog with a C-chain of the sequence GGGPRR and additional substitutions in the A-chain and B-chain (SEQ ID NO: 4) was developed by The Department of Biochemistry, Case Western Reserve University School of Medicine and the Department of Medicine, University of Chicago (see Hua, Q.-x, Nakagawa, S. H., Jia, W., Huang, K., Phillips, N. B., Hu, S.-q., Weiss, M. A., (2008) J. Biol. Chem Vol. 283, No. 21 pp 14703-14716). In this example, at position 8 of the A-chain (i.e., A8), histidine is substituted for threonine; at position 10 of the B-chain (i.e., B10), aspartic acid is substituted for histidine; at position 28 of the B-chain (i.e., B28), aspartic acid is substituted for proline; and at position 29 of the B-chain (i.e., B29), proline is substituted for lysine. SEQ ID NO: 4 is listed below with each of the non-native amino acids bolded:

(SEQ ID NO: 4)
FVNQHLCGSDLVEALYLVCGERGFFYTDPTGGGPRRGIVEQCCHSICSL

YQLENYCN

In embodiments, alanine may be substituted for tyrosine at position 16 from the N-terminus of the B-chain (i.e., B16) in SEQ ID NO: 4 to produce SEQ ID NO: 5, as an alanine substitution in this position is known to be less capable of activating insulin-specific T cells (Alleva, D. G., Gaur, A., Jin, L., Wegmann, D., Gottlieb, P. A., Pahuja, A., Johnson, E. B., Motheral, T., Putnam, A., Crowe, P. D., Ling, N., Boehme, S. A., Conlon, P. J., (2002) Diabetes Vol. 51, No.

7 pp 2126-2134). SEQ ID NO: 5 is listed below with each of the non-native amino acids bolded:

(SEQ ID NO: 5)
FVNQHLCGSDLVEALALVCGERGFFYTDPTGGGPRRGIVEQCCHSICSL
YQLENYCN

In some embodiments, it was unexpectedly discovered that specific amino acids in SEQ ID NO: 4 and SEQ ID NO: 5 led to the development of neutralizing anti-drug antibodies after repeated subcutaneous injections in the target animal (e.g., dog or cat). The anti-drug antibodies led to an unacceptable reduction in the NAOC after multiple injections (e.g., a NAOCR value after the third injection of less than 0.5), rendering the associated insulin-Fc fusion proteins non-viable. Specifically, it was discovered in the steps leading up to the invention of this disclosure that the A8 mutation to histidine and the B10 mutation to aspartic acid accounted for the vast majority of the anti-drug antibody specificity and thus represented immunogenic "hot spots" (e.g., immunogenic epitopes) on the insulin-polypeptide. Therefore, in preferred embodiments, the insulin-polypeptide does not contain histidine at position A8 or aspartic acid at position B10 of the insulin polypeptide.

In an embodiment, it was confirmed that simply keeping the A8 and B10 amino acids as their native threonine and histidine, respectively, does eliminate the anti-drug antibody response, but the resulting insulin-Fc fusion protein is not bioactive in the target species (e.g., the NAOC is less than 150% FBGL·days·kg/mg). Therefore, it was necessary to experiment with various A-chain, B-chain, and C-chain variations to find a suitable solution. Most variants failed to achieve homodimer titers greater than 50 mg/L, and many of those that did meet those objectives did not reach acceptable levels of bioactivity in the target species (e.g., acceptable NAOC values of greater than 150% FBGL·days·kg/mg). Having screened over 120 variants, the following insulin polypeptide of SEQ ID NO: 6_NULL was deemed suitable with respect to achieving homodimer titers of greater than 50 mg/L, NAOC values in the target species of greater than 150% FBGL·days·kg/mg, minimal immunogenicity, and NAOCR values after the third injection in the target species of greater than 0.5 of the associated insulin-Fc fusion proteins (non-native amino acids bolded and deleted native amino acids represented with a bolded Z:

(SEQ ID NO: 6_NULL)
FVNQHLCGS$X_1$LVEALELVCGERGFHYZZZZGGGGGSGGGGGIVEQCC
$X_2$STCSLDQLENYC$X_3$ where $X_1$ is not D, $X_2$ is not H, and $X_3$ is absent or N.

In specific embodiments, in SEQ ID NO: 6_NULL, $X_1$ is H, $X_2$ is T, and $X_3$ is absent or N resulting in the following SEQ ID NO: 7_NULL (with non-native amino acids bolded and deleted native amino acids represented with a bolded Z):

(SEQ ID NO: 7_NULL)
FVNQHLCGSHLVEALELVCGERGFHYZZZZGGGGGSGGGGGIVEQCCT
STCSLDQLENYC$X_3$ where $X_3$ is absent or N.

In a specific embodiment, in SEQ ID NO: 7_NULL, $X_3$ is absent resulting in the following SEQ ID NO: 8 NULL (with non-native amino acids bolded and deleted native amino acids represented with a bolded Z):

(SEQ ID NO: 8_NULL)
FVNQHLCGSHLVEALELVCGERGFHYZZZZGGGGGSGGGGGIVEQCCT
STCSLDQLENYCZ

In a specific embodiment, in SEQ ID NO: 7_NULL, $X_3$ is N resulting in the following SEQ ID NO: 9_NULL (with non-native amino acids bolded and deleted native amino acids represented with a bolded Z):

(SEQ ID NO: 9_NULL)
FVNQHLCGSHLVEALELVCGERGFHYZZZZGGGGGSGGGGGIVEQCCT
STCSLDQLENYCN

In some embodiments, the Fc fragment was mutated to prevent glycosylation during synthesis and potentially reduce the immunogenicity of the resulting insulin-Fc fusion protein in the target animal (e.g., dog or cat). Unexpectedly, it was discovered that there was an interaction between the insulin polypeptide and the mutated Fc fragment such that yet another amino acid mutation was required on the insulin polypeptide in order to render the insulin-Fc fusion protein sufficiently manufacturable (e.g., with a homodimer titer greater than 50 mg/L) and non-immunogenic with an NAOC value in the target species of greater than 150% FBGL·days·kg/mg and a NAOCR value after the third injection in the target species of greater than 0.5. Specifically, it was discovered that mutating the B16 amino acid to an alanine on the insulin polypeptide was required when it was linked to specific, mutated, non-glycosylated Fc fragments resulting in the following insulin polypeptide SEQ ID NO: 10 NULL (with non-native amino acids bolded and deleted native amino acids represented with a bolded Z):

(SEQ ID NO: 10_NULL)
FVNQHLCGS$X_1$LVEALALVCGERGFHYZZZZGGGGGSGGGGGIVEQCC
$X_2$STCSLDQLENYCZ where $X_1$ is not D and $X_2$ is not H.

In a specific embodiment, in SEQ ID NO: 10_NULL, $X_1$ is H and $X_2$ is T resulting in the following SEQ ID NO: 11_NULL (with non-native amino acids bolded and deleted native amino acids represented with a bolded Z):

SEQ ID NO: 11_NULL
FVNQHLCGSHLVEALALVCGERGFHYZZZZGGGGGSGGGGGIVEQCCT
STCSLDQLENYCZ-

The following are restatements of the sequences shown above but with the absent amino acids of symbol Z removed from the notation of the insulin polypeptide sequences. Again, in all cases the non-native amino acids bolded. To avoid confusion, each original sequence containing Z symbols is listed above the new sequence with the Z symbols removed. Despite the two separate notations, the paired sequences refer to exactly the same insulin polypeptide.
SEQ ID NO: 6_NULL restated as:

FVNQHLCGSX₁LVEALELVCGERGFHYGGGGGSGGGGIVEQCCX₂ST (SEQ ID NO: 6)

CSLDQLENYCX₃ where X₁ is not D, X₂ is not H, and X₃ is absent or N.
SEQ ID NO: 7_NULL restated as:

FVNQHLCGSHLVEALELVCGERGFHYGGGGGSGGGGIVEQCCTSTCS (SEQ ID NO: 7)

LDQLENYCX₃ where X₃ is absent or N.
SEQ ID NO: 8_NULL restated as:

FVNQHLCGSHLVEALELVCGERGFHYGGGGGSGGGGIVEQCCTSTCS (SEQ ID NO: 8)

LDQLENYC

SEQ ID NO: 9_NULL restated as:

FVNQHLCGSHLVEALELVCGERGFHYGGGGGSGGGGIVEQCCTSTCS (SEQ ID NO: 9)

LDQLENYCN

SEQ ID NO: 10_NULL restated as:

FVNQHLCGSX₁LVEALALVCGERGFHYGGGGGSGGGGIVEQCCX₂ST (SEQ ID NO: 10)

CSLDQLENYC where X₁ is not D and X₂ is not H.
SEQ ID NO: 11_NULL restated as:

FVNQHLCGSHLVEALALVCGERGFHYGGGGGSGGGGIVEQCCTSTCS (SEQ ID NO: 11)

LDQLENYC

Linker

The successful construction of a recombinantly made insulin-Fc fusion protein requires a linker connecting the insulin polypeptide to the Fc fragment. In embodiments, an insulin-Fc fusion protein described herein comprises a peptide linker between the insulin polypeptide and the Fc fragment comprising amino acids (e.g., natural or unnatural amino acids). In embodiments, the peptide linker can be encoded by a nucleic acid molecule, for example such that a single nucleic acid molecule can encode the various peptides within an insulin polypeptide as well as the peptide linker and the Fc fragment. The choice of peptide linker (for example, the length, composition, hydrophobicity, and secondary structure) could impact the manufacturability (i.e., the homodimer titer), the chemical and enzymatic stability, the bioactivity (i.e., the NAOC value), and the immunogenicity of the insulin-Fc fusion protein (Chen, X., Zaro, J., Shen, W. C., Adv Drug Deliv Rev. 2013 Oct. 15; 65(10): 1357-1369). Table 1 lists several linkers used in the design of an insulin-Fc fusion protein with the goal of improving the homodimer titer and the bioactivity.

TABLE 1

Peptide Linker Between A-chain and Fc Fragment in an Insulin-Fc Fusion Protein

GGGGAGGGG (SEQ ID NO: 12)

GGGGSGGGG (SEQ ID NO: 13)

GGGGGAGGGG (SEQ ID NO: 126)

GGGGSGGGGSGGGGSGGGG (SEQ ID NO: 127)

GGGGKGGGGKGGGGKGGGG (SEQ ID NO: 128)

GGGGGQGGGQGGGGQGGGGG (SEQ ID NO: 14)

GGGGGAGGGGAGGGGAGGGG (SEQ ID NO: 129)

SGGGGQGGGGQGGGGQGGGGG (SEQ ID NO: 130)

HGGGGQGGGGQGGGGQGGGGG (SEQ ID NO: 131)

PGGGGQGGGGQGGGGQGGGGG (SEQ ID NO: 132)

In embodiments, the peptide linker comprises the sequence:

GGGGAGGGG. (SEQ ID NO: 12)

In other embodiments, the peptide linker comprises the sequence:

GGGGSGGGG. (SEQ ID NO: 13)

In preferred embodiments, the peptide linker comprises the sequence:

GGGGGQGGGGQGGGGQGGGGG. (SEQ ID NO: 14)

In constructing a recombinantly made insulin-Fc fusion protein with a peptide linker like the one of SEQ ID NO: 14, attention must be paid to the possibility of unwanted enzymatic cleavage between the C-terminus of the insulin A-chain and the N-terminus of the peptide linker. Cleavage of the linker and Fc-fragment from the insulin polypeptide would render the insulin-Fc fusion protein incapable of providing an extended duration of bioactivity. A known enzymatic cleavage site exits between asparagine-glycine bonds (Vlasak, J., Ionescu, R., (2011) MAbs Vol. 3, No. 3 pp 253-263). In many peptide linker embodiments, including the preferred peptide linker of SEQ ID NO: 14, the N-terminal amino acid is a glycine. Furthermore, the C-terminus of the insulin A-chain (i.e., the 21st amino acid from the N-terminus of the A-chain (i.e., A21)) is an asparagine. Therefore, the A21 asparagine is omitted in the insulin polypeptides of SEQ ID NO: 8, SEQ ID NO: 10, and SEQ ID NO: 11 to eliminate the potentially enzymatically cleavable asparagine-glycine bond that would form between the A-chain and the peptide linker. Unexpectedly, an insulin-Fc fusion protein constructed from the insulin polypeptide of SEQ ID NO: 9, which retains the asparagine at the C-terminus of the A-chain, demonstrates manufacturability in mammalian cells with an acceptable homodimer titer (i.e., a homodimer titer greater than 50 mg/L), an acceptable bioactivity in vivo (i.e., a NAOC greater than 150% FBGL·days·kg/mg in the target animal), and sustained levels of bioactivity after multiple doses (i.e., a NAOCR values after the third injection in the target animal of greater than 0.5). The results indicate that, contrary to expectations based on prior teachings, there is no risk of enzymatic cleavage or deactivation of insulin-Fc fusion proteins containing the asparagine-glycine link between the insulin polypeptide and peptide linker, at least for insulin-Fc fusion proteins comprising the Fc fragment sequences disclosed herein.

Fc Fragment

The terms "Fc fragment," "Fc region," "Fc domain," or "Fc polypeptide," are used herein to define a C-terminal region of an immunoglobulin heavy chain. The Fc fragment, region, domain or polypeptide may be a native sequence Fc region or a variant/mutant Fc region. Although the boundaries of the Fc region of an immunoglobulin heavy chain may vary, they generally comprise some or all of the hinge region of the heavy chain, the CH2 region of the heavy chain, and the CH3 region of the heavy chain. The hinge region of a canine or feline Fc fragment comprises amino acid sequences that connect the CH1 domain of the heavy chain to the CH2 region of the heavy chain and contains one or more cysteines that form one or more interheavy chain disulfide bridges to form a homodimer of an Fc fusion protein from two identical but separate monomers of the Fc fusion protein. The hinge region may comprise all or part of a naturally occurring amino acid sequence or a non-naturally occurring amino acid sequence.

An Fc receptor (FcR) refers to a receptor that binds to an Fc fragment or to the Fc region of an antibody. In embodiments, the FcR is a native sequence of the canine or feline FcR. In embodiments, the FcR is one which binds an Fc fragment or the Fc region of an IgG antibody (a gamma receptor) and includes without limitation, receptors of the Fc(gamma) receptor I, Fc(gamma) receptor IIa, Fc(gamma) receptor IIb, and Fc(gamma) receptor III subclasses, including allelic variants and alternatively spliced forms of these receptors. "FcR" also includes the neonatal receptor, FcRn, which is responsible for the transfer of maternal IgG molecules to the fetus (Guyer et al., 1976 J. Immunol., 117:587; and Kim et al., 1994, J. Immunol., 24:249) and is also responsible for the prolonged in vivo elimination half-lives of antibodies and Fc-fusion proteins in vivo. In embodiments, FcR of human origin are used in vitro (e.g., in an assay) to measure the binding of insulin-Fc fusion proteins comprising Fc fragments of canine or feline origin so as to assess their FcR binding properties. Those skilled in the art will understand that mammalian FcR from one species (e.g., FcR of human origin) are sometimes capable of in vitro binding of Fc fragments from a second species (e.g., FcR of canine or feline origin). In embodiments, FcR of canine origin are used in vitro (e.g., in an assay) to measure the binding of insulin-Fc fusion proteins comprising Fc fragments of both canine or feline origin so as to assess their FcR binding properties. Those skilled in the art will understand that mammalian FcR from one species (e.g., FcR of canine origin) are capable of in vitro binding of insulin-Fc fusion proteins comprising Fc fragments from the same species (e.g., of canine origin) and also sometimes insulin-Fc fusion proteins comprising Fc fragments originating from another mammalian species (e.g., of feline origin).

In embodiments, the Fc fragment comprises the Fc region (e.g., hinge region, CH2 domain, and CH3 domain) of a mammalian IgG, for example a canine IgGA Fc fragment (SEQ ID NO: 15), a canine IgGB Fc fragment (SEQ ID NO: 16), a canine IgGC Fc fragment (SEQ ID NO: 17), or a canine IgGD Fc fragment (SEQ ID NO: 18) or a feline IgG1a fragment (SEQ ID NO: 19), a feline IgG1b Fc fragment (SEQ ID NO: 20), or a feline IgG2 Fc fragment (SEQ ID NO: 21). In embodiments, the C-terminal lysine that is often found in native canine or feline IgG isotype Fc fragment amino acid sequences (i.e., the lysine that represents the last amino acid of the Fc fragment sequence) is omitted to prevent the accidental production of unwanted amino acid sequence variants during manufacturing (e.g., Fc fragments containing the C-terminal lysine becoming mixed with Fc fragments where the C-terminal lysine is omitted, which can occur during production of the desired protein within cells (Dick, L W., (2008) Biotechnol Bioeng. August 15; 100 (6) pp 1132-43). Therefore, in embodiments, the canine and feline Fc fragment sequences lacking a C-terminal lysine are:

(SEQ ID NO: 15)
RCTDTPPCPVPEPLGGPSVLIFPPKPKDILRITRTPEVTCVVLDLGRED

PEVQISWFVDGKEVHTAKTQSREQQFNGTYRVVSVLPIEHQDWLTGKEF

KCRVNHIDLPSPIERTISKARGRAHKPSVYVLPPSPKELSSSDTVSITC

LIKDFYPPDIDVEWQSNGQQEPERKHRMTPPQLDEDGSYFLYSKLSVDK

SRWQQGDPFTCAVMHETLQNHYTDLSLSHSPG (SEQ ID NO: 16)
DCPKCPAPEMLGGPSVFIFPPKPKDTLLIARTPEVTCVVVDLDPEDPEV

QISWFVDGKQMQTAKTQPREEQFNGTYRVVSVLPIGHQDWLKGKQFTCK

VNNKALPSPIERTISKARGQAHQPSVYVLPPSREELSKNTVSLTCLIKD

FFPPDIDVEWQSNGQQEPESKYRTTPPQLDEDGSYFLYSKLSVDKSRWQ

RGDTFICAVMHEALHNHYTQESLSHSPG (SEQ ID NO: 17)
CNNCPCPGCGLLGGPSVFIFPPKPKDILVTARTPTVTCVVVDLDPENPE

VQISWFVDSKQVQTANTQPREEQSNGTYRVVSVLPIGHQDWLSGKQFKC

KVNNKALPSPIEEIISKTPGQAHQPNVYVLPPSRDEMSKNTVTLTCLVK

DFFPPEIDVEWQSNGQQEPESKYRMTPPQLDEDGSYFLYSKLSVDKSRW

QRGDTFICAVMHEALHNHYTQISLSHSPG (SEQ ID NO: 18)
CISPCPVPESLGGPSVFIFPPKPKDILRITRTPEITCVVLDLGREDPEV

QISWFVDGKEVHTAKTQPREQQFNSTYRVVSVLPIEHQDWLTGKEFKCR

VNHIGLPSPIERTISKARGQAHQPSVYVLPPSPKELSSSDTVTLTCLIK

DFFPPEIDVEWQSNGQPEPESKYHTTAPQLDEDGSYFLYSKLSVDKSRW

QQGDTFTCAVMHEALQNHYTDLSLSHSPG (SEQ ID NO: 19)
DCPKCPPPEMLGGPSIFIFPPKPKDTLSISRTPEVTCLVVDLGPDDSDV

QITWFVDNTQVYTAKTSPREEQFNSTYRVVSVLPILHQDWLKGKEFKCK

VNSKSLPSPIERTISKAKGQPHEPQVYVLPPAQEELSRNKVSVTCLIKS

FHPPDIAVEWEITGQPEPENNYRTTPPQLDSDGTYFVYSKLSVDRSHWQ

RGNTYTCSVSHEALHSHHTQKSLTQSPG (SEQ ID NO: 20)
DCPKCPPPEMLGGPSIFIFPPKPKDTLSISRTPEVTCLVVDLGPDDSDV

QITWFVDNTQVYTAKTSPREEQFNSTYRVVSVLPILHQDWLKGKEFKCK

VNSKSLPSPIERTISKDKGQPHEPQVYVLPPAQEELSRNKVSVTCLIEG

-continued

FYPSDIAVEWEITGQPEPENNYRTTPPQLDSDGTYFLYSRLSVDRSRWQ

RGNTYTCSVSHEALHSHHTQKSLTQSPG (SEQ ID NO: 21)
GEGPKCPVPEIPGAPSVFIFPPKPKDTLSISRTPEVTCLVVDLGPDDSN

VQITWFVDNTEMHTAKTRPREEQFNSTYRVVSVLPILHQDWLKGKEFKC

KVNSKSLPSAMERTISKAKGQPHEPQVYVLPPTQEELSENKVSVTCLIK

GFHPPDIAVEWEITGQPEPENNYQTTPPQLDSDGTYFLYSRLSVDRSHW

QRGNTYTCSVSHEALHSHHTQKSLTQSPG

Replacing the human Fc with canine IgGA is preferable to minimize any unwanted immunogenicity in dogs due to the IgGA isotype's lack of Fc(gamma) effector function in dogs (much like the human IgG2 isotype in humans). However, in an embodiment containing the insulin polypeptide of SEQ ID NO: 5 and the peptide linker of SEQ ID NO: 12, it was unexpectedly discovered that the insulin-Fc fusion protein comprising the canine IgGA fragment (SEQ ID NO: 15) was highly aggregated with low titers of the desired homodimer (i.e., homodimer titers less than 50 mg/L). Furthermore, the compound was non-bioactive in dogs (i.e., the NAOC value was less than 150% FBGL·days·kg/mg), presumably due to its high level of aggregation (e.g., low % homodimer). Despite mutating the insulin polypeptide of SEQ ID NO: 5, the canine IgGA Fc fragment (SEQ ID NO: 15), and/or the linker, there was no embodiment based on the canine IgGA Fc fragment with a low enough degree of aggregation and a high enough titer of the desired homodimer. On the other hand, replacing of the canine IgGA Fc fragment (SEQ ID NO: 15) with the canine IgGB Fc fragment (SEQ ID NO: 16) yielded a much less aggregated compound with a comparatively high titer of the desired homodimer. Furthermore, the compound containing the insulin polypeptide of SEQ ID NO: 5 and the canine IgGB Fc fragment (SEQ ID NO: 16) was bioactive in dogs, exhibiting glucose lowering bioactivity over multiple days (i.e., the NAOC value was greater than 150% FBGL·days·kg/mg).

The preference for the canine IgGB Fc fragment over the canine IgGA Fc fragment was confirmed in embodiments containing the insulin polypeptide of SEQ ID NO: 8 and the peptide linker of SEQ ID NO: 14, both of which vary considerably from the insulin polypeptide of SEQ ID NO: 5 and the peptide linker of SEQ ID NO: 12. Insulin-Fc fusion proteins containing the insulin polypeptide of SEQ ID NO: 8 and the peptide linker of SEQ ID NO: 14 were synthesized using Fc fragments from the canine IgGA (SEQ ID NO: 15), canine IgGB (SEQ ID NO: 16), canine IgGC (SEQ ID NO: 17), or canine IgGD (SEQ ID NO: 18) immunoglobulins. Using the conventional purification method, only the compounds comprising the canine IgGA and the canine IgGB showed any appreciable protein yields. However, just like before, the canine IgGA version of the compound was highly aggregated with low levels of bioactivity, whereas the canine IgGB version of the compound exhibited a low degree of aggregation (i.e., high % homodimer), a high titer of the desired homodimer (i.e., a homodimer titer greater than 50 mg/L), and appreciable levels of long-duration glucose lowering bioactivity in dogs (i.e., the NAOC value was greater than 150% FBGL·days·kg/mg). Using an alternative purification method, the canine IgGC version of the compound was recovered with low degrees of aggregation, but it was minimally bioactive in dogs (i.e., the NAOC value was less than 150% FBGL·days·kg/mg), presumably due to its low affinity for the FcRn receptor. Therefore, with respect to a dog-specific product, the canine IgGB (SEQ ID NO: 16) is the preferred Fc fragment for all insulin-Fc fusion proteins used in dogs, regardless of the choice of insulin polypeptide.

Replacing the human Fc with feline IgG2 is preferable to minimize any unwanted immunogenicity in cats due to the IgG2 isotype's lack of Fc(gamma) effector function in cats (much like the human IgG2 isotype in humans). Unlike the case with the dogs, in embodiments containing the insulin polypeptide of SEQ ID NO: 4, it was discovered that insulin-Fc fusion proteins comprising the feline IgG2 fragment (SEQ ID NO: 21) and the feline IgG1b fragment (SEQ ID NO: 20) were similarly high yielding with low degrees of aggregation (i.e., homodimer titers greater than 50 mg/L) and appreciable insulin receptor affinity (i.e., insulin receptor IC50 values less than 5000 nM). However, unexpectedly when the insulin polypeptide was changed to SEQ ID NO: 7, the insulin-Fc fusion protein comprising the feline IgG2 fragment (SEQ ID NO: 21) was not bioactive in cats (i.e., the NAOC was less than 150% FBGL·days·kg/mg), whereas the insulin-Fc fusion protein comprising the feline IgG1b fragment (SEQ ID NO: 20) exhibited a low degree of aggregation (i.e., high % homodimer), a high titer of the desired homodimer (i.e., a homodimer titer greater than 50 mg/L), and appreciable levels of long-duration glucose lowering bioactivity in cats (i.e., the NAOC value was greater than 150% FBGL·days·kg/mg). Therefore, with respect to a cat-specific product, the feline IgG1b fragment (SEQ ID NO: 20) is the preferred Fc fragment when the insulin polypeptide sequence comprises SEQ ID NO: 7.

Given that the canine IgGB and feline IgG1b isotypes interact with their respective species-specific Fc(gamma) receptors with higher affinities than their canine IgGA and feline IgG2 isotype counterparts, there may or may not be a risk of unwanted immunogenicity after repeated injections. One method for reducing the Fc(gamma) interaction involves deglycosylating or preventing the glycosylation of the Fc fragment during synthesis in the host cell. Each IgG fragment contains a conserved asparagine (N)-glycosylation site in the CH2 domain of each heavy chain of the Fc region. Herein, the notation used to refer to the conserved N-glycosylation site is "cNg". One way to remove the attached glycan from a synthesized insulin-Fc fusion protein is to mutate the cNg site to prevent the attachment of glycans altogether during production in the host cell. Herein, the notation used to describe a cNg mutation is cNg-(substituted amino acid). For example, if the asparagine at the cNg site is mutated to serine, this mutation is notated as "cNg-S".

The absolute position of the cNg site from the N-terminus of the B-chain of the insulin-Fc fusion protein varies depending on the length of the insulin polypeptide, the length of the linker, and any omitted amino acids in the Fc fragment prior to the cNg site. Herein, the notation used to refer to the absolute position of the cNg site in a given insulin-Fc fusion protein sequence (as measured counting from the N-terminus of the B-chain of the insulin-Fc fusion protein) is "NB(number)". For example, if the cNg site is found at the 151$^{st}$ amino acid position as counted from the N-terminus of the B-chain, the absolute position of this site is referred to as cNg-NB151. As a further example, if the cNg site is found at the 151$^{st}$ amino acid position as counted from the N-terminus of the B-chain, and the asparagine at this site is mutated to serine, this mutation is noted as "cNg-NB151-S".

In embodiments containing the insulin polypeptide of SEQ ID NO: 5 and the canine IgGB Fc fragment with the cNg-Q, cNg-S, cNg-D, and cNg-K mutations, it was unexpectedly discovered that only the compounds containing the cNg-K and cNg-S mutations exhibited the requisite homodimer titer greater than 50 mg/L and lowest Fc(gamma)RI binding affinities. On the other hand, in an embodiment containing the insulin polypeptide of SEQ ID NO: 8 and the canine IgGB Fc fragment with the cNg-S mutation, it was unexpectedly discovered that the resulting compound was significantly less bioactive in dogs compared to the native canine IgGB Fc-containing counterpart (i.e., the NAOC value was significantly lower for the counterpart containing the native glycosylation site amino acid, e.g., cNg-N). The bioactivity was unexpectedly restored in the cNg-S mutant (i.e., the NAOC value increased significantly) when the B16 amino acid was mutated to alanine as described above for insulin polypeptide SEQ ID NO: 11. Taken together, there is an unexpected and significant interaction between the choice of cNg mutation and the composition of the insulin polypeptide such that experimentation is required to identify the preferred embodiments. In specific embodiments, the canine IgGB Fc mutant containing the cNg-S mutation is preferred and the sequence with bolded cNg-S is shown as:

(SEQ ID NO: 22)

DCPKCPAPEMLGGPSVFIFPPKPKDTLLIARTPEVTCVVVDLDPEDPEV

QISWFVDGKQMQTAKTQPREEQFSGTYRVVSVLPIGHQDWLKGKQFTCK

VNNKALPSPIERTISKARGQAHQPSVYVLPPSREELSKNTVSLTCLIKD

FFPPDIDVEWQSNGQQEPESKYRTTPPQLDEDGSYFLYSKLSVDKSRWQ

RGDTFICAVMHEALHNHYTQESLSHSPG

In specific embodiments, the feline IgG1b Fc mutant containing the cNg-S mutation is preferred:

(SEQ ID NO: 23)

DCPKCPPPEMLGGPSIFIFPPKPKDTLSISRTPEVTCLVVDLGPDDSDV

QITWFVDNTQVYTAKTSPREEQFSSTYRVVSVLPILHQDWLKGKEFKCK

VNSKSLPSPIERTISKDKGQPHEPQVYVLPPAQEELSRNKVSVTCLIEG

FYPSDIAVEWEITGQPEPENNYRTTPPQLDSDGTYFLYSRLSVDRSRWQ

RGNTYTCSVSHEALHSHHTQKSLTQSPG

Insulin-Fe Fusion Proteins

Provided herein are insulin-Fc fusion proteins comprising an insulin polypeptide, an Fc fragment, and a linker between the insulin polypeptide and the Fc fragment. In embodiments, the insulin polypeptide comprises domains in the following orientation from N- to C-termini: (N-terminus)-B-chain-C-chain-A-chain-(C-terminus). In embodiments, the insulin polypeptide is located on the N-terminal side of the Fc fragment. In embodiments, the fusion protein comprises domains in the following orientation from N- to C-termini: (N-terminus)-insulin polypeptide-linker-Fc fragment-(C-terminus) (e.g., (N-terminus)-B-chain-C-chain-A-chain-linker-Fc fragment-(C-terminus)) as illustrated in FIG. 1.

In preferred embodiments, the preferred non-immunogenic, bioactive insulin polypeptide of SEQ ID NO: 6 is combined with the preferred canine IgGB Fc fragment of SEQ ID NO: 16 using the preferred linker of SEQ ID NO: 14 to produce a family of high homodimer titer-yielding, non-aggregated, bioactive, non-immunogenic insulin-Fc fusion proteins of SEQ ID NO: 24 that exhibit homodimer titers greater than 50 mg/L, NAOC values greater than 150% FBGL·days·kg/mg in dogs, and NAOCR values greater than 0.5 after the third injection in a series of repeated injections in dogs. The following shows SEQ ID NO: 24 with non-native amino acids bolded:

(SEQ ID NO: 24)

FVNQHLCGSX$_1$LVEALELVCGERGFHYGGGGGGSGGGGGIVEQCCX$_2$ST

CSLDQLENYCX$_3$GGGGGQGGGGQGGGGQGGGGGDCPKCPAPEMLGGPSV

FIFPPKPKDTLLIARTPEVTCVVVDLDPEDPEVQISWFVDGKQMQTAKT

QPREEQFNGTYRVVSVLPIGHQDWLKGKQFTCKVNNKALPSPIERTISK

ARGQAHQPSVYVLPPSREELSKNTVSLTCLIKDFFPPDIDVEWQSNGQQ

EPESKYRTTPPQLDEDGSYFLYSKLSVDKSRWQRGDTFICAVMHEALHN

HYTQESLSHSPG where $X_1$ is not D, $X_2$ is not H, and $X_3$ is absent or N.

In preferred embodiments comprising SEQ ID NO: 24, the $X_1$ is H, $X_2$ is T, and $X_3$ is absent or N. The selections produce the high homodimer titer-yielding, non-aggregated, bioactive, non-immunogenic insulin-Fc fusion proteins of SEQ ID NO: 25 that exhibit homodimer titers greater than 50 mg/L, NAOC values greater than 150% FBGL·days·kg/mg in dogs, and NAOCR values greater than 0.5 after the third injection in a series of repeated injections in dogs. The following shows SEQ ID NO: 25 with non-native amino acids bolded:

(SEQ ID NO: 25)

FVNQHLCGSHLVEALELVCGERGFHYGGGGGGSGGGGGIVEQCCTSTCS

LDQLENYCX$_3$GGGGGQGGGGQGGGGQGGGGGDCPKCPAPEMLGGPSVFI

FPPKPKDTLLIARTPEVTCVVVDLDPEDPEVQISWFVDGKQMQTAKTQP

REEQFNGTYRVVSVLPIGHQDWLKGKQFTCKVNNKALPSPIERTISKAR

GQAHQPSVYVLPPSREELSKNTVSLTCLIKDFFPPDIDVEWQSNGQQEP

ESKYRTTPPQLDEDGSYFLYSKLSVDKSRWQRGDTFICAVMHEALHNHY

TQESLSHSPG where $X_3$ is absent or N.

In preferred embodiments, $X_3$ is absent in SEQ ID NO: 25 to produce the high homodimer-yielding, non-aggregated, bioactive, non-immunogenic insulin-Fc fusion protein of SEQ ID NO: 32 that exhibits a homodimer titer greater than 50 mg/L, a NAOC value greater than 150% FBGL·days·kg/mg in dogs, and a NAOCR value greater than 0.5 after the third injection in a series of repeated injections in dogs. The following shows SEQ ID NO: 32 with non-native amino acids bolded:

(SEQ ID NO: 32)

FVNQHLCGSHLVEALELVCGERGFHYGGGGGGSGGGGGIVEQCCTSTCS

LDQLENYCGGGGGQGGGGQGGGGQGGGGGDCPKCPAPEMLGGPSVFIFP

PKPKDTLLIARTPEVTCVVVDLDPEDPEVQISWFVDGKQMQTAKTQPRE

EQFNGTYRVVSVLPIGHQDWLKGKQFTCKVNNKALPSPIERTISKARGQ

AHQPSVYVLPPSREELSKNTVSLTCLIKDFFPPDIDVEWQSNGQQEPES

KYRTTPPQLDEDGSYFLYSKLSVDKSRWQRGDTFICAVMHEALHNHYTQ

ESLSHSPG

In preferred embodiments, $X_3$ is N in SEQ ID NO: 25 to produce the high homodimer titer-yielding, non-aggregated, bioactive, non-immunogenic insulin-Fc fusion protein of SEQ ID NO: 34 that exhibits a homodimer titer greater than 50 mg/L, a NAOC value greater than 150% FBGL·days·kg/mg in dogs, and a NAOCR value greater than 0.5 after the third injection in a series of repeated injections in dogs. The following shows SEQ ID NO: 34 with non-native amino acids bolded:

(SEQ ID NO: 34)
FVNQHLCGSHLVEALELVCGERGFHYGGGGGGSGGGGGIVEQCCTSTCS

LDQLENYCNGGGGGQGGGGQGGGGQGGGGGDCPKCPAPEMLGGPSVFIF

PPKPKDTLLIARTPEVTCVVVDLDPEDPEVQISWFVDGKQMQTAKTQPR

EEQFNGTYRVVSVLPIGHQDWLKGKQFTCKVNNKALPSPIERTISKARG

QAHQPSVYVLPPSREELSKNTVSLTCLIKDFFPPDIDVEWQSNGQQEPE

SKYRTTPPQLDEDGSYFLYSKLSVDKSRWQRGDTFICAVMHEALHNHYT

QESLSHSPG

In preferred embodiments, the preferred non-glycosylated, cNg-S mutated canine IgGB Fc fragment of SEQ ID NO: 22 is combined with the preferred B16A mutated insulin polypeptide sequence of SEQ ID NO: 10 using the preferred linker of SEQ ID NO: 14 to produce a family of high homodimer titer-yielding, non-aggregated, bioactive, non-immunogenic insulin-Fc fusion proteins of SEQ ID NO: 26 that exhibit homodimer titers greater than 50 mg/L, NAOC values greater than 150% FBGL·days·kg/mg in dogs, and NAOCR values greater than 0.5 after the third injection in a series of repeated injections in dogs. The following shows SEQ ID NO: 26 with non-native amino acids bolded:

(SEQ ID NO: 26)
FVNQHLCGS$X_1$LVEALALVCGERGFHYGGGGGGSGGGGGIVEQCC$X_2$ST

CSLDQLENYCGGGGGQGGGGQGGGGQGGGGGDCPKCPAPEMLGGPSVFI

FPPKPKDTLLIARTPEVTCVVVDLDPEDPEVQISWFVDGKQMQTAKTQP

REEQFSGTYRVVSVLPIGHQDWLKGKQFTCKVNNKALPSPIERTISKAR

GQAHQPSVYVLPPSREELSKNTVSLTCLIKDFFPPDIDVEWQSNGQQEP

ESKYRTTPPQLDEDGSYFLYSKLSVDKSRWQRGDTFICAVMHEALHNHY

TQESLSHSPG where $X_1$ is not D and $X_2$ is not H.

In a preferred embodiment, the $X_1$ is H and $X_2$ is T in SEQ ID NO: 26 to produce the high homodimer titer-yielding, non-aggregated, bioactive, non-immunogenic insulin-Fc fusion protein of SEQ ID NO: 36 that exhibits a homodimer titer greater than 50 mg/L, a NAOC value greater than 150% FBGL·days·kg/mg in dogs, and a NAOCR value greater than 0.5 after the third injection in a series of repeated injections in dogs. The following shows SEQ ID NO: 36 with non-native amino acids bolded:

(SEQ ID NO: 36)
FVNQHLCGSHLVEALALVCGERGFHYGGGGGGSGGGGGIVEQCCTSTCS

LDQLENYCGGGGGQGGGGQGGGGQGGGGGDCPKCPAPEMLGGPSVFIFP

PKPKDTLLIARTPEVTCVVVDLDPEDPEVQISWFVDGKQMQTAKTQPRE

EQFSGTYRVVSVLPIGHQDWLKGKQFTCKVNNKALPSPIERTISKARGQ

AHQPSVYVLPPSREELSKNTVSLTCLIKDFFPPDIDVEWQSNGQQEPES

KYRTTPPQLDEDGSYFLYSKLSVDKSRWQRGDTFICAVMHEALHNHYTQ

ESLSHSPG

In preferred embodiments, the preferred non-immunogenic, bioactive insulin polypeptide of SEQ ID NO: 6 where $X_3$ is absent is combined with the preferred feline IgG1b Fc fragment of SEQ ID NO: 20 using the preferred linker of SEQ ID NO: 14 to produce a family of high homodimer titer-yielding, non-aggregated, bioactive, non-immunogenic insulin-Fc fusion proteins of SEQ ID NO: 27 that exhibit homodimer titers greater than 50 mg/L, NAOC values greater than 150% FBGL·days·kg/mg in cats, and NAOCR values greater than 0.5 after the third injection in a series of repeated injections in cats. The following shows SEQ ID NO: 27 with non-native amino acids bolded:

(SEQ ID NO: 27)
FVNQHLCGS$X_1$LVEALELVCGERGFHYGGGGGGSGGGGGIVEQCC$X_2$ST

CSLDQLENYCGGGGGQGGGGQGGGGQGGGGGDCPKCPPPEMLGGPSIFI

FPPKPKDTLSISRTPEVTCLVVDLGPDDSDVQITWFVDNTQVYTAKTSP

REEQFNSTYRVVSVLPILHQDWLKGKEFKCKVNSKSLPSPIERTISKDK

GQPHEPQVYVLPPAQEELSRNKVSVTCLIEGFYPSDIAVEWEITGQPEP

ENNYRTTPPQLDSDGTYFLYSRLSVDRSRWQRGNTYTCSVSHEALHSHE

ITQKSLTQSPG where $X_1$ is not D and $X_2$ is not H.

In a preferred embodiment, the $X_1$ is H and $X_2$ is T in SEQ ID NO: 27 to produce the high homodimer titer-yielding, non-aggregated, bioactive, non-immunogenic insulin-Fc fusion protein of SEQ ID NO: 38 that exhibits a homodimer titer greater than 50 mg/L, a NAOC value greater than 150% FBGL·days·kg/mg in cats, and a NAOCR value greater than 0.5 after the third injection in a series of repeated injections in cats. The following shows SEQ ID NO: 38 with non-native amino acids bolded:

(SEQ ID NO: 38)
FVNQHLCGSHLVEALELVCGERGEHYGGGGGGSGGGGGIVEQCCTSTCS

LDQLENYCGGGGGQGGGGQGGGGQGGGGGDCPKCPPPEMLGGPSIFIFP

PKPKDTLSISRTPEVTCLVVDLGPDDSDVQITWFVDNTQVYTAKTSPRE

EQFNSTYRVVSVLPILHQDWLKGKEFKCKVNSKSLPSPIERTISKDKGQ

PHEPQVYVLPPAQEELSRNKVSVTCLIEGFYPSDIAVEWEITGQPEPEN

NYRTTPPQLDSDGTYFLYSRLSVDRSRWQRGNTYTCSVSHEALHSHHTQ

KSLTQSPG

In preferred embodiments, the preferred non-glycosylated, cNg-S mutated feline IgG1b Fc fragment of SEQ TD NO: 23 is combined with the preferred B16A mutated insulin polypeptide sequence of SEQ ID NO: 10 using the preferred linker of SEQ ID NO: 14 to produce a family of high homodimer titer-yielding, non-aggregated, bioactive, non-immunogenic insulin-Fc fusion proteins of SEQ ID NO: 28 that exhibit homodimer titers greater than 50 mg/L, NAOC values greater than 150% FBGL·days·kg/mg in cats, and NAOCR values greater than 0.5 after the third injection in a series of repeated injections in cats. The following shows SEQ ID NO: 28 with non-native amino acids bolded:

(SEQ ID NO: 28)

FVNQHLCGS$X_1$LVEALALVCGERGFHYGGGGGGSGGGGGIVEQCC$X_2$ST

CSLDQLENYCGGGGGQGGGGQGGGGQGGGGGDCPKCPPPEMLGGPSIFI
FPPKPKDTLSISRTPEVTCLVVDLGPDDSDVQITWFVDNTQVYTAKTSP
REEQFSSTYRVVSVLPILHQDWLKGKEFKCKVNSKSLPSPIERTISKDK

GQPHEPQVYVLPPAQEELSRNKVSVTCLIEGFYPSDIAVEWEITGQPEP

ENNYRTTPPQLDSDGTYFLYSRLSVDRSRWQRGNTYTCSVSHEALHSHH

TQKSLTQSPG where $X_1$ is not D and $X_2$ is not H.

In a preferred embodiment, the $X_1$ is H and $X_2$ is T in SEQ ID NO: 28 to produce the high homodimer titer-yielding, non-aggregated, bioactive, non-immunogenic insulin-Fc fusion protein of SEQ ID NO: 40 that exhibits a homodimer titer greater than 50 mg/L, a NAOC value greater than 150% FBGL·days·kg/mg in cats, and a NAOCR value greater than 0.5 after the third injection in a series of repeated injections in dogs. The following shows SEQ ID NO: 40 with non-native amino acids bolded:

(SEQ ID NO: 40)

FVNQHLCGSHLVEALALVCGERGFHYGGGGGGSGGGGGIVEQCCTSTCS

LDQLENYCGGGGGQGGGGQGGGGQGGGGGDCPKCPPPEMLGGPSIFIFP

PKPKDTLSISRTPEVTCLVVDLGPDDSDVQITWFVDNTQVYTAKTSPRE

EQFSSTYRVVSVLPILHQDWLKGKEFKCKVNSKSLPSPIERTISKDKGQ

PHEPQVYVLPPAQEELSRNKVSVTCLIEGFYPSDIAVEWEITGQPEPEN

NYRTTPPQLDSDGTYFLYSRLSVDRSRWQRGNTYTCSVSHEALHSHHTQ

KSLTQSPG

In some embodiments, an insulin-Fc fusion protein described herein does not include a leader amino acid sequence at the N-terminus. In other embodiments, an insulin-Fc fusion protein described herein includes a leader sequence, e.g., at the N-terminus. An exemplary leader sequence includes the amino acid sequence MEWSWVFLF-FLSVTTGVHS (SEQ ID NO: 30). In some embodiments, an insulin-Fc fusion protein described herein is encoded by a nucleic acid molecule comprising a leader sequence, e.g., for expression (e.g., recombinant expression) in cells (e.g., eukaryotic, e.g., mammalian cells). In certain embodiments, the leader sequence is cleaved off, e.g., in the cell culture, during expression. An exemplary nucleic acid sequence encoding a leader sequence includes the nucleic acid sequence: atggaatggagctgggtctttctcttcttcctgtcagtaacg-actggtgtccactcc (SEQ ID NO: 29).

Also disclosed herein are nucleic acid sequences (e.g., cDNA) encoding the insulin-Fc fusion proteins of SEQ ID NOs: 032, 034, 036, 038, and 040.

In the embodiment comprising the insulin-Fc fusion protein of SEQ ID NO: 32, the nucleic acid sequence (leader sequence bolded) is:

(SEQ ID NO: 31)

atggaatggagctgggtctttctcttcttcctgtcagtaacgactggtgtc cactccttcgtgaaccagcacctgtgcggctcccacctggtggaagctctg gaactcgtgtgcggcgagcggggcttccactacgggggtggcggaggaggt tctggtggcggcggaggcatcgtggaacagtgctgcacctccacctgctcc ctggaccagctggaaaactactgcggtggcggaggtggtcaaggaggcggt ggacagggtggaggtgggcagggaggaggcgggggagactgccccaagtgc cccgctcccgagatgctgggcggacccagcgtgttcatcttccctcccaag cccaaggacacactgctgatcgccaggaccccggaggtgacctgcgtggtg gtggacctggatcccgaagaccccgaggtgcagatcagctggttcgtggat ggaaagcagatgcagaccgccaagacccaaccccgggaagagcagttcaac ggcacctacagggtggtgagtgtgttgcccatcggccaccaggactggctg aaggggaagcaattcacatgcaaggttaataacaaggccctgcccagcccc atcgagaggaccatcagcaaggccaggggccaggcccaccagccatctgtg tacgtgctgcccccatctagggaggaactgagcaagaacacagtcagcctt acttgcctgatcaaggacttcttcccaccggacatagacgtggagtggcag agtaacggccagcaggagcccgagagcaagtataggaccacaccgccccaa ctggacgaggacggaagctacttcctctacagcaaattgagcgttgacaaa agcaggtggcagcgaggcgacaccttcatctgcgccgtgatgcacgaggct ttgcataaccactacacccaggagagcctgtcccacagccccggatag In the embodiment comprising the insulin-Fc fusion protein of SEQ ID NO: 34, the nucleic acid sequence (leader sequence bolded) is:

(SEQ ID NO: 33)

atggaatggagctgggtctttctcttcttcctgtcagtaacgactggtgtc cactccttcgtgaaccagcacctgtgcggctcccacctggtggaagctctg gaactcgtgtgcggcgagcggggcttccactacgggggtggcggaggaggt tctggtggcggcggaggcatcgtggaacagtgctgcacctccacctgctcc ctggaccagctggaaaactactgcaacggtggcggaggtggtcaaggaggc ggtggacagggtggaggtgggcagggaggaggcgggggagactgccccaag tgccccgctcccgagatgctgggcggacccagcgtgttcatcttccctccc aagcccaaggacacactgctgatcgccaggaccccggaggtgacctgcgtg gtggtggacctggatcccgaagaccccgaggtgcagatcagctggttcgtg gatggaaagcagatgcagaccgccaagacccaaccccgggaagagcagttc aacggcacctacagggtggtgagtgtgttgcccatcggccaccaggactgg ctgaaggggaagcaattcacatgcaaggttaataacaaggccctgcccagc cccatcgagaggaccatcagcaaggccaggggccaggcccaccagccatct gtgtacgtgctgcccccatctagggaggaactgagcaagaacacagtcagc cttacttgcctgatcaaggacttcttcccaccggacatagacgtggagtgg -continued
cagagtaacggccagcaggagcccgagagcaagtataggaccacaccgccc caactggacgaggacggaagctacttcctctacagcaaattgagcgttgac aaaagcaggtggcagcgaggcgacaccttcatctgcgccgtgatgcacgag gctttgcataaccactacacccaggagagcctgtcccacagccccggatag In the embodiment comprising the insulin-Fc fusion protein of SEQ ID NO: 36, the nucleic acid sequence (leader sequence bolded) is:

(SEQ ID NO: 35)
atggaatggagctgggtctttctcttcttcctgtcagtaacgactggtgtc cactccttcgtgaaccagcacctgtgcggctcccacctggtggaagctctg gcactcgtgtgcggcgagcggggcttccactacgggggtggcggaggaggt tctggtggcggcggaggcatcgtggaacagtgctgcacctccacctgctcc ctggaccagctggaaaactactgcggtggcggaggtggtcaaggaggcggt ggacagggtggaggtgggcagggaggaggcggggagactgccccaagtgc cccgctcccgagatgctgggcggacccagcgtgttcatcttccctcccaag cccaaggacacactgctgatcgccaggaccccggaggtgacctgcgtggtg gtggacctggatcccgaagaccccgaggtgcagatcagctggttcgtggat ggaaagcagatgcagaccgccaagacccaaccccgggaagagcagttctca ggcacctacagggtggtgagtgtgttgcccatcggccaccaggactggctg aaggggaagcaattcacatgcaaggttaataacaaggccctgcccagcccc atcgagaggaccatcagcaaggccaggggccaggccaccagccatctgtg tacgtgctgcccccatctagggaggaactgagcaagaacacagtcagcctt acttgcctgatcaaggacttcttcccaccggacatagacgtggagtggcag agtaacggccagcaggagcccgagagcaagtataggaccacaccgccccaa ctggacgaggacggaagctacttcctctacagcaaattgagcgttgacaaa agcaggtggcagcgaggcgacaccttcatctgcgccgtgatgcacgaggct ttgcataaccactacacccaggagagcctgtcccacagccccggatag In the embodiment comprising the insulin-Fc fusion protein of SEQ ID NO: 38, the nucleic acid sequence (leader sequence bolded) is:

(SEQ ID NO: 37)
atggaatggagctgggtctttctcttcttcctgtcagtaacgactggtgtc cactccttcgtgaaccagcacctgtgcggctcccacctggtggaagctctg gaactcgtgtgcggcgagcggggcttccactacgggggtggcggaggaggt tctggtggcggcggaggcatcgtggaacagtgctgcacctccacctgctcc ctggaccagctggaaaactactgcggtggcggaggtggtcaaggaggcggt ggacagggtggaggtgggcagggaggaggcggggagactgccccaaatgt cctccgcctgagatgctgggtggccctagcatcttcatcttcccgcccaag cccaaggatactctgtccattagcaggaccccgaggtgacctgcctggtg gtggacctggggccagacgactctgacgtgcagatcacctggttcgtagac aacacccaggtttacactgccaagaccagtcccagggaggagcagttcaac agcacatacagggtggtgagcgttctgcccatcctgcaccaggactggctg aaaggcaaagagttcaagtgtaaggtgaacagcaagagcctgcccagcccc attgaaaggaccatcagcaaggacaagggccagccgcacgagcccaagtc tacgtgctgcccccagcacaggaagagctgagcaggaacaaggttagcgtg acatgcctgatcgagggtttctaccccagcgacatcgccgtggagtgggaa atcaccggccaacccgagcccgagaacaactacaggaccactccgccgcaa ctggacagcgacgggacctacttcttgtatagcaggctgagcgtggaccgg agcaggtggcagaggggcaacacctacacttgcagcgtgagccacgaggcc ttgcacagccaccacactcagaagagtctgacccagagcccgggatag In the embodiment comprising the insulin-Fc fusion protein of SEQ ID NO: 40, the nucleic acid sequence (leader sequence bolded) is:

(SEQ ID NO: 39)
atggaatggagctgggtctttctcttcttcctgtcagtaacgactggtgtc cactccttcgtgaaccagcacctgtgcggctcccacctggtggaagctctg gcactcgtgtgcggcgagcggggcttccactacgggggtggcggaggaggt tctggtggcggcggaggcatcgtggaacagtgctgcacctccacctgctcc ctggaccagctggaaaactactgcggtggcggaggtggtcaaggaggcggt ggacagggtggaggtgggcagggaggaggcggggagactgccccaaatgt cctccgcctgagatgctgggtggccctagcatcttcatcttcccgcccaag cccaaggatactctgtccattagcaggaccccgaggtgacctgcctggtg gtggacctggggccagacgactctgacgtgcagatcacctggttcgtagac aacacccaggtttacactgccaagaccagtcccagggaggagcagttcagc agcacatacagggtggtgagcgttctgcccatcctgcaccaggactggctg aaaggcaaagagttcaagtgtaaggtgaacagcaagagcctgcccagcccc attgaaaggaccatcagcaaggacaagggccagccgcacgagcccaagtc tacgtgctgcccccagcacaggaagagctgagcaggaacaaggttagcgtg acatgcctgatcgagggtttctaccccagcgacatcgccgtggagtgggaa atcaccggccaacccgagcccgagaacaactacaggaccactccgccgcaa ctggacagcgacgggacctacttcttgtatagcaggctgagcgtggaccgg agcaggtggcagaggggcaacacctacacttgcagcgtgagccacgaggcc ttgcacagccaccacactcagaagagtctgacccagagcccgggatag Insulin-Fc Fusion Protein Production In embodiments, a fusion protein can be expressed by a cell as described in more detail in the Examples section.

Expression and Purification

In embodiments, an insulin-Fc fusion protein can be expressed recombinantly, e.g., in a eukaryotic cell, e.g., mammalian cell or non-mammalian cell. Exemplary mammalian cells used for expression include HEK cells (e.g., HEK293 cells) or CHO cells. CHO cells can be subdivided into various strains or subclasses, (e.g., CHO DG44, CHO-M, and CHO-K1), and some of these cell strains may be genetically engineered for optimal use with a particular type of nucleic acid molecule (e.g., a vector comprising DNA) or a particular cell growth media composition as described in the Examples section. In embodiments, cells are transfected with a nucleic acid molecule (e.g., vector) encoding the insulin-Fc fusion protein (e.g., where the entire insulin-Fc fusion protein is encoded by a single nucleic acid molecule). In embodiments, HEK293 cells are transfected with a vector that encodes for the insulin-Fc fusion protein, but only results in temporary expression of the insulin-Fc fusion protein for a period of time (e.g., 3 days, 4 days, 5, days, 7 days, 10 days, 12 days, 14 days, or more) before the host cell stops expressing appreciable levels of the insulin-Fc fusion protein (i.e., transient transfection). HEK293 cells that are transiently transfected with nucleic acid sequences encoding for insulin-Fc fusion proteins often allow for more rapid production of recombinant proteins which facilitates making and screening multiple insulin-Fc fusion protein candidates. In embodiments, CHO cells are transfected with a vector that is permanently incorporated into the host cell DNA and leads to consistent and permanent expression (i.e., stable transfection) of the insulin-Fc fusion protein as long as the cells are cultured appropriately. CHO cells and CHO cell lines that are stably transfected with nucleic acids encoding for insulin-Fc fusion proteins often take longer to develop, but they often produce higher protein yields and are more amenable to manufacturing low cost products (e.g., products for use in the veterinary pharmaceutical market). Cells and cell lines can be cultured using standard methods in the art. In preferred embodiments, HEK cells comprising any one of the cDNA sequences with SEQ ID NOs: 31, 33, 35, 37, and 39 are used to express insulin-Fc fusion proteins. In preferred embodiments, CHO cells comprising any one of the cDNA sequences with SEQ ID NOs: 31, 33, 35, 37, and 39 are used to express insulin-Fc fusion proteins.

In some embodiments, the insulin-Fc fusion protein is purified or isolated from the cells (e.g., by lysis of the cells). In other embodiments, the insulin-Fc fusion protein is secreted by the cells and purified or isolated from the cell culture media in which the cells were grown. Purification of the insulin-Fc fusion protein can include using column chromatography (e.g., affinity chromatography) or using other separation methods based on differences in size, charge, and/or affinity for certain molecules. In embodiments, purification of the insulin-Fc fusion protein involves selecting or enriching for proteins containing an Fc fragment, e.g., by using Protein A beads or a Protein A column that cause proteins containing an Fc fragment to become bound with high affinity at neutral solution pH to the Protein A covalently conjugated to the Protein A beads. The bound insulin-Fc fusion protein may then be eluted from the Protein A beads by a change in a solution variable (e.g., a decrease in the solution pH). Other separation methods such as ion exchange chromatography and/or gel filtration chromatography can also be employed alternatively or additionally. In embodiments, purification of the insulin-Fc fusion protein further comprises filtering or centrifuging the protein preparation. In embodiments, further purification of the insulin-Fc fusion protein comprises dialfiltration, ultrafiltration, and filtration through porous membranes of various sizes, as well as final formulation with excipients.

The purified insulin-Fc fusion protein can be characterized, e.g., for purity, protein yield, structure, and/or activity, using a variety of methods, e.g., absorbance at 280 nm (e.g., to determine protein yield), size exclusion or capillary electrophoresis (e.g., to determine the molecular weight, percent aggregation, and/or purity), mass spectrometry (MS) and/or liquid chromatography (LC-MS) (e.g., to determine purity and/or glycosylation), and/or ELISA (e.g., to determine extent of binding, e.g., affinity, to an anti-insulin antibody). Exemplary methods of characterization are also described in the Examples section.

In embodiments, the protein yield of an insulin-Fc fusion protein after production in transiently transfected HEK cells and protein A purification is greater than 5 mg/L, 10 mg/L, or 20 mg/L. In preferred embodiments, the protein yield of an insulin-Fc fusion protein after production in transiently transfected HEK cells and protein A purification is greater than 50 mg/L (e.g., greater than 60 mg/L, greater than 70 mg/L, greater than 80 mg/L, greater than 90 mg/L, greater than 100 mg/L). In embodiments, the % homodimer of an insulin-Fc fusion protein after production in transiently transfected HEK cells and protein A purification is greater than 70% (e.g., greater than 80%, greater than 85%, greater than 90%, greater than 95%, greater than 96%, greater than 97%, greater than 98%, greater than 99%). In embodiments, the homodimer titer of an insulin-Fc fusion protein after production in transiently transfected HEK cells and protein A purification, calculated as the product between the insulin-Fc fusion protein yield and the % homodimer is greater than 50 mg/L (e.g., greater than 60 mg/L, greater than 70 mg/L, greater than 80 mg/L, greater than 90 mg/L, greater than 100 mg/L). Only candidates with a homodimer titer of greater than 50 mg/L were considered useful in the present invention, because experience has demonstrated that homodimer titers less than this level will not likely result in commercial production titers in CHO cells that meet the stringently low manufacturing cost requirements for veterinary products.

In embodiments, the protein yield of an insulin-Fc fusion protein after production in stably transfected CHO cells (e.g., CHO cell lines or CHO cell clones) and protein A purification is greater than 100 mg of insulin-Fc fusion protein per L (e.g., mg/L of culture media). In preferred embodiments, the protein yield of an insulin-Fc fusion protein after production in stably transfected CHO cells (e.g., CHO cell lines or CHO cell clones) and protein A purification is greater than 150 mg insulin-Fc fusion protein/L of culture media (e.g., greater than 200 mg/L, greater than 300 mg/L, greater than 400 mg/L, greater than 500 mg/L, greater than 600 mg/L or more). In embodiments, the % homodimer of an insulin-Fc fusion protein after production in stably transfected CHO cells (e.g., CHO cell lines or CHO cell clones) and protein A purification is greater than 70% (e.g., greater than 80%, greater than 85%, greater than 90%, greater than 95%, greater than 96%, greater than 97%, greater than 98%, greater than 99%). In embodiments, the homodimer titer of an insulin-Fc fusion protein after production in stably transfected CHO cells (e.g., CHO cell lines or CHO cell clones) and protein A purification, calculated as the product between the insulin-Fc fusion protein yield and the % homodimer is greater than 150 mg/L (e.g., greater than 200 mg/L, greater than 300 mg/L, greater than 400 mg/L, greater than 500 mg/L, greater than 600 mg/L or more).

Functional Features of Insulin-Fc Fusion Proteins

Described herein are methods for interacting with the insulin receptors to lower blood glucose in companion animals (e.g., dogs or cats), wherein the method comprises administering to a subject an insulin-Fc fusion protein, e.g., a fusion protein described herein. In some embodiments, the subject has been diagnosed with diabetes (e.g., canine diabetes or feline diabetes).

In embodiments, an insulin-Fc fusion protein described herein binds to the insulin receptor with an appreciable affinity as measured by the IC50 in the 4° C. IM-9 insulin receptor binding assay described in Example 7 (e.g., IC50 less than 5000 nM, IC50 less than 4000 nM, IC50 less than 3000 nM, IC50 less than 2500 nM). Based on experience, only compounds exhibiting insulin receptor activity IC50 values less than 5000 nM were deemed likely to exhibit bioactivity in the target species. Generally, higher affinity insulin receptor binding (i.e., lower IC50 values) is preferred. However, it is well-known that the clearance of insulin and insulin analogs (e.g., insulin polypeptides described herein) is governed primarily through binding to the insulin receptor followed by insulin receptor internalization and degradation within the cell. Therefore, insulin-Fc fusion proteins with too high of an insulin receptor binding affinity (i.e., too low of an IC50) may be cleared too quickly from circulation resulting in a lower than desired duration of glucose-lowering bioactivity in the target animal.

In embodiments, an insulin-Fc fusion protein described herein is capable of lowering glucose levels (e.g., blood glucose levels) after administration in a subject. In embodiments, the glucose lowering activity of the insulin-Fc fusion protein is greater than that of an insulin reference standard. In some embodiments, the duration of activity of the insulin-Fc fusion protein can be measured by a decrease, e.g., a statistically significant decrease, in fasting blood glucose relative to a pre-dose fasting blood glucose level. In embodiments, the duration of activity of the insulin-Fc fusion protein (e.g., the time during which there is a statistically significant decrease in fasting blood glucose level in a subject relative to a pre-dose level) is longer than about 2 hours. In embodiments, the duration of activity of the insulin-Fc fusion protein (e.g., the time during which there is a statistically significant decrease in blood glucose level in a subject relative to a pre-dose level) is longer than about 6 hours, 9 hours, 12 hours, 18 hours, 1 day, 1.5 days, 2 days, 2.5 days, 3 days, 4 days, 5 days, 6 days, 7 days, or longer. In embodiments, the insulin-Fc fusion protein is long-acting (e.g., has a long half-life, e.g., in serum).

In embodiments, the serum half-life of the insulin-Fc fusion protein in the target animal (e.g., dog or cat) is longer than that of an insulin reference standard or control formulation. In embodiments, the serum half-life of the insulin-Fc fusion protein (e.g., in the blood of a subject upon administration) in the target animal (e.g., dog or cat) is longer than about 2 hours. In embodiments, the serum half-life of the insulin-Fc fusion protein in the target animal (e.g., dog or cat) is about 0.5 days, 1 day, 2 days, or 2.5 days. In preferred embodiments, the serum half-life of the insulin-Fc fusion protein in the target animal (e.g., dog or cat) is about 3 days or longer.

In embodiments, the combination of potency and duration of bioactivity may be quantified by calculating the area over the percent fasting blood glucose (% FBGL) curve normalized to a given dose in mg/kg (NAOC) with units of % FBGL·days·kg/mg. In embodiments, the NAOC of the insulin-Fc fusion protein is greater than 150% FBGL·days·kg/mg (e.g., greater than 200% FBGL·days·kg/mg, greater than 250% FBGL·days·kg/mg or more). Again, based on experience, at NAOC values greater than 150% FBGL·days·kg/mg, the dose requirements in the target species will be sufficiently low so as to achieve an acceptable treatment cost. In embodiments, the NAOC of the insulin-Fc fusion protein must be maintained after repeated dosing in the target species (i.e., the ratio of the NAOC after the third dose to the NAOC after the first dose of the insulin-Fc fusion protein is greater than 0.50 (e.g., greater than 0.60, greater than 0.70, greater than 0.80, greater than 0.90, or more).

In some embodiments, the insulin-Fc fusion protein described herein binds to the Fc(gamma) receptor with an affinity that is lower than that of an insulin-Fc fusion protein reference standard as measured according to Example 8. In some embodiments, the ratio of the Fc(gamma) receptor affinity of the insulin-Fc fusion protein to that of an insulin-Fc fusion protein reference standard is less than 0.50 (e.g., less than 0.40, less than 0.30, less than 0.20).

Methods of Treatment and Characteristics of Subject Selection

Described herein are methods for treating diabetes (e.g., canine diabetes or feline diabetes), the methods comprising the administration of an insulin-Fc fusion protein (e.g., an insulin-Fc fusion protein described herein) to a subject.

In embodiments, a reference standard used in any method described herein comprises a reference treatment or reference therapy. In some embodiments, the reference comprises a standard of care agent for diabetes treatment (e.g., a standard of care agent for canine diabetes or a standard of care agent for feline diabetes). In some embodiments, the reference standard is a commercially available insulin or insulin analog. In some embodiments, the reference standard comprises a long-lasting insulin, intermediate-lasting insulin, short-lasting insulin, rapid-acting insulin, short-acting, intermediate-acting, long-acting insulin. In some embodiments, the reference standard comprises Vetsulin®, Prozinc®, insulin NPH, insulin glargine (Lantus®), or recombinant human insulin.

In embodiments, a reference standard used in any method described herein includes an outcome, e.g., outcome described herein, of a diabetes therapy (e.g., a canine diabetes therapy or a feline diabetes therapy).

In embodiments, a reference standard is a level of a marker (e.g., blood glucose or fructosamine) in the subject prior to initiation of a therapy, e.g., an insulin-Fc fusion protein therapy described herein; where the subject has diabetes. In embodiments, the blood glucose level in a companion animal (e.g., dog or cat) is greater than 200 mg/dL (e.g., greater than 250 mg/dL, 300 mg/dL, 350 mg/dL, 400 mg/dL or more) prior to initiation of therapy. In embodiments, the fructosamine level in a companion animal (e.g., dog or cat) is greater than 250 micromol/L, 350 micromol/L (e.g., greater than 400 micromol/L, 450 micromol/L, 500 micromol/L, 550 micromol/L, 600 micromol/L, 650 micromol/L, 700 micromol/L, 750 micromol/L or more) prior to initiation of therapy. In embodiments, a reference standard is a measure of the presence of or the progression of or the severity of the disease. In embodiments, a reference standard is a measure of the presence of or the severity of the disease symptoms prior to initiation of a therapy, e.g., an insulin-Fc fusion protein therapy described herein, e.g., where the subject has diabetes.

Pharmaceutical Compositions and Routes of Administration

Provided herein are pharmaceutical compositions containing an insulin-Fc fusion protein described herein that can be used to lower blood glucose in companion animals (e.g., dogs or cats). The amount and concentration of the insulin-Fc fusion protein in the pharmaceutical compositions, as well as the quantity of the pharmaceutical composition administered to a subject, can be selected based on clinically relevant factors, such as medically relevant characteristics of the subject (e.g., age, weight, gender, other medical conditions, and the like), the solubility of compounds in the pharmaceutical compositions, the potency and activity of the compounds, and the manner of administration of the pharmaceutical compositions. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

Formulations of the present disclosure include those suitable for parenteral administration. The phrases "parenteral administration" and "administered parenterally" as used herein means modes of administration other than enteral and topical administration, usually by intravenous or subcutaneous injection.

Examples of suitable aqueous and non-aqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants, e.g., Tween-like surfactants. In some embodiments, the pharmaceutical composition (e.g., as described herein) comprises a Tween-like surfactant, e.g., polysorbate-20, Tween-20 or Tween-80. In some embodiments, the pharmaceutical composition (e.g., as described herein) comprises a Tween-like surfactant, e.g., Tween-80, at a concentration between about 0.001% and about 2%, or between about 0.005% and about 0.1%, or between about 0.01% and about 0.5%.

In some embodiments, the concentration of the insulin-Fc fusion protein in the aqueous carrier is about 3 mg/mL. In some embodiments, the concentration of the insulin-Fc fusion protein in the aqueous carrier is about 6 mg/mL. In some embodiments, the concentration of the insulin-Fc fusion protein in the aqueous carrier is about 8 mg/mL, 9 mg/mL, 10 mg/mL, 12 mg/mL, 15 mg/mL or more.

In some embodiments, the insulin-Fc fusion protein is administered as a bolus, infusion, or an intravenous push. In some embodiments, the fusion protein is administered through syringe injection, pump, pen, needle, or indwelling catheter. In some embodiments, the insulin-Fc fusion protein is administered by a subcutaneous bolus injection. Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Dosages

Actual dosage levels of the insulin-Fc fusion protein can be varied so as to obtain an amount of the active ingredient that is effective to achieve the desired therapeutic response for a particular subject (e.g., dog or cat). The selected dosage level will depend upon a variety of factors including the activity of the particular fusion protein employed, or the ester, salt or amide thereof, the route of administration, the time of administration, the rate of excretion of the particular compound being employed, the duration of the treatment, other drugs, compounds and/or materials used in combination with the particular fusion protein employed, the age, sex, weight, condition, general health and prior medical history of the subject being treated, and like factors well known in the medical arts.

In general, a suitable dose of an insulin-Fc fusion protein will be the amount that is the lowest dose effective to produce a therapeutic effect. Such an effective dose will generally depend upon the factors described above. Generally, intravenous and subcutaneous doses of the insulin-Fc fusion protein for a dog or cat will range from about 0.001 to about 1 mg per kilogram (e.g., mg/kg) of body weight per day, e.g., about 0.001 to 1 mg/kg/day, about 0.01 to 0.1 mg/kg/day, about 0.1 to 1 mg/kg/day, or about 0.01 to 1 mg/kg/day. In still other embodiments, the fusion protein is administered at a dose between 0.025 and 4 mg per kilogram of body weight per week, e.g., between 0.025 and 0.5 mg/kg/week.

The present disclosure contemplates formulation of the insulin-Fc fusion protein in any of the aforementioned pharmaceutical compositions and preparations. Furthermore, the present disclosure contemplates administration via any of the foregoing routes of administration. One of skill in the art can select the appropriate formulation and route of administration based on the condition being treated and the overall health, age, and size of the patient being treated.

EXAMPLES

The present technology is further illustrated by the following Examples, which should not be construed as limiting in any way.

General Methods, Assays, and Materials

Example 1: Synthesis and Methods of Making an Insulin-Fc Fusion Protein in HEK293 Cells Insulin-Fc fusion proteins were synthesized as follows. A gene sequence of interest was constructed using proprietary software (LakePharma, Belmont, Calif.) and was cloned into a high expression mammalian vector. HEK293 cells were seeded in a shake flask 24 hours before transfection and were grown using serum-free chemically defined media. A DNA expression construct that encodes the insulin-Fc fusion protein of interest was transiently transfected into a suspension of HEK293 cells using the (LakePharma, Belmont, Calif.) standard operating procedure for transient transfection. After 20 hours, the cells were counted to determine the viability and viable cell count, and the titer was measured by FortéBio® Octet® (Pall FortéBio LLC, Fremont, Calif.). Additional readings were taken throughout the transient transfection production run. The culture was harvested on or after day 5.

Example 2: Synthesis and Methods of Making an Insulin-Fc Fusion Protein in CHO Cells A CHO cell line was originally derived from CHO-K1 (LakePharma, Belmont, Calif.), and the endogenous glutamine synthetase (GS) genes were knocked out by recombinant technology using methods known in the art. Stable expression DNA vectors were designed and optimized for CHO expression and GS selection and incorporated into a high expression mammalian vector (LakePharma, Belmont, Calif.). The sequence of each completed construct was confirmed prior to initiating scale up experiments. The suspension-adapted CHO cells were cultured in a humidified 5% $CO_2$ incubator at 37° C. in a chemically defined media (CD OptiCHO; Invitrogen, Carlsbad, Calif.). No serum or other animal-derived products were used in culturing the CHO cells.

Approximately 80 million suspension-adapted CHO cells, growing in CD OptiCHO media during the exponential growth phase, were transfected by electroporation using MaxCyte® STX® system (MaxCyte, Inc., Gaithersburg, Md.) with 80 µg DNA to a create a stable CHO cell line for each insulin-Fc fusion protein (DNA construct contains the full-length sequence of the insulin-Fc fusion protein). After twenty-four hours, the transfected cells were counted and placed under selection for stable integration of the insulin-Fc fusion genes. The transfected cells were seeded into CD OptiCHO selection media containing between 0-100 µM methionine sulfoximine (MSX) at a cell density of $0.5 \times 10^6$ cells/mL in a shaker flask and incubated at 37° C. with 5% $CO_2$. During a selection process, the cells were spun down and resuspended in fresh selection media every 2-3 days until the CHO stable pool recovered its growth rate and viability. The cell culture was monitored for growth and titer.

The cells were grown to $2.5 \times 10^6$ cells per mL. At the time of harvest for cell banking, the viability was above 95%. The cells were then centrifuged, and the cell pellet was resuspended in the CD OptiCHO media with 7.5% dimethyl sulfoxide (DMSO) to a cell count of $15 \times 10^6$ cells per mL per vial. Vials were cryopreserved for storage in liquid nitrogen.

A small-scale-up production was performed using the CHO cells as follows. The cells were scaled up for production in CD OptiCHO growth medium containing 100 µM MSX at 37° C. and fed every 2-4 days as needed, with CD OptiCHO growth medium supplemented with glucose and additional amino acids as necessary for approximately 14-21 days. The conditioned media supernatant harvested from the stable pool production run was clarified by centrifuge spinning. The protein was run over a Protein A (MabSelect, GE Healthcare, Little Chalfont, United Kingdom) column pre-equilibrated with binding buffer. Washing buffer was then passed through the column until the OD280 value (Nano-Drop, Thermo Scientific) was measured to be at or near background levels. The insulin-Fc fusion protein was eluted using a low pH buffer, elution fractions were collected, and the OD280 value of each fraction was recorded. Fractions containing the target insulin-Fc fusion protein were pooled and optionally further filtered using a 0.2 µM membrane filter.

The cell line was optionally further subcloned to monoclonality and optionally further selected for high titer insulin-Fc-fusion protein-expressing clones using the method of limiting dilution, a method known to those skilled in the art. After obtaining a high titer, monoclonal insulin-Fc fusion protein-expressing cell line, production of the insulin-Fc fusion protein was accomplished as described above in growth medium without MSX, or optionally in growth medium containing MSX, to obtain a cell culture supernatant containing the recombinant, CHO-made, insulin-Fc fusion protein. The MSX concentration was optionally increased over time to exert additional selectivity for clones capable of yielding higher product titers.

Example 3: Purification of an Insulin-Fc Fusion Protein

Purification of an insulin-Fc fusion protein was performed as follows. Conditioned media supernatants containing the secreted insulin-Fc fusion protein were harvested from the transiently or stably transfected HEK production runs and were clarified by centrifugation. The supernatant containing the desired insulin-Fc fusion protein was run over a Protein A or a Protein G column and eluted using a low pH gradient. Optionally, recovery of the insulin-Fc fusion proteins could be enhanced by reloading of the initial Protein A or Protein G column eluent again onto a second Protein A or Protein G column. Afterwards, the eluted fractions containing the desired protein were pooled and buffer exchanged into 200 mM HEPES, 100 mM NaCl, 50 mM NaOAc, pH 7.0 buffer. A final filtration step was performed using a 0.2 µm membrane filter. The final protein concentration was calculated from the solution optical density at 280 nm. Further optional purification by ion-exchange chromatography (e.g., using an anion exchange bead resin or a cation exchange bead resin), gel filtration chromatography, or other methods was performed as necessary.

Example 4: Structure Confirmation by Non-Reducing and Reducing CE-SDS

Capillary electrophoresis sodium dodecyl sulfate (CE-SDS) analysis was performed in a LabChip® GXJJ (Perkin Elmer, Waltham, Mass.) on a solution of a purified insulin-Fc fusion protein dissolved in 200 mM HEPES, 100 mM NaCl, 50 mM NaOAc, pH 7.0 buffer, and the electropherogram was plotted. Under non-reducing conditions, the sample was run against known molecular weight (MW) protein standards, and the eluting peak represented the 'apparent' MW of the insulin-Fc fusion protein homodimer. Under reducing conditions (e.g., using beta-mercaptoethanol to break disulfide bonds of the insulin-Fc fusion homodimer), the apparent MW of the resulting insulin-Fc fusion protein monomer is compared against half the molecular weight of the insulin-Fc fusion protein homodimer as a way of determining that the structural purity of the insulin-Fc fusion protein is likely to be correct.

Example 5: Sequence Identification by LC-MS with Glycan Removal

To obtain an accurate estimate of the insulin-Fc mass via mass spectroscopy (MS), the sample is first treated to remove naturally occurring glycan that might interfere with the MS analysis. 100 µL of a 2.5 mg/mL insulin-Fc fusion protein dissolved in 200 mM HEPES, 100 mM NaCl, 50 mM NaOAc, pH 7.0 buffer solution is first buffer exchanged into 0.1 M Tris, pH 8.0 buffer containing 5 mM EDTA using a Zeba desalting column (Pierce, ThermoFisher Scientific, Waltham, Mass.). 1.67 µL of PNGase F enzyme (Prozyme N-glycanase) is added to this solution in order to remove N-linked glycan present in the fusion protein (e.g., glycan linked to the side chain of the asparagine located at the cNg-N site), and the mixture is incubated at 37° C. overnight in an incubator. The sample is then analyzed via LC-MS (NovaBioassays, Woburn, Mass.) resulting in a molecular mass of the molecule which corresponds to the desired homodimer without the glycan. This mass is then further corrected since the enzymatic process used to cleave the glycan from the cNg-asparagine also deaminates the asparagine side chain to form an aspartic acid, and in doing so the enzymatically treated homodimer gains 2 Da overall, corresponding to a mass of 1 Da for each chain present in the homodimer. Therefore, the actual molecular mass is the measured mass minus 2 Da to correct for the enzymatic modification of the insulin-Fc fusion protein structure in the analytical sample.

Example 6: % Homodimer by Size-Exclusion Chromatography

Size-exclusion chromatography (SEC-HPLC) of insulin-Fc fusion proteins was carried out using a Waters 2795HT HPLC (Waters Corporation, Milford, Mass.) connected to a 2998 Photodiode array at a wavelength of 280 nm. 100 µL or less of a sample containing an insulin-Fc fusion protein of interest was injected into a MAbPac SEC-1, 5 µm, 4×300 mm column (ThermoFisher Scientific, Waltham, Mass.) operating at a flow rate of 0.2 mL/min and with a mobile phase comprising 50 mM sodium phosphate, 300 mM NaCl, and 0.05% w/v sodium azide, pH 6.2. The MAbPac SEC-1 column operates on the principle of molecular size separation. Therefore, larger soluble insulin-Fc aggregates (e.g., multimers of insulin-Fc fusion protein homodimers) eluted at earlier retention times, and the non-aggregated homodimers eluted at later retention times. In separating the mixture of homodimers from aggregated multimeric homodimers via analytical SEC-HPLC, the purity of the insulin-Fc fusion protein solution in terms of the percentage of non-aggregated homodimer was ascertained.

Example 7: In Vitro IM-9 Insulin Receptor Binding of an Exemplary Insulin-Fc Fusion Protein at 4° C.

Human IM-9 cells (ATTC #CCL-159) that express human insulin receptor were cultured and maintained in complete RPMI 5% FBS medium at 70-80% confluency. Cultures of IM-9 cells were centrifuged at 250×g (~1000 rpm) for 10 min to pellet the cells. Cells were washed once with HBSS or PBS buffer, resuspended in cold FACS staining medium (HBSS/2 mM EDTA/0.1% Na-azide+4% horse serum) to a concentration of $8 \times 10^6$ cells/mL and kept on ice or 4° C. until test solutions were made. The insulin-Fc protein was diluted in FACS buffer in 1:3 serial dilutions as 2×concentrations in 1.2 mL tubes (approx. 60 µL volume of each dilution), and the solutions were kept cold on ice until ready for pipetting.

Biotinylated-RHI was diluted in FACS staining medium to a concentration of 1.25 µg/mL. 40 µL of the serially diluted test compound and 8 µL of 1.25 µg/mL Biotin-RHI were added into each well of a V bottom microtiter plate, mixed by slow vortexing, and placed on ice. 40 µL of an IM-9 cell suspension ($8 \times 10^6$ cells/mL) was then added to each well by multichannel pipette, mixed again gently and incubated on ice for 30 min to allow competitive binding on the insulin receptor on IM-9 cells. Cells were then washed twice with 275 µL of ice-cold FACS wash buffer (HBSS/2 mM EDTA/0.1% Na-azide+0.5% horse serum) by centrifuging the V-bottom plate at 3000 rpm for 3 min and aspirating the supernatant. Cells were then resuspended in 40 µL of FACS staining medium containing 1:100 diluted Streptavidin-PE (Life Technologies) for 20 min on ice. Cells were then washed once with 275 µL of ice-cold FACS buffer and finally fixed with 3% paraformaldehyde for 10 min at room temp. Cells were then washed once with 275 µL of ice-cold FACS buffer and resuspended in 250 µl of FACS buffer for analysis.

The V-bottom plates containing cells were then analyzed on a Guava 8-HT flow cytometer (Millipore). Biotinylated-RHI binding to insulin receptor was quantitated by the median fluorescence intensity (MFI) of the cells on the FACS FL-2 channel for each concentration of the test compound. Control wells were labeled only with biotinylated-RHI and were used to calculate the percent (%) inhibition resulting from each test compound concentration. The % inhibition by test compounds of biotinylated-RHI binding on IM-9 cells was plotted against log concentrations of the test compound, and the resulting IC50 values were calculated using GraphPad Prism (GraphPad Software, La Jolla, Calif.) for the test compounds. Lower IC50 values of the test compound therefore indicate greater levels of biotinylated-RHI inhibition at lower concentrations indicating stronger binding of the insulin-Fc fusion protein to the insulin receptor. A control compound, such as unlabeled recombinant human insulin (RHI) was also used as an internal standard to generate an RHI IC50 against which a given compound IC50 could be ratioed (IC50(compound)/IC50(RHI)). Lower IC50 ratios have more similar binding to RHI (stronger binding to insulin receptor), while higher IC50 ratios have weaker binding to the insulin receptor relative to RHI.

Example 8: In Vitro Fc(Gamma) Receptor I Binding Affinity Assay

The binding of insulin-Fc fusion proteins to the Fc(gamma) receptor I at pH 7.4 was conducted using an ELISA assay as follows. Since neither canine nor feline Fc(gamma) receptor I was not commercially available, human Fc(gamma) receptor I (i.e., rhFc(gamma) receptor I) was used as a surrogate mammalian receptor. Insulin-Fc compounds were diluted to 10 µg/mL in sodium bicarbonate buffer at pH 9.6 and coated on Maxisorp (Nunc) microtiter plates overnight at 4° C., after which the microplate strips were washed 5 times with PBST (PBS/0.05% Tween-20) buffer and blocked with Superblock blocking reagent (ThermoFisher). Serial dilutions of biotinylated rhFc(gamma) receptor I (recombinant human Fc(gamma)R-I; R&D Systems) were prepared in PBST/10% Superblock buffer from 6000 ng/mL to 8.2 ng/mL and loaded at 100 µL/well onto the microplate strips coated with insulin-Fc fusion protein. The microtiter plate was incubated for 1 hour at room temperature after which the microplate strips were washed 5 times with PBST and then loaded with 100 µL/well of streptavidin-HRP diluted 1:10000 in PBST/10% Superblock buffer. After incubating for 45 min, the microplate strips were washed again 5 times with PBST. TMB was added to reveal the bound Fc(gamma) receptor I proteins and stopped with ELISA stop reagent (Boston Bioproducts). The plate was read in an ELISA plate reader at 450 nm, and the OD values (proportional to the binding of rhFc(gamma) receptor I to insulin-Fc protein) were plotted against log concentrations of rhFc(gamma) receptor I added to each well to generate binding curves using GraphPad Prism software.

Example 9: In Vitro Measurement of Insulin-Fc Fusion Protein Affinity for the Canine FcRn Receptor In vitro binding affinity of insulin-Fc fusion proteins containing Fc fragments of canine or feline IgG origin to the canine FcRn receptor was measured via an ELISA technique conducted at a solution pH of 5.5. The slightly acidic pH is the preferred binding environment for Fc fragment-containing molecules to bind to the FcRn receptor. In vivo, cells express FcRn on their surfaces and internally in the endosomes. As molecules containing Fc fragments are brought into the cell through natural processes (e.g., pinocytosis or endocytosis), the pH changes to a lower pH in the endosomes, where the FcRn receptor binds to Fc fragment-containing molecules that would otherwise be degraded in the endosomal-lysosomal compartments, thereby allowing these molecules to recycle back to the cellular surface where the pH is closer to neutral (e.g., pH 7.0-7.4). Neutral pH disfavors binding to the FcRn receptor and allows release of the Fc-fragment containing molecules back into circulation. This is a primary mechanism by which Fc fragment-containing molecules exhibit prolonged circulatory pharmacokinetic half-lives in vivo.

Insulin-Fc fusion proteins comprising Fc fragments of canine or feline origin were diluted to 10 µg/ml in sodium bicarbonate pH 9.6 buffer and coated in duplicate on Maxisorb ELISA plate strips for 1-2 hours at RT. The strips were then washed 4 times with PBST (PBS/0.1% Tween-20) buffer and blocked with Superblock blocking reagent (ThermoFisher). Strips for FcRn binding were then washed again twice with pH 5.5 MES/NaCl/Tween (50 mM MES/150 mM NaCl/0.1% Tween-20) buffer before addition of the FcRn reagent (biotinylated canine FcRn; Immunitrack). Since no feline FcRn reagent was found to be commercially available, insulin-Fc fusion proteins containing either a canine Fc fragment or a feline Fc fragment were assayed for binding to the canine FcRn. Serial dilutions (1:3× dilutions) of biotinylated FcRn reagent were prepared in pH 5.5 MES/NaCl/Tween/10% Superblock buffer at concentrations from 1000 ng/ml to 0.45 ng/ml and loaded at 100 µL/well using a multichannel pipettor onto the strips coated with the insulin-Fc fusion protein compounds. The assay plate was then incubated for 1 hour at room temperature. FcRn binding strips were washed 4 times with pH 5.5 MES/NaCl/Tween buffer and then loaded with 100 µl/well streptavidin-HRP diluted 1:10000 in pH 5.5 MES/NaCl/10% Superblock buffer. After incubating for 45 minutes, strips were washed again 4 times with pH 5.5 MES/NaCl/Tween buffer. TMB was finally added to reveal the bound biotinylated-canine FcRn reagent, and the color development was stopped with the ELISA stop reagent. The plate was read in an ELISA plate reader at a wavelength of 450 nm. The OD values (proportional to the binding of canine-FcRn to the insulin-Fc fusion protein test compounds) were plotted against log concentrations of FcRn added to each well to generate binding curves using GraphPad Prism software. EC50 values for each binding curve were calculated to compare between different compounds.

Example 10: Generalized Procedure for Determination of In Vivo Pharmacodynamics (PD) after Single Administration of Insulin Fc-Fusion Proteins in Dogs or Cats Insulin-Fc fusion proteins were assessed for their effects on fasting blood glucose levels as follows. N=1, 2, 3 or more healthy, antibody-naïve, dogs weighing approximately 10-15 kg or cats weighing approximately 5 kg were used, one for each insulin-Fc fusion protein. Animals were also observed twice daily for signs of anaphylaxis, lethargy, distress, pain, etc., and, optionally for some compounds, treatment was continued for an additional three weekly subcutaneous injections or more to observe if the glucose lowering capability of the compounds lessened over time, a key sign of potential induction of neutralizing anti-drug antibodies. On day 0, the animals received a single injection either via intravenous or subcutaneous administration of a pharmaceutical composition containing an insulin Fc-fusion protein homodimer at a concentration between 1 and 10 mg/mL in a solution of between 10-50 mM sodium hydrogen phosphate, 50-150 mM sodium chloride, 0.005-0.05% v/v Tween-80, and optionally a bacteriostat (e.g. phenol, m-cresol, or methylparaben) at a concentration of between 0.02-1.00 mg/mL, at a solution pH of between 7.0-8.0, at a dose of 0.08-0.80 mg insulin-Fc fusion protein/kg (or approximately equivalent to 1.2-12.3 nmol/kg or approximately equivalent to 0.4-4.0 U/kg insulin equivalent on molar basis). On day 0, blood was collected from a suitable vein immediately prior to injection and at 15, 30, 45, 60, 120, 240, 360, and 480 min and at 1, 2, 3, 4, 5, 6, and 7 days post injection.

For each time point, a minimum of 1 mL of whole blood was collected. A glucose level reading was immediately determined using a glucose meter (ACCU-CHEK® Aviva Plus), which required approximately one drop of blood. Average % fasting blood glucose levels (% FBGL) from day 0 to day 7 were plotted to assess the bioactivity of a given insulin-Fc fusion protein.

Example 11: Generalized Procedure for Determination of In Vivo Pharmacodynamics (PD) after Repeated Administration of Insulin-Fc Fusion Proteins in Canines or Felines Insulin-Fc fusion proteins were assessed for their effects on blood glucose levels over repeated injections as follows. Healthy, antibody-naïve, dogs or cats weighing approximately between 5 and 20 kg were used, and each animal was administered doses of an insulin-Fc fusion protein. Animals were observed twice daily for signs of anaphylaxis, lethargy, distress, pain, and other negative side effects, and optionally for some compounds, treatment was continued for up to an additional two to five subcutaneous injections to observe if the glucose lowering capability of the compounds decreased over time, indicating the possible presence of neutralizing anti-drug antibodies in vivo. On day 0, the animals received a single subcutaneous injection of a pharmaceutical composition containing an insulin Fc-fusion protein in a solution of 10-50 mM sodium hydrogen phosphate, 50-150 mM sodium chloride, 0.005-0.05% v/v Tween-80, and optionally a bacteriostat (e.g. phenol, m-cresol, or methylparaben) at a concentration of between 0.02-1.00 mg/mL, at a solution pH of between 7.0-8.0, at a dose of 0.08-0.80 mg insulin-Fc fusion protein/kg (or approximately equivalent to 1.2-12.3 nmol/kg or approximately equivalent to 0.4-4.0 U/kg insulin equivalent on molar basis). On day 0, blood was collected from a suitable vein immediately prior to injection and at 15, 30, 45, 60, 120, 240, 360, and 480 min and at 1, 2, 3, 4, 5, 6, and 7 days post injection.

Subsequent subcutaneous injections were given no more frequently than once-weekly, and in some cases the injections were given at different intervals based on the pharmacodynamics of a given insulin-Fc fusion protein formulation. Subsequent injections for each insulin-Fc fusion protein were adjusted to higher or lower doses, depending on the demonstrated pharmacodynamics of the insulin-Fc fusion protein. For instance, if the dose of a first injection on day 0 was found to be ineffective at lowering blood glucose, the subsequent dose levels of injected insulin-Fc fusion protein were adjusted upward. In a similar manner, if the dose of a first injection on day 0 was found to lower glucose in too strong a manner, then subsequent dose levels of injected insulin-Fc fusion protein were adjusted downward. It was also found that interim doses or final doses could be adjusted in a similar manner as needed. For each dose, blood was collected from a suitable vein just immediately prior to injection and at 15, 30, 45, 60, 120, 240, 360, and 480 min and at 1, 2, 3, 4, 5, 6, 7 days (and optionally 14 days) post injection. For each time point, a minimum of 1 mL of whole blood was collected. A glucose level reading was immediately determined using a glucose meter (ACCU-CHEK® Aviva Plus), which required approximately one drop of blood. Average % fasting blood glucose levels (% FBGL) from throughout the study were plotted against time which allows the bioactivity of a fusion protein to be determined.

To determine the bioactivity of each dose, an area-over-the-curve (AOC) analysis was conducted as follows. After constructing the % FBGL versus time data, the data was then entered into data analysis software (GraphPad Prism, GraphPad Software, San Diego Calif.). The software was used to first conduct an area-under-the curve analysis (AUC) to integrate the area under the % FBGL vs. time curve for each dose. To convert the AUC data into the desired AOC data, the following equation was used: AOC=TPA−AUC; where TPA is the total possible area obtained by multiplying each dose lifetime (e.g., 7 days, 14 days, etc.) by 100% (where 100% represents the y=100% of the % FBGL vs. time curve). For example, given a dose lifetime of 7 days and a calculated AUC of 500% FBGL·days, gives the following for AOC: AOC=(100% FBGL×7 days)−(500% FBGL·days) =200% FBGL·days. The analysis can be performed for each injected dose in a series of injected doses to obtain the AOC values for injection 1, injection 2, injection 3, etc.

As the doses of insulin-Fc fusion protein may vary as previously discussed, it is often more convenient to normalize all calculated AOC values for a given insulin-Fc fusion protein to a particular dose of that insulin-Fc fusion protein. Doing so allows for convenient comparison of the glucose-lowering potency of an insulin-Fc fusion protein across multiple injections, even if the dose levels change across the injections of a given study. Normalized AOC (NAOC) for a given dose is calculated as follows: NAOC=AOC/D with units of % FBGL·days·kg/mg; where D is the actual dose injected into the animal in mg/kg. NAOC values may be calculated for each injection in a series of injections for a given animal and may be averaged across a group of animals receiving the same insulin-Fc fusion protein formulation.

The NAOC ratio (NAOCR) may also be calculated for each injection in a series of injections for a given animal by taking the NAOC values for each injection (e.g., injections 1, 2, 3, . . . N) and dividing each NAOC for a given injection by the NAOC from injection 1 as follows: NAOCR=(NAOC (Nth injection)/NAOC(injection 1)). By evaluating the NAOCR of a given insulin-Fc homodimer fusion protein formulation for the Nth injection in a series of injections, it is possible to determine whether the in vivo glucose lowering activity of a given insulin-Fc fusion protein has substantially retained its bioactivity over a series of N doses (e.g., NAOCR for the Nth dose of greater than 0.5) or whether the in vivo glucose lowering activity of a given insulin-Fc fusion protein has lost a substantial portion of its potency (e.g., NAOCR of the Nth dose is less than 0.5) over a course of N doses, indicating the potential formation of neutralizing anti-drug antibodies in vivo. In preferred embodiments, the ratio of NAOC following the third subcutaneous injection to the NAOC following the first subcutaneous injection is greater than 0.5 (i.e., the NAOCR of the third subcutaneous injection is greater than 0.5).

Example 12: Generalized Procedure for the Determination of In Vivo Pharmacokinetics (PK) in Canine and Feline Serum An assay was constructed for measuring the concentrations of insulin-Fc fusion proteins comprising Fc fragments of a canine isotype in canine serum as follows. The assay comprises a sandwich ELISA format in which therapeutic compounds in serum samples are captured by an anti-insulin/proinsulin monoclonal antibody (mAb) coated on the ELISA plates and then detected by a HRP-conjugated anti-canine IgG Fc specific antibody followed by use of a TMB substrate system for color development. Maxisorp ELISA Plates (Nunc) are coated with the anti-insulin mAb clone D6C4 (Biorad) in coating buffer (pH=9.6 sodium carbonate-sodium biocarbonate buffer) at 5 µg/ml overnight at 4° C. Plates are then washed 5× with PBST (PBS+0.05% Tween 20) and blocked for a minimum of one hour at room temperature (or overnight at 4 C) with SuperBlock blocking solution (ThermoFisher). Test serum samples are diluted to 1:20 in PBST/SB/20% HS sample dilution buffer (PBS+ 0.1% Tween 20+10% SuperBlock+20% horse serum). For making a standard curve, the insulin-Fc fusion protein of interest is diluted in sample dilution buffer (PBST/SB/20% HS)+5% of pooled beagle serum (BioIVT) from a concentration range of 200 ng/ml to 0.82 ng/ml in 1:2.5 serial dilutions. Standards and diluted serum samples are added to the blocked plates at 100 µl/well in duplicate and are incubated for 1 hour at room temperature. Following incubation, samples and standards are washed 5× with PBST. HRP-conjugated goat anti-canine IgG Fc (Sigma) detection antibody is diluted to about 1:15,000 in PBST/SB/20% HS buffer and 100 µl is added to all the wells and incubated for 45 minutes at room temperature in the dark. Plates are washed 5× with PBST and once with deionized water and developed by the addition of 100 µl/well TMB (Invitrogen) for 8-10 minutes at room temperature. Color development is then stopped by the addition of 100 µl/well ELISA Stop Solution (Boston Bioproducts) and the absorbance is read at 450 nm using a SpectraMax plate reader (Molecular Devices) within 30 minutes. Concentrations of insulin-Fc fusion protein compounds in the samples are calculated by interpolation on a 4-PL curve using SoftMaxPro software.

Similarly, an assay was constructed for measuring the concentrations of insulin-Fc fusion proteins comprising Fc fragments of a feline isotype in feline serum as follows. The assay comprises a sandwich ELISA format in which therapeutic compounds in serum samples are captured by an anti-insulin/proinsulin mAb coated on the ELISA plates and then detected by a HRP-conjugated goat anti-feline IgG Fc specific antibody followed by use of a TMB substrate system for color development. Maxisorp ELISA Plates (Nunc) are coated with the anti-insulin mAb clone D6C4 (Biorad) in coating buffer (pH=9.6 sodium carbonate-sodium biocarbonate buffer) at 5 µg/ml overnight at 4° C. Plates are then washed 5× with PBST (PBS+0.05% Tween 20) and blocked for a minimum of one hour at room temperature (or overnight at 4 C) with SuperBlock blocking solution (ThermoFisher). Test serum samples are diluted to 1:20 in PBST/SB/20% HS sample dilution buffer (PBS+0.1% Tween 20+10% SuperBlock+20% horse serum). For making a standard curve, the insulin-Fc fusion protein compound of interest is diluted in sample dilution buffer (PBST/SB/20% HS)+5% of normal cat serum (Jackson Immunoresearch) from a concentration range of 200 ng/ml to 0.82 ng/ml in 1:2.5 serial dilutions. Standards and diluted serum samples are added to the blocked plates at 100 µl/well in duplicate and are incubated for 1 hour at room temperature. Following incubation, samples and standards are washed 5× with PBST. HRP-conjugated goat anti-feline IgG Fc (Bethyl Lab) detection antibody is diluted to about 1:20,000 in PBST/SB/20% HS buffer and 100 µl is added to all the wells and incubated for 45 minutes at room temperature in the dark. Plates are washed 5× with PBST and once with deionized water and developed by the addition of 100 µl/well TMB (Invitrogen) for 8-10 minutes at room temperature. Color development is then stopped by the addition of 100 µl/well ELISA Stop Solution (Boston Bioproducts) and absorbance is read at 450 nm using a SpectraMax plate reader (Molecular Devices) within 30 minutes. Concentrations of insulin-Fc fusion protein compounds in the samples are calculated by interpolation on a 4-PL curve using SoftMaxPro software.

Example 13: Assay Protocol for Measuring Anti-Drug Antibodies in Canine Serum

Maxisorp ELISA Plates (Nunc) are coated with the insulin-Fc fusion protein of interest diluted in coating buffer (pH=9.6 Carbonate-Biocarbonate buffer) at 10 μg/mL overnight at 4° C. for measuring ADAs against the test compound. For measuring ADAs against the insulin portion of the insulin-Fc fusion protein containing an Fc fragment of canine IgG origin, plates are coated with purified insulin at 30 μg/mL in coating buffer. Plates are then washed 5× with PBST (PBS+0.05% Tween 20) and blocked for at least 1 hour (or overnight) with SuperBlock blocking solution (ThermoFisher, Waltham Mass.). For calculating the ADAs in canine IgG units, strips are directly coated with 1:2 serial dilutions of canine IgG (Jackson Immunoresearch Laboratories, West Grove Pa.) in pH=9.6 Carb-Biocarb coating buffer at concentrations between 300-4.69 ng/ml overnight at 4° C. and used to create a 7-point pseudo-standard curve. The standards strip plates are also washed and blocked with SuperBlock blocking solution for at least 1 hour (or overnight).

Test serum samples are diluted to greater than or equal to 1:100 (typically tested as 1:200) in PBST/SB/20% HS sample dilution buffer (PBS+0.1% Tween 20+10% SuperBlock+20% horse serum) and added to the insulin-Fc fusion protein coated (or RHI coated) strips at 100 μL/well in duplicate. Duplicate strips of canine IgG coated standard strips are also added to each plate and filled with PBST/SB (PBS+0.1% Tween 20+10% SuperBlock) buffer at 100 μL/well. Plates are incubated for 1 hour at RT and then washed 5× with PBST. For detection of ADAs, HRP-conjugated Goat anti-feline IgG F(ab')2 (anti-feline IgG F(ab')2 reagent is cross-reacts to canine antibodies; Jackson Immunoresearch Laboratories, West Grove Pa.), which is diluted in PBST/SB to 1:10000 and added at 100 μL/well to both sample and standard wells and incubated for 45 minutes at RT in dark. Plates are washed 5× with PBST and then one time with deionized water and then developed by adding 100 μL/well TMB substrate (Invitrogen, ThermoFisher Scientific, Waltham Mass.) for 15-20 minutes at room temperature in the dark. Color development is then stopped by addition of 100 μL/well of ELISA Stop Solution (Boston Bioproducts) and the absorbance is read at 450 nm using a SpectraMax plate reader within 30 minutes. The anti-drug antibody concentration is determined by interpolating the OD values in the 4-PL pseudo-standard curve using SoftMax Pro Software (Molecular Devices, San Jose Calif.).

To demonstrate the specificity of the detected ADAs, an "inhibition" assay is carried out. In the drug inhibition ADA assay, serum samples are diluted 1:100 in PBST/SB/20% HS buffer and mixed with an equal volume of 300 μg/mL of the relevant therapeutic compound (final sample dilution at 1:200 and final inhibitory compound at 150 μg/mL) and incubated for 30-40 minutes at room temperature to allow anti-drug antibodies to bind the free inhibitor (i.e., the therapeutic compound). After pre-incubation, the samples are added to insulin-Fc fusion protein coated (or RHI coated) strips at 100 μL/well in duplicate. Samples diluted 1:200 in PBST/SB/20% HS buffer without the inhibitory compound are also tested in the sample plates along with duplicate strips of canine IgG coated standards. Remaining steps of the assay procedure are carried out as described above. The ADAs measured in the drug-inhibited wells are matched with the non-inhibited ADA concentrations to assess the specificity of the ADAs. If significant inhibition of ADA signals is observed in the drug-inhibited wells, this means the ADAs are specific to the therapeutic compound.

Example 14: Assay Protocol for Measuring Anti-Drug Antibodies in Feline Serum

Maxisorp ELISA Plates (Nunc) are coated with the insulin-Fc fusion protein of interest diluted in coating buffer (pH=9.6 Carbonate-Biocarbonate buffer) at 10 μg/mL overnight at 4° C. for measuring ADAs against the insulin-Fc fusion protein containing an Fc fragment of feline IgG origin. For measuring ADAs against the insulin portion of the insulin-Fc fusion protein, plates are coated with purified insulin at 30 μg/mL in coating buffer. Plates are then washed 5× with PBST (PBS+0.05% Tween 20) and blocked for at least 1 hour (or overnight) with SuperBlock blocking solution (ThermoFisher, Waltham Mass.). For calculating the ADAs in feline IgG units, strips are directly coated with 1:2 serial dilutions of feline IgG (Jackson Immunoresearch Laboratories, West Grove Pa.) in pH=9.6 sodium carbonate-sodium bicarbonate coating buffer at concentrations between 300-4.69 ng/mL overnight at 4° C. and used to create a 7-point pseudo-standard curve. The standards strip plates are also washed and blocked with SuperBlock blocking solution for at least 1 hour (or overnight).

Test serum samples are diluted to greater than or equal to 1:100 (typically tested as 1:200) in PBST/SB/20% HS sample dilution buffer (PBS+0.1% Tween 20+10% SuperBlock+20% horse serum) and added to the insulin-Fc fusion protein coated (or RHI coated) strips at 100 μL/well in duplicate. Duplicate strips of feline IgG coated standard strips are also added to each plate and filled with PBST/SB (PBS+0.1% Tween 20+10% SuperBlock) buffer at 100 μL/well. Plates are incubated for 1 hour at room temperature and then washed 5× with PBST. For detection of ADAs, HRP-conjugated goat anti-feline IgG F(ab')2 (Jackson Immunoresearch Laboratories, West Grove Pa.) is diluted in PBST/SB by a factor of 1:10000 and added at 100 μL/well to both sample and standard wells and incubated for 45 minutes at room temperature in the dark. Plates are washed 5× with PBST and one time with deionized water and developed by the adding 100 μL/well TMB substrate (Invitrogen) for 15-20 minutes at room temperature in the dark. Color development is then stopped by addition of 100 μL/well of ELISA Stop Solution (Boston Bioproducts, Ashland Mass.) and the absorbance is read at 450 nm using a SpectraMax plate reader within 30 minutes. Anti-drug antibody concentration is determined by interpolating the OD values in the 4-PL pseudo-standard curve using SoftMax Pro Software (Molecular Devices, San Jose Calif.).

Example 15: Assay Procedure for Immunogenic Epitope Identification

Maxisorp ELISA microplates (Nunc) are coated with a library of insulin-Fc fusion protein homodimer compounds with known amino acid sequences, and the coated plates are blocked in a similar manner as described in the anti-drug antibody ELISA assay Examples 13 and 14, except that each compound in the library is coated on a separate individual strip of ELISA microplate wells. The compounds in the library comprise a range of insulin-Fc fusion proteins with different insulin polypeptide amino acid compositions, including various B-chain, C-chain, and A-chain amino acid mutations, different linker compositions, and different Fc fragment compositions, including some of human origin. Separately, some plate strip wells are directly coated with 1:2 serial dilutions of canine or feline IgG (Jackson Immunoresearch Laboratories, West Grove Pa.) for calculating the anti-drug antibodies (ADA) in canine or feline IgG units, respectively, as described in Examples 13 and 14.

Serum obtained from individual dogs or cats receiving repeated doses of an insulin-Fc fusion protein is first screened on the anti-drug antibody ELISA assay (Example 13 for dogs and Example 14 for cats). Serum samples demonstrating moderate or high positivity (e.g., moderate or high titers of antibodies) on the assay of Example 13 or Example 14 are serially diluted (1:200 to 1:8000) in PBST/SB/20% HS sample dilution buffer (PBS+0.1% Tween 20+10% SuperBlock+20% horse serum) and added to the plates coated with the library of insulin-Fc fusion protein compounds for 1 hour at RT. Following incubation, the plates are washed 5 times with PBST. For detection of canine or feline antibodies capable of cross-reacting to the coated compound library, HRP conjugated goat anti-feline IgG F(ab')2 (Jackson Immunoresearch Laboratories, West Grove Pa.), which is cross-reactive to both canine and feline IgGs, is diluted in PBST/SB to 1:10000 and added at 100 μL/well to both sample and standard wells and incubated for 45 min at RT in the dark. Plates are washed 5 times with PBST, once with deionized water, and developed by the adding 100 μL/well TMB substrate (Invitrogen, ThermoFisher Scientific, Waltham Mass.) for 15-20 min at RT in the dark. Color development is then stopped by addition of 100 μL/well of ELISA Stop Solution (Boston Bioproducts, Ashland Mass.) and absorbance is read at 450 nm using a SpectraMax plate reader within 30 min. Anti-compound cross-reactive antibody concentrations present in the serum samples are determined by interpolating the OD values in the 4-PL pseudo-standard curve against the directly coated canine or feline IgG antibody controls using SoftMax Pro Software (Molecular Devices, San Jose Calif.).

By correlating the resulting antibody concentrations from the assay with the known amino acid compositions of the coated insulin-Fc fusion protein library, one can determine whether particular amino acid mutations or epitopes are responsible for causing none, some, most, or all of the total antibody signal on the assay, indicating no binding, weak binding, or strong binding to various insulin-Fc fusion protein homodimers. The mutations or epitopes responsible for moderate or strong binding are herein referred to as immunogenic "hot spots".

Example 16: Design Process for Obtaining Insulin-Fc Fusion Proteins with High Homodimer Titers and Acceptable Levels of Acute and Repeated Dose Bioactivity in the Target Species The process for meeting the design goals described in the Detailed Description of the Invention comprised the following steps. First, the insulin polypeptide of SEQ ID NO: 4 or SEQ ID NO: 5 was combined with a species-specific Fc fragment of a particular IgG isotype and a linker such that the resulting insulin-Fc fusion protein was most likely to yield a long acting bioactivity product with minimal immunogenicity (e.g., a species-specific IgG isotype was chosen with minimal Fc(gamma)receptor I binding). The DNA sequence coding for the desired fusion protein was prepared, cloned into a vector (LakePharma, San Carlos, Calif.), and the vector was then used to transiently transfect HEK cells according to the procedure described in Example 1. The insulin-Fc fusion protein was then purified according to Examples 3 and the overall protein yield and % homodimer measured according to Example 6. Only candidates with a homodimer titer of greater than 50 mg/L were considered acceptable, because titers less than this level are not likely to result in commercial production titers that meet the stringently low manufacturing cost requirements for veterinary products. Selected insulin-Fc fusion proteins were then screened for indicators of bioactivity through in vitro insulin receptor binding studies as described in Example 7. Based on experience, only compounds that exhibited IR activity IC50 values less than 5000 nM were deemed likely to exhibit bioactivity in the target species. Although the in vitro IR IC50 value is a useful qualitative screening tool, it utilizes human IM-9 cells which express the human insulin receptor and therefore it may not capture some of the small differences in affinity between the canine or feline IR and the human IR. Furthermore, factors other than insulin receptor binding may influence a compound's bioactivity in vivo (e.g., affinity for canine or feline FcRn to allow for extended pharmacokinetic elimination half-lives in vivo). Therefore, selected insulin-Fc fusion proteins that were acceptable from a manufacturing and IR activity IC50 value standpoint were further screened for bioactivity in the animal of interest (e.g., dog or cat) to screen out any materials with less than the desired potency and/or duration of bioactivity (e.g., NAOC of less than 150% FBGL·days·kg/mg). Again, based on experience, at NAOC values of greater than 150% FBGL·days·kg/mg, the dose requirements in the target species will be sufficiently low so as to reach an acceptable treatment cost. Lastly, an additional evaluation criterion was added which is mentioned rarely if ever in the art. As discussed in more detail in the Examples below, many insulin-Fc fusion protein embodiments that exhibit acceptable NAOC levels in the target species after the first dose, unexpectedly fail to maintain that level of bioactivity after repeated doses. Furthermore, in most cases the reduction in repeated dose bioactivity in the target species is correlated with the development of neutralizing anti-drug antibodies. This propensity to generate anti-drug antibodies and the failure to maintain activity render such insulin-Fc fusion proteins impractical for use in treating a chronic disease such as canine diabetes or feline diabetes. Therefore, only the insulin-Fc fusions proteins exhibiting acceptable levels of repeated dose bioactivity (e.g., NAOCR values greater than 0.50 for the third dose relative to the first dose) with minimal levels of anti-drug antibodies were deemed acceptable for use in the present invention.

Results—Insulin-Fc Fusion Proteins Comprising a Canine Fc Fragment

Example 17: Canine Insulin-Fc Fusion Protein Comprising the Canine Fc IgGA Isotype An attempt was made to produce an insulin-Fc fusion protein comprising the insulin polypeptide sequence of SEQ ID NO: 5 and the Fc fragment of the canine IgGA isotype (SEQ ID NO: 15) using the peptide linker of SEQ ID NO: 12. The full amino acid sequence for the resulting insulin-Fc fusion protein is as follows:

```
                                            (SEQ ID NO: 42)
FVNQHLCGSDLVEALALVCGERGFFYTDPTGGGPRRGIVEQCCHSICSLYQ

LENYCNGGGGAGGGGRCTDTPPCPVPEPLGGPSVLIFPPKPKDILRITRTP

EVTCVVLDLGREDPEVQISWFVDGKEVHTAKTQSREQQFNGTYRVVSVLPI

EHQDWLTGKEFKCRVNHIDLPSPIERTISKARGRAHKPSVYVLPPSPKELS

SSDTVSITCLIKDFYPPDIDVEWQSNGQQEPERKHRMTPPQLDEDGSYFLY

SKLSVDKSRWQQGDPFTCAVMHETLQNHYTDLSLSHSPG
```

The insulin-Fc fusion protein of SEQ ID NO: 42 was synthesized in HEK cells according to Example 1 and purified according to Example 3. The protein yield was 22 mg/L after the Protein A purification step. The structure of the insulin-Fc fusion protein was confirmed according to Example 4 by non-reducing and reducing CE-SDS, and the sequence was further identified by LC-MS with glycan removal according to Example 5. The % homodimer was measured by size-exclusion chromatography according to Example 6 and determined to be 24%, indicating a high degree of homodimer aggregates. The resulting homodimer titer was therefore only 5 mg/L. In summary, manufacturing of the insulin-Fc fusion protein of SEQ ID NO: 42 in HEK cells resulted in a high level of aggregates and a low homodimer titer (5 mg/L), which did not meet the design goal of a homodimer titer of greater than 50 mg/L.

Nevertheless, the insulin-Fc fusion protein of SEQ ID NO: 42 as evaluated for bioactivity. First, the insulin receptor binding of the insulin-Fc fusion protein of SEQ ID NO: 42 was measured according to Example 7, resulting in an IC50 value of 2,733 nM indicating that the compound is likely to be bioactive in vivo (i.e., IC50 less than 5000 nM).

Figure 2:
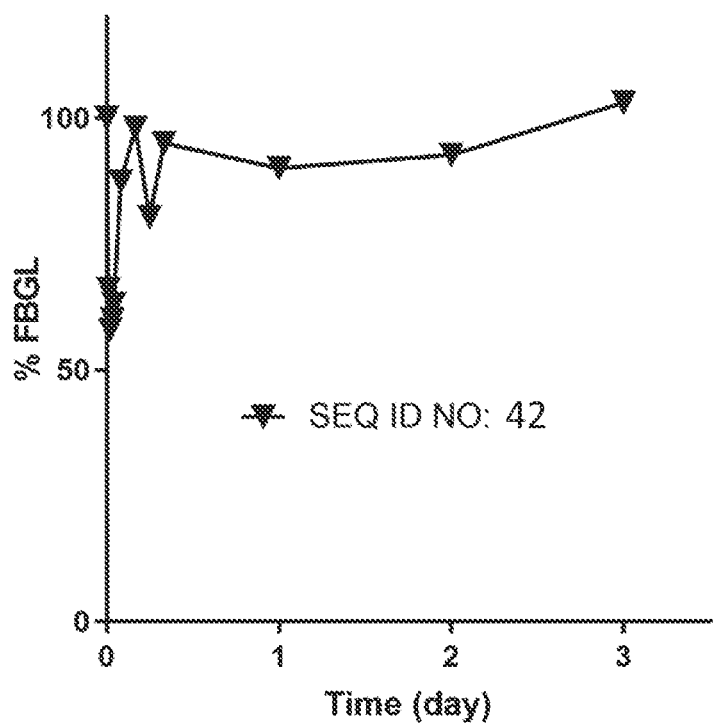
FIG. 2 shows average % fasting blood glucose levels from Day 0 to Day 3 for N=3 dogs dosed intravenously on Day 0 at 0.2 mg/kg with the homodimer of SEQ ID NO: 42.

Next, the in vivo pharmacodynamics (PD) of the insulin-Fc fusion protein of SEQ ID NO: 42 was measured after a single intravenous administration of the compound to N=3 canines, according to Example 10. FIG. 2 shows the percent fasting blood glucose level of SEQ NO: 42 as a function of time. The NAOC for SEQ ID NO: 42 was calculated to be 105% FBGL-days-kg/mg according to the procedure of Example 11. The in vivo half-life of SEQ ID NO: 42 was calculated to be less than one day using the method of Example 12. The relatively low NAOC was likely the result of the high amount of aggregates in the sample (i.e., low % homodimer), but what soluble homodimer remained in circulation still only had a pharmacokinetic elimination half-life of less than one day which was deemed unlikely support of once-weekly administration.

Example 18: Mutations of the Fc Fragment Region of Insulin-Fc Fusion Proteins Comprising the Canine IgGA Isotype In an attempt to increase the % homodimer content, improve the bioactivity, and increase the half-life of the insulin-Fc fusion protein of SEQ ID NO: 42, mutations were inserted into the Fc fragment CH3 region to try to prevent intermolecular association (e.g., Fc fragment-Fc fragment interactions between molecules) and encourage stronger binding to the FcRn receptor (e.g., higher affinity for the FcRn) to increase recycling and systemic circulation time. The following insulin-Fc fusion proteins were synthesized in HEK cells according to Example 1, purified according to Examples 3, and tested according to Examples 4-7, which are shown below. The sequence alignment of SEQ ID NOs: 44, 46, 48, and 50 against SEQ ID NO: 42 and the differences in amino acid sequences are shown in FIG. 3.

(SEQ ID NO: 44)
FVNQHLCGSDLVEALALVCGERGFFYTDPTGGGPRRGIVEQCCHSICSLYQ

LENYCNGGGGAGGGGRCTDTPPCPVPEPLGGPSVLIFPPKPKDILRITRTP

EVTCVVLDLGREDPEVQISWFVDGKEVHTAKTQSREQQFNGTYRVVSVLPI

EHQDWLTGKEFKCRVNHIDLPSPIERTISKARGRAHKPSVYVLPPSPKELS

SSDTVSITCLIKDFYPPDIDVEWQSNGQQEPERKHRMTPPQLDEDGSYFLY

SKLSVDKSRWQQGDPFTCAVLHEALHSHYTQKSLSLSPG (SEQ ID NO: 46)
FVNQHLCGSDLVEALALVCGERGFFYTDPTGGGPRRGIVEQCCHSICSLYQ

LENYCNGGGGAGGGGRCTDTPPCPVPEPLGGPSVLIFPPKPKDILRITRTP

EVTCVVLDLGREDPEVQISWFVDGKEVHTAKTQSREQQFNGTYRVVSVLPI

EHQDWLTGKEFKCRVNHIDLPSPIERTISKARGRAHKPSVYVLPPSPKELS

SSDTVSITCLIKDFYPPDIDVEWQSNGQQEPERKHRMTPPQLDEDGSYFLY

SKLSVDKSRWQQGDPFTCAVLHETLQSHYTDLSLSHSPG (SEQ ID NO: 48)
FVNQHLCGSDLVEALALVCGERGFFYTDPTGGGPRRGIVEQCCHSICSLYQ

LENYCNGGGGAGGGGRCTDTPPCPVPEPLGGPSVLIFPPKPKDILRITRTP

EVTCVVLDLGREDPEVQISWFVDGKEVHTAKTQSREQQFNGTYRVVSVLPI

EHQDWLTGKEFKCRVNHIDLPSPIERTISKARGRAHKPSVYVLPPSPKELS

SSDTVSITCLIKDFYPPDIDVEWQSNGQQEPERKHRMTPPQLDEDGSYFLY

SKLSVDKSRWQQGDPFTCAVMHETLQSHYTDLSLSHSPG (SEQ ID NO: 50)
FVNQHLCGSDLVEALALVCGERGFFYTDPTGGGPRRGIVEQCCHSICSLYQ

LENYCNGGGGAGGGGRCTDTPPCPVPEPLGGPSVLIFPPKPKDILRITRTP

EVTCVVLDLGREDPEVQISWFVDGKEVHTAKTQSREQQFNGTYRVVSVLPI

EHQDWLTGKEFKCRVNHIDLPSPIERTISKARGRAHKPSVYVLPPSPKELS

SSDTVSITCLIKDFYPPDIDVEWQSNGQQEPERKHRMTPPQLDEDGSYFLY

SKLSVDKSRWQQGDPFTCAVLHETLQNHYTDLSLSHSPG

The insulin-Fc fusion proteins based on canine IgGA variants are listed in Table 2 along with the corresponding protein yields, % homodimer, and homodimer titers. The results show that the various mutations to the IgGA Fc fragment, instead of improving the % homodimer and homodimer titer, gave rise to highly aggregated proteins with extremely low homodimer titers of less than 5 mg/L. As such, the in vivo bioactivity and pharmacokinetics of the compounds could not be evaluated.

TABLE 2

Homodimer titers for sequences utilizing a native or mutated canine IgGA Fc fragment CH3 region

| SEQ ID NO: | Protein Yield (mg/L) | % Homodimer | Homodimer Titer (mg/L) |
| --- | --- | --- | --- |
| SEQ ID NO: 42 | 22 | 24% | 5 |
| SEQ ID NO: 44 | 33 | 0% | 0 |
| SEQ ID NO: 46 | 57 | 0% | 0 |
| SEQ ID NO: 48 | 67 | 0% | 0 |
| SEQ ID NO: 50 | 80 | 0% | 0 |

Example 19: Canine Insulin-Fc Fusion Protein Using Other Canine Fc Fragment Isotypes As described above, canine IgGA is thought to be the preferred isotype for the Fc fragment to produce non-immunogenic insulin-Fc fusion protein for dogs due to its lack of Fc(gamma) I effector function in canines (much like the human IgG2 isotype in humans). However, insulin-Fc fusion proteins manufactured with a canine IgGA Fc fragment were highly aggregated with an unacceptably low homodimer titer and unacceptably low levels of bioactivity and duration of action. Therefore, Fc fragments from the other canine IgG isotypes (canine IgGB of SEQ ID NO: 16), canine IgGC of SEQ ID NO: 17, and canine IgGD of SEQ ID NO: 18) were evaluated as replacements for the canine IgGA Fc fragment of the insulin-Fc fusion of SEQ ID NO: 42. The three insulin-Fc fusion proteins containing Fc fragments based on the canine IgGB, IgGC, and IgGD isotypes were synthesized using the same insulin polypeptide of SEQ ID NO: 5 and peptide linker of SEQ ID NO: 12 as were used to make the insulin-Fc fusion protein of SEQ ID NO: 42. The proteins were manufactured in HEK293 cells according to Example 1. The insulin-Fc fusion proteins were then purified using a Protein A column according to Example 3. The structures of the insulin-Fc fusion proteins were confirmed according to Example 4 by non-reducing and reducing CE-SDS, and the sequences were further identified by LC-MS with glycan removal according to Example 5. The % homodimer was measured by size-exclusion chromatography according to Example 6. Their sequences are shown below and their sequence alignment comparison against SEQ ID NO: 42 is shown in FIG. 4:

(SEQ ID NO: 52)
FVNQHLCGSDLVEALALVCGERGFFYTDPTGGGPRRGIVEQCCHSICSLYQ

LENYCNGGGGAGGGGDCPKCPAPEMLGGPSVFIFPPKPKDTLLIARTPEVT

CVVVDLDPEDPEVQISWFVDGKQMQTAKTQPREEQFNGTYRVVVLPIGHQD

WLKGKQFTCKVNNKALPSPIERTISKARGQAHQPSVYVLPPSREELSKNTV

SLTCLIKDFFPPDIDVEWQSNGQQEPESKYRTTPPQLDEDGSYFLYSKLSV

DKSRWQRGDTFICAVMHEALHNHYTQESLSHSPG (SEQ ID NO: 54)
FVNQHLCGSDLVEALALVCGERGFFYTDPTGGGPRRGIVEQCCHSICSLYQ

LENYCNGGGGAGGGGCNNCPCPGCGLLGGPSVFIFPPKPKDILVTARTPTV

TCVVVDLDPENPEVQISWFVDSKQVQTANTQPREEQSNGTYRVVSVLPIGH

QDWLSGKQFKCKVNNKALPSPIEEIISKTPGQAHQPNVYVLPPSRDEMSKN

TVTLTCLVKDFFPPEIDVEWQSNGQQEPESKYRMTPPQLDEDGSYFLYSKL

SVDKSRWQRGDTFICAVMHEALHNHYTQISLSHSPG (SEQ ID NO: 56)
FVNQHLCGSDLVEALALVCGERGFFYTDPTGGGPRRGIVEQCCHSICSLYQ

LENYCNGGGGAGGGGCISPCPVPESLGGPSVFIFPPKPKDILRITRTPEIT

CVVLDLGREDPEVQISWFVDGKEVHTAKTQPREQQFNSTYRVVSVLPIEHQ

DWLTGKEFKCRVNHIGLPSPIERTISKARGQAHQPSVYVLPPSPKELSSSD

TVTLTCLIKDFFPPEIDVEWQSNGQPEPESKYHTTAPQLDEDGSYFLYSKL

SVDKSRWQQGDTFTCAVMHEALQNHYTDLSLSHSPG

The resulting protein yields, % homodimer, and homodimer titers are given in Table 3. Unexpectedly, only the insulin-Fc fusion protein of SEQ ID NO: 52 comprising an Fc fragment based on the canine IgGB isotype demonstrated a homodimer titer which met the design criteria of greater than 50 mg/L. The insulin-Fc fusion protein of SEQ ID NO: 54 comprising an Fc fragment based on the canine IgGC isotype did not yield any compound at all, and the insulin-Fc fusion protein of SEQ ID NO: 56 comprising an Fc fragment based on the canine IgGD isotype demonstrated an appreciable protein yield but with a high degree of aggregation and therefore an unacceptably low homodimer titer.

In vitro insulin receptor binding for the insulin-Fc fusion proteins of SEQ ID NO: 52 and SEQ ID NO: 56 was tested according to the procedure of Example 7. The insulin-Fc fusion protein of SEQ ID NO: 56 demonstrated an IC50 of greater than 5000 nM, indicating that the compound was highly unlikely to show bioactivity in vivo. However, the insulin-Fc fusion protein of SEQ ID NO: 52 demonstrated an IC50 of 28 nM indicating that this sequence was likely to be bioactive in vivo.

TABLE 3

Homodimer titers for sequences utilizing native canine IgGB, IgGC, and IgGD Fc fragments

| SEQ ID NO: | IgG Fragment | Protein Yield (mg/L) | % Homo-dimer | Homo-dimer Titer (mg/L) | IR Binding, IC50 (nM) |
|---|---|---|---|---|---|
| SEQ ID NO: 42 (Example 17) | IgGA | 21 | 24% | 5 | 2,733 |
| SEQ ID NO: 52 | IgGB | 80 | 93% | 74 | 28 |
| SEQ ID NO: 54 | IgGC | 0 | 0% | 0 | DNM* |
| SEQ ID NO: 56 | IgGD | 134 | 12% | 16 | >5000 |

*DNM = Did Not Measure

Figure 5:
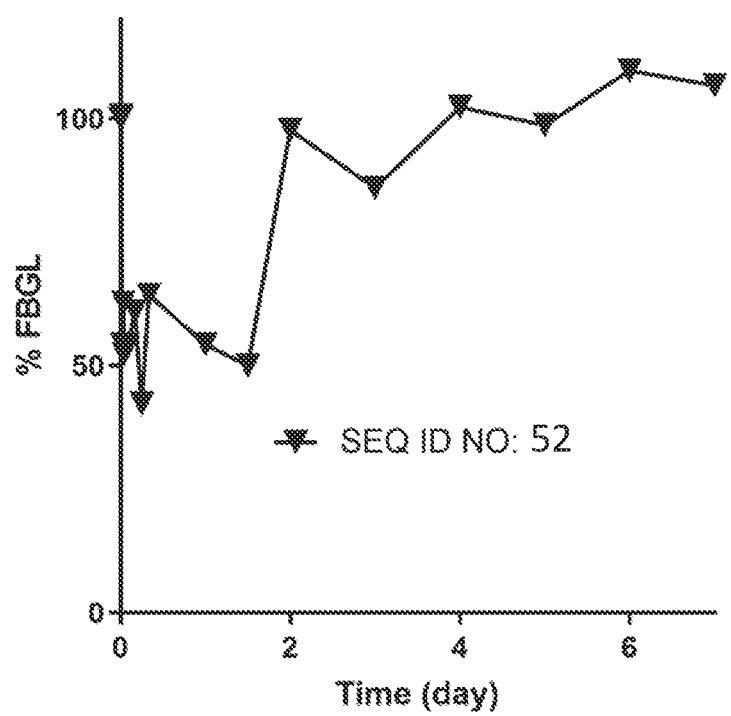
FIG. 5 shows average % fasting blood glucose levels from Day 0 to Day 7 for N=3 dogs dosed intravenously on Day 0 at 0.2 mg/kg with the homodimer of SEQ ID NO: 52.
Figure 6:
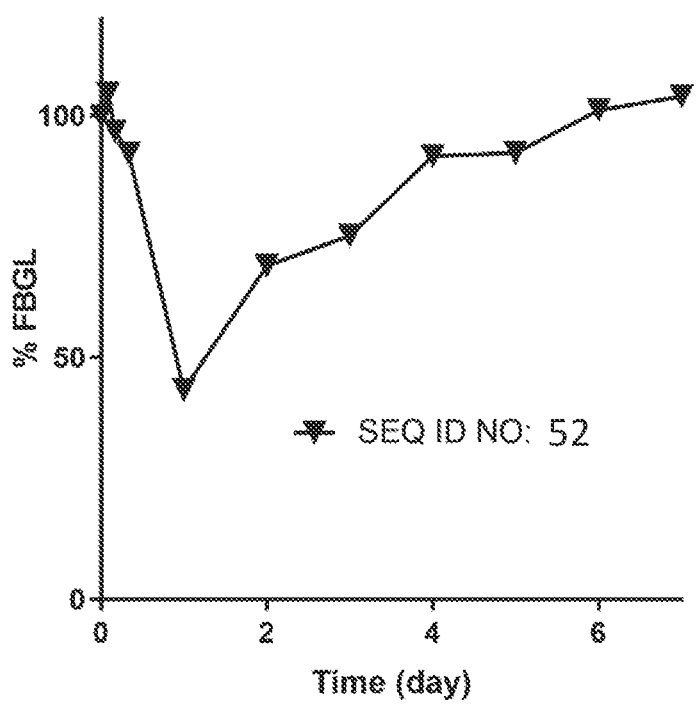
FIG. 6 shows average % fasting blood glucose levels from Day 0 to Day 7 for N=6 dogs dosed subcutaneously on Day 0 at 0.33 mg/kg with the homodimer of SEQ ID NO: 52.

Example 20: In Vivo Efficacy of an Insulin-Fc Fusion Protein Comprising the Insulin Polypeptide of SEQ ID NO: 5 with a Canine IgGB Isotype Fc Fragment Given the promising homodimer titer and insulin receptor activity results in Example 19, the insulin-Fc fusion protein of SEQ ID NO: 52 was tested for in vivo bioactivity according to Example 10 following an intravenous injection in each of N=3 healthy, antibody-naïve, beagle dogs weighing approximately 10 kg. In a separate experiment, the compound was administered subcutaneously to N=3 naïve beagle dogs. FIG. 5 shows the % FBGL versus time for a single intravenous administration of the insulin-Fc fusion protein of SEQ ID NO: 52, and FIG. 6 shows the % FBGL vs. time for a single subcutaneous administration of the insulin-Fc fusion protein of SEQ ID NO: 52, both of which demonstrate that the insulin-Fc fusion protein of SEQ ID NO: 52 is significantly bioactive in dogs.

The NAOC was calculated according to the procedure of Example 11 to determine the relative bioactivity and duration of action of the insulin-Fc fusion protein. The NAOC of the insulin-Fc fusion protein of SEQ ID NO: 52 injected intravenously was 399% FBGL·days·kg/mg which was 3.8 times the NAOC of the insulin-Fc fusion protein of SEQ ID NO: 42 injected intravenously, illustrating significantly increased bioactivity for the insulin-Fc fusion protein comprising the canine IgGB Fc fragment versus the insulin-Fc fusion protein comprising the canine IgGA Fc fragment. The NAOC of the insulin-Fc fusion protein of SEQ ID NO: 52 injected subcutaneously was 366% FBGL·days·kg/mg, demonstrating a level of bioactivity via subcutaneous administration that is similar to that obtained via intravenous administration.

Example 21: In Vivo Immunogenicity Screening after Repeated Subcutaneous Doses of the Insulin-Fc Fusion Protein Comprising the Insulin Polypeptide of SEQ ID NO: 5 with a Canine IgGB Isotype Fc Fragment Next, the repeated dose subcutaneous bioactivity of the insulin-Fc fusion protein of SEQ ID NO: 52 was tested in dogs as per the method described in Example 11. N=3 animals were dosed subcutaneously at day 0, at day 35, and at day 42, and the % FBGL was measured for the 7-day window after each dose according to Example 11. The NAOC and NAOCR were calculated according to the procedure of Example 11 for each repeated subcutaneous injection. As illustrated in Table 4, repeated subcutaneous dosing in dogs unexpectedly revealed a significant decay in bioactivity by the third dose as measured by a significant decrease in the NAOCR (i.e., the NAOC for the third injection was only 0.40, or 40%, of the NAOC for the first injection).

TABLE 4

NAOC per dose and NAOCR for repeated doses of SEQ ID NO: 52

| Injection Number of SEQ ID NO: 52 | NAOC (% FBGL · days · kg/mg) | NAOCR (ratioed to Week 1) |
|---|---|---|
| 1 | 330 | 1.0 |
| 2 | 339 | 1.1 |
| 3 | 115 | 0.4 |

Without being bound to any particular explanation, it was postulated that the cause of the significant reduction in bioactivity of the insulin-Fc fusion protein of SEQ ID NO: 52 after the third repeated subcutaneous dose in dogs was due to the development of anti-drug antibodies that neutralized its biological activity. Anti-drug antibodies may be directed against the insulin polypeptide, linker, or Fc-fragment portions of an insulin-Fc fusion protein. The immunogenic response manifests as interactions between antigen presenting cells, T-helper cells, B-cells, and their associated cytokines, which may lead to the production of endogenous antibodies against the drug (e.g., anti-drug antibodies). Binding antibodies are all isotypes capable of binding the insulin-Fc fusion protein, and these may be detected in an immunoassay as described in Example 13. Neutralizing antibodies that inhibit functional activity of the insulin-Fc fusion protein are generally directed against an epitope that is required for bioactivity. To assess whether this was the case, serum that was collected prior to the administration of each dose and at the end of the experiment described in Examples 11 and 12 was tested to quantify the levels of anti-drug antibodies according to Example 13. As shown in FIG. 7, levels of anti-drug antibodies did indeed increase with multiple subcutaneous administrations of the compound, indicating that the generation of neutralizing anti-drug antibodies were the likely cause for the reduction in the NAOCR after the third injection of the insulin Fc-fusion protein of SEQ ID NO: 52.

Example 22: Non-Glycosylated Insulin-Fc Fusion Protein Comprising the Insulin Polypeptide of SEQ ID NO: 5 with Canine IgGB Isotype Fc Fragments to Reduce the Potential Risk of Immunogenicity As shown in Examples 19 and 20, the insulin-Fc fusion protein of SEQ ID NO: 52 showed acceptable % homodimer content, homodimer titer, and bioactivity in dogs; however, its use for a chronic disease such as diabetes is compromised by the reduction in bioactivity (Example 21) and generation of anti-drug antibodies (Example 21) with repeated subcutaneous dosing. Without being bound to any particular theory, one possible cause of the generation of anti-drug antibodies and the reduction in bioactivity is the increased interaction of the canine IgGB Fc fragment with various receptors of the canine immune system (e.g., Fc(gamma) receptors, e.g., Fc(gamma)RI). Nevertheless, the canine IgGB isotype was the only one of the four canine IgG isotypes that, when used for the Fc fragment, resulted in an insulin-Fc fusion protein meeting the manufacturability and single-dose bioactivity design goals (Example 16). As described in the Detailed Description of the Invention, one method for reducing the Fc(gamma) interaction involves mutating the Fc fragment cNg site to prevent glycosylation during synthesis in the host cell. Therefore, cNg site mutations were made to the Fc fragment region of SEQ ID NO: 52 to reduce the binding affinity of the Fc fragment for Fc(gamma) receptors in vivo, as measured by binding in an in vitro human Fc(gamma)RI assay described in Example 8. Verification of the lack of glycan were performed using the LC-MS method of Example 5, but with omission of the PNGase F treatment step. The position of the cNg site in the insulin-Fc fusion protein of SEQ ID NO: 52 is cNg-NB139. Mutations to SEQ ID NO: 52 included SEQ ID NO: 58 comprising a mutation of cNg-NB139-Q, SEQ ID NO: 60 comprising a mutation of cNg-NB139-S, SEQ ID NO: 62 comprising a mutation of cNg-NB139-D, and SEQ ID NO: 64 comprising a mutation of cNg-NB139-K. The full amino acid sequences of the cNg-mutated insulin-Fc fusion proteins are listed below (with the NB139 position bolded) and the resulting sequence alignments are shown in FIG. 8 (Clustal Omega):

(SEQ ID NO: 58)
FVNQHLCGSDLVEALALVCGERGFFYTDPTGGGPRRGIVEQCCHSICSLYQ

LENYCNGGGGAGGGGDCPKCPAPEMLGGPSVFIFPPKPKDTLLIARTPEVT

CVVVDLDPEDPEVQISWFVDGKQMQTAKTQPREEQFQGTYRVVSVLPIGHQ

DWLKGKQFTCKVNNKALPSPIERTISKARGQAHQPSVYVLPPSREELSKNT

VSLTCLIKDFFPPDIDVEWQSNGQQEPESKYRTTPPQLDEDGSYFLYSKLS

VDKSRWQRGDTFICAVMHEALHNHYTQESLSHSPG (SEQ ID NO: 60)
FVNQHLCGSDLVEALALVCGERGFFYTDPTGGGPRRGIVEQCCHSICSLYQ

LENYCNGGGGAGGGGDCPKCPAPEMLGGPSVFIFPPKPKDTLLIARTPEVT

CVVVDLDPEDPEVQISWFVDGKQMQTAKTQPREEQFSGTYRVVSVLPIGHQ

DWLKGKQFTCKVNNKALPSPIERTISKARGQAHQPSVYVLPPSREELSKNT

VSLTCLIKDFFPPDIDVEWQSNGQQEPESKYRTTPPQLDEDGSYFLYSKLS

VDKSRWQRGDTFICAVMHEALHNHYTQESLSHSPG (SEQ ID NO: 62)
FVNQHLCGSDLVEALALVCGERGFFYTDPTGGGPRRGIVEQCCHSICSLYQ

LENYCNGGGGAGGGGDCPKCPAPEMLGGPSVFIFPPKPKDTLLIARTPEVT

CVVVDLDPEDPEVQISWFVDGKQMQTAKTQPREEQFDGTYRVVSVLPIGHQ

DWLKGKQFTCKVNNKALPSPIERTISKARGQAHQPSVYVLPPSREELSKNT

VSLTCLIKDFFPPDIDVEWQSNGQQEPESKYRTTPPQLDEDGSYFLYSKLS

VDKSRWQRGDTFICAVMHEALHNHYTQESLSHSPG (SEQ ID NO: 64)
FVNQHLCGSDLVEALALVCGERGFFYTDPTGGGPRRGIVEQCCHSICSLYQ

LENYCNGGGGAGGGGDCPKCPAPEMLGGPSVFIFPPKPKDTLLIARTPEVT

CVVVDLDPEDPEVQISWFVDGKQMQTAKTQPREEQFKGTYRVVSVLPIGHQ

-continued

DWLKGKQFTCKVNNKALPSPIERTISKARGQAHQPSVYVLPPSREELSKNT

VSLTCLIKDFFPPDIDVEWQSNGQQEPESKYRTTPPQLDEDGSYFLYSKLS

VDKSRWQRGDTFICAVMHEALHNHYTQESLSHSPG

The insulin-Fc fusion proteins were manufactured in HEK293 cells according to Example 1 and purified using a Protein A column according to Example 3. The structures of the insulin-Fc fusion proteins were confirmed according to Example 4 by non-reducing and reducing CE-SDS, and the sequences were further identified by LC-MS with glycan removal according to Example 5. The % homodimer was measured by size-exclusion chromatography according to Example 6. As shown in Table 5, the homodimer titers of the insulin-Fc fusion proteins of SEQ ID NO: 60, SEQ ID NO: 62, and SEQ ID NO: 64 meet the design goal, while unexpectedly the insulin-Fc fusion protein of SEQ ID NO: 58 containing the cNg-NB139-Q mutation did not meet the design goal for homodimer titer.

TABLE 5

Homodimer titers for cNg variations of SEQ ID NO: 52

| SEQ ID NO: | cNg Mutation | Protein Yield (mg/L) | % Homodimer | Homodimer Titer (mg/L) |
|---|---|---|---|---|
| SEQ ID NO: 58 | cNg-Q | 37 | 98% | 36 |
| SEQ ID NO: 60 | cNg-S | 77 | 98% | 75 |
| SEQ ID NO: 62 | cNg-D | 88 | 98% | 86 |
| SEQ ID NO: 64 | cNg-K | 68 | 98% | 67 |

To determine which of the remaining three compounds was most likely to exhibit reduced immunogenicity, the Fc(gamma) receptor binding was measured according to the procedure of Example 8. Low Fc(gamma) receptor binding is most likely to correlate with minimum immunogenicity. Table 6 compares the Fc(gamma) receptor I binding of these insulin-Fc fusion proteins with the Fc(gamma) receptor binding of the insulin-Fc fusion protein of SEQ ID NO: 52 demonstrating unexpectedly that the insulin-Fc fusion protein of SEQ ID NO: 62, containing the cNg-D mutation, exhibits an Fc (gamma) receptor binding activity that is approximately twice that of the insulin-Fc fusion proteins of SEQ ID NO: 60, containing the cNg-S mutation and SEQ ID NO: 64 containing the cNg-K mutation. Therefore, only the insulin-Fc fusion proteins comprising the latter two compounds containing the cNg-S mutation and the cNg-K mutations were deemed suitable for repeated dose bioactivity testing in dogs.

TABLE 6

Fc(gamma) receptor binding for cNg variations of SEQ ID NO: 52

| SEQ ID NO: | cNg Mutation | OD450 nm Log[Fc(gamma) RI] (ng/mL) | OD450 nm Minus Assay Background | Ratio to SEQ ID NO: 52 |
|---|---|---|---|---|
| SEQ ID NO: 52 | Native cNg | 0.386 | 0.323 | 1.00 |
| SEQ ID NO: 60 | cNg-S | 0.140 | 0.077 | 0.24 |
| SEQ ID NO: 62 | cNg-D | 0.204 | 0.141 | 0.44 |
| SEQ ID NO: 64 | cNg-K | 0.126 | 0.063 | 0.20 |
| Assay background (no compound) | N/A | 0.063 | 0.000 | N/A |

Example 23: Evaluation of In Vivo Bioactivity and Immunogenicity of an Insulin Polypeptide of SEQ ID NO: 5 with the Non-Glycosylated cNg-K and cNg-S Canine IgGB Isotype Fc Fragments To determine if the insulin-Fc fusion protein of SEQ ID NO: 60, containing the cNg-S mutation, improved the repeated dose bioactivity performance in dogs, the compound was administered subcutaneously to N=1 dog on day 0, day 7, day 14, and on day 28 according to the procedure of Example 11. When the dog's % FBGL dropped too low, the dog was given food to raise the blood glucose to a safe level. The NAOC for the first injection was 191% FBGL·days·kg/mg, showing that the insulin-Fc fusion protein of SEQ ID NO: 60 was satisfactorily bioactive in vivo. The NAOC and NAOCR were also measured for each subsequent dose according to the general procedure of Example 11, calculated from the time the dose was administered until just before the next dose was administered. The NAOC and the NAOCR shown in Table 7 illustrate that the insulin-Fc fusion protein of SEQ ID NO: 60 exhibited an NAOCR that decreased significantly on doses 3 and 4 of a four dose regimen. Therefore, the insulin-Fc fusion protein of SEQ ID NO: 60, containing the cNg-S mutation, was unable to demonstrate repeated dose bioactivity in dogs despite having a low Fc(gamma)RI binding four times lower than that of the insulin-Fc fusion protein of SEQ ID NO: 52.

TABLE 7

NAOC per dose for repeated doses of SEQ ID NO: 60

| Injection Number of SEQ ID NO: 60 | NAOC (% FBGL · days · kg/mg) | NAOCR |
|---|---|---|
| 1 | 191 | 1.0 |
| 2 | 240 | 1.3 |
| 3 | 0 | 0.0 |
| 4 | 39 | 0.2 |

To determine if the insulin-Fc fusion protein of SEQ ID NO: 64, containing the cNg-K mutation, improved the repeated dose bioactivity performance in dogs, the compound was administered subcutaneously to N=1 dog on day 0, day 7, day 14, and on day 28 according to the procedure of Example 11. When the dog's % FBGL dropped too low, the dog was given food to raise the blood glucose to a safe level. The NAOC for the first injection was 449% FBGL·days·kg/mg, showing that the insulin-Fc fusion protein of SEQ ID NO: 64 was satisfactorily bioactive in vivo. The pharmacokinetic profile of the compound was also measured by the method of Example 12 using ELISA, and a two-compartment model was fit to the data to determine its elimination half-life which was about 0.9 days. The NAOC and NAOCR were also measured for each subsequent dose according to the general procedure of Example 11, calculated from the time the dose was administered until just before the next dose was administered. The NAOC and the NAOCR shown in Table 8 illustrate that the insulin-Fc fusion protein of SEQ ID NO: 64 maintains an NAOCR greater than 0.6 throughout the four doses. Therefore, unexpectedly, the insulin-Fc fusion protein of SEQ ID NO: 64, containing the cNg-K mutation, was the only non-glycosylated mutant of the insulin-Fc fusion protein of SEQ ID NO: 52 resulting in significantly improved repeated dose bioactivity in dogs.

TABLE 8

NAOC per dose for repeated doses of SEQ ID NO: 64

| Injection Number of SEQ ID NO: 64 | NAOC (% FBGL · days · kg/mg) | NAOCR |
|---|---|---|
| 1 | 449 | 1.0 |
| 2 | 361 | 0.8 |
| 3 | 259 | 0.6 |
| 4 | 638 | 1.4 |

Figure 9:
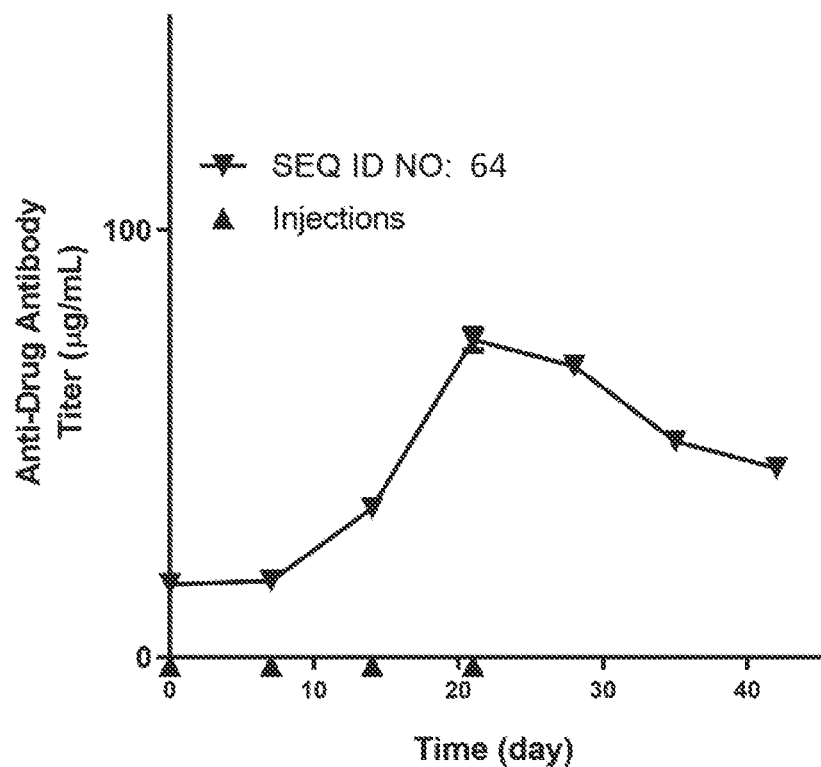
FIG. 9 shows the average anti-drug antibody titer (µg/mL) for N=1 dog dosed subcutaneously on Day 0 (0.33 mg/kg), Day 7 (0.50 mg/kg), Day 14 (0.50 mg/kg), and Day 21 (0.50 mg/kg) with the homodimer of SEQ ID NO: 64.

The levels of anti-drug and anti-insulin antibodies were also measured throughout the course of treatment (28 days) and for an additional two weeks according to Example 13. FIG. 9 illustrates that the insulin-Fc fusion protein of SEQ ID NO: 64 still generated anti-drug antibodies with repeated subcutaneous dosing in dogs, but the anti-drug antibody titers were much lower than those generated by the insulin-Fc fusion protein of SEQ ID NO: 52 (Example 19).

Example 24: Screening of Canine Serum Containing Anti-Drug Antibodies and Identification of Potential Immunogenic Epitopes at the B10D and A8H Positions of the Insulin Polypeptide Mutating the cNg site of the canine IgGB Fc fragment to a Lys (i.e., cNg-K) did improve the repeated dose bioactivity of the insulin-fusion protein comprising the insulin polypeptide of SEQ ID NO: 5 and the peptide linker of SEQ ID NO: 12 (Example 23), but the resulting insulin-Fc fusion protein of SEQ ID NO: 64 still gave rise to anti-drug antibodies (Example 23). It was hypothesized, therefore, that the insulin polypeptide of SEQ ID NO: 5 may unexpectedly contain specific epitopes (i.e., immunogenic "hot spots") against which the dog's immune system is directed. Therefore, the binding specificity of the antibodies present in the serum samples described in Example 13 were evaluated according to the general procedure of Example 15. The analysis of the antibody-containing serum samples from the repeated dosing of the insulin-Fc fusion protein of SEQ ID NO: 52 (Example 19) against the coated insulin-Fc fusion protein library demonstrated that there were unexpectedly two primary "hot spots" present within the insulin polypeptide sequence of SEQ ID NO: 5: the aspartic acid mutation at the 10th position from the N-terminus of the B-chain (i.e., B10), and, separately, the histidine mutation at the 8th position from the N-terminal end of the A-chain (i.e., A8). The results suggest that insulin-Fc fusion proteins comprising insulin polypeptide amino acid compositions containing these two particular amino acid mutations are likely to be immunogenic in dogs and therefore likely to give rise to anti-drug antibodies that neutralize the bioactivity after repeated injections. Therefore, it was determined that insulin polypeptides that do not contain the B10 aspartic acid and A8 histidine are preferred for insulin-Fc fusion proteins that need to be repeatedly dosed in dogs over long periods long-term (e.g., to treat canine diabetes).

Example 25: An Insulin-Fc Fusion Protein Comprising the Insulin Polypeptide of SEQ ID NO: 5 and a Non-Glycosylated Canine IgGB Isotype Fc Fragment in which the B10D and A8H Mutations of the Insulin Polypeptide are Restored to Native Compositions to Reduce the Potential Risk of Immunogenicity To evaluate whether replacing the "hot spot" mutations would improve the immunogenicity and repeated dose bioactivity of insulin-Fc fusion proteins comprising the insulin polypeptide of SEQ ID NO: 5 and the canine IgGB isotype fragment, an exemplary insulin-Fc fusion protein (SEQ ID NO: 66) was synthesized in which the B10 and A8 amino acids of the insulin polypeptide were restored to their native histidine and threonine compositions, respectively (SEQ ID NO: 125) listed below with non-native amino acids bolded).

(SEQ ID NO: 125)
FVNQHLCGSHLVEALALVCGERGFFYTDPTGGGPRRGIVEQCCTSICSLYQ

LENYCN

Furthermore, given the additional potential benefits of the non-glycosylated cNg mutants, the insulin-Fc fusion protein of SEQ ID NO: 66 contains the cNg-Q mutation. The entire amino acid sequence of the insulin-Fc fusion protein of SEQ ID NO: 66 is given below:

(SEQ ID NO: 66)
FVNQHLCGSHLVEALALVCGERGFFYTDPTGGGPRRGIVEQCCTSICSLYQ

LENYCNGGGGAGGGGDCPKCPAPEMLGGPSVFIFPPKPKDTLLIARTPEVT

CVVVDLDPEDPEVQISWFVDGKQMQTAKTQPREEQFQGTYRVVSVLPIGHQ

DWLKGKQFTCKVNNKALPSPIERTISKARGQAHQPSVYVLPPSREELSKNT

VSLTCLIKDFFPPDIDVEWQSNGQQEPESKYRTTPPQLDEDGSYFLYSKLS

VDKSRWQRGDTFICAVMHEALHNHYTQESLSHSPG

The insulin-Fc fusion protein of SEQ ID NO: 66 was manufactured in HEK293 cells according to Example 1 and purified using a Protein A column according to Example 3. The resulting protein yield was only 21 mg/L. The structure was confirmed according to Example 4 by non-reducing and reducing CE-SDS, and the sequence was further identified by LC-MS with glycan removal according to Example 5. The % homodimer as measured by size-exclusion chromatography according to Example 6, was 98.0% indicating that the protein was relatively free of aggregates.

Figure 10:
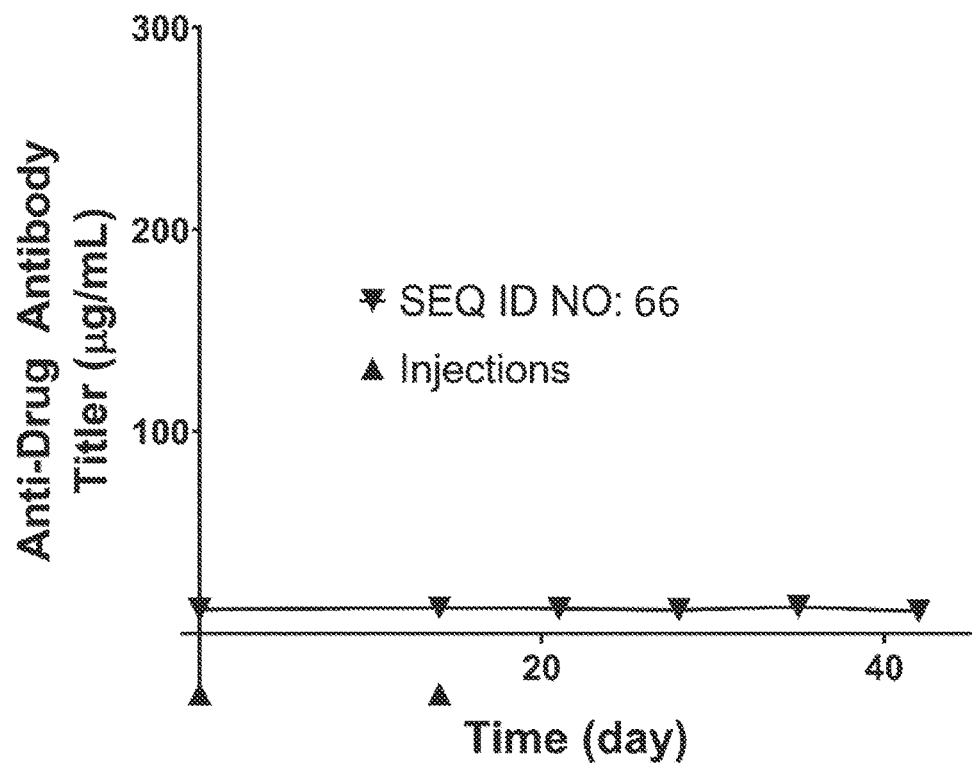
FIG. 10 shows the average anti-drug antibody titer (µg/mL) for N=1 dogs dosed subcutaneously on Day 0 (0.33 mg/kg) and Day 14 (0.16 mg/kg) with the homodimer of SEQ ID NO: 66.

Despite the relatively low homodimer titer of 21 mg/L, the insulin-Fc fusion protein of SEQ ID NO: 66 was evaluated in dogs for in vivo bioactivity and immunogenicity according to the procedures of Examples 11-13, respectively. FIG. 10 demonstrates that restoration of the B10D and A8H mutations to their native amino acids (i.e., B10H and A8T) in the insulin-Fc fusion protein of SEQ ID NO: 66 did significantly reduce the immunogenicity of the parent compound (SEQ ID NO: 52).

Figure 11:
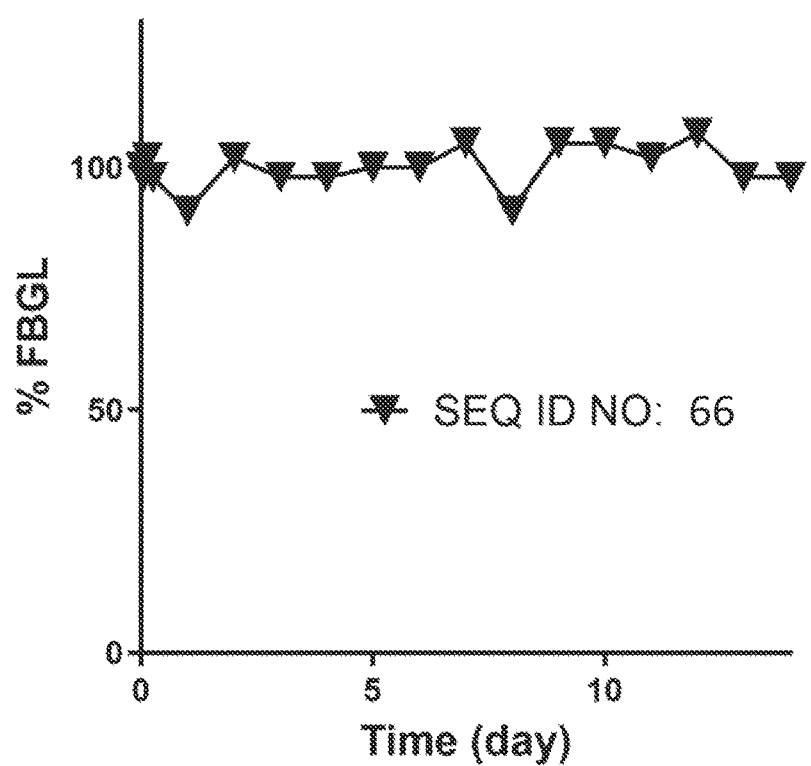
FIG. 11 shows average % fasting blood glucose levels from Day 0 to Day 7 for N=2 dogs dosed subcutaneously on Day 0 at 0.33 mg/kg with the homodimer of SEQ ID NO: 66.

However, as shown in FIG. 11, the insulin-Fc fusion protein of SEQ ID NO: 66 containing the native B10 and A8 amino acids was not bioactive (i.e., the NAOC was essentially zero).

Example 26: Attempts to Incorporate Additional B-Chain and A-Chain Mutations into the Insulin Polypeptide of SEQ ID NO: 125 to Improve the Bioactivity of the Associated Insulin-Fc Fusion Proteins Containing the Canine IgGB Fc Fragment The fact that the insulin-Fc fusion protein of SEQ ID NO: 66 did not generate anti-drug antibodies (Example 25) compared to the insulin-Fc fusion protein of SEQ ID NO: 52 (Example 20) provides strong evidence for the theory that the B10D and A8H mutations in the insulin polypeptide of SEQ ID NO: 5 are likely the immunogenic epitopes responsible for the production of anti-drug antibodies. However, the lack of in vivo potency of the insulin-Fc fusion protein of SEQ ID NO: 66 compared to that of SEQ ID NO: 52 indicates that these two amino acid mutations are also responsible for achieving acceptable levels of bioactivity. The lack of in vivo potency for the insulin-Fc fusion protein of SEQ ID NO: 66 correlates with its high IC50 (shown in Table 9 below) as measured by the insulin receptor binding assay according to the method of Example 7. Therefore, further efforts were required to increase the insulin-Fc fusion protein bioactivity (i.e., decrease the insulin receptor binding assay IC50 value to less than 5000 nM, or more preferably less than 4000 nM, or even more preferably less than 3000 nM) while maintaining a low degree of immunogenicity by keeping the native B10 and A8 amino acids in the insulin polypeptide.

It is known that various portions of the insulin B-chain and A-chain are required for strong binding to the IR (Hubbard S. R., "Structural biology: Insulin meets its receptor", Nature. 2013; 493(7431):171-172). Therefore, portions of the B-chain or A-chain were modified while keeping the B10 and A8 the same as in native insulin and the C-chain and peptide linker constant. Several of these insulin-Fc fusion proteins were manufactured in HEK293 cells according to Example 1 and purified using a Protein A column according to Example 3. Their structures were confirmed according to Example 4 by non-reducing and reducing CE-SDS, and the sequences were further identified by LC-MS with glycan removal according to Example 5. Their % homodimer content was measured by size-exclusion chromatography according to Example 6, and their insulin receptor binding affinities were measured according to Example 7. Their sequences are shown below, and the resulting sequence alignments against SEQ ID NO: 66 are shown in FIG. 12 (Clustal Omega).

(SEQ ID NO: 68)
FVNQHLCGSHLVQALYLVCGERGFFYTDPTGGGPRRGIVEQCCTSICSLYQ

LENYCGGGGAGGGGDCPKCPAPEMLGGPSVFIFPPKPKDTLLIARTPEVTC

VVVDLDPEDPEVQISWFVDGKQMQTAKTQPREEQFSGTYRVVSVLPIGHQD

WLKGKQFTCKVNNKALPSPIERTISKARGQAHQPSVYVLPPSREELSKNTV

SLTCLIKDFFPPDIDVEWQSNGQQEPESKYRTTPPQLDEDGSYFLYSKLSV

DKSRWQRGDTFICAVMHEALHNHYTQESLSHSPG (SEQ ID NO: 70)
FVNQHLCGSELVEALALVCGERGFFYTDPTGGGPRRGIVEQCCTSICSLYQ

LENYCGGGGAGGGGDCPKCPAPEMLGGPSVFIFPPKPKDTLLIARTPEVTC

VVVDLDPEDPEVQISWFVDGKQMQTAKTQPREEQFSGTYRVVSVLPIGHQD

WLKGKQFTCKVNNKALPSPIERTISKARGQAHQPSVYVLPPSREELSKNTV

SLTCLIKDFFPPDIDVEWQSNGQQEPESKYRTTPPQLDEDGSYFLYSKLSV

DKSRWQRGDTFICAVMHEALHNHYTQESLSHSPG (SEQ ID NO: 72)
FVNQHLCGSHLVEALALVCGEAGFFYTDPTGGGPRRGIVEQCCTSICSLYQ

LENYCGGGGAGGGGDCPKCPAPEMLGGPSVFIFPPKPKDTLLIARTPEVTC

VVVDLDPEDPEVQISWFVDGKQMQTAKTQPREEQFSGTYRVVSVLPIGHQD

WLKGKQFTCKVNNKALPSPIERTISKARGQAHQPSVYVLPPSREELSKNTV

SLTCLIKDFFPPDIDVEWQSNGQQEPESKYRTTPPQLDEDGSYFLYSKLSV

DKSRWQRGDTFICAVMHEALHNHYTQESLSHSPG (SEQ ID NO: 74)
FVNQHLCGSHLVEALALVCGERGFYYTDPTGGGPRRGIVEQCCTSICSLYQ

LENYCGGGGAGGGGDCPKCPAPEMLGGPSVFIFPPKPKDTLLIARTPEVTC

VVVDLDPEDPEVQISWFVDGKQMQTAKTQPREEQFSGTYRVVSVLPIGHQD

WLKGKQFTCKVNNKALPSPIERTISKARGQAHQPSVYVLPPSREELSKNTV

SLTCLIKDFFPPDIDVEWQSNGQQEPESKYRTTPPQLDEDGSYFLYSKLSV

DKSRWQRGDTFICAVMHEALHNHYTQESLSHSPG (SEQ ID NO: 76)
FVNQHLCGSHLVEALALVCGERGFFYTDPTGGGPRRGIVEQCCTSICSLYQ

LENYCGGGGAGGGGDCPKCPAPEMLGGPSVFIFPPKPKDTLLIARTPEVTC

VVVDLDPEDPEVQISWFVDGKQMQTAKTQPREEQFSGTYRVVSVLPIGHQD

WLKGKQFTCKVNNKALPSPIERTISKARGQAHQPSVYVLPPSREELSKNTV

SLTCLIKDFFPPDIDVEWQSNGQQEPESKYRTTPPQLDEDGSYFLYSKLSV

DKSRWQRGDTFICAVMHEALHNHYTQESLSHSPG

TABLE 9

% homodimer, homodimer titers, and IR IC50 values for various SEQ ID NOs.

| SEQ ID NO: | % Homodimer | HEK homodimer titer (mg/L) | IR IC50 (nM) |
| --- | --- | --- | --- |
| SEQ ID NO: 66 | 98.0% | 21 | >5000 |
| SEQ ID NO: 68 | 97.6% | 9 | 2624 |
| SEQ ID NO: 70 | 81.4% | 17 | 633 |
| SEQ ID NO: 72 | 99.1% | 22 | >5000 |
| SEQ ID NO: 74 | 96.6% | 25 | 2402 |
| SEQ ID NO: 76 | 98.0% | 6 | >5000 |

In only three cases (SEQ ID NOs: 68, 70, and 74 did the proposed mutations improve the IR binding (i.e., lower the IC50 value) as compared to SEQ ID NO: 66. However, none of the mutations resulted in compounds that meet the manufacturing design goal of a homodimer titer greater than 50 mg/L, and in some cases, the mutations lead to significantly reduced manufacturability (e.g., homodimer titers less than 20 mg/L).

Example 27: Attempts to Incorporate C-Chain Mutations into the Insulin Polypeptide of SEQ ID NO: 125 to Improve the Bioactivity of the Associated Insulin-Fc Fusion Proteins Containing the Canine IgGB Fc Fragment The results obtained in Example 26 showed that all attempts to mutate the A-chain and B-chain of the insulin polypeptide of SEQ ID NO: 125 resulted in unacceptably low HEK homodimer titers of the associated insulin-Fc fusion (i.e., homodimer titers less than or equal to 25 mg/L). Therefore, there was a need for further experimentation. In the present example, the C-chain composition of the insulin polypeptide of SEQ ID NO: 125 was mutated by making it longer or by increasing its flexibility. Native insulin (e.g., human insulin) has been shown to undergo a significant conformational change that involves movement of both the B-chain and A-chain folding as it binds to the insulin receptor (e.g., as described by Menting, et al., Nature, 2013; 493(7431): pp241-245). Native insulin, unlike the insulin polypeptides of the present invention, is freely able to undergo this conformational change at the insulin receptor, because it is a two-chain polypeptide in its native form, connected only through two disulfide bonds with no C-chain constraining the mobility of the A- and B-chains. Without being bound by any particular theory, it was hypothesized that the C-chain contained within the insulin polypeptide of SEQ ID NO: 125 was too inflexible (e.g. an amino acid composition and sequence that does not permit facile movement between the B-chain and A-chain) and/or too short (e.g. not enough amino acids between the C-terminus of the B-chain and the N-terminus of the A-chain) thus preventing the insulin polypeptide from undergoing the necessary change in molecular shape required for strong binding to the insulin receptor. Therefore, several insulin-Fc fusion proteins were synthesized based on the insulin-Fc fusion protein of SEQ ID NO: 66 with variations in the insulin polypeptide C-chain as shown below with the resulting sequence alignments against SEQ ID NO: 66 shown in FIG. 13 (Clustal Omega).

(SEQ ID NO: 78)
FVNQHLCGSHLVQALYLVCGERGFFYTDPTQRGGGGGQRGIVEQCCTSICS

LYQLENYCGGGGAGGGGDCPKCPAPEMLGGPSVFIFPPKPKDTLLIARTPE

VTCVVVDLDPEDPEVQISWFVDGKQMQTAKTQPREEQFSGTYRVVSVLPIG

HQDWLKGKQFTCKVNNKALPSPIERTISKARGQAHQPSVYVLPPSREELSK

NTVSLTCLIKDFFPPDIDVEWQSNGQQEPESKYRTTPPQLDEDGSYFLYSK

LSVDKSRWQRGDTFICAVMHEALHNHYTQESLSHSPG (SEQ ID NO: 80)
FVNQHLCGSHLVEALALVCGERGFFYTDPTGGGGGGSGGGGIVEQCCTSI

CSLYQLENYCGGGGAGGGGDCPKCPAPEMLGGPSVFIFPPKPKDTLLIART

PEVTCVVVDLDPEDPEVQISWFVDGKQMQTAKTQPREEQFSGTYRVVSVLP

IGHQDWLKGKQFTCKVNNKALPSPIERTISKARGQAHQPSVYVLPPSREEL

SKNTVSLTCLIKDFFPPDIDVEWQSNGQQEPESKYRTTPPQLDEDGSYFLY

SKLSVDKSRWQRGDTFICAVMHEALHNHYTQESLSHSPG (SEQ ID NO: 82)
FVNQHLCGSHLVEALALVCGERGFFYTDPGGGGGGGGGIVEQCCTSICSLY

QLENYCGGGGAGGGGDCPKCPAPEMLGGPSVFIFPPKPKDTLLIARTPEVT

CVVVDLDPEDPEVQISWFVDGKQMQTAKTQPREEQFSGTYRVVSVLPIGHQ

DWLKGKQFTCKVNNKALPSPIERTISKARGQAHQPSVYVLPPSREELSKNT

VSLTCLIKDFFPPDIDVEWQSNGQQEPESKYRTTPPQLDEDGSYFLYSKLS

VDKSRWQRGDTFICAVMHEALHNHYTQESLSHSPG (SEQ ID NO: 84)
FVNQHLCGSHLVEALALVCGERGFFYTPGGGGGGGGGIVEQCCTSICSLYQ

LENYCGGGGAGGGGDCPKCPAPEMLGGPSVFIFPPKPKDTLLIARTPEVTC

VVVDLDPEDPEVQISWFVDGKQMQTAKTQPREEQFSGTYRVVSVLPIGHQD

WLKGKQFTCKVNNKALPSPIERTISKARGQAHQPSVYVLPPSREELSKNTV

SLTCLIKDFFPPDIDVEWQSNGQQEPESKYRTTPPQLDEDGSYFLYSKLSV

DKSRWQRGDTFICAVMHEALHNHYTQESLSHSPG

TABLE 10

% homodimer, homodimer titers, and IR IC50 values for various SEQ ID NOs.

| SEQ ID NO: | % Homodimer | HEK homodimer titer (mg/L) | IR IC50 (nM) |
|---|---|---|---|
| SEQ ID NO: 66 | 98.0% | 21 | >5000 |
| SEQ ID NO: 78 | 94.0% | 8 | 4176 |
| SEQ ID NO: 80 | 99.6% | 37 | 1609 |
| SEQ ID NO: 82 | 98.3% | 42 | >5000 |
| SEQ ID NO: 84 | 98.6% | 33 | 4720 |

The insulin-Fc fusion proteins were manufactured in HEK293 cells according to Example 1 and purified using a Protein A column according to Example 3. Their structures were confirmed according to Example 4 by non-reducing and reducing CE-SDS, and the sequences were further identified by LC-MS with glycan removal according to Example 5. Their % homodimer content was measured by size-exclusion chromatography according to Example 6, and their insulin receptor binding affinities were measured according to Example 7. In only one case, (SEQ ID NO: 80) which comprises the longest C-chain (GGGGGGSGGGG—SEQ ID NO: 133), did a C-chain mutation significantly improve the insulin receptor binding affinity (IC50 less than 3000 nM) compared to that of the insulin-Fc fusion protein of SEQ ID NO: 66. However, none of these C-chain-mutated insulin-Fc fusion proteins exhibited a homodimer titer greater than the manufacturing design goal of 50 mg/L. In fact, in one case (SEQ ID NO: 78) the C-chain mutation unexpectedly led to significantly lower homodimer titers.

Example 28: Attempts to Incorporate Peptide Linker Mutations into Insulin-Fc Fusion Proteins Containing the Insulin Polypeptide of SEQ ID NO: 125 and the Canine IgGB Fc Fragment to Improve Bioactivity Without being bound by any particular theory, another possible reason for the poor insulin receptor binding of the insulin-Fc fusion protein of SEQ ID NO: 66 was thought to involve the steric hindrance between the insulin polypeptide and the insulin receptor resulting from the close proximity of the much larger Fc fragment molecule attached to the insulin polypeptide through the peptide linker. Shorter peptide linkers or more tightly folded peptide linkers were thought to potentially exacerbate this issue, while longer peptide linkers or peptide linkers that are resistant to folding back on themselves (e.g., linkers with more molecular stiffness) may alleviate this issue by creating more space between the insulin polypeptide and the Fc fragment. The increased space between the insulin polypeptide and the Fc fragment would also increase the distance between the insulin receptor and the Fc fragment leading to less interference during insulin receptor binding. The peptide linker of SEQ ID NO: 12 (i.e., GGGGAGGGG) used to construct the insulin-Fc fusion protein of SEQ ID NO: 66 was hypothesized to be potentially too short and/or too flexible, because the amino acids that comprise the linker contain no side chains (i.e., it contains only glycine and alanine amino acids). Therefore, to test this hypothesis, two other insulin-Fc fusion protein variants of the insulin-Fc fusion protein of SEQ ID NO: 66 were synthesized. The insulin-Fc fusion protein of SEQ ID NO: 76 contained the same peptide linker as was used to construct the insulin-Fc fusion protein of SEQ ID NO: 66 but with an insulin polypeptide in which the asparagine at the 21st position from the N-terminus of the A chain (i.e., A21) was absent (i.e., des-A21). This particular mutation was incorporated to see whether the junction between the A-chain and the peptide linker affects the protein yield and/or bioactivity of the molecule. The other insulin-Fc fusion protein of SEQ ID NO: 86 contains this des-A21N A-chain mutation and a peptide linker that is more than twice the length of that used to construct the insulin-Fc fusion protein of SEQ ID NO: 66. In this longer peptide linker, alanine is disfavored and instead is replaced with a glutamine, which contains a polar amide side chain. The glutamine substitutions were expected to increase the hydrophilic nature of the peptide linker and potentially prevent the linker from folding back against itself. The sequences are shown below with the resulting sequence alignments against SEQ ID NO: 66 shown in FIG. 14 (Clustal Omega).

(SEQ ID NO: 86)
FVNQHLCGSHLVEALALVCGERGFFYTDPTGGGPRRGIVEQCCTSICSLYQ

LENYCGGGGQGGGGQGGGGQGGGGGDCPKCPAPEMLGGPSVFIFPPKPKD

TLLIARTPEVTCVVVDLDPEDPEVQISWFVDGKQMQTAKTQPREEQFSGTY

RVVSVLPIGHQDWLKGKQFTCKVNNKALPSPIERTISKARGQAHQPSVYVL

PPSREELSKNTVSLTCLIKDFFPPDIDVEWQSNGQQEPESKYRTTPPQLDE

DGSYFLYSKLSVDKSRWQRGDTFICAVMHEALHNHYTQESLSHSPG (SEQ ID NO: 76)
FVNQHLCGSHLVEALALVCGERGFFYTDPTGGGPRRGIVEQCCTSICSLYQ

LENYCGGGGAGGGGDCPKCPAPEMLGGPSVFIFPPKPKDTLLIARTPEVTC

VVVDLDPEDPEVQISWFVDGKQMQTAKTQPREEQFSGTYRVVSVLPIGHQD

WLKGKQFTCKVNNKALPSPIERTISKARGQAHQPSVYVLPPSREELSKNTV

SLTCLIKDFFPPDIDVEWQSNGQQEPESKYRTTPPQLDEDGSYFLYSKLSV

DKSRWQRGDTFICAVMHEALHNHYTQESLSHSPG

TABLE 11

% homodimer, homodimer titers, and IR
IC50 values for various SEQ ID NOs.

| SEQ ID NO: | % Homodimer | HEK Homodimer titer (mg/L) | IR IC50 (nM) |
| --- | --- | --- | --- |
| SEQ ID NO: 66 | 98.0% | 21 | >5000 |
| SEQ ID NO: 76 | 98.0% | 6 | >5000 |
| SEQ ID NO: 86 | 99.6% | 11 | 1281 |

The two insulin-Fc fusion proteins were manufactured in HEK293 cells according to Example 1 and purified using a Protein A column according to Example 3. Their structures were confirmed according to Example 4 by non-reducing and reducing CE-SDS, and the sequences were further identified by LC-MS with glycan removal according to Example 5. Their % homodimer content was measured by size-exclusion chromatography according to Example 6, and their insulin receptor binding affinities were measured according to Example 7. The incorporation of a longer peptide linker of different composition (GGGGGQGGGGQGGGGQGGGGG (SEQ ID NO: 14) for SEQ ID NO: 86 vs. GGGGAGGGG (SEQ ID NO: 12) for SEQ ID NO: 66) did improve the insulin receptor binding as measured by a significant reduction in the IC50 value, indicating that longer linkers may be a strategy for increasing insulin receptor binding for other insulin-Fc fusion proteins. However, the incorporation of a longer linker still did not improve the homodimer titers to above the manufacturing design goal of greater than 50 mg/L.

Example 29: Attempts to Delete Portions of the B-Chain of the Insulin Polypeptide of SEQ ID NO: 125 to Improve the Homodimer Titer of the Associated Insulin-Fc Fusion Proteins Containing the Canine IgGB Fc Fragment The results from Example 28 demonstrate that the peptide linker can be modified to increase the insulin receptor binding affinity of the insulin-Fc fusion protein of SEQ ID NO: 66, which contains the native B10 and A8 amino acids. However, the peptide linker mutation failed to increase the homodimer titer enough to meet the manufacturing design goal. Because the homodimer titer is a function of several properties, including the intracellular synthesis and processing within cells, it was hypothesized that perhaps the insulin-Fc molecule was self-associating (i.e., aggregating) during and after synthesis either intramolecularly between the two monomers of the homodimer or intermolecularly between two or more separate homodimers. This aggregation would lead to unacceptably low homodimer titers obtained from the cell culture supernatants during the production process described in Examples 1, 3, and 6. This potential interaction between the insulin-Fc fusion protein molecules could be due, in part, to insulin's well-known propensity to self-associate and form aggregates. One method known in the art to reduce the propensity for insulin to self-associate involves mutating the amino acids near the C-terminus of the B-chain. For example, insulin lispro (B28K; B29P mutations) and insulin aspart (B28D mutation) are well-known commercial two-chain insulins with non-native B-chain mutations that prevent association and aggregation thus giving rise to a predominantly monomeric form of insulin in solution. Another approach to prevent aggregation involves amino acid structural deletions. For example, a two-chain insulin known as despentapeptide insulin (DPPI; see Brange J., Dodson G. G., Edwards J., Holden P. H., Whittingham J. L. 1997b. "A model of insulin fibrils derived from the x-ray crystal structure of a monomeric insulin (despentapeptide insulin)" Proteins 27 507-516), is identical to native two-chain human insulin except that the five C-terminal amino acids of the B-chain (YTPKT) are removed. DPPI has a lower binding affinity to the insulin receptor as compared to the native two-chain human insulin, but it is completely monomeric in solution, meaning that there is no significant association or aggregation between DPPI molecules. Therefore, in an attempt to decrease the potential for intramolecular and intermolecular self-association and improve the insulin-Fc fusion protein homodimer titer, several variants of the insulin-Fc fusion protein of SEQ ID NO: 66 were constructed using partial B-chain amino acid truncation and B-chain amino acid mutations as described above for DPPI, insulin lispro, and insulin aspart. The sequences are shown below with the resulting sequence alignments against SEQ ID NO: 66 shown in FIG. 15 (Clustal Omega).

(SEQ ID NO: 82)
FVNQHLCGSHLVEALALVCGERGFFYTDPGGGGGGGGGIVEQCCTSICSLY

QLENYCGGGGAGGGGDCPKCPAPEMLGGPSVFIFPPKPKDTLLIARTPEVT

CVVVDLDPEDPEVQISWFVDGKQMQTAKTQPREEQFSGTYRVVSVLPIGHQ

DWLKGKQFTCKVNNKALPSPIERTISKARGQAHQPSVYVLPPSREELSKNT

```
                                                        (SEQ ID NO: 84)
FVNQHLCGSHLVEALALVCGERGFFYTPGGGGGGGGIVEQCCTSICSLYQ

LENYCGGGGAGGGGDCPKCPAPEMLGGPSVFIFPPKPKDTLLIARTPEVTC

VVVDLDPEDPEVQISWFVDGKQMQTAKTQPREEQFSGTYRVVSVLPIGHQD

WLKGKQFTCKVNNKALPSPIERTISKARGQAHQPSVYVLPPSREELSKNTV

SLTCLIKDFFPPDIDVEWQSNGQQEPESKYRTTPPQLDEDGSYFLYSKLS

VDKSRWQRGDTFICAVMHEALHNHYTQESLSHSPG (SEQ ID NO: 84)
FVNQHLCGSHLVEALALVCGERGFFYTPGGGGGGGGIVEQCCTSICSLYQ

LENYCGGGGAGGGGDCPKCPAPEMLGGPSVFIFPPKPKDTLLIARTPEVTC

VVVDLDPEDPEVQISWFVDGKQMQTAKTQPREEQFSGTYRVVSVLPIGHQD

WLKGKQFTCKVNNKALPSPIERTISKARGQAHQPSVYVLPPSREELSKNTV

SLTCLIKDFFPPDIDVEWQSNGQQEPESKYRTTPPQLDEDGSYFLYSKLSV

DKSRWQRGDTFICAVMHEALHNHYTQESLSHSPG (SEQ ID NO: 88)
FVNQHLCGSHLVEALALVCGERGFFYTQGGGGGGGGIVEQCCTSICSLYQ

LENYCGGGGAGGGGDCPKCPAPEMLGGPSVFIFPPKPKDTLLIARTPEVTC

VVVDLDPEDPEVQISWFVDGKQMQTAKTQPREEQFSGTYRVVSVLPIGHQD

WLKGKQFTCKVNNKALPSPIERTISKARGQAHQPSVYVLPPSREELSKNTV

SLTCLIKDFFPPDIDVEWQSNGQQEPESKYRTTPPQLDEDGSYFLYSKLSV

DKSRWQRGDTFICAVMHEALHNHYTQESLSHSPG
```

TABLE 12

% homodimer, homodimer titers, and IR IC50 values for various SEQ ID NOs.

| SEQ ID NO: | % Homodimer | HEK Homodimer titer (mg/L) | IR IC50 (nM) |
| --- | --- | --- | --- |
| SEQ ID NO: 66 | 98.0% | 21 | >5000 |
| SEQ ID NO: 82 | 98.3% | 42 | 1915 |
| SEQ ID NO: 88 | 99.4% | 22 | 2195 |
| SEQ ID NO: 84 | 98.6% | 33 | 1930 |

The insulin-Fc fusion proteins were manufactured in HEK293 cells according to Example 1 and purified using a Protein A column according to Example 3. Their structures were confirmed according to Example 4 by non-reducing and reducing CE-SDS, and the sequences were further identified by LC-MS with glycan removal according to Example 5. Their % homodimer content was measured by size-exclusion chromatography according to Example 6, and their insulin receptor binding affinities were measured according to Example 7. The homodimer titer of the resulting compounds was only significantly increased in one case (SEQ ID NO: 82), but unexpectedly, the insulin receptor affinity was improved for all of the mutated compounds (SEQ ID NOs: 82, 88, and 84).

Example 30: Attempts to Combine B-Chain, C-Chain, and A-Chain Mutations, B-Chain Truncation, and Linker Mutations to the Insulin-Fc Fusion Protein of SEQ ID NO: 66 to Further Improve Homodimer Titer and Bioactivity As shown in Examples 26, 27, 28, and 29, no single strategy successfully incorporated an insulin polypeptide comprising the non-immunogenic native B10 and A8 amino acids with the canine IgGB Fc fragment to form an insulin-Fc fusion protein with acceptable insulin receptor activity and homodimer titer. Therefore, the concepts of a longer C-chain, a longer peptide linker, and truncation of the C-terminal amino acids of the B-chain were combined. In addition, to potentially further decrease the propensity for self-association and aggregation, additional point mutations were introduced to the native insulin hydrophobic amino acid residue sites using less hydrophobic amino acids, including those with side groups that are negatively or positively charged at physiological pH. Example mutations included tyrosine to alanine, tyrosine to glutamic acid, isoleucine to threonine, and phenylalanine to histidine. Furthermore, to simplify the analysis, in all cases the cNg site of the canine IgGB Fc fragment was restored to its native asparagine. The sequences for these insulin-Fc fusion protein variants are shown below with the resulting sequence alignments against SEQ ID NO: 66 shown in FIG. 16 (Clustal Omega).

```
                                                        (SEQ ID NO: 90)
FVNQHLCGSHLVEALELVCGERGFFYTPKTGGSGGGGIVEQCCTSTCSLDQLENYCGGGG

GQGGGGQGGGGQGGGGGDCPKCPAPEMLGGPSVFIFPPKPKDTLLIARTPEVTCVVVDLDP

EDPEVQISWFVDGKQMQTAKTQPREEQFNGTYRVVSVLPIGHQDWLKGKQFTCKVNNKA

LPSPIERTISKARGQAHQPSVYVLPPSREELSKNTVSLTCLIKDFFPPDIDVEWQSNGQQEPES

KYRTTPPQLDEDGSYFLYSKLSVDKSRWQRGDTFICAVMHEALHNHYTQESLSHSPG (SEQ ID NO: 92)
FVNQHLCGSHLVEALELVCGERGFHYGGGGGSGGGGIVEQCCTSTCSLDQLENYCNHG

GGGQGGGQGGGQGGGGDCPKCPAPEMLGGPSVFIFPPKPKDTLLIARTPEVTCVVVD

LDPEDPEVQISWFVDGKQMQTAKTQPREEQFNGTYRVVSVLPIGHQDWLKGKQFTCKVNN

KALPSPIERTISKARGQAHQPSVYVLPPSREELSKNTVSLTCLIKDFFPPDIDVEWQSNGQQE

PESKYRTTPPQLDEDGSYFLYSKLSVDKSRWQRGDTFICAVMHEALHNHYTQESLSHSPG (SEQ ID NO: 34)
FVNQHLCGSHLVEALELVCGERGFHYGGGGGSGGGGIVEQCCTSTCSLDQLENYCNGG

GGGQGGGQGGGQGGGGDCPKCPAPEMLGGPSVFIFPPKPKDTLLIARTPEVTCVVVD

LDPEDPEVQISWFVDGKQMQTAKTQPREEQFNGTYRVVSVLPIGHQDWLKGKQFTCKVNN
```

-continued

KALPSPIERTISKARGQAHQPSVYVLPPSREELSKNTVSLTCLIKDFFPPDIDVEWQSNGQQE

PESKYRTTPPQLDEDGSYFLYSKLSVDKSRWQRGDTFICAVMHEALHNHYTQESLSHSPG (SEQ ID NO: 32)
FVNQHLCGSHLVEALELVCGERGFHYGGGGGGSGGGGGIVEQCCTSTCSLDQLENYCGGG

GGQGGGGQGGGGQGGGGDCPKCPAPEMLGGPSVFIFPPKPKDTLLIARTPEVTCVVVDL

DPEDPEVQISWFVDGKQMQTAKTQPREEQFNGTYRVVSVLPIGHQDWLKGKQFTCKVNN

KALPSPIERTISKARGQAHQPSVYVLPPSREELSKNTVSLTCLIKDFFPPDIDVEWQSNGQQE

PESKYRTTPPQLDEDGSYFLYSKLSVDKSRWQRGDTFICAVMHEALHNHYTQESLSHSPG (SEQ ID NO: 94)
FVNQHLCGSHLVEALELVCGERGFFYGGGGGGSGGGGGIVEQCCTSTCSLDQLENYCGGG

GGQGGGGQGGGGQGGGGDCPKCPAPEMLGGPSVFIFPPKPKDTLLIARTPEVTCVVVDL

DPEDPEVQISWFVDGKQMQTAKTQPREEQFNGTYRVVSVLPIGHQDWLKGKQFTCKVNN

KALPSPIERTISKARGQAHQPSVYVLPPSREELSKNTVSLTCLIKDFFPPDIDVEWQSNGQQE

PESKYRTTPPQLDEDGSYFLYSKLSVDKSRWQRGDTFICAVMHEALHNHYTQESLSHSPG

TABLE 13

% homodimer, homodimer titers, and IR IC50 values for various SEQ ID NOs.

| SEQ ID NO: | % Homodimer | HEK homodimer titer (mg/L) | IR IC50 (nM) |
|---|---|---|---|
| SEQ ID NO: 66 | 98.0% | 21 | >5000 |
| SEQ ID NO: 90 | 97.9% | 69 | 3869 |
| SEQ ID NO: 92 | 99.5% | 101 | 554 |
| SEQ ID NO: 34 | 99.7% | 107 | 1247 |
| SEQ ID NO: 94 | 99.7% | 128 | 2043 |
| SEQ ID NO: 32 | 99.4% | 187 | 2339 |

The insulin-Fc fusion proteins were manufactured in HEK293 cells according to Example 1 and purified using a Protein A column according to Example 3. Their structures were confirmed according to Example 4 by non-reducing and reducing CE-SDS, and the sequences were further identified by LC-MS with glycan removal according to Example 5. Their % homodimer content was measured by size-exclusion chromatography according to Example 6, and their insulin receptor binding affinities were measured according to Example 7. The results show that a combination of decreasing the hydrophobicity of certain B-chain and A-chain amino acids, using longer and more flexible C-peptide sequences, truncating several C-terminal B-chain amino acids, and using a longer peptide linker resulted in several useful insulin-Fc fusion proteins that meet the minimum homodimer titer and insulin receptor binding activity design criteria. SEQ ID NOs: 92, 34, 32, and 94 (368d), (366d), (218d), and (375d) showed more preferable insulin receptor IC50 values (less than 3000 nM) and more preferable HEK homodimer titer values (greater than 100 mg/L) than either SEQ ID NO: 66 or SEQ ID NO: 90. Surprisingly, changing just a few amino acids leads to a multifold improvement in insulin receptor affinity, and, in the case of the insulin-Fc fusion protein of SEQ ID NO: 32 a dramatic increase in homodimer titer over the original insulin-Fc fusion protein of SEQ ID NO: 66.

Example 31: In Vivo Bioactivity, Repeated Dose Bioactivity, and Immunogenicity of Insulin-Fc Fusion Proteins Constructed from the Insulin Polypeptide of SEQ ID NO: 7, the Peptide Linker of SEQ ID NO: 14, and the Canine IgGB Fc Fragment of SEQ ID NO: 16

Given the positive homodimer titer and insulin receptor binding activity results from Example 30, two of the most promising insulin-Fc fusion proteins (SEQ ID NOs: 32 and 34) were tested in dogs to evaluate the repeated dose bioactivity and immunogenicity. Each compound comprises the longer, more hydrophilic peptide linker of SEQ ID NO: 14 and the more manufacturable, less aggregated canine IgGB Fc fragment of SEQ ID NO: 16. Most importantly, both insulin-Fc fusion proteins comprise insulin polypeptides with the putatively less immunogenic native B10 and A8 amino acids (i.e., general SEQ ID NO: 7). In the case of the insulin-Fc fusion protein of SEQ ID NO: 34, the asparagine at position A21 is present (i.e., the insulin polypeptide comprises SEQ ID NO: 9). In the case of the insulin-Fc fusion protein of SEQ ID NO: 32, the asparagine at position A21 is absent (i.e., the insulin polypeptide comprises SEQ ID NO: 8).

Figure 17:
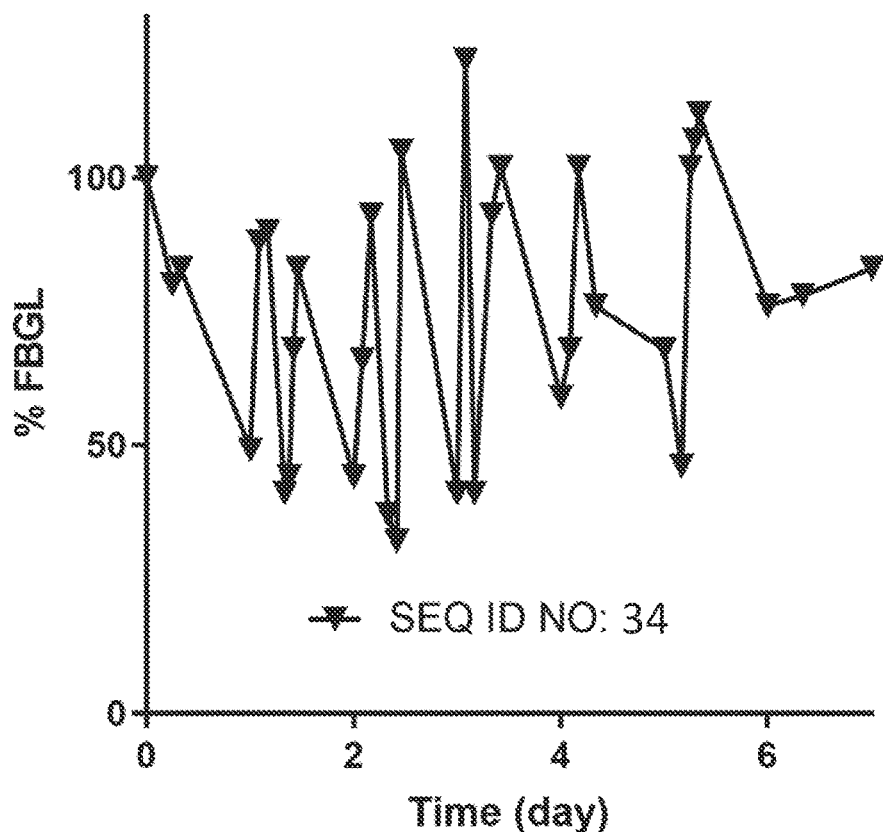
FIG. 17 shows % fasting blood glucose levels from Day 0 to Day 7 for N=1 dog dosed subcutaneously on Day 0 at 0.16 mg/kg with the homodimer of SEQ ID NO: 34.

The in vivo bioactivity of the insulin-Fc fusion protein of SEQ ID NO: 34 was tested in N=1 dog according to the procedure of Example 10. The results shown in FIG. 17 for a single subcutaneous dose demonstrate that the insulin-Fc fusion protein of SEQ ID NO: 34 is indeed bioactive in vivo with an NAOC of 1076% FBGL·days·kg/mg calculated according to the procedure in Example 11. The insulin-Fc fusion protein of SEQ ID NO: 34 pharmacokinetic profile was measured by the method of Example 12 using ELISA, and a two-compartment model was fit to the data to determine its elimination half-life which was 3.5 days.

The repeated dose bioactivity was then evaluated by continuing to subcutaneously administer the insulin-Fc fusion protein of SEQ ID NO: 34 to N=1 dog on day 14, day 28, and day 42 after the initial injection according to the procedure of Example 8. When the dog's % FBGL dropped too low, the dog was given food to raise the blood glucose to a safe level. The NAOC and NAOCR were measured for each subsequent dose according to the general procedure of Example 11, calculated from the time the dose was administered until just before the next dose was administered. The NAOC and the NAOCR shown in Table 14 illustrate that the insulin-Fc fusion protein of SEQ ID NO: 34 maintains an NAOCR greater than 0.8 throughout the four doses thus meeting the repeated dose bioactivity design goal.

TABLE 14

NAOC per dose for repeated doses of SEQ ID NO: 34

| Injection# | Day | NAOC (% FBGL · days · kg/mg) | NAOCR |
|---|---|---|---|
| 1 | 0 | 1076 | 1.0 |
| 2 | 14 | 1005 | 0.9 |
| 3 | 28 | 900 | 0.8 |
| 4 | 42 | 838 | 0.8 |

Figure 18:
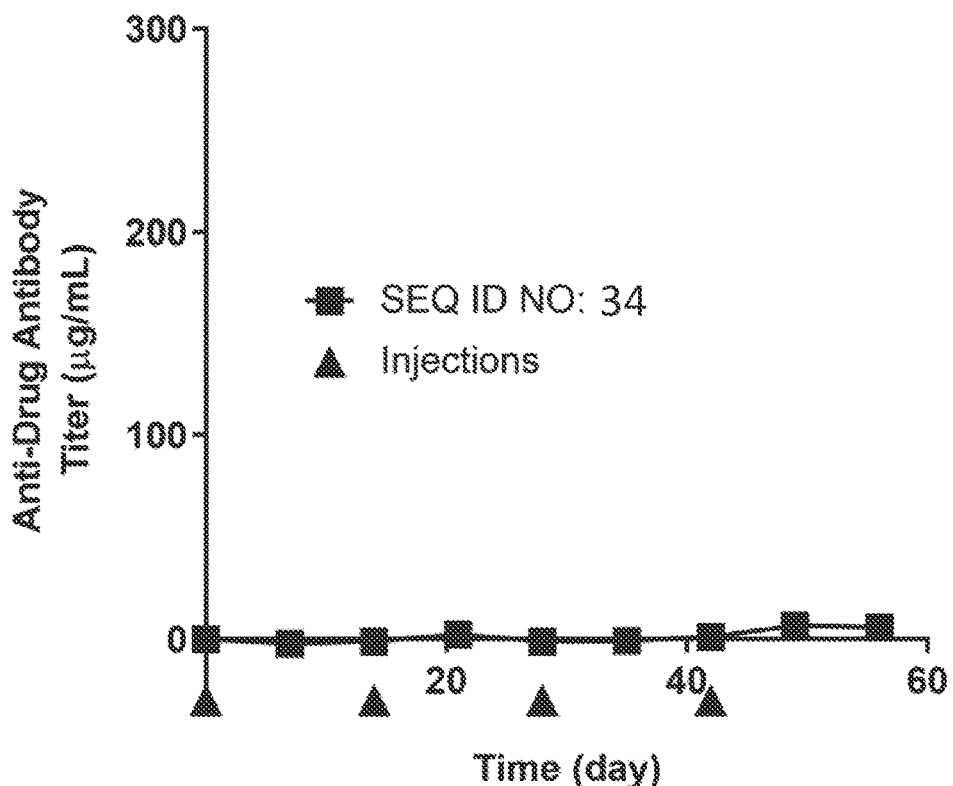
FIG. 18 shows the anti-drug antibody titer (µg/mL) for N=1 dog dosed subcutaneously on Day 0 (0.16 mg/kg), Day 14 (0.16 mg/kg), Day 28 (0.16 mg/kg), and Day 42 (0.16 mg/kg) with the homodimer of SEQ ID NO: 34.

The immunogenicity of the insulin-Fc fusion protein of SEQ ID NO: 34 was tested according to the procedure of Example 13. FIG. 18 demonstrates that the insulin-Fc fusion protein of SEQ ID NO: 34 exhibits no apparent immunogenicity in vivo in agreement with the maintenance of in vivo bioactivity throughout the repeated dose experiment.

Figure 19:
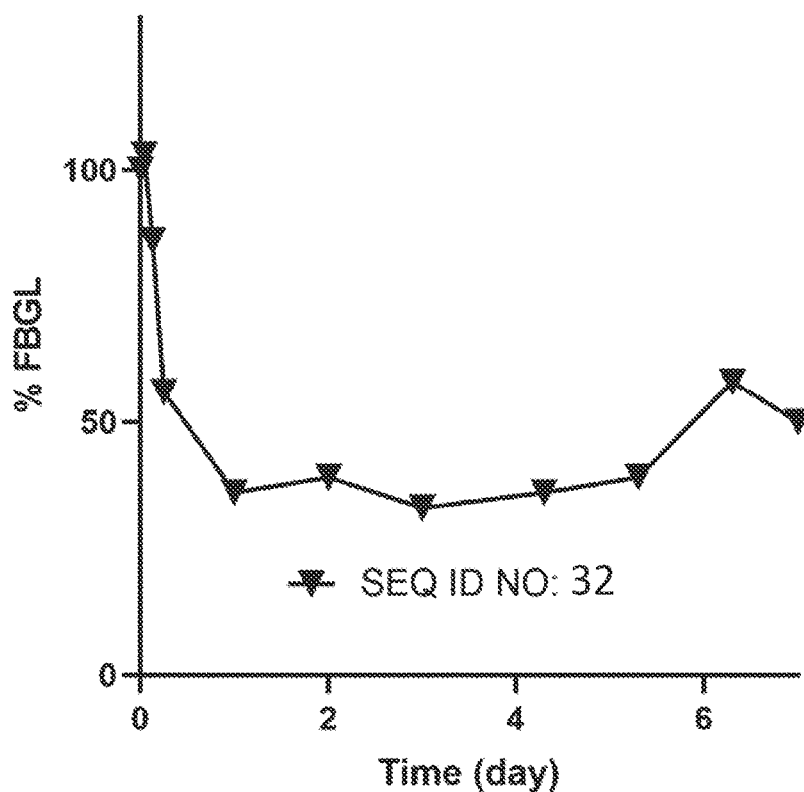
FIG. 19 shows % fasting blood glucose levels from Day 0 to Day 7 for N=1 dog dosed subcutaneously on Day 0 at 0.33 mg/kg with the homodimer of SEQ ID NO: 32.
Figure 20:
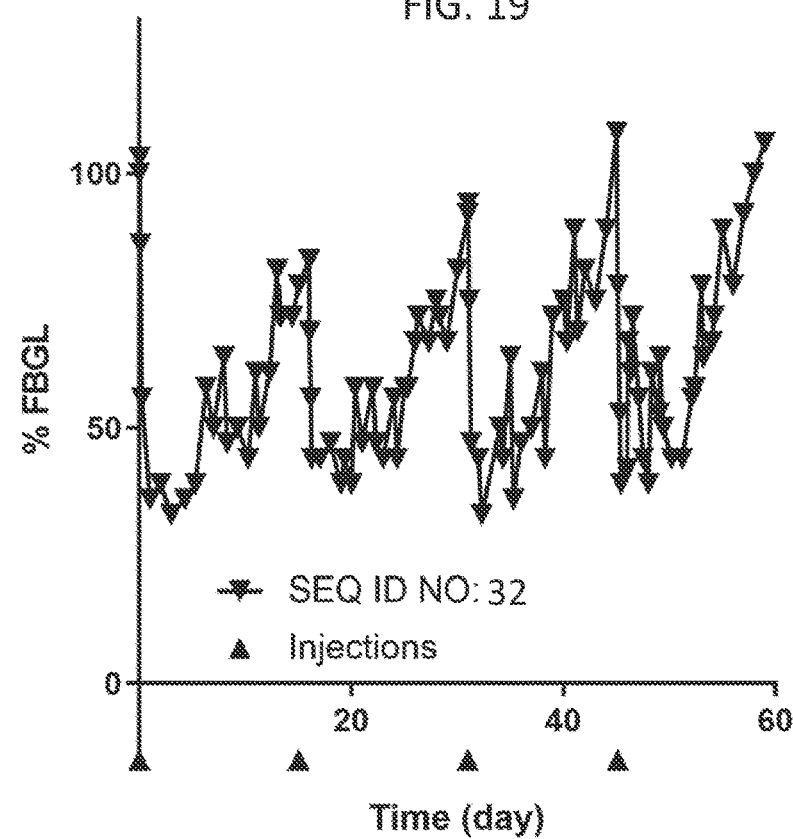
FIG. 20 shows % fasting blood glucose levels from Day 0 to Day 60 for N=1 dog dosed subcutaneously on Day 0 (0.33 mg/kg), Day 15 (0.16 mg/kg), Day 31 (0.16 mg/kg) and Day 45 (0.15 mg/kg) with the homodimer of SEQ ID NO: 32.

The insulin-Fc fusion protein of SEQ ID NO: 32, with the asparagine at A21 of the insulin polypeptide chain absent, was also evaluated for repeated dose bioactivity performance in dogs. The compound was administered subcutaneously to N=1 dog on day 0, day 14, day 28, and on day 42 according to the procedure of Example 11. When the dog's % FBGL dropped too low, the dog was given food to raise the blood glucose to a safe level. The NAOC for the first injection was an impressive 2278% FBGL·days·kg/mg, showing that the insulin-Fc fusion protein of SEQ ID NO: 32 was satisfactorily bioactive in vivo at almost twice the potency of the insulin-Fc fusion protein of SEQ ID NO: 34. The pharmacokinetic profile of the insulin-Fc fusion protein was measured by the method of Example 12 using ELISA, and a two-compartment model was fit to the data to determine its elimination half-life which was 4.1+0.7 days. FIGS. 19 and 20 show the single dose blood glucose control and the multidose, multiweek blood glucose control for animals receiving the homodimer of SEQ ID NO: 32. The NAOC and NAOCR were also measured for each subsequent dose according to the general procedure of Example 11, calculated from the time the dose was administered until just before the next dose was administered. The NAOC and the NAOCR shown in Table 15 illustrate that the insulin-Fc fusion protein of SEQ ID NO: 32 maintains an NAOCR greater than or equal to 1.0 throughout the four doses thus meeting the repeated dose bioactivity design goal described in Example 16.

Figure 21:
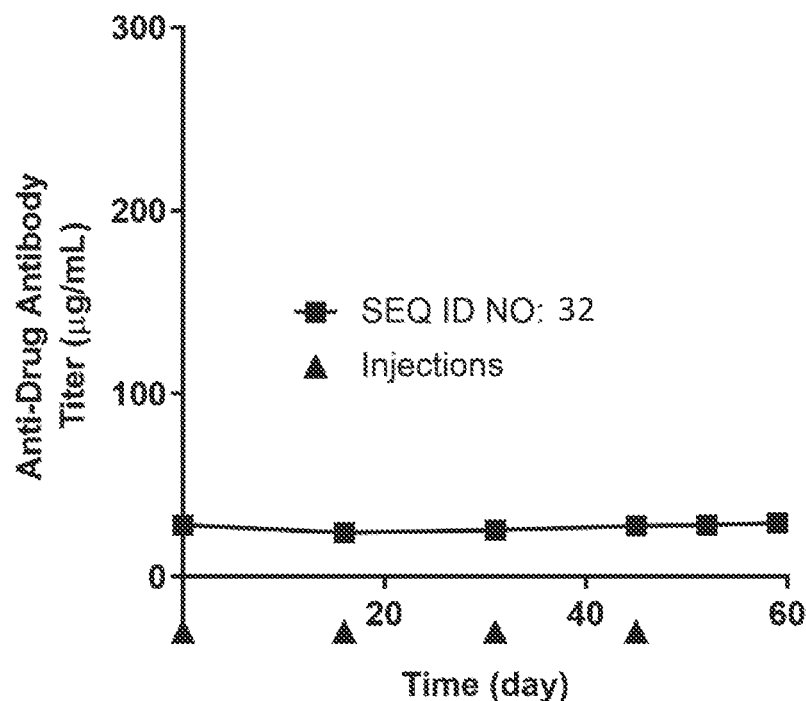
FIG. 21 shows the anti-drug antibody titer (µg/mL) for N=1 dogs dosed subcutaneously on Day 0 (0.33 mg/kg), Day 15 (0.16 mg/kg), Day 31 (0.16 mg/kg) and Day 45 (0.15 mg/kg) with the homodimer of SEQ ID NO: 32.

The immunogenicity of the insulin-Fc fusion protein of SEQ ID NO: 32 was tested according to the procedure of Example 13. FIG. 21 demonstrates that the insulin-Fc fusion protein of SEQ ID NO: 32 exhibits no apparent immunogenicity in vivo in agreement with the maintenance of in vivo bioactivity throughout the repeated dose experiment.

TABLE 15

NAOC per dose for repeated doses of SEQ ID NO: 32

| Injection# | Day | NAOC (% FBGL · days · kg/mg) | NAOCR |
|---|---|---|---|
| 1 | 0 | 2278 | 1.0 |
| 2 | 14 | 4029 | 1.8 |
| 3 | 28 | 3450 | 1.5 |
| 4 | 42 | 3257 | 1.4 |

As discussed in the Detailed Description of the invention, a known enzymatic cleavage site exists between asparagine-glycine bonds (Vlasak, J., Ionescu, R., (2011) MAbs Vol. 3, No. 3 pp 253-263). Omitting the asparagine at the 21st amino acid in the A chain (i.e., A21) in the insulin polypeptide of SEQ ID NO: 8 contained in the insulin-Fc fusion protein of SEQ ID NO: 32 with the peptide linker of SEQ ID NO: 14, eliminates the possibility of enzymatic cleavage of the asparagine-glycine bond between the C-terminus of the A-chain and the N-terminus of the peptide linker. However, the insulin-Fc fusion protein of SEQ ID NO: 34 comprises the peptide linker of SEQ ID NO: 14 and the insulin polypeptide of SEQ ID NO: 8, which keeps the asparagine at A21. Therefore, it would have been expected that the insulin-Fc fusion protein of SEQ ID NO: 34 would have been enzymatically digested during synthesis or in vivo following subcutaneous administration. However, rather unexpectedly the insulin-Fc fusion protein of SEQ ID NO: 34 was manufacturable in HEK cells with an acceptable homodimer titer and demonstrated acceptable bioactivity in vivo with no signs of enzymatic digestion compromising its bioactivity.

Example 32: Confirmation of the Canine IgGB Isotype Fc Fragment for Optimal Manufacturability and In Vivo Efficacy of Insulin-Fc Fusion Proteins Comprising the Preferred Insulin Polypeptide of SEQ ID NO: 8 and the Preferred Peptide Linker of SEQ ID NO: 14

Having discovered a new insulin polypeptide and peptide linker combination resulting in non-immunogenic, high yielding, high purity, and highly bioactive insulin-Fc fusion proteins as described in Examples 30 and 31, a question remained as to whether the canine IgGB Fc fragment was still the preferred isotype with respect to homodimer titer and bioactivity as was the case for the insulin-Fc fusion proteins in Examples 19 and 20. Therefore, additional insulin-Fc fusion proteins were designed wherein the insulin polypeptide (SEQ ID NO: 8) and peptide linker (SEQ ID NO: 14) of the insulin-Fc fusion protein of SEQ ID NO: 32 were kept constant, and the canine IgGB Fc fragment of SEQ ID NO: 16 was replaced by the canine IgGA Fc fragment of SEQ ID NO: 15, the canine IgGC Fc fragment of SEQ ID NO: 17, or the canine IgGD Fc fragment of SEQ ID NO: 18. The sequences for these resulting insulin-Fc fusion protein variants are shown below:

(SEQ ID NO: 32)
FVNQHLCGSHLVEALELVCGERGFHYGGGGGSGGGGGIVEQCCTSTCSLDQLENYCGGG

GGQGGGGQGGGGQGGGGGDCPKCPAPEMLGGPSVFIFPPKPKDTLLIARTPEVTCVVVDL

DPEDPEVQISWFVDGKQMQTAKTQPREEQFNGTYRVVSVLPIGHQDWLKGKQFTCKVNN

KALPSPIERTISKARGQAHQPSVYVLPPSREELSKNTVSLTCLIKDFFPPDIDVEWQSNGQQE

PESKYRTTPPQLDEDGSYFLYSKLSVDKSRWQRGDTFICAVMHEALHNHYTQESLSHSPG (SEQ ID NO: 96)
FVNQHLCGSHLVEALELVCGERGFHYGGGGGSGGGGGIVEQCCTSTCSLDQLENYCGGG

GGQGGGGQGGGGQGGGGGRCTDTPPCPVPEPLGGPSVLIFPPKPKDILRITRTPEVTCVVLD

LGREDPEVQISWFVDGKEVHTAKTQSREQQFNGTYRVVSVLPIEHQDWLTGKEFKCRVNHI

DLPSPIERTISKARGRAHKPSVYVLPPSPKELSSSDTVSITCLIKDFYPPDIDVEWQSNGQQEP

ERKHRMTPPQLDEDGSYFLYSKLSVDKSRWQQGDPFTCAVMHETLQNHYTDLSLSHSPG (SEQ ID NO: 98)
FVNQHLCGSHLVEALELVCGERGFHYGGGGGSGGGGGIVEQCCTSTCSLDQLENYCGGG

GGQGGGGQGGGGQGGGGGCNNCPCPGCGLLGGPSVFIFPPKPKDILVTARTPTVTCVVVD

LDPENPEVQISWFVDSKQVQTANTQPREEQSNGTYRVVSVLPIGHQDWLSGKQFKCKVNN

KALPSPIEEIISKTPGQAHQPNVYVLPPSRDEMSKNTVTLTCLVKDFFPPEIDVEWQSNGQQE

PESKYRMTPPQLDEDGSYFLYSKLSVDKSRWQRGDTFICAVMHEALHNHYTQISLSHSPG (SEQ ID NO: 100)
FVNQHLCGSHLVEALELVCGERGFHYGGGGGSGGGGGIVEQCCTSTCSLDQLENYCGGG

GGQGGGGQGGGGQGGGGGCISPCPVPESLGGPSVFIFPPKPKDILRITRTPEITCVVLDLGRE

DPEVQISWFVDGKEVHTAKTQPREQQFNSTYRVVSVLPIEHQDWLTGKEFKCRVNHIGLPS

PIERTISKARGQAHQPSVYVLPPSPKELSSSDTVTLTCLIKDFFPPEIDVEWQSNGQPEPESKY

HTTAPQLDEDGSYFLYSKLSVDKSRWQQGDTFTCAVMHEALQNHYTDLSLSHSPG

The insulin-Fc fusion proteins were manufactured in HEK293 cells according to Example 1 and purified using a Protein A or Protein G columns according to Example 3. Their structures were confirmed according to Example 4 by non-reducing and reducing CE-SDS, and the sequences were further identified by LC-MS with glycan removal according to Example 5. Their % homodimer content was measured by size-exclusion chromatography according to Example 6, and their insulin receptor binding affinities were measured according to Example 7. Additionally, the insulin-Fc fusion protein affinities for the canine FcRn receptor were measured according to Example 8. As is shown in Table 16, the insulin-Fc fusion protein of SEQ ID NO: 32 comprising the canine IgGB Fc fragment demonstrated the highest homodimer titer of these sequences. The insulin-Fc fusion protein of SEQ ID NO: 96 comprising the canine IgGA Fc fragment exhibited poor homodimer titer when purified using a Protein A column; however, when it purified using a Protein G column, the homodimer titer was significantly improved, exceeding the design goal of greater than 50 mg/L. The same was true for the insulin-Fc fusion protein of SEQ ID NO: 98 comprising the canine IgGC Fc fragment. The insulin-Fc fusion protein of SEQ ID NO: 100 comprising the canine IgGD Fc fragment did not yield any compound when purified with either a Protein A or a Protein G column. Therefore, as was demonstrated with the insulin-Fc fusion protein of SEQ ID NO: 52 containing a different insulin polypeptide (SEQ ID NO: 5 and peptide linker (SEQ ID NO: 12), the canine IgGB was the preferred Fc fragment with respect to homodimer titer (see Example 19).

TABLE 16

Homodimer titers, IR binding, and FcRn binding for sequences utilizing native canine IgGA, IgGB, IgGC, and IgGD Fc fragments

| SEQ ID NO: | Fc Fragment IgG Isotype | Protein Yield Protein A/ (Protein G) mg/L) | % Homo-dimer Protein A/ (Protein G) | Homo-dimer Titer (mg/L) | IR Binding, IC50 (nM) | FcRn Binding, EC50 (ng/mL) | First dose NAOC (% FBGL · days · kg/mg) |
|---|---|---|---|---|---|---|---|
| SEQ ID NO: 32 | IgGB | 187/(DNM) | 99%/(DNM) | 185 | 2339 | 599 | 2278 |
| SEQ ID NO: 96 | IgGA | 10/(69) | 45%/(91%) | 62‡ | 2586# | 1610 | 174 |

TABLE 16-continued

Homodimer titers, IR binding, and FcRn binding for sequences utilizing native canine IgGA, IgGB, IgGC, and IgGD Fc fragments

| SEQ ID NO: | Fc Fragment IgG Isotype | Protein Yield Protein A/ (Protein G) mg/L) | % Homo-dimer Protein A/ (Protein G) | Homo-dimer Titer (mg/L) | IR Binding, IC50 (nM) | FcRn Binding, EC50 (ng/mL) | First dose NAOC (% FBGL · days · kg/mg) |
|---|---|---|---|---|---|---|---|
| SEQ ID NO: 98 | IgGC | 0/(86) | 0%/(94%) | 81‡ | 2084‡ | >200000 | 39 |
| SEQ ID NO: 100 | IgGD | 0/(0) | (DNM)/(DNM) | 0 | DNM | DNM | DNM |

DNM = did not measure;
# = purified via Protein A;
‡ = purified by Protein G.

Figure 22:
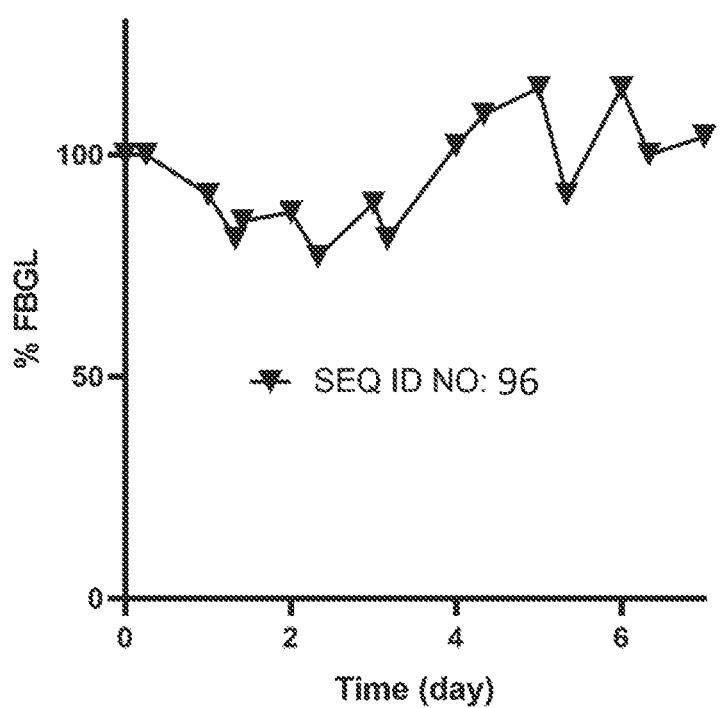
FIG. 22 shows % fasting blood glucose levels from Day 0 to Day 7 for N=1 dog dosed subcutaneously on Day 0 at 0.16 mg/kg with the homodimer of SEQ ID NO: 96.

The in vivo bioactivity of the insulin-Fc fusion protein of SEQ ID NO: 96 comprising the canine IgGA Fc fragment that was purified via Protein G was tested according to the procedure of Example 10. The results illustrated in FIG. 22 show that the insulin-Fc fusion protein of SEQ ID NO: 96 is only somewhat bioactive in vivo with a NAOC of only 174% FBGL·days·kg/mg calculated according to Example 11.

The in vivo bioactivity of the insulin-Fc fusion protein of SEQ ID NO: 98 comprising the canine IgGC Fc fragment was purified via Protein G tested according to the procedure of Example 10. The results illustrated in FIG. 23 show that the insulin-Fc fusion protein of SEQ ID NO: 98 is only somewhat bioactive in vivo with a NAOC of only 39% FBGL·days·kg/mg calculated according to Example 11.

Therefore, as was demonstrated with the insulin-Fc fusion protein of SEQ ID NO: 52 containing a different insulin polypeptide (SEQ ID NO: 5) and peptide linker (SEQ ID NO: 12), the canine IgGB was the preferred Fc fragment with respect to bioactivity (see Examples 19 and 20 and Table 16 above).

Example 33: Non-Glycosylated Insulin-Fc Fusion Proteins Comprising the Insulin Polypeptide of SEQ ID NO: 8, the Peptide Linker of SEQ ID NO: 14, and the Canine IgGB Fc Fragment to Reduce the Potential Risk of Immunogenicity While the insulin-Fc fusion protein of SEQ ID NO: 32 meets all of the design goals (Example 16), there may or may not be a risk of immunogenicity over extended periods of treatment (e.g., 6 months, 1 year, 2 years or more) which could compromise the use of this insulin-Fc fusion protein for treating diabetes should this occur. As described in the Detailed Description of the Invention and in Examples 21 and 22, one possible cause of a reduction in bioactivity after repeated doses is the unwanted interaction of the canine IgGB Fc fragment with the dog's immune system resulting in the production of neutralizing anti-drug antibodies. However, the results shown in Example 32 demonstrate that unexpectedly, the canine IgGB isotype was the only option of the four canine IgG isotypes that yielded the desired manufacturability and bioactivity. Therefore, further Fc mutations were explored to achieve non-glycosylated insulin-Fc fusion proteins with low Fc(gamma)RI receptor binding, which should reduce the long-term, chronic immunogenicity risk.

As described in the Detailed Description of the Invention, one method for reducing the Fc(gamma)RI interaction involves mutating the Fc fragment cNg site to prevent glycosylation during synthesis in the host cell. Therefore, cNg site mutations were made to the Fc fragment region of SEQ ID NO: 32 to reduce the binding affinity of the Fc fragment for Fc(gamma) receptors in vivo, as measured by binding in an in vitro human Fc(gamma)RI assay described in Example 8. The position of the cNg site in the insulin-Fc fusion protein of SEQ ID NO: 32 is cNg-NB151. Mutations to SEQ ID NO: 32 included SEQ ID NO: 104 comprising a cNg-NB151-S mutation and SEQ ID NO: 102 comprising the same cNg-NB151-S mutation as well as a NB119-A mutation. The NB119-A was incorporated in a further attempt to reduce the interaction with Fc(gamma)RI as has been described only for use in mouse antibodies by Lo, M. et al. "Effector attenuating substitutions that maintain antibody stability and reduce toxicity in mice", J. Biol. Chem. (2017), pp. 1-20. The full amino acid sequences of the resulting insulin-Fc fusion proteins are listed below (NB119 and NB151 sites bolded for clarity) along with their sequence alignments (Clustal Omega) which are shown in FIG. 24:

(SEQ ID NO: 102)
FVNQHLCGSHLVEALELVCGERGFHYGGGGGSGGGGGIVEQCC

TSTCSLDQLENYCGGGGGQGGGGQGGGGQGGGGGDCPKCPAPEM

LGGPSVFIFPPKPKDTLLIARTPEVTCVVVALDPEDPEVQISWF

VDGKQMQTAKTQPREEQFSGTYRVVSVLPIGHQDWLKGKQFTCK

VNNKALPSPIERTISKARGQAHQPSVYVLPPSREELSKNTVSLT

CLIKDFFPPDIDVEWQSNGQQEPESKYRTTPPQLDEDGSYFLYS

KLSVDKSRWQRGDTFICAVMHEALHNHYTQESLSHSPG (SEQ ID NO: 104)
FVNQHLCGSHLVEALELVCGERGFHYGGGGGSGGGGGIVEQCC

TSTCSLDQLENYCGGGGGQGGGGQGGGGQGGGGGDCPKCPAPEM

LGGPSVFIFPPKPKDTLLIARTPEVTCVVVDLDPEDPEVQISWF

VDGKQMQTAKTQPREEQFSGTYRVVSVLPIGHQDWLKGKQFTCK

VNNKALPSPIERTISKARGQAHQPSVYVLPPSREELSKNTVSLT

CLIKDFFPPDIDVEWQSNGQQEPESKYRTTPPQLDEDGSYFLYS

KLSVDKSRWQRGDTFICAVMHEALHNHYTQESLSHSPG

The insulin-Fc fusion proteins were manufactured in HEK293 cells according to Example 1 and purified using a Protein A column according to Example 3. Their structures were confirmed according to Example 4 by non-reducing and reducing CE-SDS, and the sequences were further identified by LC-MS with glycan removal according to Example 5. Their % homodimer content was measured by size-exclusion chromatography according to Example 6, and their insulin receptor binding affinities were measured according to Example 7. As shown in Table 17, incorporating the cNg-NB151-S mutations on the Fc fragment decreased the % homodimer, indicating an unacceptably high level of aggregation (i.e., the % homodimer dropped to just above 70%).

days. The sequence of SEQ ID NO: 36 is shown below (B16A and cNg-NB151-S mutations bolded for clarity).

(SEQ ID NO: 36)
FVNQHLCGSHLVEALALVCGERGFHYGGGGGSGGGGGIVEQCCTSTCS

LDQLENYCGGGGGQGGGGQGGGGQGGGGDCPKCPAPEMLGGPSVFIFP

TABLE 17

Homodimer titers for non-glycosylated insulin-Fc fusion proteins of SEQ ID NO: 102 and 104

| SEQ ID NO: | IgG Fragment | Relevant Mutations | Protein Yield (mg/L) | % Homodimer | % Homodimer Titer (mg/L) | IR Binding, IC50 (nM) |
|---|---|---|---|---|---|---|
| SEQ ID NO: 32 | IgGB | cNg-NB-151-N | 187 | 99% | 185 | 2339 |
| SEQ ID NO: 102 | IgGB | cNg-NB-151-S, NB119-A | 78 | 73% | 57 | 3093 |
| SEQ ID NO: 104 | IgGB | cNg-NB151-S | 130 | 71% | 93 | 2302 |

Figure 25:
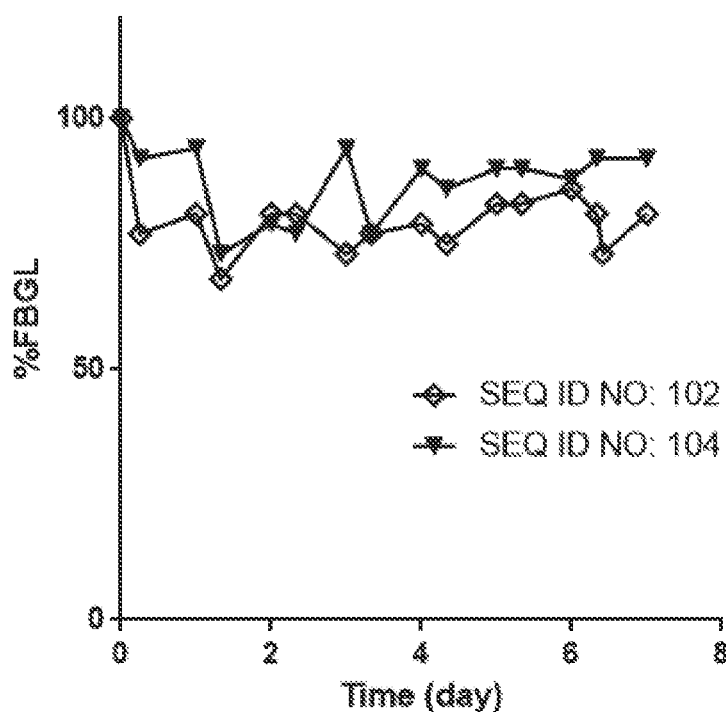
FIG. 25 shows % fasting blood glucose levels from Day 0 to Day 7 for N=1 dog dosed subcutaneously on Day 0 at 0.16 mg/kg with the homodimer of SEQ ID NO: 102, and % fasting blood glucose levels from Day 0 to Day 7 for N=1 dog dosed subcutaneously on Day 0 at 0.16 mg/kg with the homodimer of SEQ ID NO: 104.

The in vivo bioactivity of the insulin-Fc fusion proteins of SEQ ID NO: 102 and SEQ ID NO: 104 were tested in N=1 dog each according to the procedure of Example 10. The results shown in FIG. 25 for a single subcutaneous dose demonstrate that both compounds were significantly less bioactive in vivo than the insulin-Fc fusion protein of SEQ ID NO: 32 (NAOC for SEQ ID NO: 104=574% FBGL-days-kg/mg; NAOC for SEQ ID NO: 102=921% FBGL-days-kg/mg). The results indicate that incorporating cNg-NB151-S mutations on the Fc fragment to produce non-glycosylated versions of the insulin-Fc fusion protein of SEQ ID NO: 32 unexpectedly decreased the in vivo bioactivity of the resulting compounds.

In an attempt to lessen the degree of aggregation and improve the bioactivity of the insulin-Fc fusion protein of SEQ ID NO: 104 containing the cNg-NB151-S site mutation, various insulin-polypeptide B-chain variants were investigated with mutations in the region thought to be responsible for aggregation. The insulin-Fc fusion proteins were manufactured in HEK293 cells according to Example 1 and purified using a Protein A column according to Example 3. Their structures were confirmed according to Example 4 by non-reducing and reducing CE-SDS, and the sequences were further identified by LC-MS with glycan removal according to Example 5. Their % homodimer content was measured by size-exclusion chromatography according to Example 6. Among the B-chain variants tested, one insulin Fc-fusion protein (SEQ ID NO: 36) containing a tyrosine to alanine substitution at the 16$^{th}$ amino acid from the N-terminus of the B-chain (i.e., B16) was unexpectedly found to have high homodimer titers (105 mg/L) with low aggregation (99% homodimer), resulting in a homodimer titer of 104 mg/L. The insulin receptor binding measured according to Example 7 was acceptable with an IC50 of 2040 nM. The FcRn receptor binding affinity EC50 value measured according to Example 9 was 1194 ng/mL. The pharmacokinetic profile of the insulin-Fc fusion protein of SEQ ID NO: 36 was measured by the method of Example 12 using ELISA, and a two-compartment model was fit to the data to determine its elimination half-life which was 4.1±0.7

-continued
PKPKDTLLIARTPEVTCVVVDLDPEDPEVQISWFVDGKQMQTAKTQPRE

EQFSGTYRVVSVLPIGHQDWLKGKQFTCKVNNKALPSPIERTISKARGQ

AHQPSVYVLPPSREELSKNTVSLTCLIKDFFPPDIDVEWQSNGQQEPES

KYRTTPPQLDEDGSYFLYSKLSVDKSRWQRGDTFICAVMHEALHNHYTQ

ESLSHSPG

Figure 26:
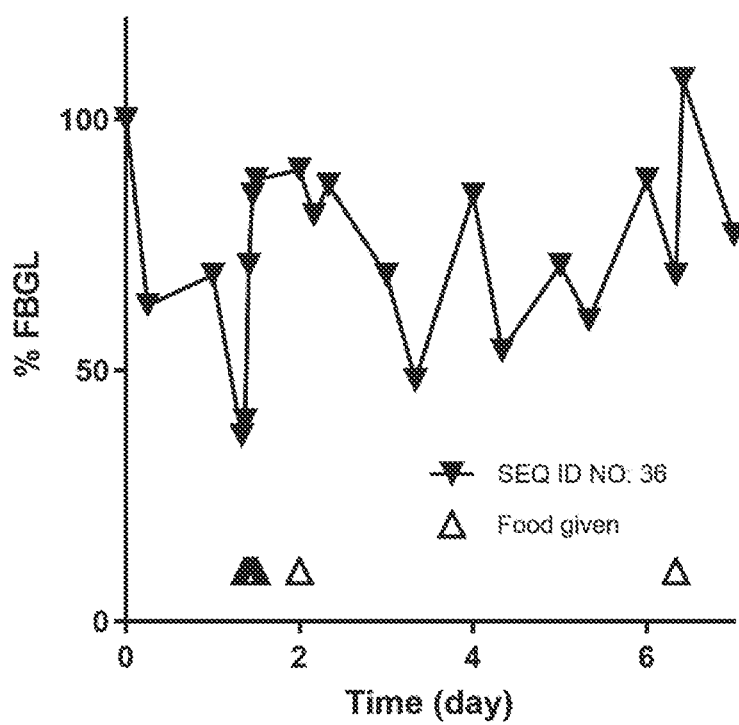
FIG. 26 shows % fasting blood glucose levels from Day 0 to Day 7 for N=1 dog dosed subcutaneously c with the homodimer of SEQ ID NO: 36 in addition to the times that the dog was given food.

The insulin-Fc fusion protein of SEQ ID NO: 36 was then evaluated for repeated dose bioactivity performance in dogs. The compound was administered subcutaneously to N=1 dog on day 0, day 7, day 14, and on day 28 according to the procedure of Example 11. When the dog's % FBGL dropped too low, the dog was given food to raise the blood glucose to a safe level. Unexpectedly, compared to the insulin-Fc fusion protein of SEQ ID NO: 104, the NAOC for the first injection of the insulin-Fc fusion protein of SEQ ID NO: 36 containing the B16A mutation, was significantly higher (1185% FBGL-days-kg/mg). The first dose in vivo bioactivity plot is shown in FIG. 26. The pharmacokinetic profile of the compound was also measured by the method of Example 12 using ELISA, and a two-compartment model was fit to the data to determine its elimination half-life which was 3.5 days. The NAOC and NAOCR were also measured for each subsequent dose according to the general procedure of Example 11, calculated from the time the dose was administered until just before the next dose was administered. The NAOC and the NAOCR shown in Table 18 illustrate that the insulin-Fc fusion protein of SEQ ID NO: 36 maintains an NAOCR greater than or equal to 0.6 throughout the four doses thus meeting the repeated dose bioactivity design goal. Taken together, the results indicate that it was necessary to mutate the insulin B-chain sequence to obtain a suitable, non-glycosylated cNg-S variant of SEQ ID NO: 32. Therefore, the insulin polypeptide of SEQ ID NO: 11 was preferred for non-glycosylated insulin-Fc fusion proteins comprising cNg-mutated canine IgGB Fc fragments.

TABLE 18

NAOC per dose for repeated doses of SEQ ID NO: 36

| Injection# | Day | NAOC (% FBGL · days · kg/mg) | NAOCR |
|---|---|---|---|
| 1 | 0 | 1185 | 1.0 |
| 2 | 7 | 954 | 0.8 |
| 3 | 14 | 764 | 0.6 |
| 4 | 28 | 991 | 0.8 |

Finally, select compounds were tested for their likelihood to interact with the immune system by measuring their Fc(gamma) receptor binding activity according to the procedure of Example 8. Table 19 compares the Fc(gamma) receptor I binding of these insulin-Fc fusion proteins with the Fc(gamma) receptor binding of the insulin-Fc fusion protein of SEQ ID NO: 52. It can be seen that the non-glycosylated insulin-Fc fusion proteins (achieved through a cNg-S mutation) exhibited the lowest Fc(gamma) receptor binding ratio to SEQ ID NO: 52.

TABLE 19

Fc(gamma) receptor binding for cNg variations of SEQ ID NO: 52

| SEQ ID NO: | Species / Fc Isotype | Glycosylation Mutation | OD450 nm at a Fc(gamma) RI concentration of 3000 (ng/mL) | OD450 nm Minus Assay Background | Ratio to SEQ ID NO: 52 |
|---|---|---|---|---|---|
| SEQ ID NO: 52 | Canine / IgGB | Native cNg | 0.428 | 0.371 | 1.00 |
| SEQ ID NO: 32 | Canine / IgGB | Native cNg | 0.368 | 0.311 | 0.84 |
| SEQ ID NO: 96 | Canine / IgGA | Native cNg | 0.253 | 0.196 | 0.53 |
| SEQ ID NO: 104 | Canine / IgGB | cNg-S | 0.175 | 0.118 | 0.32 |
| SEQ ID NO: 102 | Canine / IgGB | cNg-S and NB119-A | 0.166 | 0.109 | 0.29 |
| SEQ ID NO: 36 | Canine / IgGB | cNg-S and B16A | 0.177 | 0.120 | 0.32 |

Example 34: Exemplary CHO-Based Production Runs Using Preferred Insulin-Fc Fusion Proteins Comprising Fc Fragments of Canine IgGB Origin Made Via Stably Transfected CHO Cell Lines Separate CHO cell lines stably transfected with vectors encoding for SEQ TD NO: 32, or SEQ ID NO: 36 were constructed as described in Example 2. Fed-batch shake flask 14-day production runs (0.5-2.0 L media scale) were seeded at 0.5 million cells/mL in an incubator-shaker set at 37° C. and 5% carbon dioxide, and the runs were conducted as described in Example 2 above, except that CD OptiCHO was substituted for Dynamis as the growth media (ThermoFisher) and Efficient Feed C (ThermoFisher) was used as the feed. Feed was added at 3% v/v starting on production run day 3, and on day 4, the shake-flask temperature was adjusted to 32° C. and the incubator-shaker carbon dioxide concentration was lowered from 5% to 2%. During the run, the cells increased to between 8-14 million cells/mL, and on Day 14 the production run was harvested to remove the cells and the culture supernatant was purified and tested to obtain the insulin-Fc fusion protein as described in Examples 3, 4, 5, and 6. Table 20 describes the manufacturing data obtained from the production runs with stably transfected CHO cell lines.

TABLE 20

Homodimer titers for non-glycosylated insulin-Fc fusion proteins of SEQ ID NO: 32 and SEQ ID NO: 36

| SEQ ID NO: | Protein Yield (mg/L) | % Homodimer | Homodimer Titer (mg/L) |
|---|---|---|---|
| SEQ ID NO: 32 | 485 | 99.3% | 482 |
| SEQ ID NO: 36 | 260 | 99.0% | 257 |

Example 35: Exemplary CHO-Based Production Runs Using Preferred Insulin-Fc Fusion Proteins Comprising Fc Fragments of Canine IgGB Origin Made Via Stably Transfected CHO Cell Lines A CHO cell line stably transfected with vectors encoding for SEQ ID NO: 34 is constructed as described in Example 2. Fed-batch shake flask 14-day production runs (0.5-2.0 L media scale) is seeded at 0.5 million cells/mL in an incubator-shaker set at 37° C. and 5% carbon dioxide, and the run is conducted as described in Example 2, except that CD OptiCHO is substituted for Dynamis as the growth media (ThermoFisher) and Efficient Feed C (ThermoFisher) is used as the feed. Feed is added at 3% v/v starting on production run day 3, and on day 4, the shake-flask temperature is adjusted to 32° C. and the incubator-shaker carbon dioxide concentration is lowered from 5% to 2%. On Day 14, the production run is harvested to remove the cells, and the culture supernatant is purified and tested to obtain the insulin-Fc fusion protein as described in Example 3, 4, 5, and 6. The resulting production run gives a protein yield of greater than 200 mg/L, greater than 95% homodimer, and greater than 190 mg/L homodimer titer of SEQ ID NO: 34.
Results—Insulin-Fc Fusion Proteins Comprising a Feline Fc Fragment

Example 36: An Insulin-Fc Fusion Protein Comprising an Fc Fragment of the Feline IgG2 Isotype To develop a product suitable for use in cats, an attempt was made to produce an insulin-Fc fusion protein comprising the insulin polypeptide sequence of SEQ ID NO: 4 and the Fc fragment of the feline IgG2 isotype (SEQ ID NO: 21) using the peptide linker of SEQ ID NO: 13 with the following amino acid sequence:

```
                                          (SEQ ID NO: 106)
FVNQHLCGSDLVEALYLVCGERGFFYTDPTGGGPRRGIVEQCCHSICS

LYQLENYCNGGGGSGGGGGEGPKCPVPEIPGAPSVFIFPPKPKDTLSI

SRTPEVTCLVVDLGPDDSNVQITWFVDNTEMHTAKTRPREEQFNSTYR

VVSVLPILHQDWLKGKEFKCKVNSKSLPSAMERTISKAKGQPHEPQVY

VLPPTQEELSENKVSVTCLIKGFHPPDIAVEWEITGQPEPENNYQTTP

PQLDSDGTYFLYSRLSVDRSHWQRGNTYTCSVSHEALHSHHTQKSLTQ

SPG
```

The insulin-Fc fusion protein of SEQ ID NO: 106 was synthesized in HEK cells according to Example 1 and purified according to Example 3. The structure of the insulin-Fc fusion protein was confirmed according to Example 4 by non-reducing and reducing CE-SDS, and the sequence was further identified by LC-MS with glycan removal according to Example 5. The % homodimer of the resulting compound, measured by size-exclusion chromatography according to Example 6, was 88%. The resulting homodimer titer was only 20 mg/L, which resulted from the inability for the HEK cells to make the product in high yield (i.e., the protein yield after Protein a purification was only 23 mg/L). In summary, manufacturing of the insulin-Fc fusion protein of SEQ ID NO: 106 in HEK cells resulted in a moderate level of aggregates and a low homodimer titer of 20 mg/L, which did not meet the design goal of a homodimer titer of greater than 50 mg/L.

Nevertheless, the insulin-Fc fusion protein of SEQ ID NO: 106 was evaluated for bioactivity. First, the insulin receptor binding of the insulin-Fc fusion protein of SEQ ID NO: 106 was measured according to Example 7, resulting in an IC50 value of 22 nM indicating that the compound is likely to be bioactive in vivo (i.e., IC50 less than 5000 nM).

Next, the in vivo pharmacodynamics (PD) of the insulin-Fc fusion protein of SEQ ID NO: 106 was measured after a single subcutaneous administration of the compound to N=3 cats at a dose of 0.8 mg/kg according to Example 10. FIG. 27 shows the percent fasting blood glucose level for the insulin-Fc fusion protein of SEQ NO: 106 (161c) as a function of time. The NAOC for the insulin-Fc fusion protein was calculated to be 215% FBGL-days-kg/mg according to the procedure of Example 11. Surprisingly, unlike the analogous insulin-Fc fusion protein for dogs of SEQ ID NO: 42 comprising the insulin polypeptide of SEQ ID NO: 5 and the peptide linker of SEQ ID NO: 12, the insulin-Fc fusion protein for cats of SEQ NO: 106 was found to be much less aggregated and significantly more bioactive in the target animal.

Since the NAOC was acceptable and the pharmacokinetic data was supportive of a once-weekly administration, the cats were given additional subcutaneous doses on day 28, day 35, day 42 and day 49 and the % FBGL was measured for the 7-day window after each dose according to Example 11. The NAOC and NAOCR were calculated according to the procedure of Example 11 for each repeated subcutaneous injection. As illustrated in Table 21, repeated subcutaneous dosing in cats revealed a significant decay in bioactivity by the third dose as measured by a significant decrease in the NAOCR (i.e., the NAOC for the third injection was only 0.40, or 40%, of the NAOC for the first injection, and the NAOC for the fourth injection was only 0.10, or 10%, of the NAOC for the first injection). The significant decay in bioactivity for the insulin-Fc fusion protein of SEQ ID NO: 106 after repeated dosing in cats was similar to that observed for the insulin-Fc fusion protein of SEQ ID NO: 52 in dogs shown in Example 20.

TABLE 21

NAOC per dose for repeated doses of SEQ ID NO: 106

| Injection# | Day | NAOC (% FBGL · days · kg/mg) | NAOCR |
|---|---|---|---|
| 1 | 0 | 215 | 1.0 |
| 2 | 28 | 161 | 0.7 |
| 3 | 35 | 120 | 0.6 |
| 4 | 42 | 80 | 0.4 |
| 5 | 49 | 21 | 0.1 |

Example 37: Evaluation of Insulin Polypeptide Mutations and the Choice of Feline IgG1b or IgG2 Fc Fragments on Protein Yield, Purity, and Insulin Receptor Activity In an attempt to increase the % homodimer content and protein yield of the insulin-Fc fusion protein of SEQ ID NO: 106, mutations were inserted into the sequences of the insulin polypeptide B-chain (e.g., the B16A mutation) and the peptide linker. Furthermore, the feline IgG1b Fc fragment (SEQ ID NO: 20) was evaluated in addition to the feline IgG2 Fc fragment (SEQ ID NO: 21) that was used to construct the insulin-Fc fusion protein of SEQ ID NO: 106. The resulting insulin-Fc fusion protein sequences are shown below with the resulting sequence alignments against SEQ ID NO: 106 shown in FIG. 28 (Clustal Omega).

(SEQ ID NO: 108)
FVNQHLCGSDLVEALALVCGERGFFYTDPTGGGPRRGIVEQCCHSICS

LYQLENYCNGGGGSGGGGDCPKCPPPEMLGGPSIFIFPPKPKDTLSIS

RTPEVTCLVVDLGPDDSDVQITWFVDNTQVYTAKTSPREEQFNSTYRV

VSVLPILHQDWLKGKEFKCKVNSKSLPSPIERTISKDKGQPHEPQVYV

LPPAQEELSRNKVSVTCLIEGFYPSDIAVEWEITGQPEPENNYRTTPP

QLDSDGTYFLYSRLSVDRSRWQRGNTYTCSVSHEALHSHHTQKSLTQS

PG (SEQ ID NO: 110)
FVNQHLCGSDLVEALALVCGERGFFYTDPTGGGPRRGIVEQCCHSICS

LYQLENYCNGGGGAGGGGGEGPKCPVPEIPGAPSVFIFPPKPKDTLSI

SRTPEVTCLVVDLGPDDSNVQITWFVDNTEMEITAKTRPREEOFNSTY

RVVSVLPILHODWLKGKEFKCKVNSKSLPSAMERTISKAKGOPHEPQV

YVLPPTQEELSENKVSVTCLIKGFHPPDIAVEWEITGQPEPENNYQTT

PPQLDSDGTYFLYSRLSVDRSHWQRGNTYTCSVSHEALHSHHTQKSLT

QSPG (SEQ ID NO: 112)
FVNQHLCGSDLVEALALVCGERGFFYTDPTGGGPRRGIVEQCCHSICS

LYQLENYCNGGGGSGGGGGEGPKCPVPEIPGAPSVFIFPPKPKDTLSI

SRTPEVTCLVVDLGPDDSNVQITWFVDNTEMHTAKTRPREEQFNSTYR

VVSVLPILHQDWLKGKEFKCKVNSKSLPSAMERTISKAKGQPHEPQVY

VLPPTQEELSENKVSVTCLIKGFHPPDIAVEWEITGQPEPENNYQTTP

PQLDSDGTYFLYSRLSVDRSHWQRGNTYTCSVSHEALHSHHTQKSLTQ

SPG

The insulin-Fc fusion proteins were manufactured in HEK293 cells according to Example 1 and purified using a Protein A column according to Example 3. Their structures were confirmed according to Example 4 by non-reducing and reducing CE-SDS, and the sequences were further identified by LC-MS with glycan removal according to Example 5. Their % homodimer content was measured by size-exclusion chromatography according to Example 6, and their insulin receptor binding affinities were measured according to Example 7. The insulin-Fc fusion protein variants are listed in Table 22 along with the corresponding protein yields, % homodimer, and homodimer titer. The results show that the various mutations, when combined with the feline IgG1b isotype Fc fragment to produce the insulin-Fc fusion protein of SEQ ID NO: 108, gave rise to a much higher protein yield, but the resulting protein was more aggregated (e.g., lower % homodimer than SEQ ID NO: 106). This was surprising as the feline IgG1b is more similar in function to the canine IgGB Fc fragment isotype, which was the highly preferred Fc isotype for the production of canine insulin-Fc fusion proteins (Example 32). Of the mutated feline compositions containing the feline IgG2 isotype, the ones comprising B16A mutation of the insulin polypeptide B-chain (i.e., SEQ ID NO: 110 and SEQ ID NO: 112) led to improved protein yield and homodimer titers. However, the mutated linker present in SEQ ID NO: 110 (i.e., GGGGAGGGG (SEQ ID NO: 12)) seems to have provided a further doubling in protein yield and homodimer titer as compared to SEQ ID NO: 112.

TABLE 22

Manufacturing and IR Binding for insulin-Fc fusion proteins utilizing feline IgG1b and IgG2 Fc fragments

| SEQ ID NO: | IgG Fragment | Protein Yield (mg/L) | % Homodimer | Homodimer Titer (mg/L) | IR Binding, IC50 (nM) |
|---|---|---|---|---|---|
| SEQ ID NO: 106 | IgG2 | 23 | 88.0% | 20 | 22 |
| SEQ ID NO: 108 | IgG1b | 127 | 49.0% | 62 | 62 |
| SEQ ID NO: 110 | IgG2 | 122 | 89.7% | 109 | 41 |
| SEQ ID NO: 112 | IgG2 | 64 | 80.4% | 51 | 53 |

Example 38: In Vivo Immunogenicity Screening after Repeated Subcutaneous Doses of the Insulin-Fc Fusion Protein Comprising the Insulin Polypeptide of SEQ ID NO: 4 with a Feline IgG2 Isotype Fc Fragment Without being bound to any particular explanation, it was postulated that the cause of the significant reduction in bioactivity of the insulin-Fc fusion protein of SEQ ID NO: 106 after the fourth repeated subcutaneous dose in cats (Example 36) was due to the development of anti-drug antibodies that neutralized its biological activity. Anti-drug antibodies may be directed against the insulin polypeptide, linker, or Fc-fragment portions of an insulin-Fc fusion protein. The immunogenic response manifests as interactions between antigen presenting cells, T-helper cells, B-cells, and their associated cytokines, which may lead to the production of endogenous antibodies against the drug (e.g., anti-drug antibodies). Binding antibodies are all isotypes capable of binding the insulin-Fc fusion protein, and these may be detected in an immunoassay as described in Example 14. Neutralizing antibodies that inhibit functional activity of the insulin-Fc fusion protein are generally directed against a biologically active site. To assess whether this was the case, serum that was collected prior to the administration of each dose and at the end of the experiment described in Example 11 was tested to quantify the levels of anti-drug antibodies according to Example 14. As shown in FIG. 29, levels of anti-drug antibodies did indeed increase with multiple subcutaneous administrations of the compound, indicating that the generation of neutralizing anti-drug antibodies was the likely cause for the reduction in the NAOCR after the fourth injection of the insulin Fc-fusion protein of SEQ ID NO: 106.

Example 39: Screening of Feline Serum Containing Anti-Drug Antibodies and Identification of Potential Immunogenic Epitopes at the B10D and A8H Positions of the Insulin Polypeptide As was observed for SEQ ID NO: 52 in dogs (Example 20), the repeated dose bioactivity of the insulin-fusion protein of SEQ ID NO: 106 comprising the insulin polypeptide of SEQ ID NO: 4 and the peptide linker of SEQ ID NO: 13 still gave rise to anti-drug antibodies (Example 38). It was hypothesized, therefore, that the insulin polypeptide of SEQ ID NO: 4 may unexpectedly contain specific epitopes (i.e., immunogenic "hot spots") against which a cat's immune system is directed. Therefore, the binding specificity of the antibodies present in the serum samples described in Example 38 were evaluated according to the general procedure of Example 15. The analysis of the antibody-containing feline serum samples from the repeated dosing of the insulin-Fc fusion protein of SEQ ID NO: 106 (Example 38) against the coated insulin-Fc fusion protein library demonstrated that there were unexpectedly two primary "hot spots" present within the insulin polypeptide sequence of SEQ ID NO: 4: the B10D site mutation (i.e., the aspartic acid mutation at the 10th position from the N-terminus of the B-chain (i.e., B10)), and, separately, the A8H site mutation (i.e., the histidine mutation at the 8th position from the N-terminal end of the A-chain (i.e., A8)). The results suggest that insulin-Fc fusion proteins comprising insulin polypeptide amino acid compositions containing these two particular amino acid mutations are likely to be immunogenic in cats and therefore likely to give rise anti-drug antibodies that neutralize the bioactivity after repeated injections. Therefore, it was determined that insulin polypeptides that do not contain the B10D and A8H are preferred for insulin-Fc fusion proteins that need to be repeatedly dosed in cats over long periods long-term (e.g., to treat feline diabetes).

Example 40: Insulin-Fc Fusion Proteins Comprising the Insulin Polypeptide of SEQ ID NO: 4 and Glycosylated and Non-Glycosylated Feline IgG1b and IgG2 Isotype Fc Fragments in which the B0, A8, and Other Sites of the Insulin Polypeptide are Further Mutated to Reduce the Potential Risk of Immunogenicity To evaluate whether replacing the "hot spot" mutations would improve the immunogenicity and repeated dose bioactivity of insulin-Fc fusion proteins comprising the insulin polypeptide of SEQ ID NO: 4 and the feline IgG2 isotype fragment, exemplary insulin-Fc fusion proteins of SEQ ID NOs: 114, 116, and 118 were synthesized in which the B10 and A8 amino acids of the insulin polypeptide were restored to their native histidine and alanine compositions, respectively, and the histidine at B16 was replaced with alanine (i.e., B16A) as was the case for the insulin polypeptide of SEQ ID NO: 5 used for many of the canine insulin-Fc fusion proteins. The A21N site of the native insulin was also deleted. For this example, other insulin polypeptide amino acids were mutated to make the structure more similar to native feline insulin (e.g., B30A, A8A, A10V, and A18H). The sequence of the resulting insulin polypeptide (SEQ ID NO: 120) is listed below with the non-native amino acids to feline insulin bolded.

(SEQ ID NO: 120)
FVNQHLCGSHLVEALALVCGERGFFYTDPAGGGPRRGIVE

QCCASVCSLYQLEHYC

Furthermore, given the additional potential benefits of the non-glycosylated cNg mutants discussed in Examples 22 and 33, two of the evaluated insulin-Fc fusion proteins (SEQ ID NOs: 116 and 118) contain the cNg-S mutation. The entire amino acid sequences of the insulin-Fc fusion proteins are shown below with the resulting sequence alignments against SEQ ID NO: 108 shown in FIG. 30 (Clustal Omega).

(SEQ ID NO: 114)
FVNQHLCGSHLVEALALVCGERGFFYTDPAGGGPRRGIVEQCCASVCS

LYQLEHYCGGGGAGGGGGEGPKCPVPEIPGAPSVFIFPPKPKDTLSIS

RTPEVTCLVVDLGPDDSNVQITWFVDNTEMHTAKTRPREEQFNSTYRV

VSVLPILHQDWLKGKEFKCKVNSKSLPSAMERTISKAKGQPHEPQVYV

LPPTQEELSENKVSVTCLIKGFHPPDIAVEWEITGQPEPENNYQTTPP

QLDSDGTYFLYSRLSVDRSHWQRGNTYTCSVSHEALHSHHTQKSLTQS

P (SEQ ID NO: 116)
FVNQHLCGSHLVEALALVCGERGFFYTDPAGGGPRRGIVEQCCASVCS

LYQLEHYCGGGGAGGGGGEGPKCPVPEIPGAPSVFIFPPKPKDTLSIS

RTPEVTCLVVDLGPDDSNVQITWFVDNTEMHTAKTRPREEQFSSTYRV

VSVLPILHQDWLKGKEFKCKVNSKSLPSAMERTISKAKGQPHEPQVYV

LPPTQEELSENKVSVTCLIKGFHPPDIAVEWEITGQPEPENNYQTTPP

QLDSDGTYFLYSRLSVDRSHWQRGNTYTCSVSHEALHSHHTQKSLTQS

PG (SEQ ID NO: 118)
FVNQHLCGSHLVEALALVCGERGFFYTDPAGGGPRRGIVEQCCASVCS

LYQLEHYCGGGGAGGGGDCPKCPPPEMLGGPSIFIFPPKPKDTLSISR

TPEVTCLVVALGPDDSDVQITWFVDNTQVYTAKTSPREEQFSSTYRVV

SVLPILHQDWLKGKEFKCKVNSKSLPSPIERTISKDKGQPHEPQVYVL

PPAQEELSRNKVSVTCLIEGFYPSDIAVEWEITGQPEPENNYRTTPPQ

LDSDGTYFLYSRLSVDRSRWQRGNTYTCSVSHEALHSHHTQKSLTQSP

G

The insulin-Fc fusion proteins were manufactured in HEK293 cells according to Example 1 and purified using a Protein A column according to Example 3. Their structures were confirmed according to Example 4 by non-reducing and reducing CE-SDS, and the sequences were further identified by LC-MS with glycan removal according to Example 5. Their % homodimer content was measured by size-exclusion chromatography according to Example 6, and their insulin receptor binding affinities were measured according to Example 7. Table 23 below illustrates the manufacturability and in vitro IR binding parameters for the resulting compounds.

Manufacturing and IR Binding for insulin-Fc fusion proteins utilizing feline IgG1b and IgG2 Fc fragments

| SEQ ID NO: | IgG Fragment | Protein Yield (mg/L) | % Homo-dimer | Homo-dimer Titer (mg/L) | IR Binding, IC50 (nM) |
|---|---|---|---|---|---|
| SEQ ID NO: 108 | IgG1b | 127 | 48.6% | 62 | 62 |
| SEQ ID NO: 118 | IgG1b | 18 | 97.5% | 18 | >5000 |
| SEQ ID NO: 114 | IgG2 | 25 | 90.5% | 23 | 3,480 |
| SEQ ID NO: 116 | IgG2 | 1 | 73.0% | 1 | 707 |

Unexpectedly, all three insulin-Fc fusion proteins gave much lower protein yields compared to that of the insulin-Fc fusion protein of SEQ ID NO: 108. In fact, although it had a sufficiently high insulin receptor binding affinity (IC50 of 707 nM), the insulin-Fc fusion protein of SEQ ID NO: 116 gave almost no protein yield. The insulin-Fc fusion protein of SEQ ID NO: 118 gave unacceptably low protein yield and homodimer titer and was deemed unlikely to be bioactive in vivo due to its high IR binding IC50 value greater than 5000 nM. The protein of SEQ ID NO: 114 also gave an unacceptably low protein yield and a much lower insulin receptor binding affinity (higher IR IC50 value) compared to that of the insulin-Fc fusion protein of SEQ ID NO: 108.

Example 41: An Insulin-Fc Fusion Protein Comprising the Insulin Polypeptide of SEQ ID NO: 8, Linker of SEQ ID NO: 14 and a Feline IgG2 Isotype Fc Fragment In an attempt to obtain an acceptable protein yield of an insulin-Fc fusion protein comprising an insulin polypeptide sequence without the immunogenic "hot spot" mutations (i.e., B10D and A8H), learnings were obtained from the simultaneous and parallel development of canine insulin-Fc fusion proteins that had shown that the use of an insulin polypeptide of SEQ ID NO: 8 and a peptide linker of SEQ ID NO: 14 on a canine IgGB isotype Fc fragment resulted in high protein and homodimer titers and acceptable IR binding affinity. Therefore, a feline insulin-Fc fusion protein was constructed using the insulin polypeptide of SEQ ID NO: 8 and the peptide linker of SEQ ID NO: 14 on a feline IgG2 Fc fragment of SEQ ID NO: 21 to produce the following sequence:

(SEQ ID NO: 122)
FVNQHLCGSHLVEALELVCGERGFHYGGGGGGSGGGGGIVEQC

CTSTCSLDQLENYCGGGGQGGGGQGGGGQGGGGGEGPKCPV

PEIPGAPSVFIFPPKPKDTLSISRTPEVTCLVVDLGPDDSNVQ

ITWFVDNTEMHTAKTRPREEQFNSTYRVVSVLPILHQDWLKGK

EFKCKVNSKSLPSAMERTISKAKGQPHEPQVYVLPPTQEELSE

NKVSVTCLIKGFHPPDIAVEWEITGQPEPENNYQTTPPQLDSD

GTYFLYSRLSVDRSHWQRGNTYTCSVSHEALHSHHTQKSLTQS

PG

The sequence alignment of SEQ ID NO: 122 against the Example 37 sequences SEQ ID NOs: 106 and 112 are shown in FIG. 31 (Clustal Omega).

TABLE 24

Manufacturing and IR Binding for insulin-Fc fusion proteins utilizing feline IgG1b and IgG2 Fc fragments

| SEQ ID NO: | IgG Fragment | Protein Yield (mg/L) | % Homo-dimer | Homo-dimer Titer (mg/L) | IR Binding, IC50 (nM) |
|---|---|---|---|---|---|
| SEQ ID NO: 106 | IgG2 | 23 | 88.0% | 20 | 22 |
| SEQ ID NO: 112 | IgG2 | 64 | 80.4% | 51 | 53 |
| SEQ ID NO: 122 | IgG2 | 146 | 99.0% | 145 | 2,536 |

The insulin-Fc fusion protein of SEQ ID NO: 122 was manufactured in HEK293 cells according to Example 1 and purified using a Protein A column according to Example 3. Their structures were confirmed according to Example 4 by non-reducing and reducing CE-SDS, and the sequences were further identified by LC-MS with glycan removal according to Example 5. Their % homodimer content was measured by size-exclusion chromatography according to Example 6, and their insulin receptor binding affinities were measured according to Example 7. The FcRn receptor binding affinity was measured according to Example 9. The protein yield was 146 mg/L, and the % homodimer was determined to be 99%, resulting in a homodimer titer of 145 mg/L which meets the manufacturing design goal. The IR binding affinity IC50 value was 2,536 nM indicating that the compound is likely to be bioactive in vivo. The FcRn receptor binding affinity EC50 value was 3114 ng/mL. Therefore, the insulin-Fc fusion protein of SEQ ID NO: 122 was a potential candidate for further testing in vivo.

Example 42: In Vivo Bioactivity of an Insulin-Fc Fusion Protein Constructed from the Insulin Polypeptide of SEQ ID NO: 8, the Peptide Linker of SEQ ID NO: 14, and the Feline IgG2 Fc Fragment of SEQ ID NO: 21

The insulin-Fc fusion protein of SEQ ID NO: 122 was tested for bioactivity in vivo according to Example 10. A healthy, antibody-naïve, cat weighing approximately 5 kg was used. On day 0 the cat received a single injection of a pharmaceutical composition containing the insulin Fc-fusion protein of SEQ ID NO: 122. On day 0, blood was collected from a suitable vein immediately prior to injection and at 15, 30, 45, 60, 120, 240, 360, and 480 min and at 1, 2, 3, 4, 5, 6, and 7 days post injection. If the subject's blood glucose dropped to dangerous levels, food and/or dextrose injections were given to prevent symptomatic hypoglycemia.

FIG. 32 shows the % FBGL for a single administration, illustrating that, unexpectedly, the insulin-Fc fusion protein of SEQ ID NO: 122 was only marginally bioactive in vivo (NAOC of essentially 0% FBGL·days·kg/mg). This result was surprising, especially since the insulin-Fc fusion protein was not aggregated (i.e., had a high % homodimer content), and the molecule exhibited an IR affinity in a similar range as the canine insulin-Fc fusion proteins that were found to exhibit significant bioactivity in dogs (Example 31). Due to the lack of bioactivity on the first administration, repeat administrations were not performed.

Example 43: Evaluation of the Substitution of Feline IgG1b for the Feline IgG2 Fc Fragment on the Yield, Purity, Bioactivity, and Immunogenicity of an Insulin-Fc Fusion Protein Comprising the Insulin Polypeptide of SEQ ID NO: 8 and the Peptide Linker of SEQ ID NO: 14

Because the dog and cat long-acting insulin research programs were conducted in parallel, some of the learnings of the canine insulin-Fc fusion protein research program were applied to the feline insulin-Fc protein research program. One key learning from the canine insulin-Fc research program was how the selection of different IgG isotype Fc fragments (e.g., canine IgGA, canine IgGB, canine IgGC, and canine IgGD isotypes) led to dramatically different manufacturing and in vivo efficacy performance. Therefore, the feline IgG2 Fc fragment of SEQ ID NO: 122 was replaced with the feline IgG1b Fc fragment of SEQ ID NO: 20 while keeping the insulin polypeptide of SEQ ID NO: 8 and the peptide linker of SEQ ID NO: 14 resulting in the following amino acid sequence:

```
                                       (SEQ ID NO: 38)
FVNQHLCGSHLVEALELVCGERGEHYGGGGGSGGGGIVEQCC

TSTCSLDQLENYCGGGGGQGGGGQGGGGQGGGGDCPKCPPPEM

LGGPSIFIFPPKPKDTLSISRTPEVTCLVVDLGPDDSDVQITWF

VDNTQVYTAKTSPREEQFNSTYRVVSVLPILHQDWLKGKEFKCK

VNSKSLPSPIERTISKDKGQPHEPQVYVLPPAQEELSRNKVSVT

CLIEGFYPSDIAVEWEITGQPEPENNYRTTPPQLDSDGTYFLYS

RLSVDRSRWQRGNTYTCSVSHEALHSHHTQKSLTQSPG
```

The insulin-Fc fusion protein of SEQ ID NO: 38 was synthesized in HEK293 cells according to the procedure of Example 1 and purified using a Protein A column according to Example 3. The structure was confirmed according to Example 4 by non-reducing and reducing LC-MS, and the sequence was further identified by LC-MS with glycan removal according to Example 5. The protein yield was 158 mg/L at this stage. The % homodimer for the sequence was measured by size-exclusion chromatography according to Example 6 and was determined to be 99.5% resulting in a homodimer titer of 157 mg/L which meets the manufacturing design goal. The in vitro IM-9 insulin receptor binding IC50 value, measured according to Example 7, was 2398 nM which also meets the design goal. The FcRn receptor binding affinity EC50 value was measured according to Example 9 and found to be 1552 ng/mL.

The insulin-Fc fusion protein of SEQ ID NO: 38 was then tested for bioactivity in vivo according to Example 10. A healthy, antibody-naïve, cat weighing approximately 5 kg received a single subcutaneous injection of a pharmaceutical composition containing the insulin Fc-fusion protein of SEQ ID NO: 38 at a dose of 0.16 mg insulin-Fc fusion protein/kg. On day 0, blood was collected from a suitable vein immediately prior to injection and at 15, 30, 45, 60, 120, 240, 360, and 480 min and at 1, 2, 3, 4, 5, 6, and 7 days post injection. If the subject's blood glucose dropped to dangerous levels, food and/or dextrose injections were given to prevent symptomatic hypoglycemia.

Figure 33:
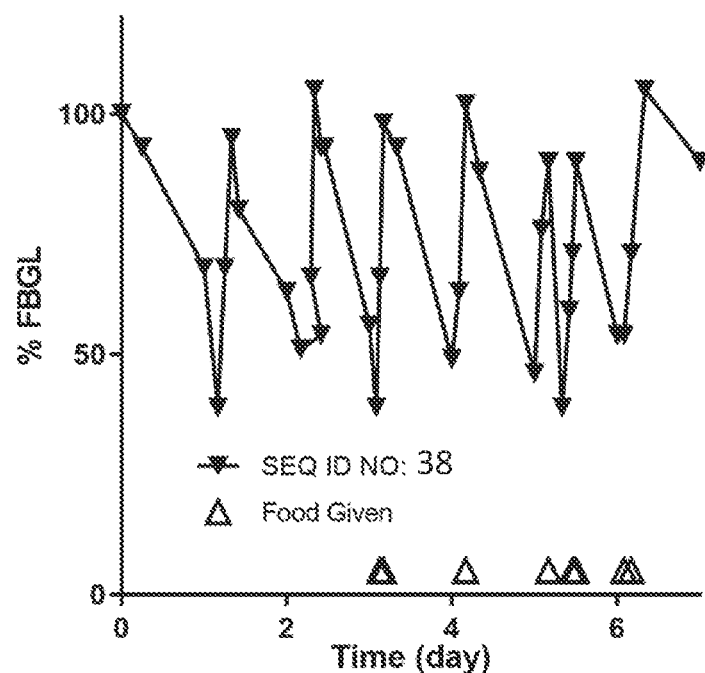
FIG. 33 shows % fasting blood glucose levels from Day 0 to Day 7 for N=1 cat dosed subcutaneously on Day 0 (0.16 mg/kg) with the homodimer of SEQ ID NO: 38, in addition to the times that the cat was given food.

FIG. 33 shows the % FBGL after the first administration. Food was given to the animal regularly to prevent symptomatic hypoglycemia, illustrating that the insulin-Fc fusion protein of SEQ ID NO: 38 was significantly bioactive in vivo with a NAOC of 1838% FBGL·days·kg/mg. The pharmacokinetic profile of the compound was also measured by the method of Example 12 using ELISA, and a two-compartment model was fit to the data to determine its elimination half-life which was 6.3+0.5. The difference in biological activity (in vitro and in vivo) between the insulin-Fc fusion protein of SEQ ID NO: 38 and that of SEQ ID NO: 122 demonstrates that, unexpectedly, the feline IgG1b isotype is preferred over the feline IgG2 isotype for the Fc fragment when the insulin polypeptide sequence is modified as in SEQ ID NO: 8.

Since the NAOC was acceptable and the pharmacokinetic data was supportive of a once-weekly administration, the cat was given additional subcutaneous doses on day 14, day 28, and on day 42, and the % FBGL was measured for the 7-day window after each dose according to Example 11. The NAOC and NAOCR were calculated according to the procedure of Example 11 for each repeated subcutaneous injection. As illustrated in Table 25, the insulin-Fc fusion protein of SEQ ID NO: 38 demonstrated acceptable bioactivity in vivo after multiple doses.

TABLE 25

NAOC per dose for repeated doses of SEQ ID NO: 38

| Injection# | Day | NAOC (% FBGL · days · kg/mg) | NAOCR |
|---|---|---|---|
| 1 | 0 | 1838 | 1.0 |
| 2 | 14 | 1431 | 0.8 |
| 3 | 28 | 1900 | 1.0 |
| 4 | 42 | 2400 | 1.3 |

In addition, serum was collected prior to the administration of each dose and once a week for two weeks after the end of the experiment in order to test for the presence and quantify the levels of any anti-drug antibodies according to Example 14. As shown in FIG. 34, there was no measurable increase in anti-drug antibodies above baseline after multiple administrations of the compound. Therefore, in order to obtain a feline insulin-Fc fusion protein candidate (e.g. SEQ ID NO: 38) that meets the design criteria of acceptable homodimer titer, in vivo bioactivity, and sustained bioactivity after repeated weekly injections in cats, it was necessary to replace the insulin polypeptide of SEQ ID NO: 4 with the insulin polypeptide of SEQ ID NO: 8 and use the feline IgG1b Fc fragment of SEQ ID NO: 20 instead of the feline IgG2 Fc fragment of SEQ ID NO: 21.

Example 44: Non-Glycosylated Insulin-Fc Fusion Proteins Comprising the Insulin Polypeptide of SEQ ID NO: 8, the Peptide Linker of SEQ ID NO: 14, and the Feline IgG1b Fc Fragment to Reduce the Potential Risk of Immunogenicity While the insulin-Fc fusion protein of SEQ ID NO: 38 meets all of the design goals (Example 43), there may or may not be a risk of immunogenicity over extended periods of treatment (e.g., 6 months, 1 year, 2 years or more), which could compromise the use of this insulin-Fc fusion protein for treating diabetes should this occur. As described in the Detailed Description of the Invention, one possible cause of a reduction in bioactivity after repeated doses is the unwanted interaction of the feline IgG1b Fc fragment with the cat's immune system resulting in the production of neutralizing anti-drug antibodies. However, the results shown in Example 43 demonstrate that unexpectedly, the feline IgG1b isotype was preferable over the less immunogenic feline IgG2 isotype with respect to in vivo bioactivity. Therefore, further Fc mutations were explored to achieve non-glycosylated insulin-Fc fusion proteins with low Fc(gamma)RI receptor binding, which should reduce the long-term, chronic immunogenicity risk.

As described in the Detailed Description of the Invention, one method for reducing the Fc(gamma)RI interaction involves mutating the Fc fragment cNg site to prevent glycosylation during synthesis in the host cell. Therefore, cNg site mutations were made to the Fc fragment region of SEQ ID NO: 38 to reduce the binding affinity of the Fc fragment for Fc(gamma) receptors in vivo, as measured by binding in an in vitro human Fc(gamma)RI assay described in Example 8. The position of the cNg site in the insulin-Fc fusion protein of SEQ ID NO: 38 is cNg-NB151. Again, capitalizing on the learnings from the canine insulin-Fc fusion proteins described in Example 33, a cNg-NB151-S mutation was introduced into the Fc fragment of SEQ ID NO: 38. The full amino acid sequence of the resulting insulin-Fc fusion protein is listed below (cNg-NB151-S bolded for clarity):

(SEQ ID NO: 124)
FVNQHLCGSHLVEALELVCGERGEHYGGGGGSGGGGGIVEQCCTS

TCSLDQLENYCGGGGQGGGGQGGGQGGGGDCPKCPPPEMLGGP

SIFIFPPKPKDTLSISRTPEVTCLVVDLGPDDSDVQITWFVDNTQV

YTAKTSPREEQFSSTYRVVSVLPILHQDWLKGKEFKCKVNSKSLPS

PIERTISKDKGQPHEPQVYVLPPAQEELSRNKVSVTCLIEGFYPSD

IAVEWEITGQPEPENNYRTTPPQLDSDGTYFLYSRLSVDRSRWQRG

NTYTCSVSHEALHSHHTQKSLTQSPG

The insulin-Fc fusion protein of SEQ ID NO: 124 was synthesized in HEK293 cells according to the procedure of Example 1 and purified using a Protein A column according to Example 3. The structure of the insulin-Fc fusion protein was confirmed according to Example 4 by non-reducing and reducing LC-MS, and the sequence was further identified by LC-MS with glycan removal according to Example 5. The protein yield was 202 mg/L at this stage. The % homodimer for the sequence was measured by size-exclusion chromatography according to Example 6 and was determined to be 99%, resulting in a homodimer titer of 200 mg/L which meets the manufacturing design goal. However, the in vitro IM-9 insulin receptor binding IC50 value, measured according to Example 7, was greater than 5000 nM, which is outside the design goal for in vitro bioactivity. The FcRn receptor binding affinity EC50 value was measured according to Example 9 and was 6922 ng/mL.

Although the insulin-Fc fusion protein of SEQ ID NO: 124 did not meet the insulin receptor binding design goal, it was tested for bioactivity in vivo according to Example 10. A healthy, antibody-naïve, cat weighing approximately 5 kg was used. On day 0 the cat received a single injection of a pharmaceutical composition containing the insulin Fc-fusion protein of SEQ ID NO: 124 at a dose of 0.16 mg insulin-Fc fusion protein/kg. On day 0, blood was collected from a suitable vein immediately prior to injection and at 15, 30, 45, 60, 120, 240, 360, and 480 min and at 1, 2, 3, 4, 5, 6, and 7 days post injection. If the subject's blood glucose dropped to dangerous levels, food and/or dextrose injections were given to prevent symptomatic hypoglycemia.

FIG. 35 shows the % FBGL for a single administration, illustrating that the insulin-Fc fusion protein of SEQ ID NO: 124 is only somewhat bioactive in vivo with an NAOC of 65% FBGL·days·kg/mg. Due to the lack of bioactivity on the first administration, repeat administrations were not performed.

Unexpectedly, as was the case in Example 33 for the canine insulin Fc-fusion protein of SEQ ID NO: 36, it was found that mutating the insulin polypeptide sequence of SEQ ID NO: 124 such that the 16th amino acid from the N-terminus of the B-chain (B16) was mutated from tyrosine to alanine (i.e., B16A) rendered the resulting insulin-Fc fusion protein of SEQ ID NO: 40 bioactive. The amino acid sequence of the resulting insulin-Fc fusion protein is shown below (B16A and cNg-NB151-S mutations bolded for clarity):

(SEQ ID NO: 40)
FVNQHLCGSHLVEALALVCGERGFHYGGGGGSGGGGGIVEQCCTSTC

SLDQLENYCGGGGQGGGGQGGGQGGGGDCPKCPPPEMLGGPSIFI

FPPKPKDTLSISRTPEVTCLVVDLGPDDSDVQITWFVDNTQVYTAKTS

-continued

PREEQFSSTYRVVSVLPILHQDWLKGKEFKCKVNSKSLPSPIERTISK

DKGQPHEPQVYVLPPAQEELSRNKVSVTCLIEGFYPSDIAVEWEITGQ

PEPENNYRTTPPQLDSDGTYFLYSRLSVDRSRWQRGNTYTCSVSHEAL

HSHHTQKSLTQSPG

The insulin-Fc fusion protein of SEQ ID NO: 40 was synthesized in HEK293 cells according to the procedure of Example 1 and purified using a Protein A column according to Example 3. The structure of the insulin-Fc fusion protein was confirmed according to Example 4 by non-reducing and reducing CE-SDS, and the sequence was further identified by LC-MS with glycan removal according to Example 5. The protein yield was 174 mg/L at this stage. The % homodimer for the sequence was measured by size-exclusion chromatography according to Example 6 and was determined to be 98.9% resulting in a homodimer titer of 172 mg/L which meets the manufacturing design criteria. The in vitro IM-9 insulin receptor binding IC50 value of 4635 nM, measured according to Example 7, also meets the design goal. The Fc(gamma) receptor activity was measured according to Example 8 and found to be approximately four times less than that obtained for the insulin-Fc fusion protein of SEQ ID NO: 38 using the same procedure indicating that the insulin-Fc fusion protein is less likely to adversely interact with the cat's immune system. The FcRn receptor binding affinity EC50 value was measured according to Example 9 and was 8157 ng/mL.

The insulin-Fc fusion protein of SEQ ID NO: 40 was then tested for bioactivity in vivo according to Example 11. A healthy, antibody-naïve, cat weighing approximately 5 kg was used. On day 0, day 7, and day 21 the cat received a single subcutaneous injection of a pharmaceutical composition containing an insulin Fc-fusion protein of SEQ ID NO: 40 at a dose of 0.1 mg insulin-Fc fusion protein/kg. On day 0, blood was collected from a suitable vein immediately prior to injection and at 15, 30, 45, 60, 120, 240, 360, and 480 min and at 1, 2, 3, 4, 5, 6, and 7 days post injection. If the subject's blood glucose dropped to dangerous levels, food and/or dextrose injections were given to prevent symptomatic hypoglycemia.

FIG. 36 shows the % FBGL after the first administration, illustrating that the insulin-Fc fusion protein of SEQ ID NO: 40 is bioactive in vivo with a NAOC of 159% FBGL·days·kg/mg for a subcutaneous dose of 0.1 mg insulin-Fc fusion protein/kg. A second higher subcutaneous dose of 0.2 mg insulin-Fc fusion protein/kg gave a much higher NAOC of 702% FBGL·days·kg/mg and is shown in FIG. 37. The pharmacokinetic profile is measured by the method of Example 12 using ELISA, and a two-compartment model is fit to the data to determine its elimination half-life which is greater than 3 days. These results are in contrast to the results obtained with the insulin-Fc fusion protein of SEQ ID NO: 124 which showed that the same compound comprising a tyrosine at B16 instead of an alanine was only very weakly bioactive at approximately the same dose (0.16 mg insulin-Fc fusion protein/kg). Therefore, the insulin polypeptide of SEQ ID NO: 11 was preferred for non-glycosylated insulin-Fc fusion proteins comprising cNg mutated feline IgG1b Fc fragments.

To analyze the repeatable bioactivity after multiple doses, the cat was given a further dose of the insulin-Fc fusion protein of SEQ ID NO: 40 on day 7, on day 21, and on day 35. When the cat's % FBGL dropped too low, the cat was given food to raise the blood glucose to a safe level. The NAOC and NAOCR were measured for each subsequent dose according to the general procedure of Example 11, calculated from the time the dose was administered until just before the next dose was administered. The NAOC and the NAOCR shown in Table 26 illustrate that the insulin-Fc fusion protein of SEQ ID NO: 40 is bioactive in vivo after multiple doses.

TABLE 26

NAOC per dose for repeated doses of SEQ ID NO: 40

| Injection# | Day | NAOC (% FBGL · days · kg/mg) | NAOCR |
|---|---|---|---|
| 1 | 0 | 159 | 1.0 |
| 2 | 7 | 702 | 4.4 |
| 3 | 21 | 462 | 2.9 |
| 4 | 35 | 670 | 4.2 |

In addition, serum was collected prior to the administration of each dose and at the end of the experiment in order to test for the presence and quantify the levels of any anti-drug antibodies according to Example 14. There is no measurable increase in anti-drug antibodies above baseline after multiple administrations of the compound. Therefore, in order to obtain a feline insulin-Fc fusion protein meeting the manufacturing and bioactivity design criteria with significantly reduced Fc(gamma) receptor activity, it was not only necessary to mutate the cNg to serine but also to mutate the insulin polypeptide B16 amino acid to alanine.

Example 45: Exemplary CHO-Based Production Runs Using Preferred Insulin-Fc Fusion Proteins Comprising Fc Fragments of Feline IgG1b Origin Made Via Stably Transfected CHO Cell Lines A CHO cell line stably transfected with vectors encoding for SEQ ID NO: 38 was constructed as described in Example 2 above. Fed-batch shake flask 14-day production runs (0.5-2.0 L media scale) were seeded at 0.5 million cells/mL in an incubator-shaker set at 37° C. and 5% carbon dioxide, and the runs were conducted as described in Example 2 above, except that CD OptiCHO was substituted for Dynamis as the growth media (ThermoFisher) and Efficient Feed C (ThermoFisher) was used as the feed. Feed was added at 3% v/v starting on production run day 3, and on day 4, the shake-flask temperature was adjusted to 32° C. and the incubator-shaker carbon dioxide concentration was lowered from 5% to 2%. During the run, the cell density increased to between 8-14 million cells/mL, and on Day 14 the production run was harvested to remove the cells, and the culture supernatant was purified and characterized to obtain the insulin-Fc fusion protein as described in Example 3, 4, 5, and 6. Table 27 describes the manufacturing data for the insulin-Fc fusion protein obtained via these stably transfected CHO cell line production runs.

TABLE 27

Homodimer titers for non-glycosylated insulin-Fc fusion proteins of SEQ ID NO: 38

| SEQ ID NO: | Protein Yield (mg/L) | % Homodimer | Homodimer Titer (mg/L) |
|---|---|---|---|
| SEQ ID NO: 38 | 633 | 96.3% | 610 |

Example 46: Exemplary CHO-Based Production Runs Using Preferred Insulin-Fc Fusion Proteins of Feline IgG1b Origin Made Via Stably Transfected CHO Cell Lines A CHO cell line stably transfected with vectors encoding for SEQ ID NO: 40 is constructed as described in Example 2 above. A fed-batch shake flask 14-day production run (0.5-2.0 L media scale) is seeded at 0.5 million cells/mL in an incubator-shaker set at 37° C. and 5% carbon dioxide, and the run is conducted as described in Example 2 above, except that CD OptiCHO is substituted for Dynamis as the growth media (ThermoFisher) and Efficient Feed C (ThermoFisher) is used as the feed. Feed is added at 3% v/v starting on production run day 3, and on day 4, the shake-flask temperature is adjusted to 32° C. and the incubator-shaker carbon dioxide concentration is lowered from 5% to 2%. On Day 14, the production run is harvested to remove the cells, and the culture supernatant is purified and characterized to obtain the insulin-Fc fusion protein as described in Example 3, 4, 5, and 6. The resulting production run gives a protein yield of greater than 200 mg/L, greater than 95% homodimer, and greater than 190 mg/L homodimer titer of SEQ ID NO: 40.

Example 47: Exemplary Insulin-Fc Fusion Protein Domains and Sequences

Exemplary insulin-Fc fusion protein amino acid sequences and corresponding DNA sequences used in the above Examples are shown FIGS. 38, 39, 40, 41, and 42.

EQUIVALENTS

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should be understood that, in general, where the disclosure, or aspects of the disclosure, is/are referred to as comprising particular elements and/or features, certain embodiments of the disclosure or aspects of the disclosure consist, or consist essentially of, such elements and/or features. For purposes of simplicity, those embodiments have not been specifically set forth in haec verba herein. It is also noted that the terms "comprise(s)," "comprising," "contain(s)," and "containing" are intended to be open and the use thereof permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the disclosure, to the tenth of the unit of the lower limit of the range, unless the context clearly dictates otherwise.

The invention claimed is:

1. A fusion protein comprising an insulin polypeptide and an Fc fragment, wherein the Fc fragment comprises the following sequence:

(SEQ ID NO: 22)
DCPKCPAPEMLGGPSVFIFPPKPKDTLLIARTPEVTCVVVDLDPEDPEV

QISWFVDGKQMQTAKTQPREEQFSGTYRVVSVLPIGHQDWLKGKQFTCK

VNNKALPSPIERTISKARGQAHQPSVYVLPPSREELSKNTVSLTCLIKD

FFPPDIDVEWQSNGQQEPESKYRTTPPQLDEDGSYFLYSKLSVDKSRWQ

RGDTFICAVMHEALHNHYTQESLSHSPG wherein the insulin polypeptide and the Fc fragment are connected by a linker, and wherein the insulin polypeptide comprises a B-chain and an A-chain, said insulin polypeptide comprising an alanine substitution at B16.

2. The fusion protein of claim 1, wherein the insulin polypeptide and the Fc fragment are connected by a linker, comprising the following sequence:

(SEQ ID NO: 14)
GGGGGQGGGGQGGGGQGGGGG.

3. The fusion protein of claim 1 comprising domains in the following orientation from N- to C-terminus: (N-terminus)-insulin polypeptide-linker-Fc fragment-(C-terminus).

4. The fusion protein of claim 1, wherein the B-chain and the A-chain are linked by a C-chain comprising the following sequence:

(SEQ ID NO: 133)
GGGGGGSGGGG.

5. The fusion protein of claim 1, wherein the fusion protein is a homodimer.

6. The fusion protein of claim 5, wherein the percentage homodimer of the fusion protein is greater than 90%.

7. The fusion protein of claim 5, wherein the fusion protein is made using one of HEK293 or CHO cells, and the resulting homodimer titer after purification using Protein A beads or a Protein A column is greater than 50 mg/L.

8. The fusion protein of claim 1, wherein the fusion protein is formulated as a pharmaceutical composition.

9. The fusion protein of claim 8, wherein the fusion protein is present in the pharmaceutical composition at a concentration of about 3 mg/mL or greater.

10. The fusion protein of claim 8, wherein the composition is suitable for subcutaneous administration.

11. A method for lowering the blood glucose of a target animal, the method comprising administering a physiologically effective amount of the fusion protein of claim 1 or a pharmaceutical composition thereof to the target animal, and wherein the target animal is a dog.

12. The method of claim 11 in which the target animal is diagnosed with diabetes.

13. The method of claim 11, wherein the fusion protein is administered subcutaneously.

14. The method of claim 13, wherein the fusion protein is administered daily, twice weekly, or once weekly to the target animal.

15. The method of claim 13, wherein the fusion protein is administered once weekly to the target animal at a dose between 0.025 and 0.5 mg/kg/week.

* * * * *

SEQUENCE LISTING

```
<160> NUMBER OF SEQ ID NOS: 133

<210> SEQ ID NO 1
<211> LENGTH: 30
<212> TYPE: PRT
<213> ORGANISM: Artificial Sequence
<220> FEATURE:
<223> OTHER INFORMATION: hIns-B-chain

<400> SEQUENCE: 1

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 2
<211> LENGTH: 21
<212> TYPE: PRT
<213> ORGANISM: Artificial Sequence
<220> FEATURE:
<223> OTHER INFORMATION: hIns-A-chain

<400> SEQUENCE: 2

Gly Ile Val Glu Gln Cys Cys Thr Ser Ile Cys Ser Leu Tyr Gln Leu
1               5                   10                  15
```

Glu Asn Tyr Cys Asn
            20

<210> SEQ ID NO 3
<211> LENGTH: 86
<212> TYPE: PRT
<213> ORGANISM: Artificial Sequence
<220> FEATURE:
<223> OTHER INFORMATION: Human Proinsulin

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Pro
        35                  40                  45

Gly Ala Gly Ser Leu Gln Pro Leu Ala Leu Glu Gly Ser Leu Gln Lys
        50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85

<210> SEQ ID NO 4
<211> LENGTH: 57
<212> TYPE: PRT
<213> ORGANISM: Artificial Sequence
<220> FEATURE:
<223> OTHER INFORMATION: Ins Polypeptide

<400> SEQUENCE: 4

Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn
        50                  55

<210> SEQ ID NO 5
<211> LENGTH: 57
<212> TYPE: PRT
<213> ORGANISM: Artificial Sequence
<220> FEATURE:
<223> OTHER INFORMATION: Ins Polypeptide

<400> SEQUENCE: 5

Phe Val Asn Gln His Leu Cys Gly Ser Asp Leu Val Glu Ala Leu Ala
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn
        50                  55

<210> SEQ ID NO 6
<211> LENGTH: 58
<212> TYPE: PRT

```
<213> ORGANISM: Artificial Sequence
<220> FEATURE:
<223> OTHER INFORMATION: Ins Polypeptide
<220> FEATURE:
<221> NAME/KEY: Xaa
<222> LOCATION: (10)..(10)
<223> OTHER INFORMATION: Xaa is not D
<220> FEATURE:
<221> NAME/KEY: Xaa
<222> LOCATION: (45)..(45)
<223> OTHER INFORMATION: Xaa is not H
<220> FEATURE:
<221> NAME/KEY: Xaa
<222> LOCATION: (58)..(58)
<223> OTHER INFORMATION: Xaa is absent or N

<400> SEQUENCE: 6

Phe Val Asn Gln His Leu Cys Gly Ser Xaa Leu Val Glu Ala Leu Glu
1               5                   10                  15

Leu Val Cys Gly Glu Arg Gly Phe His Tyr Gly Gly Gly Gly Gly
            20                  25                  30

Ser Gly Gly Gly Gly Gly Ile Val Glu Gln Cys Cys Xaa Ser Thr Cys
        35                  40                  45

Ser Leu Asp Gln Leu Glu Asn Tyr Cys Xaa
    50                  55

<210> SEQ ID NO 7
<211> LENGTH: 58
<212> TYPE: PRT
<213> ORGANISM: Artificial Sequence
<220> FEATURE:
<223> OTHER INFORMATION: Ins Polypeptide
<220> FEATURE:
<221> NAME/KEY: Xaa
<222> LOCATION: (58)..(58)
<223> OTHER INFORMATION: Xaa is absent or N

<400> SEQUENCE: 7

Phe Val Asn Gln His Leu Cys Gly Ser His Leu Val Glu Ala Leu Glu
1               5                   10                  15

Leu Val Cys Gly Glu Arg Gly Phe His Tyr Gly Gly Gly Gly Gly
            20                  25                  30

Ser Gly Gly Gly Gly Gly Ile Val Glu Gln Cys Cys Thr Ser Thr Cys
        35                  40                  45

Ser Leu Asp Gln Leu Glu Asn Tyr Cys Xaa
    50                  55

<210> SEQ ID NO 8
<211> LENGTH: 57
<212> TYPE: PRT
<213> ORGANISM: Artificial Sequence
<220> FEATURE:
<223> OTHER INFORMATION: Ins Polypeptide

<400> SEQUENCE: 8

Phe Val Asn Gln His Leu Cys Gly Ser His Leu Val Glu Ala Leu Glu
1               5                   10                  15

Leu Val Cys Gly Glu Arg Gly Phe His Tyr Gly Gly Gly Gly Gly
            20                  25                  30

Ser Gly Gly Gly Gly Gly Ile Val Glu Gln Cys Cys Thr Ser Thr Cys
        35                  40                  45

Ser Leu Asp Gln Leu Glu Asn Tyr Cys
    50                  55
```

```
<210> SEQ ID NO 9
<211> LENGTH: 58
<212> TYPE: PRT
<213> ORGANISM: Artificial Sequence
<220> FEATURE:
<223> OTHER INFORMATION: Ins Polypeptide

<400> SEQUENCE: 9

Phe Val Asn Gln His Leu Cys Gly Ser His Leu Val Glu Ala Leu Glu
1               5                   10                  15

Leu Val Cys Gly Glu Arg Gly Phe His Tyr Gly Gly Gly Gly Gly
            20                  25                  30

Ser Gly Gly Gly Gly Gly Ile Val Glu Gln Cys Cys Thr Ser Thr Cys
        35                  40                  45

Ser Leu Asp Gln Leu Glu Asn Tyr Cys Asn
    50                  55

<210> SEQ ID NO 10
<211> LENGTH: 57
<212> TYPE: PRT
<213> ORGANISM: Artificial Sequence
<220> FEATURE:
<223> OTHER INFORMATION: Ins Polypeptide
<220> FEATURE:
<221> NAME/KEY: Xaa
<222> LOCATION: (10)..(10)
<223> OTHER INFORMATION: Xaa is not D
<220> FEATURE:
<221> NAME/KEY: Xaa
<222> LOCATION: (45)..(45)
<223> OTHER INFORMATION: Xaa is not H

<400> SEQUENCE: 10

Phe Val Asn Gln His Leu Cys Gly Ser Xaa Leu Val Glu Ala Leu Ala
1               5                   10                  15

Leu Val Cys Gly Glu Arg Gly Phe His Tyr Gly Gly Gly Gly Gly
            20                  25                  30

Ser Gly Gly Gly Gly Gly Ile Val Glu Gln Cys Cys Xaa Ser Thr Cys
        35                  40                  45

Ser Leu Asp Gln Leu Glu Asn Tyr Cys
    50                  55

<210> SEQ ID NO 11
<211> LENGTH: 57
<212> TYPE: PRT
<213> ORGANISM: Artificial Sequence
<220> FEATURE:
<223> OTHER INFORMATION: Ins Polypeptide

<400> SEQUENCE: 11

Phe Val Asn Gln His Leu Cys Gly Ser His Leu Val Glu Ala Leu Ala
1               5                   10                  15

Leu Val Cys Gly Glu Arg Gly Phe His Tyr Gly Gly Gly Gly Gly
            20                  25                  30

Ser Gly Gly Gly Gly Gly Ile Val Glu Gln Cys Cys Thr Ser Thr Cys
        35                  40                  45

Ser Leu Asp Gln Leu Glu Asn Tyr Cys
    50                  55

<210> SEQ ID NO 12
<211> LENGTH: 9
<212> TYPE: PRT
<213> ORGANISM: Artificial Sequence
<220> FEATURE:
```

```
<223> OTHER INFORMATION: Linker

<400> SEQUENCE: 12

Gly Gly Gly Gly Ala Gly Gly Gly Gly
1               5

<210> SEQ ID NO 13
<211> LENGTH: 9
<212> TYPE: PRT
<213> ORGANISM: Artificial Sequence
<220> FEATURE:
<223> OTHER INFORMATION: Linker

<400> SEQUENCE: 13

Gly Gly Gly Gly Ser Gly Gly Gly Gly
1               5

<210> SEQ ID NO 14
<211> LENGTH: 21
<212> TYPE: PRT
<213> ORGANISM: Artificial Sequence
<220> FEATURE:
<223> OTHER INFORMATION: Linker

<400> SEQUENCE: 14

Gly Gly Gly Gly Gln Gly Gly Gly Gln Gly Gly Gly Gln
1               5                   10                  15

Gly Gly Gly Gly Gly
            20

<210> SEQ ID NO 15
<211> LENGTH: 228
<212> TYPE: PRT
<213> ORGANISM: Artificial Sequence
<220> FEATURE:
<223> OTHER INFORMATION: Canine IgGA Fc Fragment

<400> SEQUENCE: 15

Arg Cys Thr Asp Thr Pro Pro Cys Pro Val Pro Glu Pro Leu Gly Gly
1               5                   10                  15

Pro Ser Val Leu Ile Phe Pro Pro Lys Pro Lys Asp Ile Leu Arg Ile
            20                  25                  30

Thr Arg Thr Pro Glu Val Thr Cys Val Val Leu Asp Leu Gly Arg Glu
        35                  40                  45

Asp Pro Glu Val Gln Ile Ser Trp Phe Val Asp Gly Lys Glu Val His
    50                  55                  60

Thr Ala Lys Thr Gln Ser Arg Glu Gln Gln Phe Asn Gly Thr Tyr Arg
65                  70                  75                  80

Val Val Ser Val Leu Pro Ile Glu His Gln Asp Trp Leu Thr Gly Lys
                85                  90                  95

Glu Phe Lys Cys Arg Val Asn His Ile Asp Leu Pro Ser Pro Ile Glu
            100                 105                 110

Arg Thr Ile Ser Lys Ala Arg Gly Arg Ala His Lys Pro Ser Val Tyr
        115                 120                 125

Val Leu Pro Pro Ser Pro Lys Glu Leu Ser Ser Asp Thr Val Ser
    130                 135                 140

Ile Thr Cys Leu Ile Lys Asp Phe Tyr Pro Pro Asp Ile Asp Val Glu
145                 150                 155                 160

Trp Gln Ser Asn Gly Gln Gln Glu Pro Glu Arg Lys His Arg Met Thr
                165                 170                 175
```

```
Pro Pro Gln Leu Asp Glu Asp Gly Ser Tyr Phe Leu Tyr Ser Lys Leu
            180                 185                 190

Ser Val Asp Lys Ser Arg Trp Gln Gln Gly Asp Pro Phe Thr Cys Ala
        195                 200                 205

Val Met His Glu Thr Leu Gln Asn His Tyr Thr Asp Leu Ser Leu Ser
    210                 215                 220

His Ser Pro Gly
225

<210> SEQ ID NO 16
<211> LENGTH: 224
<212> TYPE: PRT
<213> ORGANISM: Artificial Sequence
<220> FEATURE:
<223> OTHER INFORMATION: Canine IgGB Fc Fragment

<400> SEQUENCE: 16

Asp Cys Pro Lys Cys Pro Ala Pro Glu Met Leu Gly Gly Pro Ser Val
1               5                   10                  15

Phe Ile Phe Pro Pro Lys Pro Lys Asp Thr Leu Leu Ile Ala Arg Thr
            20                  25                  30

Pro Glu Val Thr Cys Val Val Asp Leu Asp Pro Glu Asp Pro Glu
        35                  40                  45

Val Gln Ile Ser Trp Phe Val Asp Gly Lys Gln Met Gln Thr Ala Lys
    50                  55                  60

Thr Gln Pro Arg Glu Glu Gln Phe Asn Gly Thr Tyr Arg Val Val Ser
65                  70                  75                  80

Val Leu Pro Ile Gly His Gln Asp Trp Leu Lys Gly Lys Gln Phe Thr
                85                  90                  95

Cys Lys Val Asn Asn Lys Ala Leu Pro Ser Pro Ile Glu Arg Thr Ile
            100                 105                 110

Ser Lys Ala Arg Gly Gln Ala His Gln Pro Ser Val Tyr Val Leu Pro
        115                 120                 125

Pro Ser Arg Glu Glu Leu Ser Lys Asn Thr Val Ser Leu Thr Cys Leu
    130                 135                 140

Ile Lys Asp Phe Phe Pro Pro Asp Ile Asp Val Glu Trp Gln Ser Asn
145                 150                 155                 160

Gly Gln Gln Glu Pro Glu Ser Lys Tyr Arg Thr Thr Pro Pro Gln Leu
                165                 170                 175

Asp Glu Asp Gly Ser Tyr Phe Leu Tyr Ser Lys Leu Ser Val Asp Lys
            180                 185                 190

Ser Arg Trp Gln Arg Gly Asp Thr Phe Ile Cys Ala Val Met His Glu
        195                 200                 205

Ala Leu His Asn His Tyr Thr Gln Glu Ser Leu Ser His Ser Pro Gly
    210                 215                 220

<210> SEQ ID NO 17
<211> LENGTH: 225
<212> TYPE: PRT
<213> ORGANISM: Artificial Sequence
<220> FEATURE:
<223> OTHER INFORMATION: Canine IgGC Fc Fragment

<400> SEQUENCE: 17

Cys Asn Asn Cys Pro Cys Pro Gly Cys Gly Leu Leu Gly Gly Pro Ser
1               5                   10                  15

Val Phe Ile Phe Pro Pro Lys Pro Lys Asp Ile Leu Val Thr Ala Arg
            20                  25                  30
```

Thr Pro Thr Val Thr Cys Val Val Asp Leu Asp Pro Glu Asn Pro
        35                  40                  45
Glu Val Gln Ile Ser Trp Phe Val Asp Ser Lys Gln Val Gln Thr Ala
 50                      55                  60
Asn Thr Gln Pro Arg Glu Glu Gln Ser Asn Gly Thr Tyr Arg Val Val
 65                  70                  75                  80
Ser Val Leu Pro Ile Gly His Gln Asp Trp Leu Ser Gly Lys Gln Phe
                85                  90                  95
Lys Cys Lys Val Asn Asn Lys Ala Leu Pro Ser Pro Ile Glu Glu Ile
                100                 105                 110
Ile Ser Lys Thr Pro Gly Gln Ala His Gln Pro Asn Val Tyr Val Leu
            115                 120                 125
Pro Pro Ser Arg Asp Glu Met Ser Lys Asn Thr Val Thr Leu Thr Cys
        130                 135                 140
Leu Val Lys Asp Phe Phe Pro Pro Glu Ile Asp Val Glu Trp Gln Ser
145                 150                 155                 160
Asn Gly Gln Gln Glu Pro Glu Ser Lys Tyr Arg Met Thr Pro Pro Gln
                165                 170                 175
Leu Asp Glu Asp Gly Ser Tyr Phe Leu Tyr Ser Lys Leu Ser Val Asp
            180                 185                 190
Lys Ser Arg Trp Gln Arg Gly Asp Thr Phe Ile Cys Ala Val Met His
        195                 200                 205
Glu Ala Leu His Asn His Tyr Thr Gln Ile Ser Leu Ser His Ser Pro
    210                 215                 220
Gly
225

<210> SEQ ID NO 18
<211> LENGTH: 225
<212> TYPE: PRT
<213> ORGANISM: Artificial Sequence
<220> FEATURE:
<223> OTHER INFORMATION: Canine IgGD Fc Fragment

<400> SEQUENCE: 18

Cys Ile Ser Pro Cys Pro Val Pro Glu Ser Leu Gly Gly Pro Ser Val
1               5                   10                  15
Phe Ile Phe Pro Pro Lys Pro Lys Asp Ile Leu Arg Ile Thr Arg Thr
                20                  25                  30
Pro Glu Ile Thr Cys Val Val Leu Asp Leu Gly Arg Glu Asp Pro Glu
        35                  40                  45
Val Gln Ile Ser Trp Phe Val Asp Gly Lys Glu Val His Thr Ala Lys
 50                      55                  60
Thr Gln Pro Arg Glu Gln Gln Phe Asn Ser Thr Tyr Arg Val Val Ser
 65                  70                  75                  80
Val Leu Pro Ile Glu His Gln Asp Trp Leu Thr Gly Lys Glu Phe Lys
                85                  90                  95
Cys Arg Val Asn His Ile Gly Leu Pro Ser Pro Ile Glu Arg Thr Ile
                100                 105                 110
Ser Lys Ala Arg Gly Gln Ala His Gln Pro Ser Val Tyr Val Leu Pro
            115                 120                 125
Pro Ser Pro Lys Glu Leu Ser Ser Ser Asp Thr Val Thr Leu Thr Cys
        130                 135                 140
Leu Ile Lys Asp Phe Phe Pro Pro Glu Ile Asp Val Glu Trp Gln Ser
145                 150                 155                 160

Asn Gly Gln Pro Glu Pro Glu Ser Lys Tyr His Thr Thr Ala Pro Gln
            165                 170                 175

Leu Asp Glu Asp Gly Ser Tyr Phe Leu Tyr Ser Lys Leu Ser Val Asp
        180                 185                 190

Lys Ser Arg Trp Gln Gln Gly Asp Thr Phe Thr Cys Ala Val Met His
        195                 200                 205

Glu Ala Leu Gln Asn His Tyr Thr Asp Leu Ser Leu Ser His Ser Pro
    210                 215                 220

Gly
225

<210> SEQ ID NO 19
<211> LENGTH: 224
<212> TYPE: PRT
<213> ORGANISM: Artificial Sequence
<220> FEATURE:
<223> OTHER INFORMATION: Feline IgG1a Fc Fragment

<400> SEQUENCE: 19

Asp Cys Pro Lys Cys Pro Pro Pro Glu Met Leu Gly Gly Pro Ser Ile
1               5                   10                  15

Phe Ile Phe Pro Pro Lys Pro Lys Asp Thr Leu Ser Ile Ser Arg Thr
            20                  25                  30

Pro Glu Val Thr Cys Leu Val Val Asp Leu Gly Pro Asp Asp Ser Asp
        35                  40                  45

Val Gln Ile Thr Trp Phe Val Asp Asn Thr Gln Val Tyr Thr Ala Lys
    50                  55                  60

Thr Ser Pro Arg Glu Glu Gln Phe Asn Ser Thr Tyr Arg Val Val Ser
65                  70                  75                  80

Val Leu Pro Ile Leu His Gln Asp Trp Leu Lys Gly Lys Glu Phe Lys
                85                  90                  95

Cys Lys Val Asn Ser Lys Ser Leu Pro Ser Pro Ile Glu Arg Thr Ile
            100                 105                 110

Ser Lys Ala Lys Gly Gln Pro His Glu Pro Gln Val Tyr Val Leu Pro
        115                 120                 125

Pro Ala Gln Glu Glu Leu Ser Arg Asn Lys Val Ser Val Thr Cys Leu
    130                 135                 140

Ile Lys Ser Phe His Pro Pro Asp Ile Ala Val Glu Trp Glu Ile Thr
145                 150                 155                 160

Gly Gln Pro Glu Pro Glu Asn Asn Tyr Arg Thr Thr Pro Pro Gln Leu
                165                 170                 175

Asp Ser Asp Gly Thr Tyr Phe Val Tyr Ser Lys Leu Ser Val Asp Arg
            180                 185                 190

Ser His Trp Gln Arg Gly Asn Thr Tyr Thr Cys Ser Val Ser His Glu
        195                 200                 205

Ala Leu His Ser His His Thr Gln Lys Ser Leu Thr Gln Ser Pro Gly
    210                 215                 220

<210> SEQ ID NO 20
<211> LENGTH: 224
<212> TYPE: PRT
<213> ORGANISM: Artificial Sequence
<220> FEATURE:
<223> OTHER INFORMATION: Feline IgG1b Fc Fragment

<400> SEQUENCE: 20

Asp Cys Pro Lys Cys Pro Pro Pro Glu Met Leu Gly Gly Pro Ser Ile

-continued

```
1               5                   10                  15
Phe Ile Phe Pro Pro Lys Pro Lys Asp Thr Leu Ser Ile Ser Arg Thr
            20                  25                  30

Pro Glu Val Thr Cys Leu Val Val Asp Leu Gly Pro Asp Asp Ser Asp
            35                  40                  45

Val Gln Ile Thr Trp Phe Val Asp Asn Thr Gln Val Tyr Thr Ala Lys
 50                  55                  60

Thr Ser Pro Arg Glu Glu Gln Phe Asn Ser Thr Tyr Arg Val Val Ser
 65                  70                  75                  80

Val Leu Pro Ile Leu His Gln Asp Trp Leu Lys Gly Lys Glu Phe Lys
                 85                  90                  95

Cys Lys Val Asn Ser Lys Ser Leu Pro Ser Pro Ile Glu Arg Thr Ile
                100                 105                 110

Ser Lys Asp Lys Gly Gln Pro His Glu Pro Gln Val Tyr Val Leu Pro
                115                 120                 125

Pro Ala Gln Glu Glu Leu Ser Arg Asn Lys Val Ser Val Thr Cys Leu
    130                 135                 140

Ile Glu Gly Phe Tyr Pro Ser Asp Ile Ala Val Glu Trp Glu Ile Thr
145                 150                 155                 160

Gly Gln Pro Glu Pro Glu Asn Asn Tyr Arg Thr Thr Pro Pro Gln Leu
                165                 170                 175

Asp Ser Asp Gly Thr Tyr Phe Leu Tyr Ser Arg Leu Ser Val Asp Arg
                180                 185                 190

Ser Arg Trp Gln Arg Gly Asn Thr Tyr Thr Cys Ser Val Ser His Glu
                195                 200                 205

Ala Leu His Ser His His Thr Gln Lys Ser Leu Thr Gln Ser Pro Gly
    210                 215                 220
```

<210> SEQ ID NO 21
<211> LENGTH: 225
<212> TYPE: PRT
<213> ORGANISM: Artificial Sequence
<220> FEATURE:
<223> OTHER INFORMATION: Feline IgG2 Fc Fragment

<400> SEQUENCE: 21

```
Gly Glu Gly Pro Lys Cys Pro Val Pro Glu Ile Pro Gly Ala Pro Ser
1               5                   10                  15

Val Phe Ile Phe Pro Pro Lys Pro Lys Asp Thr Leu Ser Ile Ser Arg
            20                  25                  30

Thr Pro Glu Val Thr Cys Leu Val Val Asp Leu Gly Pro Asp Asp Ser
            35                  40                  45

Asn Val Gln Ile Thr Trp Phe Val Asp Asn Thr Glu Met His Thr Ala
 50                  55                  60

Lys Thr Arg Pro Arg Glu Glu Gln Phe Asn Ser Thr Tyr Arg Val Val
 65                  70                  75                  80

Ser Val Leu Pro Ile Leu His Gln Asp Trp Leu Lys Gly Lys Glu Phe
                 85                  90                  95

Lys Cys Lys Val Asn Ser Lys Ser Leu Pro Ser Ala Met Glu Arg Thr
                100                 105                 110

Ile Ser Lys Ala Lys Gly Gln Pro His Glu Pro Gln Val Tyr Val Leu
                115                 120                 125

Pro Pro Thr Gln Glu Glu Leu Ser Glu Asn Lys Val Ser Val Thr Cys
    130                 135                 140

Leu Ile Lys Gly Phe His Pro Pro Asp Ile Ala Val Glu Trp Glu Ile
```

```
145                 150                 155                 160
Thr Gly Gln Pro Glu Pro Glu Asn Asn Tyr Gln Thr Thr Pro Pro Gln
                165                 170                 175

Leu Asp Ser Asp Gly Thr Tyr Phe Leu Tyr Ser Arg Leu Ser Val Asp
            180                 185                 190

Arg Ser His Trp Gln Arg Gly Asn Thr Tyr Thr Cys Ser Val Ser His
        195                 200                 205

Glu Ala Leu His Ser His Thr Gln Lys Ser Leu Thr Gln Ser Pro
    210                 215                 220

Gly
225

<210> SEQ ID NO 22
<211> LENGTH: 224
<212> TYPE: PRT
<213> ORGANISM: Artificial Sequence
<220> FEATURE:
<223> OTHER INFORMATION: Canine IgGB Fc Fragment with cNg-S Mutation

<400> SEQUENCE: 22

Asp Cys Pro Lys Cys Pro Ala Pro Glu Met Leu Gly Gly Pro Ser Val
1               5                   10                  15

Phe Ile Phe Pro Pro Lys Pro Lys Asp Thr Leu Leu Ile Ala Arg Thr
            20                  25                  30

Pro Glu Val Thr Cys Val Val Asp Leu Asp Pro Glu Asp Pro Glu
        35                  40                  45

Val Gln Ile Ser Trp Phe Val Asp Gly Lys Gln Met Gln Thr Ala Lys
50                  55                  60

Thr Gln Pro Arg Glu Glu Gln Phe Ser Gly Thr Tyr Arg Val Val Ser
65                  70                  75                  80

Val Leu Pro Ile Gly His Gln Asp Trp Leu Lys Gly Lys Gln Phe Thr
            85                  90                  95

Cys Lys Val Asn Asn Lys Ala Leu Pro Ser Pro Ile Glu Arg Thr Ile
        100                 105                 110

Ser Lys Ala Arg Gly Gln Ala His Gln Pro Ser Val Tyr Val Leu Pro
    115                 120                 125

Pro Ser Arg Glu Glu Leu Ser Lys Asn Thr Val Ser Leu Thr Cys Leu
130                 135                 140

Ile Lys Asp Phe Phe Pro Pro Asp Ile Asp Val Glu Trp Gln Ser Asn
145                 150                 155                 160

Gly Gln Gln Glu Pro Glu Ser Lys Tyr Arg Thr Thr Pro Pro Gln Leu
                165                 170                 175

Asp Glu Asp Gly Ser Tyr Phe Leu Tyr Ser Lys Leu Ser Val Asp Lys
            180                 185                 190

Ser Arg Trp Gln Arg Gly Asp Thr Phe Ile Cys Ala Val Met His Glu
        195                 200                 205

Ala Leu His Asn His Tyr Thr Gln Glu Ser Leu Ser His Ser Pro Gly
    210                 215                 220

<210> SEQ ID NO 23
<211> LENGTH: 224
<212> TYPE: PRT
<213> ORGANISM: Artificial Sequence
<220> FEATURE:
<223> OTHER INFORMATION: Feline IgG1b Fc Fragment with cNg-S Mutation

<400> SEQUENCE: 23
```

-continued

```
Asp Cys Pro Lys Cys Pro Pro Glu Met Leu Gly Pro Ser Ile
1               5                   10                  15

Phe Ile Phe Pro Pro Lys Pro Lys Asp Thr Leu Ser Ile Ser Arg Thr
            20                  25                  30

Pro Glu Val Thr Cys Leu Val Val Asp Leu Gly Pro Asp Asp Ser Asp
            35                  40                  45

Val Gln Ile Thr Trp Phe Val Asp Asn Thr Gln Val Tyr Thr Ala Lys
        50                  55                  60

Thr Ser Pro Arg Glu Glu Gln Phe Ser Ser Thr Tyr Arg Val Val Ser
65                  70                  75                  80

Val Leu Pro Ile Leu His Gln Asp Trp Leu Lys Gly Lys Glu Phe Lys
                    85                  90                  95

Cys Lys Val Asn Ser Lys Ser Leu Pro Ser Pro Ile Glu Arg Thr Ile
                100                 105                 110

Ser Lys Asp Lys Gly Gln Pro His Glu Pro Gln Val Tyr Val Leu Pro
            115                 120                 125

Pro Ala Gln Glu Glu Leu Ser Arg Asn Lys Val Ser Val Thr Cys Leu
        130                 135                 140

Ile Glu Gly Phe Tyr Pro Ser Asp Ile Ala Val Glu Trp Glu Ile Thr
145                 150                 155                 160

Gly Gln Pro Glu Pro Glu Asn Asn Tyr Arg Thr Thr Pro Pro Gln Leu
                165                 170                 175

Asp Ser Asp Gly Thr Tyr Phe Leu Tyr Ser Arg Leu Ser Val Asp Arg
                180                 185                 190

Ser Arg Trp Gln Arg Gly Asn Thr Tyr Thr Cys Ser Val Ser His Glu
            195                 200                 205

Ala Leu His Ser His His Thr Gln Lys Ser Leu Thr Gln Ser Pro Gly
        210                 215                 220

<210> SEQ ID NO 24
<211> LENGTH: 303
<212> TYPE: PRT
<213> ORGANISM: Artificial Sequence
<220> FEATURE:
<223> OTHER INFORMATION: Fusion Protein
<220> FEATURE:
<221> NAME/KEY: Xaa
<222> LOCATION: (10)..(10)
<223> OTHER INFORMATION: Xaa is not D
<220> FEATURE:
<221> NAME/KEY: Xaa
<222> LOCATION: (45)..(45)
<223> OTHER INFORMATION: Xaa is not H
<220> FEATURE:
<221> NAME/KEY: Xaa
<222> LOCATION: (58)..(58)
<223> OTHER INFORMATION: Xaa is absent or N

<400> SEQUENCE: 24

Phe Val Asn Gln His Leu Cys Gly Ser Xaa Leu Val Glu Ala Leu Glu
1               5                   10                  15

Leu Val Cys Gly Glu Arg Gly Phe His Tyr Gly Gly Gly Gly Gly Gly
            20                  25                  30

Ser Gly Gly Gly Gly Ile Val Glu Gln Cys Cys Xaa Ser Thr Cys
            35                  40                  45

Ser Leu Asp Gln Leu Glu Asn Tyr Cys Xaa Gly Gly Gly Gly Gln
        50                  55                  60

Gly Gly Gly Gly Gln Gly Gly Gly Gln Gly Gly Gly Gly Asp
65                  70                  75                  80
```

```
Cys Pro Lys Cys Pro Ala Pro Glu Met Leu Gly Gly Pro Ser Val Phe
                85                  90                  95

Ile Phe Pro Pro Lys Pro Lys Asp Thr Leu Leu Ile Ala Arg Thr Pro
            100                 105                 110

Glu Val Thr Cys Val Val Val Asp Leu Asp Pro Glu Asp Pro Glu Val
        115                 120                 125

Gln Ile Ser Trp Phe Val Asp Gly Lys Gln Met Gln Thr Ala Lys Thr
    130                 135                 140

Gln Pro Arg Glu Glu Gln Phe Asn Gly Thr Tyr Arg Val Val Ser Val
145                 150                 155                 160

Leu Pro Ile Gly His Gln Asp Trp Leu Lys Gly Lys Gln Phe Thr Cys
                165                 170                 175

Lys Val Asn Asn Lys Ala Leu Pro Ser Pro Ile Glu Arg Thr Ile Ser
            180                 185                 190

Lys Ala Arg Gly Gln Ala His Gln Pro Ser Val Tyr Val Leu Pro Pro
        195                 200                 205

Ser Arg Glu Glu Leu Ser Lys Asn Thr Val Ser Leu Thr Cys Leu Ile
    210                 215                 220

Lys Asp Phe Phe Pro Pro Asp Ile Asp Val Glu Trp Gln Ser Asn Gly
225                 230                 235                 240

Gln Gln Glu Pro Glu Ser Lys Tyr Arg Thr Thr Pro Pro Gln Leu Asp
                245                 250                 255

Glu Asp Gly Ser Tyr Phe Leu Tyr Ser Lys Leu Ser Val Asp Lys Ser
            260                 265                 270

Arg Trp Gln Arg Gly Asp Thr Phe Ile Cys Ala Val Met His Glu Ala
        275                 280                 285

Leu His Asn His Tyr Thr Gln Glu Ser Leu Ser His Ser Pro Gly
    290                 295                 300

<210> SEQ ID NO 25
<211> LENGTH: 303
<212> TYPE: PRT
<213> ORGANISM: Artificial Sequence
<220> FEATURE:
<223> OTHER INFORMATION: Fusion Protein
<220> FEATURE:
<221> NAME/KEY: Xaa
<222> LOCATION: (58)..(58)
<223> OTHER INFORMATION: Xaa is absent or N

<400> SEQUENCE: 25

Phe Val Asn Gln His Leu Cys Gly Ser His Leu Val Glu Ala Leu Glu
1               5                   10                  15

Leu Val Cys Gly Glu Arg Gly Phe His Tyr Gly Gly Gly Gly Gly Gly
            20                  25                  30

Ser Gly Gly Gly Gly Gly Ile Val Glu Gln Cys Cys Thr Ser Thr Cys
        35                  40                  45

Ser Leu Asp Gln Leu Glu Asn Tyr Cys Xaa Gly Gly Gly Gly Gln
    50                  55                  60

Gly Gly Gly Gly Gln Gly Gly Gly Gln Gly Gly Gly Gly Asp
65                  70                  75                  80

Cys Pro Lys Cys Pro Ala Pro Glu Met Leu Gly Gly Pro Ser Val Phe
                85                  90                  95

Ile Phe Pro Pro Lys Pro Lys Asp Thr Leu Leu Ile Ala Arg Thr Pro
            100                 105                 110

Glu Val Thr Cys Val Val Val Asp Leu Asp Pro Glu Asp Pro Glu Val
        115                 120                 125
```

```
Gln Ile Ser Trp Phe Val Asp Gly Lys Gln Met Gln Thr Ala Lys Thr
    130                 135                 140

Gln Pro Arg Glu Glu Gln Phe Asn Gly Thr Tyr Arg Val Val Ser Val
145                 150                 155                 160

Leu Pro Ile Gly His Gln Asp Trp Leu Lys Gly Lys Gln Phe Thr Cys
                165                 170                 175

Lys Val Asn Asn Lys Ala Leu Pro Ser Pro Ile Glu Arg Thr Ile Ser
                180                 185                 190

Lys Ala Arg Gly Gln Ala His Gln Pro Ser Val Tyr Val Leu Pro Pro
            195                 200                 205

Ser Arg Glu Glu Leu Ser Lys Asn Thr Val Ser Leu Thr Cys Leu Ile
    210                 215                 220

Lys Asp Phe Phe Pro Pro Asp Ile Asp Val Glu Trp Gln Ser Asn Gly
225                 230                 235                 240

Gln Gln Glu Pro Glu Ser Lys Tyr Arg Thr Thr Pro Pro Gln Leu Asp
                245                 250                 255

Glu Asp Gly Ser Tyr Phe Leu Tyr Ser Lys Leu Ser Val Asp Lys Ser
                260                 265                 270

Arg Trp Gln Arg Gly Asp Thr Phe Ile Cys Ala Val Met His Glu Ala
            275                 280                 285

Leu His Asn His Tyr Thr Gln Glu Ser Leu Ser His Ser Pro Gly
    290                 295                 300

<210> SEQ ID NO 26
<211> LENGTH: 302
<212> TYPE: PRT
<213> ORGANISM: Artificial Sequence
<220> FEATURE:
<223> OTHER INFORMATION: Fusion Protein
<220> FEATURE:
<221> NAME/KEY: Xaa
<222> LOCATION: (10)..(10)
<223> OTHER INFORMATION: Xaa is not D
<220> FEATURE:
<221> NAME/KEY: Xaa
<222> LOCATION: (45)..(45)
<223> OTHER INFORMATION: Xaa is not H

<400> SEQUENCE: 26

Phe Val Asn Gln His Leu Cys Gly Ser Xaa Leu Val Glu Ala Leu Ala
1               5                   10                  15

Leu Val Cys Gly Glu Arg Gly Phe His Tyr Gly Gly Gly Gly Gly Gly
            20                  25                  30

Ser Gly Gly Gly Gly Ile Val Glu Gln Cys Cys Xaa Ser Thr Cys
        35                  40                  45

Ser Leu Asp Gln Leu Glu Asn Tyr Cys Gly Gly Gly Gly Gln Gly
    50                  55                  60

Gly Gly Gln Gly Gly Gly Gln Gly Gly Gly Gly Asp Cys
65                  70                  75                  80

Pro Lys Cys Pro Ala Pro Glu Met Leu Gly Gly Pro Ser Val Phe Ile
                85                  90                  95

Phe Pro Pro Lys Pro Lys Asp Thr Leu Leu Ile Ala Arg Thr Pro Glu
                100                 105                 110

Val Thr Cys Val Val Val Asp Leu Asp Pro Glu Asp Pro Glu Val Gln
            115                 120                 125

Ile Ser Trp Phe Val Asp Gly Lys Gln Met Gln Thr Ala Lys Thr Gln
    130                 135                 140
```

Pro Arg Glu Glu Gln Phe Ser Gly Thr Tyr Arg Val Val Ser Val Leu
145                 150                 155                 160

Pro Ile Gly His Gln Asp Trp Leu Lys Gly Lys Gln Phe Thr Cys Lys
            165                 170                 175

Val Asn Asn Lys Ala Leu Pro Ser Pro Ile Glu Arg Thr Ile Ser Lys
            180                 185                 190

Ala Arg Gly Gln Ala His Gln Pro Ser Val Tyr Val Leu Pro Pro Ser
        195                 200                 205

Arg Glu Glu Leu Ser Lys Asn Thr Val Ser Leu Thr Cys Leu Ile Lys
    210                 215                 220

Asp Phe Phe Pro Pro Asp Ile Asp Val Glu Trp Gln Ser Asn Gly Gln
225                 230                 235                 240

Gln Glu Pro Glu Ser Lys Tyr Arg Thr Thr Pro Pro Gln Leu Asp Glu
            245                 250                 255

Asp Gly Ser Tyr Phe Leu Tyr Ser Lys Leu Ser Val Asp Lys Ser Arg
            260                 265                 270

Trp Gln Arg Gly Asp Thr Phe Ile Cys Ala Val Met His Glu Ala Leu
        275                 280                 285

His Asn His Tyr Thr Gln Glu Ser Leu Ser His Ser Pro Gly
    290                 295                 300

<210> SEQ ID NO 27
<211> LENGTH: 302
<212> TYPE: PRT
<213> ORGANISM: Artificial Sequence
<220> FEATURE:
<223> OTHER INFORMATION: Fusion Protein
<220> FEATURE:
<221> NAME/KEY: Xaa
<222> LOCATION: (10)..(10)
<223> OTHER INFORMATION: Xaa is not D
<220> FEATURE:
<221> NAME/KEY: Xaa
<222> LOCATION: (45)..(45)
<223> OTHER INFORMATION: Xaa is not H

<400> SEQUENCE: 27

Phe Val Asn Gln His Leu Cys Gly Ser Xaa Leu Val Glu Ala Leu Glu
1               5                   10                  15

Leu Val Cys Gly Glu Arg Gly Phe His Tyr Gly Gly Gly Gly Gly Gly
            20                  25                  30

Ser Gly Gly Gly Gly Gly Ile Val Glu Gln Cys Cys Xaa Ser Thr Cys
        35                  40                  45

Ser Leu Asp Gln Leu Glu Asn Tyr Cys Gly Gly Gly Gly Gly Gln Gly
    50                  55                  60

Gly Gly Gly Gln Gly Gly Gly Gln Gly Gly Gly Gly Asp Cys
65                  70                  75                  80

Pro Lys Cys Pro Pro Pro Glu Met Leu Gly Gly Pro Ser Ile Phe Ile
            85                  90                  95

Phe Pro Pro Lys Pro Lys Asp Thr Leu Ser Ile Ser Arg Thr Pro Glu
            100                 105                 110

Val Thr Cys Leu Val Val Asp Leu Gly Pro Asp Asp Ser Asp Val Gln
        115                 120                 125

Ile Thr Trp Phe Val Asp Asn Thr Gln Val Tyr Thr Ala Lys Thr Ser
    130                 135                 140

Pro Arg Glu Glu Gln Phe Asn Ser Thr Tyr Arg Val Val Ser Val Leu
145                 150                 155                 160

Pro Ile Leu His Gln Asp Trp Leu Lys Gly Lys Glu Phe Lys Cys Lys

```
                    165                 170                 175
Val Asn Ser Lys Ser Leu Pro Ser Pro Ile Glu Arg Thr Ile Ser Lys
                180                 185                 190

Asp Lys Gly Gln Pro His Glu Pro Gln Val Tyr Val Leu Pro Pro Ala
            195                 200                 205

Gln Glu Glu Leu Ser Arg Asn Lys Val Ser Val Thr Cys Leu Ile Glu
        210                 215                 220

Gly Phe Tyr Pro Ser Asp Ile Ala Val Glu Trp Glu Ile Thr Gly Gln
225                 230                 235                 240

Pro Glu Pro Glu Asn Asn Tyr Arg Thr Thr Pro Pro Gln Leu Asp Ser
                245                 250                 255

Asp Gly Thr Tyr Phe Leu Tyr Ser Arg Leu Ser Val Asp Arg Ser Arg
            260                 265                 270

Trp Gln Arg Gly Asn Thr Tyr Thr Cys Ser Val Ser His Glu Ala Leu
        275                 280                 285

His Ser His His Thr Gln Lys Ser Leu Thr Gln Ser Pro Gly
    290                 295                 300

<210> SEQ ID NO 28
<211> LENGTH: 302
<212> TYPE: PRT
<213> ORGANISM: Artificial Sequence
<220> FEATURE:
<223> OTHER INFORMATION: Fusion Protein
<220> FEATURE:
<221> NAME/KEY: Xaa
<222> LOCATION: (10)..(10)
<223> OTHER INFORMATION: Xaa is not D
<220> FEATURE:
<221> NAME/KEY: Xaa
<222> LOCATION: (45)..(45)
<223> OTHER INFORMATION: Xaa is not H

<400> SEQUENCE: 28

Phe Val Asn Gln His Leu Cys Gly Ser Xaa Leu Val Glu Ala Leu Ala
1               5                   10                  15

Leu Val Cys Gly Glu Arg Gly Phe His Tyr Gly Gly Gly Gly Gly Gly
            20                  25                  30

Ser Gly Gly Gly Gly Gly Ile Val Glu Gln Cys Cys Xaa Ser Thr Cys
        35                  40                  45

Ser Leu Asp Gln Leu Glu Asn Tyr Cys Gly Gly Gly Gly Gly Gln Gly
    50                  55                  60

Gly Gly Gln Gly Gly Gly Gly Gln Gly Gly Gly Gly Asp Cys
65                  70                  75                  80

Pro Lys Cys Pro Pro Pro Glu Met Leu Gly Gly Pro Ser Ile Phe Ile
                85                  90                  95

Phe Pro Pro Lys Pro Lys Asp Thr Leu Ser Ile Ser Arg Thr Pro Glu
            100                 105                 110

Val Thr Cys Leu Val Val Asp Leu Gly Pro Asp Asp Ser Asp Val Gln
        115                 120                 125

Ile Thr Trp Phe Val Asp Asn Thr Gln Val Tyr Thr Ala Lys Thr Ser
    130                 135                 140

Pro Arg Glu Glu Gln Phe Ser Thr Tyr Arg Val Val Ser Val Leu
145                 150                 155                 160

Pro Ile Leu His Gln Asp Trp Leu Lys Gly Lys Glu Phe Lys Cys Lys
                165                 170                 175

Val Asn Ser Lys Ser Leu Pro Ser Pro Ile Glu Arg Thr Ile Ser Lys
            180                 185                 190
```

Asp Lys Gly Gln Pro His Glu Pro Gln Val Tyr Val Leu Pro Pro Ala
        195                 200                 205

Gln Glu Glu Leu Ser Arg Asn Lys Val Ser Val Thr Cys Leu Ile Glu
    210                 215                 220

Gly Phe Tyr Pro Ser Asp Ile Ala Val Glu Trp Glu Ile Thr Gly Gln
225                 230                 235                 240

Pro Glu Pro Glu Asn Asn Tyr Arg Thr Thr Pro Pro Gln Leu Asp Ser
                245                 250                 255

Asp Gly Thr Tyr Phe Leu Tyr Ser Arg Leu Ser Val Asp Arg Ser Arg
            260                 265                 270

Trp Gln Arg Gly Asn Thr Tyr Thr Cys Ser Val Ser His Glu Ala Leu
        275                 280                 285

His Ser His His Thr Gln Lys Ser Leu Thr Gln Ser Pro Gly
    290                 295                 300

<210> SEQ ID NO 29
<211> LENGTH: 57
<212> TYPE: DNA
<213> ORGANISM: Artificial Sequence
<220> FEATURE:
<223> OTHER INFORMATION: Leader DNA

<400> SEQUENCE: 29
atggaatgga gctgggtctt tctcttcttc ctgtcagtaa cgactggtgt ccactcc      57

<210> SEQ ID NO 30
<211> LENGTH: 19
<212> TYPE: PRT
<213> ORGANISM: Artificial Sequence
<220> FEATURE:
<223> OTHER INFORMATION: Leader

<400> SEQUENCE: 30

Met Glu Trp Ser Trp Val Phe Leu Phe Phe Leu Ser Val Thr Thr Gly
1               5                   10                  15

Val His Ser

<210> SEQ ID NO 31
<211> LENGTH: 966
<212> TYPE: DNA
<213> ORGANISM: Artificial Sequence
<220> FEATURE:
<223> OTHER INFORMATION: Fusion Protein DNA

<400> SEQUENCE: 31
atggaatgga gctgggtctt tctcttcttc ctgtcagtaa cgactggtgt ccactccttc      60
gtgaaccagc acctgtgcgg ctcccacctg gtggaagctc tggaactcgt gtgcggcgag     120
cggggcttcc actacggggg tggcggagga ggttctggtg gcggcggagg catcgtggaa     180
cagtgctgca cctccacctg ctccctggac cagctggaaa actactgcgg tggcggaggt     240
ggtcaaggag gcggtggaca gggtggaggt gggcagggag gaggcggggg agactgcccc     300
aagtgccccg ctcccgagat gctgggcgga cccagcgtgt tcatcttccc tcccaagccc     360
aaggacacac tgctgatcgc caggaccccg gaggtgacct gcgtggtggt ggacctggat     420
cccgaagacc ccgaggtgca gatcagctgg ttcgtggatg aaagcagat gcagaccgcc      480 aagacccaac ccgggaaga gcagttcaac ggcacctaca gggtggtgag tgtgttgccc      540
atcggccacc aggactggct gaaggggaag caattcacat gcaaggttaa taacaaggcc     600

```
ctgcccagcc ccatcgagag gaccatcagc aaggccaggg gccaggccca ccagccatct    660
gtgtacgtgc tgcccccatc tagggaggaa ctgagcaaga acacagtcag ccttacttgc    720
ctgatcaagg acttcttccc accggacata gacgtggagt ggcagagtaa cggccagcag    780
gagcccgaga gcaagtatag gaccacaccg ccccaactgg acgaggacgg aagctacttc    840
ctctacagca aattgagcgt tgacaaaagc aggtggcagc gaggcgacac cttcatctgc    900
gccgtgatgc acgaggcttt gcataaccac tacacccagg agagcctgtc ccacagcccc    960
ggatag                                                                966
```

<210> SEQ ID NO 32
<211> LENGTH: 302
<212> TYPE: PRT
<213> ORGANISM: Artificial Sequence
<220> FEATURE:
<223> OTHER INFORMATION: Fusion Protein

<400> SEQUENCE: 32

```
Phe Val Asn Gln His Leu Cys Gly Ser His Leu Val Glu Ala Leu Glu
1               5                   10                  15

Leu Val Cys Gly Glu Arg Gly Phe His Tyr Gly Gly Gly Gly Gly Gly
            20                  25                  30

Ser Gly Gly Gly Gly Ile Val Glu Gln Cys Cys Thr Ser Thr Cys
        35                  40                  45

Ser Leu Asp Gln Leu Glu Asn Tyr Cys Gly Gly Gly Gly Gln Gly
    50                  55                  60

Gly Gly Gln Gly Gly Gly Gln Gly Gly Gly Gly Asp Cys
65                  70                  75                  80

Pro Lys Cys Pro Ala Pro Glu Met Leu Gly Gly Pro Ser Val Phe Ile
                85                  90                  95

Phe Pro Pro Lys Pro Lys Asp Thr Leu Leu Ile Ala Arg Thr Pro Glu
            100                 105                 110

Val Thr Cys Val Val Val Asp Leu Asp Pro Glu Asp Pro Glu Val Gln
        115                 120                 125

Ile Ser Trp Phe Val Asp Gly Lys Gln Met Gln Thr Ala Lys Thr Gln
    130                 135                 140

Pro Arg Glu Glu Gln Phe Asn Gly Thr Tyr Arg Val Val Ser Val Leu
145                 150                 155                 160

Pro Ile Gly His Gln Asp Trp Leu Lys Gly Lys Gln Phe Thr Cys Lys
                165                 170                 175

Val Asn Asn Lys Ala Leu Pro Ser Pro Ile Glu Arg Thr Ile Ser Lys
            180                 185                 190

Ala Arg Gly Gln Ala His Gln Pro Ser Val Tyr Val Leu Pro Pro Ser
        195                 200                 205

Arg Glu Glu Leu Ser Lys Asn Thr Val Ser Leu Thr Cys Leu Ile Lys
    210                 215                 220

Asp Phe Phe Pro Pro Asp Ile Asp Val Glu Trp Gln Ser Asn Gly Gln
225                 230                 235                 240

Gln Glu Pro Glu Ser Lys Tyr Arg Thr Thr Pro Pro Gln Leu Asp Glu
                245                 250                 255

Asp Gly Ser Tyr Phe Leu Tyr Ser Lys Leu Ser Val Asp Lys Ser Arg
            260                 265                 270

Trp Gln Arg Gly Asp Thr Phe Ile Cys Ala Val Met His Glu Ala Leu
        275                 280                 285

His Asn His Tyr Thr Gln Glu Ser Leu Ser His Ser Pro Gly
```

<210> SEQ ID NO 33
<211> LENGTH: 969
<212> TYPE: DNA
<213> ORGANISM: Artificial Sequence
<220> FEATURE:
<223> OTHER INFORMATION: Fusion Protein DNA

<400> SEQUENCE: 33

```
atggaatgga gctgggtctt tctcttcttc ctgtcagtaa cgactggtgt ccactccttc    60
gtgaaccagc acctgtgcgg ctcccacctg gtggaagctc tggaactcgt gtgcggcgag   120
cggggcttcc actacggggg tggcggagga ggttctggtg gcggcggagg catcgtggaa   180
cagtgctgca cctccacctg ctccctggac cagctggaaa actactgcaa cggtggcgga   240
ggtggtcaag gaggcggtgg acagggtgga ggtgggcagg gaggaggcgg gggagactgc   300
cccaagtgcc ccgctcccga gatgctgggc ggacccagcg tgttcatctt ccctcccaag   360
cccaaggaca cactgctgat cgccaggacc ccggaggtga cctgcgtggt ggtggacctg   420
gatcccgaag accccgaggt gcagatcagc tggttcgtgg atggaaagca gatgcagacc   480
gccaagaccc aaccccggga gagcagttc aacggcacct acagggtggt gagtgtgttg   540
cccatcggcc accaggactg gctgaagggg aagcaattca catgcaaggt taataacaag   600
gccctgccca gccccatcga gaggaccatc agcaaggcca ggggccaggc ccaccagcca   660
tctgtgtacg tgctgccccc atctagggag gaactgagca agaacacagt cagccttact   720
tgcctgatca aggacttctt cccaccggac atagacgtgg agtggcagag taacggccag   780
caggagcccg agagcaagta taggaccaca ccgccccaac tggacgagga cggaagctac   840
ttcctctaca gcaaattgag cgttgacaaa gcaggtggc agcgaggcga caccttcatc   900
tgcgccgtga tgcacgaggc tttgcataac cactacaccc aggagagcct gtcccacagc   960
cccggatag                                                           969
```

<210> SEQ ID NO 34
<211> LENGTH: 303
<212> TYPE: PRT
<213> ORGANISM: Artificial Sequence
<220> FEATURE:
<223> OTHER INFORMATION: Fusion Protein

<400> SEQUENCE: 34

```
Phe Val Asn Gln His Leu Cys Gly Ser His Leu Val Glu Ala Leu Glu
1               5                   10                  15

Leu Val Cys Gly Glu Arg Gly Phe His Tyr Gly Gly Gly Gly Gly Gly
            20                  25                  30

Ser Gly Gly Gly Gly Ile Val Glu Gln Cys Cys Thr Ser Thr Cys
        35                  40                  45

Ser Leu Asp Gln Leu Glu Asn Tyr Cys Asn Gly Gly Gly Gly Gln
    50                  55                  60

Gly Gly Gly Gly Gln Gly Gly Gly Gln Gly Gly Gly Gly Asp
65                  70                  75                  80

Cys Pro Lys Cys Pro Ala Pro Glu Met Leu Gly Gly Pro Ser Val Phe
                85                  90                  95

Ile Phe Pro Pro Lys Pro Lys Asp Thr Leu Leu Ile Ala Arg Thr Pro
            100                 105                 110

Glu Val Thr Cys Val Val Val Asp Leu Asp Pro Glu Asp Pro Glu Val
        115                 120                 125
```

```
Gln Ile Ser Trp Phe Val Asp Gly Lys Gln Met Gln Thr Ala Lys Thr
    130                 135                 140

Gln Pro Arg Glu Glu Gln Phe Asn Gly Thr Tyr Arg Val Val Ser Val
145                 150                 155                 160

Leu Pro Ile Gly His Gln Asp Trp Leu Lys Gly Lys Gln Phe Thr Cys
                165                 170                 175

Lys Val Asn Asn Lys Ala Leu Pro Ser Pro Ile Glu Arg Thr Ile Ser
                180                 185                 190

Lys Ala Arg Gly Gln Ala His Gln Pro Ser Val Tyr Val Leu Pro Pro
            195                 200                 205

Ser Arg Glu Glu Leu Ser Lys Asn Thr Val Ser Leu Thr Cys Leu Ile
    210                 215                 220

Lys Asp Phe Phe Pro Pro Asp Ile Asp Val Glu Trp Gln Ser Asn Gly
225                 230                 235                 240

Gln Gln Glu Pro Glu Ser Lys Tyr Arg Thr Thr Pro Pro Gln Leu Asp
                245                 250                 255

Glu Asp Gly Ser Tyr Phe Leu Tyr Ser Lys Leu Ser Val Asp Lys Ser
                260                 265                 270

Arg Trp Gln Arg Gly Asp Thr Phe Ile Cys Ala Val Met His Glu Ala
            275                 280                 285

Leu His Asn His Tyr Thr Gln Glu Ser Leu Ser His Ser Pro Gly
    290                 295                 300
```

<210> SEQ ID NO 35
<211> LENGTH: 966
<212> TYPE: DNA
<213> ORGANISM: Artificial Sequence
<220> FEATURE:
<223> OTHER INFORMATION: Fusion Protein DNA

<400> SEQUENCE: 35

```
atggaatgga gctgggtctt tctcttcttc ctgtcagtaa cgactggtgt ccactccttc    60
gtgaaccagc acctgtgcgg ctcccacctg gtggaagctc tggcactcgt gtgcggcgag   120
cggggcttcc actacggggg tggcggagga ggttctggtg gcggcggagg catcgtggaa   180
cagtgctgca cctccacctg ctccctggac cagctggaaa actactgcgg tggcggaggt   240
ggtcaaggag gcggtggaca gggtggaggt gggcagggag gaggcggggg agactgcccc   300
aagtgccccg ctcccgagat gctgggcgga cccagcgtgt tcatcttccc tcccaagccc   360
aaggacacac tgctgatcgc caggaccccg gaggtgacct gcgtggtggt ggacctggat   420
cccgaagacc ccgaggtgca gatcagctgg ttcgtggatg gaaagcagat gcagaccgcc   480
aagacccaac cccgggaaga gcagttctca ggcacctaca gggtggtgag tgtgttgccc   540
atcggccacc aggactggct gaaggggaag caattcacat gcaaggttaa taacaaggcc   600
ctgcccagcc ccatcgagag gaccatcagc aaggccaggg gccaggccca ccagccatct   660
gtgtacgtgc tgcccccatc tagggaggaa ctgagcaaga cacagtcagc cttacttgc   720 ctgatcaagg acttcttccc accggacata gacgtggagt ggcagagtaa cggccagcag   780
gagcccgaga gcaagtatag gaccacaccg ccccaactgg acgaggacgg aagctacttc   840
ctctacagca aattgagcgt tgacaaaagc aggtggcagc gaggcgacac cttcatctgc   900
gccgtgatgc acgaggcttt gcataaccac tacacccagg agagcctgtc ccacagcccc   960
ggatag                                                              966
```

```
<210> SEQ ID NO 36
<211> LENGTH: 302
<212> TYPE: PRT
<213> ORGANISM: Artificial Sequence
<220> FEATURE:
<223> OTHER INFORMATION: Fusion Protein

<400> SEQUENCE: 36

Phe Val Asn Gln His Leu Cys Gly Ser His Leu Val Glu Ala Leu Ala
1               5                   10                  15

Leu Val Cys Gly Glu Arg Gly Phe His Tyr Gly Gly Gly Gly Gly Gly
                20                  25                  30

Ser Gly Gly Gly Gly Gly Ile Val Glu Gln Cys Cys Thr Ser Thr Cys
            35                  40                  45

Ser Leu Asp Gln Leu Glu Asn Tyr Cys Gly Gly Gly Gly Gly Gln Gly
        50                  55                  60

Gly Gly Gly Gln Gly Gly Gly Gly Gln Gly Gly Gly Gly Gly Asp Cys
65                  70                  75                  80

Pro Lys Cys Pro Ala Pro Glu Met Leu Gly Gly Pro Ser Val Phe Ile
                85                  90                  95

Phe Pro Pro Lys Pro Lys Asp Thr Leu Leu Ile Ala Arg Thr Pro Glu
                100                 105                 110

Val Thr Cys Val Val Val Asp Leu Asp Pro Glu Asp Pro Glu Val Gln
            115                 120                 125

Ile Ser Trp Phe Val Asp Gly Lys Gln Met Gln Thr Ala Lys Thr Gln
        130                 135                 140

Pro Arg Glu Glu Gln Phe Ser Gly Thr Tyr Arg Val Val Ser Val Leu
145                 150                 155                 160

Pro Ile Gly His Gln Asp Trp Leu Lys Gly Lys Gln Phe Thr Cys Lys
                165                 170                 175

Val Asn Asn Lys Ala Leu Pro Ser Pro Ile Glu Arg Thr Ile Ser Lys
                180                 185                 190

Ala Arg Gly Gln Ala His Gln Pro Ser Val Tyr Val Leu Pro Pro Ser
            195                 200                 205

Arg Glu Glu Leu Ser Lys Asn Thr Val Ser Leu Thr Cys Leu Ile Lys
210                 215                 220

Asp Phe Phe Pro Pro Asp Ile Asp Val Glu Trp Gln Ser Asn Gly Gln
225                 230                 235                 240

Gln Glu Pro Glu Ser Lys Tyr Arg Thr Thr Pro Pro Gln Leu Asp Glu
                245                 250                 255

Asp Gly Ser Tyr Phe Leu Tyr Ser Lys Leu Ser Val Asp Lys Ser Arg
            260                 265                 270

Trp Gln Arg Gly Asp Thr Phe Ile Cys Ala Val Met His Glu Ala Leu
        275                 280                 285

His Asn His Tyr Thr Gln Glu Ser Leu Ser His Ser Pro Gly
    290                 295                 300

<210> SEQ ID NO 37
<211> LENGTH: 966
<212> TYPE: DNA
<213> ORGANISM: Artificial Sequence
<220> FEATURE:
<223> OTHER INFORMATION: Fusion Protein DNA

<400> SEQUENCE: 37
atggaatgga gctgggtctt tctcttcttc ctgtcagtaa cgactggtgt ccactccttc      60
gtgaaccagc acctgtgcgg ctcccacctg gtggaagctc tggaactcgt gtgcggcgag     120
```

```
cggggcttcc actacgggggg tggcggagga ggttctggtg gcggcggagg catcgtggaa    180
cagtgctgca cctccacctg ctccctggac cagctggaaa actactgcgg tggcggaggt    240
ggtcaaggag gcggtggaca gggtggaggt gggcaggag gaggcggggg agactgcccc     300
aaatgtcctc cgcctgagat gctgggtggc cctagcatct tcatcttccc gcccaagccc    360
aaggatactc tgtccattag caggaccccc gaggtgacct gcctggtggt ggacctgggg    420
ccagacgact ctgacgtgca gatcacctgg ttcgtagaca cacccaggt ttacactgcc    480 aagaccagtc ccagggagga gcagttcaac agcacataca gggtggtgag cgttctgccc    540
atcctgcacc aggactggct gaaaggcaaa gagttcaagt gtaaggtgaa cagcaagagc    600
ctgcccagcc ccattgaaag gaccatcagc aaggacaagg ccagccgca cgagccccaa     660 gtctacgtgc tgcccccagc acaggaagag ctgagcagga caaggttag cgtgacatgc      720 ctgatcgagg gtttctaccc cagcgacatc gccgtggagt gggaaatcac cggccaaccc    780
gagcccgaga caactacag gaccactccg ccgcaactgg acagcgacgg gacctacttc     840
ttgtatagca ggctgagcgt ggaccggagc aggtggcaga ggggcaacac ctacacttgc    900
agcgtgagcc acgaggcctt gcacagccac cacactcaga gagtctgac ccagagcccg     960 ggatag                                                                966
```

<210> SEQ ID NO 38
<211> LENGTH: 302
<212> TYPE: PRT
<213> ORGANISM: Artificial Sequence
<220> FEATURE:
<223> OTHER INFORMATION: Fusion Protein

<400> SEQUENCE: 38

```
Phe Val Asn Gln His Leu Cys Gly Ser His Leu Val Glu Ala Leu Glu
1               5                   10                  15

Leu Val Cys Gly Glu Arg Gly Phe His Tyr Gly Gly Gly Gly Gly
            20                  25                  30

Ser Gly Gly Gly Gly Ile Val Glu Gln Cys Cys Thr Ser Thr Cys
        35                  40                  45

Ser Leu Asp Gln Leu Glu Asn Tyr Cys Gly Gly Gly Gly Gln Gly
    50                  55                  60

Gly Gly Gly Gln Gly Gly Gly Gly Gln Gly Gly Gly Gly Asp Cys
65                  70                  75                  80

Pro Lys Cys Pro Pro Glu Met Leu Gly Gly Pro Ser Ile Phe Ile
                85                  90                  95

Phe Pro Pro Lys Pro Lys Asp Thr Leu Ser Ile Ser Arg Thr Pro Glu
                100                 105                 110

Val Thr Cys Leu Val Val Asp Leu Gly Pro Asp Ser Asp Val Gln
            115                 120                 125

Ile Thr Trp Phe Val Asp Asn Thr Gln Val Tyr Thr Ala Lys Thr Ser
        130                 135                 140

Pro Arg Glu Glu Gln Phe Asn Ser Thr Tyr Arg Val Val Ser Val Leu
145                 150                 155                 160

Pro Ile Leu His Gln Asp Trp Leu Lys Gly Lys Glu Phe Lys Cys Lys
                165                 170                 175

Val Asn Ser Lys Ser Leu Pro Ser Pro Ile Glu Arg Thr Ile Ser Lys
                180                 185                 190

Asp Lys Gly Gln Pro His Glu Pro Gln Val Tyr Val Leu Pro Pro Ala
            195                 200                 205
```

Gln Glu Glu Leu Ser Arg Asn Lys Val Ser Val Thr Cys Leu Ile Glu
    210                 215                 220

Gly Phe Tyr Pro Ser Asp Ile Ala Val Glu Trp Glu Ile Thr Gly Gln
225                 230                 235                 240

Pro Glu Pro Glu Asn Asn Tyr Arg Thr Thr Pro Pro Gln Leu Asp Ser
                245                 250                 255

Asp Gly Thr Tyr Phe Leu Tyr Ser Arg Leu Ser Val Asp Arg Ser Arg
            260                 265                 270

Trp Gln Arg Gly Asn Thr Tyr Thr Cys Ser Val Ser His Glu Ala Leu
        275                 280                 285

His Ser His His Thr Gln Lys Ser Leu Thr Gln Ser Pro Gly
    290                 295                 300

<210> SEQ ID NO 39
<211> LENGTH: 966
<212> TYPE: DNA
<213> ORGANISM: Artificial Sequence
<220> FEATURE:
<223> OTHER INFORMATION: Fusion Protein DNA

<400> SEQUENCE: 39
atggaatgga gctgggtctt tctcttcttc ctgtcagtaa cgactggtgt ccactccttc      60
gtgaaccagc acctgtgcgg ctcccacctg gtggaagctc tggcactcgt gtgcggcgag     120
cggggcttcc actacggggg tggcggagga ggttctggtg gcggcggagg catcgtggaa     180
cagtgctgca cctccacctg ctccctggac cagctggaaa actactgcgg tggcggaggt     240
ggtcaaggag gcggtggaca gggtggaggt gggcaggag gaggcggggg agactgcccc      300
aaatgtcctc cgcctgagat gctgggtggc cctagcatct tcatcttccc gcccaagccc     360
aaggatactc tgtccattag caggaccccc gaggtgacct gctggtggt ggacctgggg      420 ccagacgact ctgacgtgca gatcacctgg ttcgtagaca cacccaggt ttacactgcc      480 aagaccagtc ccagggagga gcagttcagc agcacataca gggtggtgag cgttctgccc     540
atcctgcacc aggactggct gaaaggcaaa gagttcaagt gtaaggtgaa cagcaagagc     600
ctgcccagcc ccattgaaag gaccatcagc aaggacaagg ccagccgca cgagccccaa      660 gtctacgtgc tgcccccagc acaggaagag ctgagcagga caaggttag cgtgacatgc      720 ctgatcgagg gtttctaccc cagcgacatc gccgtggagt gggaaatcac cggccaaccc     780
gagcccgaga caactacag gaccactccg ccgcaactgg acagcgacgg gacctacttc      840
ttgtatagca ggctgagcgt ggaccggagc aggtggcaga gggcaacac ctacacttgc      900 agcgtgagcc acgaggcctt gcacagccac cacactcaga gagtctgac ccagagcccg      960 ggatag                                                                966

<210> SEQ ID NO 40
<211> LENGTH: 302
<212> TYPE: PRT
<213> ORGANISM: Artificial Sequence
<220> FEATURE:
<223> OTHER INFORMATION: Fusion Protein

<400> SEQUENCE: 40

Phe Val Asn Gln His Leu Cys Gly Ser His Leu Val Glu Ala Leu Ala
1               5                   10                  15

Leu Val Cys Gly Glu Arg Gly Phe His Tyr Gly Gly Gly Gly Gly Gly
            20                  25                  30

-continued

```
Ser Gly Gly Gly Gly Ile Val Glu Gln Cys Cys Thr Ser Thr Cys
     35                  40                  45
Ser Leu Asp Gln Leu Glu Asn Tyr Cys Gly Gly Gly Gly Gln Gly
 50                  55                  60
Gly Gly Gly Gln Gly Gly Gly Gln Gly Gly Gly Gly Gly Asp Cys
65                  70                  75                  80
Pro Lys Cys Pro Pro Pro Glu Met Leu Gly Gly Pro Ser Ile Phe Ile
                 85                  90                  95
Phe Pro Pro Lys Pro Lys Asp Thr Leu Ser Ile Ser Arg Thr Pro Glu
                100                 105                 110
Val Thr Cys Leu Val Val Asp Leu Gly Pro Asp Asp Ser Asp Val Gln
                115                 120                 125
Ile Thr Trp Phe Val Asp Asn Thr Gln Val Tyr Thr Ala Lys Thr Ser
130                 135                 140
Pro Arg Glu Glu Gln Phe Ser Ser Thr Tyr Arg Val Val Ser Val Leu
145                 150                 155                 160
Pro Ile Leu His Gln Asp Trp Leu Lys Gly Lys Glu Phe Lys Cys Lys
                165                 170                 175
Val Asn Ser Lys Ser Leu Pro Ser Pro Ile Glu Arg Thr Ile Ser Lys
                180                 185                 190
Asp Lys Gly Gln Pro His Glu Pro Gln Val Tyr Val Leu Pro Pro Ala
                195                 200                 205
Gln Glu Glu Leu Ser Arg Asn Lys Val Ser Val Thr Cys Leu Ile Glu
                210                 215                 220
Gly Phe Tyr Pro Ser Asp Ile Ala Val Glu Trp Glu Ile Thr Gly Gln
225                 230                 235                 240
Pro Glu Pro Glu Asn Asn Tyr Arg Thr Thr Pro Pro Gln Leu Asp Ser
                245                 250                 255
Asp Gly Thr Tyr Phe Leu Tyr Ser Arg Leu Ser Val Asp Arg Ser Arg
                260                 265                 270
Trp Gln Arg Gly Asn Thr Tyr Thr Cys Ser Val Ser His Glu Ala Leu
                275                 280                 285
His Ser His His Thr Gln Lys Ser Leu Thr Gln Ser Pro Gly
                290                 295                 300
```

<210> SEQ ID NO 41
<211> LENGTH: 942
<212> TYPE: DNA
<213> ORGANISM: Artificial Sequence
<220> FEATURE:
<223> OTHER INFORMATION: Fusion Protein DNA

<400> SEQUENCE: 41

| | | |
|---|---|---|
| atggaatgga gctgggtctt tctcttcttc ctgtcagtaa cgactggtgt ccactccttc | 60 |
| gtgaaccagc acctgtgcgg ctccgacctg gtggaagctc tggctctcgt gtgcggcgag | 120 |
| cggggcttct tctacaccga tcccactgga ggcggtccac gcagaggcat cgtgaacag | 180 |
| tgctgccact ccatctgctc cctgtaccag ctggaaaact actgcaatgg cggaggtggt | 240 |
| gcaggaggcg gtggacgctg cactgacacc cctccatgcc ctgtgcccga gcccctgggt | 300 |
| ggccccagcg tactgatctt cccaccgaaa cccaaggaca tcctgaggat cacccgcacc | 360 |
| ccggaggtga cctgcgtggt gctggacctg ggcaggagg accccgaagt gcaaatcagc | 420 |
| tggttcgtgg acgaaaagga ggtgcacacc gccaagaccc aatcaaggga gcagcagttc | 480 |
| aacggcacct acagggtggt gagcgtgttg cccatagagc accaggactg gctgaccggc | 540 |

```
aaggagttca agtgccgcgt gaaccacatt gatctcccca gccccatcga gaggactatc    600
tccaaggccc gagggagggc ccacaagccc agtgtatacg tgctgccgcc ctctccgaag    660
gaactgagct ctagcgacac cgtgagcatc acctgcctga tcaaggactt ctaccctccc    720
gacatagacg tagagtggca gagcaacggc cagcaggagc ccgaaaggaa gcacaggatg    780
accccacccc aactggacga ggacggctca tactttcttt atagcaagct gagtgtggac    840
aagagcaggt ggcagcaggg cgacccttc acttgcgccg taatgcacga gaccctgcag    900
aatcactaca ccgacctgtc actgagccat agccccggat ag                      942
```

```
<210> SEQ ID NO 42
<211> LENGTH: 294
<212> TYPE: PRT
<213> ORGANISM: Artificial Sequence
<220> FEATURE:
<223> OTHER INFORMATION: Fusion Protein

<400> SEQUENCE: 42
```

```
Phe Val Asn Gln His Leu Cys Gly Ser Asp Leu Val Glu Ala Leu Ala
  1               5                  10                  15

Leu Val Cys Gly Glu Arg Gly Phe Phe Tyr Thr Asp Pro Thr Gly Gly
             20                  25                  30

Gly Pro Arg Arg Gly Ile Val Glu Gln Cys Cys His Ser Ile Cys Ser
         35                  40                  45

Leu Tyr Gln Leu Glu Asn Tyr Cys Asn Gly Gly Gly Ala Gly Gly
     50                  55                  60

Gly Gly Arg Cys Thr Asp Thr Pro Pro Cys Pro Val Pro Glu Pro Leu
 65                  70                  75                  80

Gly Gly Pro Ser Val Leu Ile Phe Pro Pro Lys Pro Lys Asp Ile Leu
                 85                  90                  95

Arg Ile Thr Arg Thr Pro Glu Val Thr Cys Val Val Leu Asp Leu Gly
            100                 105                 110

Arg Glu Asp Pro Glu Val Gln Ile Ser Trp Phe Val Asp Gly Lys Glu
        115                 120                 125

Val His Thr Ala Lys Thr Gln Ser Arg Glu Gln Gln Phe Asn Gly Thr
    130                 135                 140

Tyr Arg Val Val Ser Val Leu Pro Ile Glu His Gln Asp Trp Leu Thr
145                 150                 155                 160

Gly Lys Glu Phe Lys Cys Arg Val Asn His Ile Asp Leu Pro Ser Pro
                165                 170                 175

Ile Glu Arg Thr Ile Ser Lys Ala Arg Gly Arg Ala His Lys Pro Ser
            180                 185                 190

Val Tyr Val Leu Pro Pro Ser Pro Lys Glu Leu Ser Ser Ser Asp Thr
        195                 200                 205

Val Ser Ile Thr Cys Leu Ile Lys Asp Phe Tyr Pro Pro Asp Ile Asp
    210                 215                 220

Val Glu Trp Gln Ser Asn Gly Gln Gln Glu Pro Glu Arg Lys His Arg
225                 230                 235                 240

Met Thr Pro Pro Gln Leu Asp Glu Asp Gly Ser Tyr Phe Leu Tyr Ser
                245                 250                 255

Lys Leu Ser Val Asp Lys Ser Arg Trp Gln Gln Gly Asp Pro Phe Thr
            260                 265                 270

Cys Ala Val Met His Glu Thr Leu Gln Asn His Tyr Thr Asp Leu Ser
        275                 280                 285

Leu Ser His Ser Pro Gly
```

<210> SEQ ID NO 43
<211> LENGTH: 942
<212> TYPE: DNA
<213> ORGANISM: Artificial Sequence
<220> FEATURE:
<223> OTHER INFORMATION: Fusion Protein DNA

<400> SEQUENCE: 43

```
atggaatgga gctgggtctt tctcttcttc ctgtcagtaa cgactggtgt ccactccttc      60
gtgaaccagc acctgtgcgg ctccgacctg gtggaagctc tggctctcgt gtgcggcgag     120
cggggcttct tctacaccga tcccactgga ggcggtccac gcagaggcat cgtggaacag     180
tgctgccact ccatctgctc cctgtaccag ctggaaaact actgcaatgg cggaggtggt     240
gcaggaggcg gtggacgctg cactgacacc cctccatgcc ctgtgcccga gcccctgggt     300
ggccccagcg tactgatctt cccaccgaaa cccaaggaca tcctgaggat cacccgcacc     360
ccggaggtga cctgcgtggt gctggacctg gcaggagg accccgaagt gcaaatcagc     420
tggttcgtgg acggaaagga ggtgcacacc gccaagaccc aatcaaggga gcagcagttc     480
aacggcacct acagggtggt gagcgtgttg cccatagagc accaggactg gctgaccggc     540
aaggagttca gtgccgcgt gaaccacatt gatctcccca gccccatcga gaggactatc     600
tccaaggccc agggagggc ccacaagccc agtgtatacg tgctgccgcc ctctccgaag     660
gaactgagct ctagcgacac cgtgagcatc acctgcctga tcaaggactt ctaccctccc     720
gacatagacg tagagtggca gagcaacggc cagcaggagc cgaaaggaa gcacaggatg     780
accccacccc aactggacga ggacggctca tactttcttt atagcaagct gagtgtggac     840
aagagcaggt ggcagcaggg cgacccttc acttgcgccg tactgcacga ggccctgcac     900
tctcactaca cccagaagtc actgagcctt agccccggat ag                       942
```

<210> SEQ ID NO 44
<211> LENGTH: 294
<212> TYPE: PRT
<213> ORGANISM: Artificial Sequence
<220> FEATURE:
<223> OTHER INFORMATION: Fusion Protein

<400> SEQUENCE: 44

Phe Val Asn Gln His Leu Cys Gly Ser Asp Leu Val Glu Ala Leu Ala
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn Gly Gly Gly Ala Gly Gly
    50                  55                  60

Gly Gly Arg Cys Thr Asp Thr Pro Pro Cys Pro Val Pro Glu Pro Leu
65                  70                  75                  80

Gly Gly Pro Ser Val Leu Ile Phe Pro Pro Lys Pro Lys Asp Ile Leu
                85                  90                  95

Arg Ile Thr Arg Thr Pro Glu Val Thr Cys Val Val Leu Asp Leu Gly
            100                 105                 110

Arg Glu Asp Pro Glu Val Gln Ile Ser Trp Phe Val Asp Gly Lys Glu
        115                 120                 125

Val His Thr Ala Lys Thr Gln Ser Arg Glu Gln Gln Phe Asn Gly Thr

```
                130             135             140
Tyr Arg Val Val Ser Val Leu Pro Ile Glu His Gln Asp Trp Leu Thr
145                 150                 155                 160

Gly Lys Glu Phe Lys Cys Arg Val Asn His Ile Asp Leu Pro Ser Pro
                165                 170                 175

Ile Glu Arg Thr Ile Ser Lys Ala Arg Gly Arg Ala His Lys Pro Ser
                180                 185                 190

Val Tyr Val Leu Pro Pro Ser Pro Lys Glu Leu Ser Ser Ser Asp Thr
                195                 200                 205

Val Ser Ile Thr Cys Leu Ile Lys Asp Phe Tyr Pro Pro Asp Ile Asp
            210                 215                 220

Val Glu Trp Gln Ser Asn Gly Gln Gln Glu Pro Glu Arg Lys His Arg
225                 230                 235                 240

Met Thr Pro Pro Gln Leu Asp Glu Asp Gly Ser Tyr Phe Leu Tyr Ser
                245                 250                 255

Lys Leu Ser Val Asp Lys Ser Arg Trp Gln Gln Gly Asp Pro Phe Thr
                260                 265                 270

Cys Ala Val Leu His Glu Ala Leu His Ser His Tyr Thr Gln Lys Ser
                275                 280                 285

Leu Ser Leu Ser Pro Gly
    290
```

```
<210> SEQ ID NO 45
<211> LENGTH: 942
<212> TYPE: DNA
<213> ORGANISM: Artificial Sequence
<220> FEATURE:
<223> OTHER INFORMATION: Fusion Protein DNA

<400> SEQUENCE: 45
atggaatgga gctgggtctt tctcttcttc ctgtcagtaa cgactggtgt ccactccttc      60
gtgaaccagc acctgtgcgg ctccgacctg gtggaagctc tggctctcgt gtgcggcgag     120
cggggcttct ctacaccga tcccactgga ggcggtccac gcagaggcat cgtggaacag     180
tgctgccact ccatctgctc cctgtaccag ctggaaaaact actgcaatgg cggaggtggt     240
gcaggaggcg gtggacgctg cactgacacc cctccatgcc ctgtgcccga gcccctgggt     300
ggccccagcg tactgatctt ccaccgaaa cccaaggaca tcctgaggat cacccgcacc     360
ccggaggtga cctgcgtggt gctggacctg ggcagggagg accccgaagt gcaaatcagc     420
tggttcgtgg acggaaagga ggtgcacacc gccaagaccc aatcaaggga gcagcagttc     480
aacggcacct acagggtggt gagcgtgttg cccatagagc accaggactg gctgaccggc     540
aaggagttca gtgccgcgt gaaccacatt gatctcccca gccccatcga gaggactatc     600
tccaaggccc gagggagggc ccacaagccc agtgtatacg tgctgccgcc ctctccgaag     660
gaactgagct ctagcgacac cgtgagcatc acctgcctga tcaaggactt ctaccctccc     720
gacatagacg tagagtggca gagcaacggc cagcaggagc ccgaaaggaa gcacaggatg     780
accccacccc aactggacga ggacggctca tactttcttt atagcaagct gagtgtggac     840
aagagcaggt ggcagcaggg cgacccttc acttgcgccg tactgcacga ccctgcag     900
tctcactaca ccgacctgtc actgagccat agccccggat ag                         942

<210> SEQ ID NO 46
<211> LENGTH: 294
<212> TYPE: PRT
<213> ORGANISM: Artificial Sequence
```

<220> FEATURE:
<223> OTHER INFORMATION: Fusion Protein

<400> SEQUENCE: 46

```
Phe Val Asn Gln His Leu Cys Gly Ser Asp Leu Val Glu Ala Leu Ala
1               5                   10                  15
Leu Val Cys Gly Glu Arg Gly Phe Phe Tyr Thr Asp Pro Thr Gly Gly
            20                  25                  30
Gly Pro Arg Arg Gly Ile Val Glu Gln Cys Cys His Ser Ile Cys Ser
        35                  40                  45
Leu Tyr Gln Leu Glu Asn Tyr Cys Asn Gly Gly Gly Ala Gly Gly
50                  55                  60
Gly Gly Arg Cys Thr Asp Thr Pro Cys Pro Val Pro Glu Pro Leu
65                  70                  75                  80
Gly Gly Pro Ser Val Leu Ile Phe Pro Pro Lys Pro Lys Asp Ile Leu
            85                  90                  95
Arg Ile Thr Arg Thr Pro Glu Val Thr Cys Val Val Leu Asp Leu Gly
            100                 105                 110
Arg Glu Asp Pro Glu Val Gln Ile Ser Trp Phe Val Asp Gly Lys Glu
        115                 120                 125
Val His Thr Ala Lys Thr Gln Ser Arg Glu Gln Gln Phe Asn Gly Thr
130                 135                 140
Tyr Arg Val Val Ser Val Leu Pro Ile Glu His Gln Asp Trp Leu Thr
145                 150                 155                 160
Gly Lys Glu Phe Lys Cys Arg Val Asn His Ile Asp Leu Pro Ser Pro
            165                 170                 175
Ile Glu Arg Thr Ile Ser Lys Ala Arg Gly Arg Ala His Lys Pro Ser
        180                 185                 190
Val Tyr Val Leu Pro Pro Ser Pro Lys Glu Leu Ser Ser Ser Asp Thr
        195                 200                 205
Val Ser Ile Thr Cys Leu Ile Lys Asp Phe Tyr Pro Pro Asp Ile Asp
210                 215                 220
Val Glu Trp Gln Ser Asn Gly Gln Gln Glu Pro Glu Arg Lys His Arg
225                 230                 235                 240
Met Thr Pro Pro Gln Leu Asp Glu Asp Gly Ser Tyr Phe Leu Tyr Ser
            245                 250                 255
Lys Leu Ser Val Asp Lys Ser Arg Trp Gln Gln Gly Asp Pro Phe Thr
        260                 265                 270
Cys Ala Val Leu His Glu Thr Leu Gln Ser His Tyr Thr Asp Leu Ser
    275                 280                 285
Leu Ser His Ser Pro Gly
290
```

<210> SEQ ID NO 47
<211> LENGTH: 942
<212> TYPE: DNA
<213> ORGANISM: Artificial Sequence
<220> FEATURE:
<223> OTHER INFORMATION: Fusion Protein DNA

<400> SEQUENCE: 47

```
atggaatgga gctgggtctt tctcttcttc ctgtcagtaa cgactggtgt ccactccttc      60
gtgaaccagc acctgtgcgg ctccgacctg gtggaagctc tggctctcgt gtgcggcgag     120
cggggcttct ctctacaccga tcccactgga ggcggtccac gcagaggcat cgtgaacag     180 tgctgccact ccatctgctc cctgtaccag ctggaaaact actgcaatgg cggaggtggt     240
```

-continued

```
gcaggaggcg gtggacgctg cactgacacc cctccatgcc ctgtgcccga gcccctgggt    300
ggccccagcg tactgatctt cccaccgaaa cccaaggaca tcctgaggat cacccgcacc    360
ccggaggtga cctgcgtggt gctggacctg gcagggagg accccgaagt gcaaatcagc     420
tggttcgtgg acgaaaagga ggtgcacacc gccaagaccc aatcaaggga gcagcagttc    480
aacggcacct acagggtggt gagcgtgttg cccatagagc accaggactg gctgaccggc    540
aaggagttca gtgccgcgt gaaccacatt gatctcccca gccccatcga gaggactatc     600
tccaaggccc gagggagggc ccacaagccc agtgtatacg tgctgccgcc ctctccgaag    660
gaactgagct ctagcgacac cgtgagcatc acctgcctga tcaaggactt ctaccctccc    720
gacatagacg tagagtggca gagcaacggc cagcaggagc ccgaaaggaa gcacaggatg    780
accccacccc aactggacga ggacggctca tactttcttt atagcaagct gagtgtggac    840
aagagcaggt ggcagcaggg cgaccctttc acttgcgccg taatgcacga gaccctgcag    900
tctcactaca ccgacctgtc actgagccat agccccggat ag                      942
```

```
<210> SEQ ID NO 48
<211> LENGTH: 294
<212> TYPE: PRT
<213> ORGANISM: Artificial Sequence
<220> FEATURE:
<223> OTHER INFORMATION: Fusion Protein

<400> SEQUENCE: 48
```

```
Phe Val Asn Gln His Leu Cys Gly Ser Asp Leu Val Glu Ala Leu Ala
1               5                   10                  15

Leu Val Cys Gly Glu Arg Gly Phe Phe Tyr Thr Asp Pro Thr Gly Gly
                20                  25                  30

Gly Pro Arg Arg Gly Ile Val Glu Gln Cys Cys His Ser Ile Cys Ser
            35                  40                  45

Leu Tyr Gln Leu Glu Asn Tyr Cys Asn Gly Gly Gly Ala Gly Gly
        50                  55                  60

Gly Gly Arg Cys Thr Asp Thr Pro Pro Cys Pro Val Pro Glu Pro Leu
65                  70                  75                  80

Gly Gly Pro Ser Val Leu Ile Phe Pro Pro Lys Pro Lys Asp Ile Leu
                85                  90                  95

Arg Ile Thr Arg Thr Pro Glu Val Thr Cys Val Val Leu Asp Leu Gly
            100                 105                 110

Arg Glu Asp Pro Glu Val Gln Ile Ser Trp Phe Val Asp Gly Lys Glu
        115                 120                 125

Val His Thr Ala Lys Thr Gln Ser Arg Glu Gln Gln Phe Asn Gly Thr
    130                 135                 140

Tyr Arg Val Val Ser Val Leu Pro Ile Glu His Gln Asp Trp Leu Thr
145                 150                 155                 160

Gly Lys Glu Phe Lys Cys Arg Val Asn His Ile Asp Leu Pro Ser Pro
                165                 170                 175

Ile Glu Arg Thr Ile Ser Lys Ala Arg Gly Arg Ala His Lys Pro Ser
            180                 185                 190

Val Tyr Val Leu Pro Pro Ser Pro Lys Glu Leu Ser Ser Asp Thr
        195                 200                 205

Val Ser Ile Thr Cys Leu Ile Lys Asp Phe Tyr Pro Pro Asp Ile Asp
    210                 215                 220

Val Glu Trp Gln Ser Asn Gly Gln Gln Glu Pro Glu Arg Lys His Arg
225                 230                 235                 240
```

Met Thr Pro Pro Gln Leu Asp Glu Asp Gly Ser Tyr Phe Leu Tyr Ser
                245                 250                 255

Lys Leu Ser Val Asp Lys Ser Arg Trp Gln Gln Gly Asp Pro Phe Thr
            260                 265                 270

Cys Ala Val Met His Glu Thr Leu Gln Ser His Tyr Thr Asp Leu Ser
        275                 280                 285

Leu Ser His Ser Pro Gly
    290

<210> SEQ ID NO 49
<211> LENGTH: 942
<212> TYPE: DNA
<213> ORGANISM: Artificial Sequence
<220> FEATURE:
<223> OTHER INFORMATION: Fusion Protein DNA

<400> SEQUENCE: 49
atggaatgga gctgggtctt tctcttcttc ctgtcagtaa cgactggtgt ccactccttc      60
gtgaaccagc acctgtgcgg ctccgacctg gtggaagctc tggctctcgt gtgcggcgag     120
cggggcttct tctacaccga tcccactgga ggcggtccac gcagaggcat cgtggaacag     180
tgctgccact ccatctgctc cctgtaccag ctggaaaact actgcaatgg cggaggtggt     240
gcaggaggcg gtggacgctg cactgacacc cctccatgcc ctgtgcccga gcccctgggt     300
ggccccagcg tactgatctt cccaccgaaa cccaaggaca tcctgaggat cacccgcacc     360
ccggaggtga cctgcgtggt gctggacctg ggcagggagg accccgaagt gcaaatcagc     420
tggttcgtgg acggaaagga ggtgcacacc gccaagaccc aatcaaggga gcagcagttc     480
aacggcacct acagggtggt gagcgtgttg cccatagagc accaggactg gctgaccggc     540
aaggagttca gtgccgcgt gaaccacatt gatctcccca gccccatcga gaggactatc     600
tccaaggccc gagggagggc ccacaagccc agtgtatacg tgctgccgcc ctctccgaag     660
gaactgagct ctagcgacac cgtgagcatc acctgcctga tcaaggactt ctaccctccc     720
gacatagacg tagagtggca gagcaacggc cagcaggagc ccgaaaggaa gcacaggatg     780
accccacccc aactggacga ggacggctca tactttcttt atagcaagct gagtgtggac     840
aagagcaggt ggcagcaggg cgacccttc acttgcgccg tactgcacga ccctgcag      900 aatcactaca ccgacctgtc actgagccat agccccggat ag                       942

<210> SEQ ID NO 50
<211> LENGTH: 294
<212> TYPE: PRT
<213> ORGANISM: Artificial Sequence
<220> FEATURE:
<223> OTHER INFORMATION: Fusion Protein

<400> SEQUENCE: 50

Phe Val Asn Gln His Leu Cys Gly Ser Asp Leu Val Glu Ala Leu Ala
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn Gly Gly Gly Ala Gly Gly
    50                  55                  60

Gly Gly Arg Cys Thr Asp Thr Pro Pro Cys Pro Val Pro Glu Pro Leu
65                  70                  75                  80

Gly Gly Pro Ser Val Leu Ile Phe Pro Pro Lys Pro Lys Asp Ile Leu
                85                  90                  95

Arg Ile Thr Arg Thr Pro Glu Val Thr Cys Val Val Leu Asp Leu Gly
            100                 105                 110

Arg Glu Asp Pro Glu Val Gln Ile Ser Trp Phe Val Asp Gly Lys Glu
        115                 120                 125

Val His Thr Ala Lys Thr Gln Ser Arg Glu Gln Gln Phe Asn Gly Thr
    130                 135                 140

Tyr Arg Val Val Ser Val Leu Pro Ile Glu His Gln Asp Trp Leu Thr
145                 150                 155                 160

Gly Lys Glu Phe Lys Cys Arg Val Asn His Ile Asp Leu Pro Ser Pro
                165                 170                 175

Ile Glu Arg Thr Ile Ser Lys Ala Arg Gly Arg Ala His Lys Pro Ser
            180                 185                 190

Val Tyr Val Leu Pro Pro Ser Pro Lys Glu Leu Ser Ser Ser Asp Thr
        195                 200                 205

Val Ser Ile Thr Cys Leu Ile Lys Asp Phe Tyr Pro Pro Asp Ile Asp
    210                 215                 220

Val Glu Trp Gln Ser Asn Gly Gln Gln Glu Pro Glu Arg Lys His Arg
225                 230                 235                 240

Met Thr Pro Pro Gln Leu Asp Glu Asp Gly Ser Tyr Phe Leu Tyr Ser
                245                 250                 255

Lys Leu Ser Val Asp Lys Ser Arg Trp Gln Gln Gly Asp Pro Phe Thr
            260                 265                 270

Cys Ala Val Leu His Glu Thr Leu Gln Asn His Tyr Thr Asp Leu Ser
        275                 280                 285

Leu Ser His Ser Pro Gly
    290

<210> SEQ ID NO 51
<211> LENGTH: 930
<212> TYPE: DNA
<213> ORGANISM: Artificial Sequence
<220> FEATURE:
<223> OTHER INFORMATION: Fusion Protein DNA

<400> SEQUENCE: 51
atggaatgga gctgggtctt tctcttcttc ctgtcagtaa cgactggtgt ccactccttc      60
gtgaaccagc acctgtgcgg ctccgacctg gtggaagctc tggctctcgt gtgcggcgag     120
cggggcttct tctacaccga tcccactgga ggcggtccac gcagaggcat cgtggaacag     180
tgctgccact ccatctgctc cctgtaccag ctggaaaact actgcaatgg cggaggtggt     240
gcaggaggcg gtgagactg ccccaagtgc ccgctcccg agatgctggg cggacccagc      300
gtgttcatct ccctcccaa gcccaaggac acactgctga tcgccaggac cccggaggtg     360
acctgcgtgg tggtggacct ggatcccgaa gaccccgagg tgcagatcag ctggttcgtg     420
gatggaaagc agatgcagac cgccaagacc caaccccggg aagagcagtt caacggcacc     480
tacagggtgg tgagtgtgtt gcccatcggc caccaggact ggctgaaggg aagcaattc      540 acatgcaagg ttaataacaa ggccctgccc agccccatcg agaggaccat cagcaaggcc     600
aggggccagg cccaccagcc atctgtgtac gtgctgcccc catctaggga ggaactgagc     660
aagaacacag tcagccttac ttgcctgatc aaggacttct tcccaccgga catagacgtg     720
gagtggcaga gtaacggcca gcaggagccc gagagcaagt ataggaccac accgcccaa      780

-continued

```
ctggacgagg acggaagcta cttcctctac agcaaattga gcgttgacaa aagcaggtgg    840
cagcgaggcg acaccttcat ctgcgccgtg atgcacgagg ctttgcataa ccactacacc    900
caggagagcc tgtcccacag ccccggatag                                     930
```

<210> SEQ ID NO 52
<211> LENGTH: 290
<212> TYPE: PRT
<213> ORGANISM: Artificial Sequence
<220> FEATURE:
<223> OTHER INFORMATION: Fusion Protein

<400> SEQUENCE: 52

```
Phe Val Asn Gln His Leu Cys Gly Ser Asp Leu Val Glu Ala Leu Ala
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn Gly Gly Gly Ala Gly Gly
    50                  55                  60

Gly Gly Asp Cys Pro Lys Cys Pro Ala Pro Glu Met Leu Gly Gly Pro
65                  70                  75                  80

Ser Val Phe Ile Phe Pro Pro Lys Pro Lys Asp Thr Leu Leu Ile Ala
                85                  90                  95

Arg Thr Pro Glu Val Thr Cys Val Val Val Asp Leu Asp Pro Glu Asp
            100                 105                 110

Pro Glu Val Gln Ile Ser Trp Phe Val Asp Gly Lys Gln Met Gln Thr
        115                 120                 125

Ala Lys Thr Gln Pro Arg Glu Glu Gln Phe Asn Gly Thr Tyr Arg Val
    130                 135                 140

Val Ser Val Leu Pro Ile Gly His Gln Asp Trp Leu Lys Gly Lys Gln
145                 150                 155                 160

Phe Thr Cys Lys Val Asn Asn Lys Ala Leu Pro Ser Pro Ile Glu Arg
                165                 170                 175

Thr Ile Ser Lys Ala Arg Gly Gln Ala His Gln Pro Ser Val Tyr Val
            180                 185                 190

Leu Pro Pro Ser Arg Glu Glu Leu Ser Lys Asn Thr Val Ser Leu Thr
        195                 200                 205

Cys Leu Ile Lys Asp Phe Phe Pro Pro Asp Ile Asp Val Glu Trp Gln
    210                 215                 220

Ser Asn Gly Gln Gln Glu Pro Glu Ser Lys Tyr Arg Thr Thr Pro Pro
225                 230                 235                 240

Gln Leu Asp Glu Asp Gly Ser Tyr Phe Leu Tyr Ser Lys Leu Ser Val
                245                 250                 255

Asp Lys Ser Arg Trp Gln Arg Gly Asp Thr Phe Ile Cys Ala Val Met
            260                 265                 270

His Glu Ala Leu His Asn His Tyr Thr Gln Glu Ser Leu Ser His Ser
        275                 280                 285

Pro Gly
    290
```

<210> SEQ ID NO 53
<211> LENGTH: 933
<212> TYPE: DNA
<213> ORGANISM: Artificial Sequence
<220> FEATURE:

<223> OTHER INFORMATION: Fusion Protein DNA

<400> SEQUENCE: 53

```
atggaatgga gctgggtctt tctcttcttc ctgtcagtaa cgactggtgt ccactccttc      60
gtgaaccagc acctgtgcgg ctccgacctg gtggaagctc tggctctcgt gtgcggcgag     120
cggggcttct tctacaccga tcccactgga ggcggtccac gcagaggcat cgtggaacag     180
tgctgccact ccatctgctc cctgtaccag ctggaaaaact actgcaatgg cggaggtggt    240
gcaggaggcg gtggatgcaa caactgcccg tgtccgggat gcggcctcct gggcggaccg     300
agcgtgttca ttttccctcc taagcccaag gacattctgg tgaccgccag gacccccacg     360
gtgacctgcg tggtagtaga tctcgatccc gaaaacccag aggtgcaaat cagctggttc     420
gtggactcta gcaagtgcaa aaccgccaac acgcaacccc gcgaggaaca gagcaacggc     480
acctacaggg tggtgagcgt gctgcccatc gggcatcagg actggctgag cggcaagcag     540
tttaaatgca aggttaacaa caaggcactg cccagcccca tcgaggagat catcagcaag     600
accccgggac aggcccacca gcccaacgtg tacgtcttc ctccgagccg cgacgagatg      660
agcaagaaca ccgtgacgct gacctgtttg gtgaaggact tcttcccacc cgagatcgac     720
gtggagtggc aaagcaatgg ccagcaggag cccgagagca atacaggat gaccccaccc      780
caactggatg aggatggcag ctatttcctc tacagcaaat gtccgtgga caaaagcagg      840
tggcagaggg gcgacacctt catctgcgcc gtcatgcacg aggcccttca caatcactac     900
acccagatca gcctgagcca ctctcccgga tag                                  933
```

<210> SEQ ID NO 54
<211> LENGTH: 291
<212> TYPE: PRT
<213> ORGANISM: Artificial Sequence
<220> FEATURE:
<223> OTHER INFORMATION: Fusion Protein

<400> SEQUENCE: 54

```
Phe Val Asn Gln His Leu Cys Gly Ser Asp Leu Val Glu Ala Leu Ala
1               5                  10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn Gly Gly Gly Ala Gly Gly
    50                  55                  60

Gly Gly Cys Asn Asn Cys Pro Cys Pro Gly Cys Gly Leu Leu Gly Gly
65                  70                  75                  80

Pro Ser Val Phe Ile Phe Pro Pro Lys Pro Lys Asp Ile Leu Val Thr
                85                  90                  95

Ala Arg Thr Pro Thr Val Thr Cys Val Val Val Asp Leu Asp Pro Glu
            100                 105                 110

Asn Pro Glu Val Gln Ile Ser Trp Phe Val Asp Ser Lys Gln Val Gln
        115                 120                 125

Thr Ala Asn Thr Gln Pro Arg Glu Glu Gln Ser Asn Gly Thr Tyr Arg
    130                 135                 140

Val Val Ser Val Leu Pro Ile Gly His Gln Asp Trp Leu Ser Gly Lys
145                 150                 155                 160

Gln Phe Lys Cys Lys Val Asn Asn Lys Ala Leu Pro Ser Pro Ile Glu
                165                 170                 175
```

```
Glu Ile Ile Ser Lys Thr Pro Gly Gln Ala His Gln Pro Asn Val Tyr
            180                 185                 190

Val Leu Pro Pro Ser Arg Asp Glu Met Ser Lys Asn Thr Val Thr Leu
        195                 200                 205

Thr Cys Leu Val Lys Asp Phe Phe Pro Pro Glu Ile Asp Val Glu Trp
    210                 215                 220

Gln Ser Asn Gly Gln Gln Glu Pro Glu Ser Lys Tyr Arg Met Thr Pro
225                 230                 235                 240

Pro Gln Leu Asp Glu Asp Gly Ser Tyr Phe Leu Tyr Ser Lys Leu Ser
                245                 250                 255

Val Asp Lys Ser Arg Trp Gln Arg Gly Asp Thr Phe Ile Cys Ala Val
            260                 265                 270

Met His Glu Ala Leu His Asn His Tyr Thr Gln Ile Ser Leu Ser His
        275                 280                 285

Ser Pro Gly
    290

<210> SEQ ID NO 55
<211> LENGTH: 933
<212> TYPE: DNA
<213> ORGANISM: Artificial Sequence
<220> FEATURE:
<223> OTHER INFORMATION: Fusion Protein DNA

<400> SEQUENCE: 55
atggaatgga gctgggtctt tctcttcttc ctgtcagtaa cgactggtgt ccactccttc      60
gtgaaccagc acctgtgcgg ctccgacctg gtggaagctc tggctctcgt gtgcggcgag     120
cggggcttct tctacaccga tcccactgga ggcggtccac gcagaggcat cgtggaacag     180
tgctgccact ccatctgctc cctgtaccag ctggaaaact actgcaatgg cggaggtggt     240
gcaggaggcg gtggatgcat cagcccctgc cccgtgccgg agagcctggg tggccctagc     300
gtgttcatat ccctcccaa gcccaaggac atcctgagga tcaccaggac ccccgagatc      360
acctgtgtgg tgctggatct tggcagggaa gaccccgaag tccagatcag ctggttcgtg     420
gatggcaagg aggtgcacac cgccaagacc cagccgaggg agcagcagtt caactccacc     480
tacagggtgg tgagcgtgct gcctatcgag catcaggact ggctgaccgg caaagagttc     540
aagtgcaggg tgaaccacat cggcctgccc agcccatcg agaggaccat cagcaaagcc      600
aggggccagg cccaccagcc cagtgtgtac gtgcttcccc ctagcccaaa ggaactgagt     660
agcagcgata ccgtgaccct gacctgcctg atcaaggact ttttcccgcc agaaatagac     720
gtggagtggc agagcaacgg ccagccggag cccgagagca ataccacac accgcccct       780 caactggacg aggacgggag ctacttcctg tatagcaagc tgagcgttga caagagcagg     840
tggcaacagg gcgacacctt cacctgcgcc gtgatgcacg aagctctgca aaaccactac     900
accgacctgt cactgagcca tagccccgga tag                                 933

<210> SEQ ID NO 56
<211> LENGTH: 291
<212> TYPE: PRT
<213> ORGANISM: Artificial Sequence
<220> FEATURE:
<223> OTHER INFORMATION: Fusion Protein

<400> SEQUENCE: 56

Phe Val Asn Gln His Leu Cys Gly Ser Asp Leu Val Glu Ala Leu Ala
1               5                   10                  15
```

```
Leu Val Cys Gly Glu Arg Gly Phe Phe Tyr Thr Asp Pro Thr Gly Gly
            20                  25                  30
Gly Pro Arg Arg Gly Ile Val Glu Gln Cys Cys His Ser Ile Cys Ser
         35                  40                  45
Leu Tyr Gln Leu Glu Asn Tyr Cys Asn Gly Gly Gly Ala Gly Gly
 50                  55                  60
Gly Gly Cys Ile Ser Pro Cys Pro Val Pro Glu Ser Leu Gly Gly Pro
 65                  70                  75                  80
Ser Val Phe Ile Phe Pro Pro Lys Pro Lys Asp Ile Leu Arg Ile Thr
                 85                  90                  95
Arg Thr Pro Glu Ile Thr Cys Val Val Leu Asp Leu Gly Arg Glu Asp
            100                 105                 110
Pro Glu Val Gln Ile Ser Trp Phe Val Asp Gly Lys Glu Val His Thr
        115                 120                 125
Ala Lys Thr Gln Pro Arg Glu Gln Gln Phe Asn Ser Thr Tyr Arg Val
130                 135                 140
Val Ser Val Leu Pro Ile Glu His Gln Asp Trp Leu Thr Gly Lys Glu
145                 150                 155                 160
Phe Lys Cys Arg Val Asn His Ile Gly Leu Pro Ser Pro Ile Glu Arg
                165                 170                 175
Thr Ile Ser Lys Ala Arg Gly Gln Ala His Gln Pro Ser Val Tyr Val
            180                 185                 190
Leu Pro Pro Ser Pro Lys Glu Leu Ser Ser Ser Asp Thr Val Thr Leu
        195                 200                 205
Thr Cys Leu Ile Lys Asp Phe Phe Pro Pro Glu Ile Asp Val Glu Trp
210                 215                 220
Gln Ser Asn Gly Gln Pro Glu Pro Glu Ser Lys Tyr His Thr Thr Ala
225                 230                 235                 240
Pro Gln Leu Asp Glu Asp Gly Ser Tyr Phe Leu Tyr Ser Lys Leu Ser
                245                 250                 255
Val Asp Lys Ser Arg Trp Gln Gln Gly Asp Thr Phe Thr Cys Ala Val
            260                 265                 270
Met His Glu Ala Leu Gln Asn His Tyr Thr Asp Leu Ser Leu Ser His
        275                 280                 285
Ser Pro Gly
    290

<210> SEQ ID NO 57
<211> LENGTH: 930
<212> TYPE: DNA
<213> ORGANISM: Artificial Sequence
<220> FEATURE:
<223> OTHER INFORMATION: Fusion Protein DNA

<400> SEQUENCE: 57
atggaatgga gctgggtctt tctcttcttc ctgtcagtaa cgactggtgt ccactccttc      60
gtgaaccagc acctgtgcgg ctccgacctg gtgaagctc tggctctcgt gtgcggcgag     120
cggggcttct tctacaccga tcccactgga ggcggtccac gcagaggcat cgtggaacag    180
tgctgccact ccatctgctc cctgtaccag ctggaaaact actgcaatgg cggaggtggt    240
gcaggaggcg gtggagactg ccccaagtgc ccgctcccg agatgctggg cggacccagc    300
gtgttcatct ccctcccaa gcccaaggac acactgctga tcgccaggac cccggaggtg    360
acctgcgtgg tggtggaccct ggatcccgaa gaccccgagg tgcagatcag ctggttcgtg    420
gatggaaagc agatgcagac cgccaagacc caaccccggg aagagcagtt ccaaggcacc    480
```

```
tacagggtgg tgagtgtgtt gcccatcggc caccaggact ggctgaaggg gaagcaattc    540
acatgcaagg ttaataacaa ggccctgccc agccccatcg agaggaccat cagcaaggcc    600
aggggccagg cccaccagcc atctgtgtac gtgctgcccc catctaggga ggaactgagc    660
aagaacacag tcagccttac ttgcctgatc aaggacttct tcccaccgga catagacgtg    720
gagtggcaga gtaacggcca gcaggagccc gagagcaagt ataggaccac accgccccaa    780
ctggacgagg acggaagcta cttcctctac agcaaattga gcgttgacaa agcaggtgg     840 cagcgaggcg acaccttcat ctgcgccgtg atgcacgagg ctttgcataa ccactacacc    900
caggagagcc tgtcccacag ccccggatag                                     930
```

<210> SEQ ID NO 58
<211> LENGTH: 290
<212> TYPE: PRT
<213> ORGANISM: Artificial Sequence
<220> FEATURE:
<223> OTHER INFORMATION: Fusion Protein

<400> SEQUENCE: 58

```
Phe Val Asn Gln His Leu Cys Gly Ser Asp Leu Val Glu Ala Leu Ala
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn Gly Gly Gly Ala Gly Gly
    50                  55                  60

Gly Gly Asp Cys Pro Lys Cys Pro Ala Pro Glu Met Leu Gly Gly Pro
65                  70                  75                  80

Ser Val Phe Ile Phe Pro Pro Lys Pro Lys Asp Thr Leu Leu Ile Ala
                85                  90                  95

Arg Thr Pro Glu Val Thr Cys Val Val Val Asp Leu Asp Pro Glu Asp
            100                 105                 110

Pro Glu Val Gln Ile Ser Trp Phe Val Asp Gly Lys Gln Met Gln Thr
        115                 120                 125

Ala Lys Thr Gln Pro Arg Glu Glu Gln Phe Gln Gly Thr Tyr Arg Val
    130                 135                 140

Val Ser Val Leu Pro Ile Gly His Gln Asp Trp Leu Lys Gly Lys Gln
145                 150                 155                 160

Phe Thr Cys Lys Val Asn Asn Lys Ala Leu Pro Ser Pro Ile Glu Arg
                165                 170                 175

Thr Ile Ser Lys Ala Arg Gly Gln Ala His Gln Pro Ser Val Tyr Val
            180                 185                 190

Leu Pro Pro Ser Arg Glu Glu Leu Ser Lys Asn Thr Val Ser Leu Thr
        195                 200                 205

Cys Leu Ile Lys Asp Phe Phe Pro Pro Asp Ile Asp Val Glu Trp Gln
    210                 215                 220

Ser Asn Gly Gln Gln Glu Pro Glu Ser Lys Tyr Arg Thr Thr Pro Pro
225                 230                 235                 240

Gln Leu Asp Glu Asp Gly Ser Tyr Phe Leu Tyr Ser Lys Leu Ser Val
                245                 250                 255

Asp Lys Ser Arg Trp Gln Arg Gly Asp Thr Phe Ile Cys Ala Val Met
            260                 265                 270

His Glu Ala Leu His Asn His Tyr Thr Gln Glu Ser Leu Ser His Ser
```

Pro Gly
    290

<210> SEQ ID NO 59
<211> LENGTH: 930
<212> TYPE: DNA
<213> ORGANISM: Artificial Sequence
<220> FEATURE:
<223> OTHER INFORMATION: Fusion Protein DNA

<400> SEQUENCE: 59

```
atggaatgga gctgggtctt tctcttcttc ctgtcagtaa cgactggtgt ccactccttc      60
gtgaaccagc acctgtgcgg ctccgacctg gtggaagctc tggctctcgt gtgcggcgag     120
cggggcttct tctacaccga tcccactgga ggcggtccac gcagaggcat cgtgaacag      180
tgctgccact ccatctgctc cctgtaccag ctggaaaact actgcaatgg cggaggtggt     240
gcaggaggcg gtggagactg ccccaagtgc ccgctcccg agatgctggg cggacccagc      300
gtgttcatct tccctcccaa gcccaaggac acactgctga tcgccaggac cccggaggtg     360
acctgcgtgg tggtggacct ggatcccgaa gaccccgagg tgcagatcag ctggttcgtg     420
gatggaaagc agatgcagac cgccaagacc caaccccggg aagagcagtt cagcggcacc     480
tacagggtgg tgagtgtgtt gcccatcggc accaggact ggctgaaggg gaagcaattc     540
acatgcaagg ttaataacaa ggccctgccc agccccatcg agaggaccat cagcaaggcc     600
aggggccagg cccaccagcc atctgtgtac gtgctgcccc catctaggga ggaactgagc     660
aagaacacag tcagccttac ttgcctgatc aaggacttct tcccaccgga catagacgtg     720
gagtggcaga gtaacggcca gcaggagccc gagagcaagt ataggaccac accgccccaa     780
ctggacgagg acggaagcta cttcctctac agcaaattga gcgttgacaa aagcaggtgg     840
cagcgaggcg acaccttcat ctgcgccgtg atgcacgagg ctttgcataa ccactacacc     900
caggagagcc tgtcccacag ccccggatag                                      930
```

<210> SEQ ID NO 60
<211> LENGTH: 290
<212> TYPE: PRT
<213> ORGANISM: Artificial Sequence
<220> FEATURE:
<223> OTHER INFORMATION: Fusion Protein

<400> SEQUENCE: 60

Phe Val Asn Gln His Leu Cys Gly Ser Asp Leu Val Glu Ala Leu Ala
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn Gly Gly Gly Gly Ala Gly Gly
    50                  55                  60

Gly Gly Asp Cys Pro Lys Cys Pro Ala Pro Glu Met Leu Gly Gly Pro
65                  70                  75                  80

Ser Val Phe Ile Phe Pro Pro Lys Pro Lys Asp Thr Leu Leu Ile Ala
                85                  90                  95

Arg Thr Pro Glu Val Thr Cys Val Val Val Asp Leu Asp Pro Glu Asp
            100                 105                 110

Pro Glu Val Gln Ile Ser Trp Phe Val Asp Gly Lys Gln Met Gln Thr

```
             115                 120                 125
Ala Lys Thr Gln Pro Arg Glu Glu Gln Phe Ser Gly Thr Tyr Arg Val
    130                 135                 140

Val Ser Val Leu Pro Ile Gly His Gln Asp Trp Leu Lys Gly Lys Gln
145                 150                 155                 160

Phe Thr Cys Lys Val Asn Asn Lys Ala Leu Pro Ser Pro Ile Glu Arg
                165                 170                 175

Thr Ile Ser Lys Ala Arg Gly Gln Ala His Gln Pro Ser Val Tyr Val
            180                 185                 190

Leu Pro Pro Ser Arg Glu Glu Leu Ser Lys Asn Thr Val Ser Leu Thr
        195                 200                 205

Cys Leu Ile Lys Asp Phe Phe Pro Pro Asp Ile Asp Val Glu Trp Gln
    210                 215                 220

Ser Asn Gly Gln Gln Glu Pro Glu Ser Lys Tyr Arg Thr Thr Pro Pro
225                 230                 235                 240

Gln Leu Asp Glu Asp Gly Ser Tyr Phe Leu Tyr Ser Lys Leu Ser Val
                245                 250                 255

Asp Lys Ser Arg Trp Gln Arg Gly Asp Thr Phe Ile Cys Ala Val Met
            260                 265                 270

His Glu Ala Leu His Asn His Tyr Thr Gln Glu Ser Leu Ser His Ser
        275                 280                 285

Pro Gly
    290

<210> SEQ ID NO 61
<211> LENGTH: 930
<212> TYPE: DNA
<213> ORGANISM: Artificial Sequence
<220> FEATURE:
<223> OTHER INFORMATION: Fusion Protein DNA

<400> SEQUENCE: 61
atggaatgga gctgggtctt tctcttcttc ctgtcagtaa cgactggtgt ccactccttc      60
gtgaaccagc acctgtgcgg ctccgacctg gtggaagctc tggctctcgt gtgcggcgag     120
cggggcttct tctacaccga tcccactgga ggcggtccac gcagaggcat cgtggaacag     180
tgctgccact ccatctgctc cctgtaccag ctggaaaact actgcaatgg cggaggtggt     240
gcaggaggcg gtggagactg ccccaagtgc ccgctcccg agatgctggg cggacccagc      300
gtgttcatct ccctcccaa gcccaaggac acactgctga tcgccaggac cccggaggtg     360
acctgcgtgg tggtggacct ggatcccgaa gaccccgagg tgcagatcag ctggttcgtg     420
gatggaaagc agatgcagac cgccaagacc caaccccggg aagagcagtt cgacggcacc     480
tacagggtgg tgagtgtgtt gcccatcggc caccaggact ggctgaaggg aagcaattc      540 acatgcaagg ttaataacaa ggccctgccc agccccatcg agaggaccat cagcaaggcc     600
aggggccagg cccaccagcc atctgtgtac gtgctgcccc catctaggga ggaactgagc     660
aagaacacag tcagccttac ttgcctgatc aaggacttct tcccaccgga catagacgtg     720
gagtggcaga gtaacggcca gcaggagccc gagagcaagt ataggaccac accgccccaa     780
ctggacgagg acggaagcta cttcctctac agcaaattga gcgttgacaa agcaggtgg     840 cagcgaggcg acaccttcat ctgcgccgtg atgcacgagg ctttgcataa ccactacacc     900
caggagagcc tgtcccacag ccccggatag                                     930

<210> SEQ ID NO 62
```

<211> LENGTH: 290
<212> TYPE: PRT
<213> ORGANISM: Artificial Sequence
<220> FEATURE:
<223> OTHER INFORMATION: Fusion Protein

<400> SEQUENCE: 62

Phe Val Asn Gln His Leu Cys Gly Ser Asp Leu Val Glu Ala Leu Ala
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn Gly Gly Gly Ala Gly Gly
    50                  55                  60

Gly Gly Asp Cys Pro Lys Cys Pro Ala Pro Glu Met Leu Gly Gly Pro
65                  70                  75                  80

Ser Val Phe Ile Phe Pro Pro Lys Pro Lys Asp Thr Leu Leu Ile Ala
                85                  90                  95

Arg Thr Pro Glu Val Thr Cys Val Val Val Asp Leu Asp Pro Glu Asp
            100                 105                 110

Pro Glu Val Gln Ile Ser Trp Phe Val Asp Gly Lys Gln Met Gln Thr
        115                 120                 125

Ala Lys Thr Gln Pro Arg Glu Glu Gln Phe Asp Gly Thr Tyr Arg Val
    130                 135                 140

Val Ser Val Leu Pro Ile Gly His Gln Asp Trp Leu Lys Gly Lys Gln
145                 150                 155                 160

Phe Thr Cys Lys Val Asn Asn Lys Ala Leu Pro Ser Pro Ile Glu Arg
                165                 170                 175

Thr Ile Ser Lys Ala Arg Gly Gln Ala His Gln Pro Ser Val Tyr Val
            180                 185                 190

Leu Pro Pro Ser Arg Glu Glu Leu Ser Lys Asn Thr Val Ser Leu Thr
        195                 200                 205

Cys Leu Ile Lys Asp Phe Phe Pro Pro Asp Ile Asp Val Glu Trp Gln
    210                 215                 220

Ser Asn Gly Gln Gln Glu Pro Glu Ser Lys Tyr Arg Thr Thr Pro Pro
225                 230                 235                 240

Gln Leu Asp Glu Asp Gly Ser Tyr Phe Leu Tyr Ser Lys Leu Ser Val
                245                 250                 255

Asp Lys Ser Arg Trp Gln Arg Gly Asp Thr Phe Ile Cys Ala Val Met
            260                 265                 270

His Glu Ala Leu His Asn His Tyr Thr Gln Glu Ser Leu Ser His Ser
        275                 280                 285

Pro Gly
    290

<210> SEQ ID NO 63
<211> LENGTH: 930
<212> TYPE: DNA
<213> ORGANISM: Artificial Sequence
<220> FEATURE:
<223> OTHER INFORMATION: Fusion Protein DNA

<400> SEQUENCE: 63
atggaatgga gctgggtctt tctcttcttc ctgtcagtaa cgactggtgt ccactccttc      60
gtgaaccagc acctgtgcgg ctccgacctg gtggaagctc tggctctcgt gtgcggcgag     120

```
cggggcttct tctacaccga tcccactgga ggcggtccac gcagaggcat cgtggaacag    180
tgctgccact ccatctgctc cctgtaccag ctggaaaact actgcaatgg cggaggtggt    240
gcaggaggcg gtggagactg ccccaagtgc cccgctcccg agatgctggg cggacccagc    300
gtgttcatct tccctcccaa gcccaaggac acactgctga tcgccaggac cccggaggtg    360
acctgcgtgg tggtggacct ggatcccgaa gaccccgagg tgcagatcag ctggttcgtg    420 gatgaaagc agatgcagac cgccaagacc caaccccggg aagagcagtt caaaggcacc     480
tacagggtgg tgagtgtgtt gcccatcggc caccaggact ggctgaaggg gaagcaattc    540
acatgcaagg ttaataacaa ggccctgccc agccccatcg agaggaccat cagcaaggcc    600
aggggccagg cccaccagcc atctgtgtac gtgctgcccc catctaggga ggaactgagc    660
aagaacacag tcagccttac ttgcctgatc aaggacttct tcccaccgga catagacgtg    720
gagtggcaga gtaacggcca gcaggagccc gagagcaagt ataggaccac accgccccaa    780
ctggacgagg acggaagcta cttcctctac agcaaattga gcgttgacaa aagcaggtgg    840
cagcgaggcg acaccttcat ctgcgccgtg atgcacgagg ctttgcataa ccactacacc    900
caggagagcc tgtcccacag ccccggatag                                    930
```

```
<210> SEQ ID NO 64
<211> LENGTH: 290
<212> TYPE: PRT
<213> ORGANISM: Artificial Sequence
<220> FEATURE:
<223> OTHER INFORMATION: Fusion Protein

<400> SEQUENCE: 64

Phe Val Asn Gln His Leu Cys Gly Ser Asp Leu Val Glu Ala Leu Ala
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn Gly Gly Gly Ala Gly Gly
    50                  55                  60

Gly Gly Asp Cys Pro Lys Cys Pro Ala Pro Glu Met Leu Gly Gly Pro
65                  70                  75                  80

Ser Val Phe Ile Phe Pro Pro Lys Pro Lys Asp Thr Leu Leu Ile Ala
                85                  90                  95

Arg Thr Pro Glu Val Thr Cys Val Val Val Asp Leu Asp Pro Glu Asp
            100                 105                 110

Pro Glu Val Gln Ile Ser Trp Phe Val Asp Gly Lys Gln Met Gln Thr
        115                 120                 125

Ala Lys Thr Gln Pro Arg Glu Glu Gln Phe Lys Gly Thr Tyr Arg Val
    130                 135                 140

Val Ser Val Leu Pro Ile Gly His Gln Asp Trp Leu Lys Gly Lys Gln
145                 150                 155                 160

Phe Thr Cys Lys Val Asn Asn Lys Ala Leu Pro Ser Pro Ile Glu Arg
                165                 170                 175

Thr Ile Ser Lys Ala Arg Gly Gln Ala His Gln Pro Ser Val Tyr Val
            180                 185                 190

Leu Pro Pro Ser Arg Glu Glu Leu Ser Lys Asn Thr Val Ser Leu Thr
        195                 200                 205

Cys Leu Ile Lys Asp Phe Phe Pro Pro Asp Ile Asp Val Glu Trp Gln
    210                 215                 220
```

```
Ser Asn Gly Gln Gln Glu Pro Glu Ser Lys Tyr Arg Thr Thr Pro Pro
225                 230                 235                 240

Gln Leu Asp Glu Asp Gly Ser Tyr Phe Leu Tyr Ser Lys Leu Ser Val
                245                 250                 255

Asp Lys Ser Arg Trp Gln Arg Gly Asp Thr Phe Ile Cys Ala Val Met
            260                 265                 270

His Glu Ala Leu His Asn His Tyr Thr Gln Glu Ser Leu Ser His Ser
        275                 280                 285

Pro Gly
    290

<210> SEQ ID NO 65
<211> LENGTH: 930
<212> TYPE: DNA
<213> ORGANISM: Artificial Sequence
<220> FEATURE:
<223> OTHER INFORMATION: Fusion Protein DNA

<400> SEQUENCE: 65
atggaatgga gctgggtctt tctcttcttc ctgtcagtaa cgactggtgt ccactccttc      60
gtgaaccagc acctgtgcgg ctcccacctg gtggaagctc tggctctcgt gtgcggcgag     120
cggggcttct tctacaccga tcccactgga ggcggtccac gcagaggcat cgtggaacag     180
tgctgcacct ccatctgctc cctgtaccag ctggaaaact actgcaatgg cggaggtggt     240
gcaggaggcg gtggagactg ccccaagtgc cccgctcccg agatgctggg cggacccagc     300
gtgttcatct tccctcccaa gcccaaggac acactgctga tcgccaggac cccggaggtg     360
acctgcgtgg tggtggacct ggatcccgaa gaccccgagg tgcagatcag ctggttcgtg     420 gatgaaagc agatgcagac cgccaagacc caaccccggg aagagcagtt ccaaggcacc     480
tacagggtgg tgagtgtgtt gcccatcggc caccaggact ggctgaaggg gaagcaattc     540
acatgcaagg ttaataacaa ggccctgccc agccccatcg agaggaccat cagcaaggcc     600
aggggccagg cccaccagcc atctgtgtac gtgctgcccc catctaggga ggaactgagc     660
aagaacacag tcagccttac ttgcctgatc aaggacttct tcccaccgga catagacgtg     720
gagtggcaga gtaacggcca gcaggagccc gagagcaagt ataggaccac accgccccaa     780
ctggacgagg acggaagcta cttcctctac agcaaattga gcgttgacaa agcaggtgg     840 cagcgaggcg acaccttcat ctgcgccgtg atgcacgagg ctttgcataa ccactacacc     900
caggagagcc tgtcccacag ccccggatag                                      930

<210> SEQ ID NO 66
<211> LENGTH: 290
<212> TYPE: PRT
<213> ORGANISM: Artificial Sequence
<220> FEATURE:
<223> OTHER INFORMATION: Fusion Protein

<400> SEQUENCE: 66

Phe Val Asn Gln His Leu Cys Gly Ser His Leu Val Glu Ala Leu Ala
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys Thr Ser Ile Cys Ser
        35                  40                  45

Leu Tyr Gln Leu Glu Asn Tyr Cys Asn Gly Gly Gly Ala Gly Gly
    50                  55                  60
```

Gly Gly Asp Cys Pro Lys Cys Pro Ala Pro Glu Met Leu Gly Gly Pro
65                  70                  75                  80

Ser Val Phe Ile Phe Pro Pro Lys Pro Lys Asp Thr Leu Leu Ile Ala
                85                  90                  95

Arg Thr Pro Glu Val Thr Cys Val Val Val Asp Leu Asp Pro Glu Asp
            100                 105                 110

Pro Glu Val Gln Ile Ser Trp Phe Val Asp Gly Lys Gln Met Gln Thr
        115                 120                 125

Ala Lys Thr Gln Pro Arg Glu Glu Gln Phe Gln Gly Thr Tyr Arg Val
    130                 135                 140

Val Ser Val Leu Pro Ile Gly His Gln Asp Trp Leu Lys Gly Lys Gln
145                 150                 155                 160

Phe Thr Cys Lys Val Asn Asn Lys Ala Leu Pro Ser Pro Ile Glu Arg
                165                 170                 175

Thr Ile Ser Lys Ala Arg Gly Gln Ala His Gln Pro Ser Val Tyr Val
            180                 185                 190

Leu Pro Pro Ser Arg Glu Glu Leu Ser Lys Asn Thr Val Ser Leu Thr
        195                 200                 205

Cys Leu Ile Lys Asp Phe Phe Pro Pro Asp Ile Asp Val Glu Trp Gln
210                 215                 220

Ser Asn Gly Gln Gln Glu Pro Glu Ser Lys Tyr Arg Thr Thr Pro Pro
225                 230                 235                 240

Gln Leu Asp Glu Asp Gly Ser Tyr Phe Leu Tyr Ser Lys Leu Ser Val
                245                 250                 255

Asp Lys Ser Arg Trp Gln Arg Gly Asp Thr Phe Ile Cys Ala Val Met
            260                 265                 270

His Glu Ala Leu His Asn His Tyr Thr Gln Glu Ser Leu Ser His Ser
        275                 280                 285

Pro Gly
    290

<210> SEQ ID NO 67
<211> LENGTH: 927
<212> TYPE: DNA
<213> ORGANISM: Artificial Sequence
<220> FEATURE:
<223> OTHER INFORMATION: Fusion Protein DNA

<400> SEQUENCE: 67
atggaatgga gctgggtctt tctcttcttc ctgtcagtaa cgactggtgt ccactccttc     60
gtgaaccagc acctgtgcgg ctcccacctg gtgcaagctc tgtatctcgt gtgcggcgag    120
cggggcttct tctacaccga tcccactgga ggcggtccac gcagaggcat cgtggaacag    180
tgctgcacct ccatctgctc cctgtaccag ctggaaaact actgcggcgg aggtggtgca    240
ggaggcggtg gagactgccc caagtgcccc gctcccgaga tgctgggcgg acccagcgtg    300
ttcatcttcc ctcccaagcc caaggacaca ctgctgatcg ccaggacccc ggaggtgacc    360
tgcgtggtgg tggacctgga tcccgaagac cccgaggtgc agatcagctg gttcgtggat    420
ggaaagcaga tgcagaccgc caagacccaa ccccgggaag agcagttcag cggcacctac    480
agggtggtga gtgtgttgcc catcggccac caggactggc tgaagggaaa gcaattcaca    540
tgcaaggtta ataacaaggc cctgccagc ccatcgaga ggaccatcag caaggccagg     600
ggccaggccc accagccatc tgtgtacgtg ctgcccccat ctagggagga actgagcaag    660
aacacagtca gccttacttg cctgatcaag gacttcttcc caccggacat agacgtggag    720

```
tggcagagta acggccagca ggagcccgag agcaagtata ggaccacacc gccccaactg    780
gacgaggacg gaagctactt cctctacagc aaattgagcg ttgacaaaag caggtggcag    840
cgaggcgaca ccttcatctg cgccgtgatg cacgaggctt tgcataacca ctacacccag    900
gagagcctgt cccacagccc cggatag                                       927
```

<210> SEQ ID NO 68
<211> LENGTH: 289
<212> TYPE: PRT
<213> ORGANISM: Artificial Sequence
<220> FEATURE:
<223> OTHER INFORMATION: Fusion Protein

<400> SEQUENCE: 68

```
Phe Val Asn Gln His Leu Cys Gly Ser His Leu Val Gln Ala Leu Tyr
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys Thr Ser Ile Cys Ser
        35                  40                  45

Leu Tyr Gln Leu Glu Asn Tyr Cys Gly Gly Gly Ala Gly Gly Gly
    50                  55                  60

Gly Asp Cys Pro Lys Cys Pro Ala Pro Glu Met Leu Gly Gly Pro Ser
65                  70                  75                  80

Val Phe Ile Phe Pro Pro Lys Pro Lys Asp Thr Leu Leu Ile Ala Arg
                85                  90                  95

Thr Pro Glu Val Thr Cys Val Val Asp Leu Asp Pro Glu Asp Pro
            100                 105                 110

Glu Val Gln Ile Ser Trp Phe Val Asp Gly Lys Gln Met Gln Thr Ala
        115                 120                 125

Lys Thr Gln Pro Arg Glu Glu Gln Phe Ser Gly Thr Tyr Arg Val Val
    130                 135                 140

Ser Val Leu Pro Ile Gly His Gln Asp Trp Leu Lys Gly Lys Gln Phe
145                 150                 155                 160

Thr Cys Lys Val Asn Asn Lys Ala Leu Pro Ser Pro Ile Glu Arg Thr
                165                 170                 175

Ile Ser Lys Ala Arg Gly Gln Ala His Gln Pro Ser Val Tyr Val Leu
            180                 185                 190

Pro Pro Ser Arg Glu Glu Leu Ser Lys Asn Thr Val Ser Leu Thr Cys
        195                 200                 205

Leu Ile Lys Asp Phe Phe Pro Pro Asp Ile Asp Val Glu Trp Gln Ser
    210                 215                 220

Asn Gly Gln Gln Glu Pro Glu Ser Lys Tyr Arg Thr Thr Pro Pro Gln
225                 230                 235                 240

Leu Asp Glu Asp Gly Ser Tyr Phe Leu Tyr Ser Lys Leu Ser Val Asp
                245                 250                 255

Lys Ser Arg Trp Gln Arg Gly Asp Thr Phe Ile Cys Ala Val Met His
            260                 265                 270

Glu Ala Leu His Asn His Tyr Thr Gln Glu Ser Leu Ser His Ser Pro
        275                 280                 285

Gly
```

<210> SEQ ID NO 69
<211> LENGTH: 927
<212> TYPE: DNA

<213> ORGANISM: Artificial Sequence
<220> FEATURE:
<223> OTHER INFORMATION: Fusion Protein DNA

<400> SEQUENCE: 69

```
atggaatgga gctgggtctt tctcttcttc ctgtcagtaa cgactggtgt ccactccttc    60
gtgaaccagc acctgtgcgg ctccgagctg gtggaagctc tggctctcgt gtgcggcgag   120
cggggcttct tctacaccga tcccactgga ggcggtccac gcagaggcat cgtgaacag   180
tgctgcacat ccatctgctc cctgtaccag ctggaaaact actgcggcgg aggtggtgca   240
ggaggcggtg gagactgccc caagtgcccc gctcccgaga tgctgggcgg acccagcgtg   300
ttcatcttcc ctcccaagcc caaggacaca ctgctgatcg ccaggacccc ggaggtgacc   360
tgcgtggtgg tggacctgga tcccgaagac cccgaggtgc agatcagctg gttcgtggat   420
ggaaagcaga tgcagaccgc caagacccaa ccccgggaag agcagttcag cggcacctac   480
agggtggtga gtgtgttgcc catcggccac caggactggc tgaagggaa gcaattcaca   540
tgcaaggtta ataacaaggc cctgcccagc cccatcgaga ggaccatcag caaggccagg   600
ggccaggccc accagccatc tgtgtacgtg ctgcccccat ctagggagga actgagcaag   660
aacacagtca gccttacttg cctgatcaag gacttcttcc caccggacat agacgtggag   720
tggcagagta acggccagca ggagcccgag agcaagtata ggaccacacc gccccaactg   780
gacgaggacg gaagctactt cctctacagc aaattgagcg ttgacaaaag caggtggcag   840
cgaggcgaca ccttcatctg cgccgtgatg cacgaggctt gcataaccca tacacccag   900
gagagcctgt cccacagccc cggatag                                       927
```

<210> SEQ ID NO 70
<211> LENGTH: 289
<212> TYPE: PRT
<213> ORGANISM: Artificial Sequence
<220> FEATURE:
<223> OTHER INFORMATION: Fusion Protein

<400> SEQUENCE: 70

```
Phe Val Asn Gln His Leu Cys Gly Ser Glu Leu Val Glu Ala Leu Ala
1               5                   10                  15
Leu Val Cys Gly Glu Arg Gly Phe Phe Tyr Thr Asp Pro Thr Gly Gly
            20                  25                  30
Gly Pro Arg Arg Gly Ile Val Glu Gln Cys Cys Thr Ser Ile Cys Ser
        35                  40                  45
Leu Tyr Gln Leu Glu Asn Tyr Cys Gly Gly Gly Ala Gly Gly Gly
    50                  55                  60
Gly Asp Cys Pro Lys Cys Pro Ala Pro Glu Met Leu Gly Gly Pro Ser
65                  70                  75                  80
Val Phe Ile Phe Pro Pro Lys Pro Lys Asp Thr Leu Leu Ile Ala Arg
                85                  90                  95
Thr Pro Glu Val Thr Cys Val Val Val Asp Leu Asp Pro Glu Asp Pro
            100                 105                 110
Glu Val Gln Ile Ser Trp Phe Val Asp Gly Lys Gln Met Gln Thr Ala
        115                 120                 125
Lys Thr Gln Pro Arg Glu Glu Gln Phe Ser Gly Thr Tyr Arg Val Val
    130                 135                 140
Ser Val Leu Pro Ile Gly His Gln Asp Trp Leu Lys Gly Lys Gln Phe
145                 150                 155                 160
Thr Cys Lys Val Asn Asn Lys Ala Leu Pro Ser Pro Ile Glu Arg Thr
```

```
                  165                 170                 175
Ile Ser Lys Ala Arg Gly Gln Ala His Gln Pro Ser Val Tyr Val Leu
            180                 185                 190

Pro Pro Ser Arg Glu Glu Leu Ser Lys Asn Thr Val Ser Leu Thr Cys
        195                 200                 205

Leu Ile Lys Asp Phe Phe Pro Pro Asp Ile Asp Val Glu Trp Gln Ser
    210                 215                 220

Asn Gly Gln Gln Glu Pro Glu Ser Lys Tyr Arg Thr Thr Pro Pro Gln
225                 230                 235                 240

Leu Asp Glu Asp Gly Ser Tyr Phe Leu Tyr Ser Lys Leu Ser Val Asp
                245                 250                 255

Lys Ser Arg Trp Gln Arg Gly Asp Thr Phe Ile Cys Ala Val Met His
            260                 265                 270

Glu Ala Leu His Asn His Tyr Thr Gln Glu Ser Leu Ser His Ser Pro
        275                 280                 285

Gly

<210> SEQ ID NO 71
<211> LENGTH: 927
<212> TYPE: DNA
<213> ORGANISM: Artificial Sequence
<220> FEATURE:
<223> OTHER INFORMATION: Fusion Protein DNA

<400> SEQUENCE: 71
atggaatgga gctgggtctt tctcttcttc ctgtcagtaa cgactggtgt ccactccttc      60
gtgaaccagc acctgtgcgg ctcccacctg gtggaagctc tggctctcgt gtgcggcgag     120
gccggcttct tctacaccga tcccactgga ggcggtccac gcagaggcat cgtggaacag     180
tgctgcacct ccatctgctc cctgtaccag ctggaaaact actgcggcgg aggtggtgca     240
ggaggcggtg gagactgccc caagtgcccc gctcccgaga tgctgggcgg acccagcgtg     300
ttcatcttcc ctcccaagcc caaggacaca ctgctgatcg ccaggacccc ggaggtgacc     360
tgcgtggtgg tggacctgga tcccgaagac cccgaggtgc agatcagctg gttcgtggat     420
ggaaagcaga tgcagaccgc caagacccaa ccccgggaag agcagttcag cggcacctac     480
agggtggtga gtgtgttgcc catcggccac caggactggc tgaaggggaa gcaattcaca     540
tgcaaggtta ataacaaggc cctgcccagc ccatcgaga ggaccatcag caaggccagg     600
ggccaggccc accagccatc tgtgtacgtg ctgcccccat ctagggagga actgagcaag     660
aacacagtca gccttacttg cctgatcaag gacttcttcc caccggacat agacgtggag     720
tggcagagta acggccagca ggagcccgag agcaagtata ggaccacacc gccccaactg     780
gacgaggacg gaagctactt cctctacagc aaattgagcg ttgacaaaag caggtggcag     840
cgaggcgaca ccttcatctg cgccgtgatg cacgaggctt tgcataacca ctacacccag     900
gagagcctgt cccacagccc cggatag                                         927

<210> SEQ ID NO 72
<211> LENGTH: 289
<212> TYPE: PRT
<213> ORGANISM: Artificial Sequence
<220> FEATURE:
<223> OTHER INFORMATION: Fusion Protein

<400> SEQUENCE: 72

Phe Val Asn Gln His Leu Cys Gly Ser His Leu Val Glu Ala Leu Ala
1               5                   10                  15
```

Leu Val Cys Gly Glu Ala Gly Phe Phe Tyr Thr Asp Pro Thr Gly Gly
            20                  25                  30

Gly Pro Arg Arg Gly Ile Val Glu Gln Cys Cys Thr Ser Ile Cys Ser
            35                  40                  45

Leu Tyr Gln Leu Glu Asn Tyr Cys Gly Gly Gly Ala Gly Gly Gly
 50                  55                  60

Gly Asp Cys Pro Lys Cys Pro Ala Pro Glu Met Leu Gly Gly Pro Ser
 65                  70                  75                  80

Val Phe Ile Phe Pro Pro Lys Pro Lys Asp Thr Leu Leu Ile Ala Arg
                 85                  90                  95

Thr Pro Glu Val Thr Cys Val Val Val Asp Leu Asp Pro Glu Asp Pro
             100                 105                 110

Glu Val Gln Ile Ser Trp Phe Val Asp Gly Lys Gln Met Gln Thr Ala
             115                 120                 125

Lys Thr Gln Pro Arg Glu Glu Gln Phe Ser Gly Thr Tyr Arg Val Val
 130                 135                 140

Ser Val Leu Pro Ile Gly His Gln Asp Trp Leu Lys Gly Lys Gln Phe
145                 150                 155                 160

Thr Cys Lys Val Asn Asn Lys Ala Leu Pro Ser Pro Ile Glu Arg Thr
                 165                 170                 175

Ile Ser Lys Ala Arg Gly Gln Ala His Gln Pro Ser Val Tyr Val Leu
             180                 185                 190

Pro Pro Ser Arg Glu Glu Leu Ser Lys Asn Thr Val Ser Leu Thr Cys
             195                 200                 205

Leu Ile Lys Asp Phe Phe Pro Pro Asp Ile Asp Val Glu Trp Gln Ser
 210                 215                 220

Asn Gly Gln Gln Glu Pro Glu Ser Lys Tyr Arg Thr Thr Pro Pro Gln
225                 230                 235                 240

Leu Asp Glu Asp Gly Ser Tyr Phe Leu Tyr Ser Lys Leu Ser Val Asp
                 245                 250                 255

Lys Ser Arg Trp Gln Arg Gly Asp Thr Phe Ile Cys Ala Val Met His
             260                 265                 270

Glu Ala Leu His Asn His Tyr Thr Gln Glu Ser Leu Ser His Ser Pro
             275                 280                 285

Gly

<210> SEQ ID NO 73
<211> LENGTH: 927
<212> TYPE: DNA
<213> ORGANISM: Artificial Sequence
<220> FEATURE:
<223> OTHER INFORMATION: Fusion Protein DNA

<400> SEQUENCE: 73
atggaatgga gctgggtctt tctcttcttc ctgtcagtaa cgactggtgt ccactccttc      60
gtgaaccagc acctgtgcgg ctcccacctg gtggaagctc tggctctcgt gtgcggcgag     120
cggggcttct actacaccga tcccactgga ggcggtccac gcagaggcat cgtggaacag     180
tgctgcacct ccatctgctc cctgtaccag ctggaaaact actgcggcgg aggtggtgca     240
ggaggcggtg gagactgccc caagtgcccc gctccgaga tgctgggcgg acccagcgtg      300
ttcatcttcc ctcccaagcc caaggacaca ctgctgatcg ccaggacccc ggaggtgacc     360
tgcgtggtgg tggacctgga tcccgaagac cccgaggtgc agatcagctg gttcgtggat     420
ggaaagcaga tgcagaccgc caagacccaa ccccgggaag agcagttcag cggcacctac     480

```
agggtggtga gtgtgttgcc catcggccac caggactggc tgaaggggaa gcaattcaca      540
tgcaaggtta ataacaaggc cctgcccagc cccatcgaga ggaccatcag caaggccagg      600
ggccaggccc accagccatc tgtgtacgtg ctgcccccat ctagggagga actgagcaag      660
aacacagtca gccttacttg cctgatcaag gacttcttcc caccggacat agacgtggag      720
tggcagagta acggccagca ggagcccgag agcaagtata ggaccacacc gccccaactg      780
gacgaggacg gaagctactt cctctacagc aaattgagcg ttgacaaaag caggtggcag      840
cgaggcgaca ccttcatctg cgccgtgatg cacgaggctt tgcataacca ctacacccag      900
gagagcctgt cccacagccc cggatag                                         927

<210> SEQ ID NO 74
<211> LENGTH: 289
<212> TYPE: PRT
<213> ORGANISM: Artificial Sequence
<220> FEATURE:
<223> OTHER INFORMATION: Fusion Protein DNA

<400> SEQUENCE: 74

Phe Val Asn Gln His Leu Cys Gly Ser His Leu Val Glu Ala Leu Ala
1               5                   10                  15

Leu Val Cys Gly Glu Arg Gly Phe Tyr Tyr Thr Asp Pro Thr Gly Gly
                20                  25                  30

Gly Pro Arg Arg Gly Ile Val Glu Gln Cys Cys Thr Ser Ile Cys Ser
            35                  40                  45

Leu Tyr Gln Leu Glu Asn Tyr Cys Gly Gly Gly Ala Gly Gly Gly
        50                  55                  60

Gly Asp Cys Pro Lys Cys Pro Ala Pro Glu Met Leu Gly Gly Pro Ser
65                  70                  75                  80

Val Phe Ile Phe Pro Pro Lys Pro Lys Asp Thr Leu Leu Ile Ala Arg
                85                  90                  95

Thr Pro Glu Val Thr Cys Val Val Val Asp Leu Asp Pro Glu Asp Pro
            100                 105                 110

Glu Val Gln Ile Ser Trp Phe Val Asp Gly Lys Gln Met Gln Thr Ala
        115                 120                 125

Lys Thr Gln Pro Arg Glu Glu Gln Phe Ser Gly Thr Tyr Arg Val Val
130                 135                 140

Ser Val Leu Pro Ile Gly His Gln Asp Trp Leu Lys Gly Lys Gln Phe
145                 150                 155                 160

Thr Cys Lys Val Asn Asn Lys Ala Leu Pro Ser Pro Ile Glu Arg Thr
                165                 170                 175

Ile Ser Lys Ala Arg Gly Gln Ala His Gln Pro Ser Val Tyr Val Leu
            180                 185                 190

Pro Pro Ser Arg Glu Glu Leu Ser Lys Asn Thr Val Ser Leu Thr Cys
        195                 200                 205

Leu Ile Lys Asp Phe Phe Pro Pro Asp Ile Asp Val Glu Trp Gln Ser
    210                 215                 220

Asn Gly Gln Gln Glu Pro Glu Ser Lys Tyr Arg Thr Thr Pro Pro Gln
225                 230                 235                 240

Leu Asp Glu Asp Gly Ser Tyr Phe Leu Tyr Ser Lys Leu Ser Val Asp
                245                 250                 255

Lys Ser Arg Trp Gln Arg Gly Asp Thr Phe Ile Cys Ala Val Met His
            260                 265                 270

Glu Ala Leu His Asn His Tyr Thr Gln Glu Ser Leu Ser His Ser Pro
```

<210> SEQ ID NO 75
<211> LENGTH: 927
<212> TYPE: DNA
<213> ORGANISM: Artificial Sequence
<220> FEATURE:
<223> OTHER INFORMATION: Fusion Protein DNA

<400> SEQUENCE: 75

```
atggaatgga gctgggtctt tctcttcttc ctgtcagtaa cgactggtgt ccactccttc      60
gtgaaccagc acctgtgcgg ctcccacctg gtggaagctc tggctctcgt gtgcggcgag     120
cggggcttct tctacaccga tcccactgga ggcggtccac gcagaggcat cgtggaacag     180
tgctgcacct ccatctgctc cctgtaccag ctggaaaact actgcggcgg aggtggtgca     240
ggaggcggtg gagactgccc caagtgcccc gctcccgaga tgctgggcgg acccagcgtg     300
ttcatcttcc ctcccaagcc caaggacaca ctgctgatcg ccaggacccc ggaggtgacc     360
tgcgtggtgg tggacctgga tcccgaagac cccgaggtgc agatcagctg gttcgtggat     420
ggaaagcaga tgcagaccgc caagacccaa ccccgggaag agcagttcag cggcacctac     480
agggtggtga gtgtgttgcc catcggccac caggactggc tgaagggaa gcaattcaca      540
tgcaaggtta taacaaggc cctgccagc ccatcgaga ggaccatcag caaggccagg        600
ggccaggccc accagccatc tgtgtacgtg ctgccccat ctagggagga actgagcaag      660
aacacagtca gccttacttg cctgatcaag gacttcttcc caccggacat agacgtggag     720
tggcagagta acggccagca ggagcccgag agcaagtata ggaccacacc gccccaactg     780
gacgaggacg gaagctactt cctctacagc aaattgagcg ttgacaaaag caggtggcag     840
cgaggcgaca ccttcatctg cgccgtgatg cacgaggctt tgcataacca ctacacccag     900
gagagcctgt cccacagccc cggatag                                         927
```

<210> SEQ ID NO 76
<211> LENGTH: 289
<212> TYPE: PRT
<213> ORGANISM: Artificial Sequence
<220> FEATURE:
<223> OTHER INFORMATION: Fusion Protein

<400> SEQUENCE: 76

Phe Val Asn Gln His Leu Cys Gly Ser His Leu Val Glu Ala Leu Ala
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys Thr Ser Ile Cys Ser
        35                  40                  45

Leu Tyr Gln Leu Glu Asn Tyr Cys Gly Gly Gly Ala Gly Gly Gly
    50                  55                  60

Gly Asp Cys Pro Lys Cys Pro Ala Pro Glu Met Leu Gly Gly Pro Ser
65                  70                  75                  80

Val Phe Ile Phe Pro Pro Lys Pro Lys Asp Thr Leu Leu Ile Ala Arg
                85                  90                  95

Thr Pro Glu Val Thr Cys Val Val Val Asp Leu Asp Pro Glu Asp Pro
            100                 105                 110

Glu Val Gln Ile Ser Trp Phe Val Asp Gly Lys Gln Met Gln Thr Ala
        115                 120                 125

```
Lys Thr Gln Pro Arg Glu Glu Gln Phe Ser Gly Thr Tyr Arg Val Val
            130                 135                 140

Ser Val Leu Pro Ile Gly His Gln Asp Trp Leu Lys Gly Lys Gln Phe
145                 150                 155                 160

Thr Cys Lys Val Asn Asn Lys Ala Leu Pro Ser Pro Ile Glu Arg Thr
                165                 170                 175

Ile Ser Lys Ala Arg Gly Gln Ala His Gln Pro Ser Val Tyr Val Leu
            180                 185                 190

Pro Pro Ser Arg Glu Glu Leu Ser Lys Asn Thr Val Ser Leu Thr Cys
            195                 200                 205

Leu Ile Lys Asp Phe Phe Pro Asp Ile Asp Val Glu Trp Gln Ser
210                 215                 220

Asn Gly Gln Gln Glu Pro Glu Ser Lys Tyr Arg Thr Thr Pro Pro Gln
225                 230                 235                 240

Leu Asp Glu Asp Gly Ser Tyr Phe Leu Tyr Ser Lys Leu Ser Val Asp
                245                 250                 255

Lys Ser Arg Trp Gln Arg Gly Asp Thr Phe Ile Cys Ala Val Met His
            260                 265                 270

Glu Ala Leu His Asn His Tyr Thr Gln Glu Ser Leu Ser His Ser Pro
            275                 280                 285

Gly

<210> SEQ ID NO 77
<211> LENGTH: 936
<212> TYPE: DNA
<213> ORGANISM: Artificial Sequence
<220> FEATURE:
<223> OTHER INFORMATION: Fusion Protein DNA

<400> SEQUENCE: 77
atggaatgga gctgggtctt tctcttcttc ctgtcagtaa cgactggtgt ccactccttc    60
gtgaaccagc acctgtgcgg ctcccacctg gtgcaagctc tgtatctcgt gtgcggcgag   120
cggggcttct tctacaccga tcccactcag aggggcggtg gcggagggca aagaggcatc   180
gtggaacagt gctgcacatc catctgctcc ctgtaccagc tggaaaacta ctgcggcgga   240
ggtggtgcag gaggcggtgg agactgcccc aagtgccccg ctcccgagat gctgggcgga   300
cccagcgtgt tcatcttccc tcccaagccc aaggacacac tgctgatcgc caggaccccg   360
gaggtgacct gcgtggtggt ggacctggat cccgaagacc ccgaggtgca gatcagctgg   420
ttcgtggatg gaaagcagat gcagaccgcc aagacccaac cccgggaaga gcagttcagc   480
ggcacctaca gggtggtgag tgtgttgccc atcggccacc aggactggct gaaggggaag   540
caattcacat gcaaggttaa taacaaggcc ctgcccagcc catcgagag gaccatcagc   600 aaggccaggg gccaggccca ccagccatct gtgtacgtgc tgcccccatc tagggaggaa   660
ctgagcaaga cacagtcag ccttacttgc ctgatcaagg acttcttccc accggacata   720
gacgtggagt ggcagagtaa cggccagcag gagcccgaga gcaagtatag gaccacaccg   780
ccccaactgg acgaggacgg aagctacttc ctctacagca aattgagcgt tgacaaaagc   840
aggtggcagc gaggcgacac cttcatctgc gccgtgatgc acgaggcttt gcataaccac   900
tacacccagg agagcctgtc ccacagcccc ggatag                              936

<210> SEQ ID NO 78
<211> LENGTH: 292
<212> TYPE: PRT
```

<213> ORGANISM: Artificial Sequence
<220> FEATURE:
<223> OTHER INFORMATION: Fusion Protein

<400> SEQUENCE: 78

```
Phe Val Asn Gln His Leu Cys Gly Ser His Leu Val Gln Ala Leu Tyr
1               5                   10                  15
Leu Val Cys Gly Glu Arg Gly Phe Phe Tyr Thr Asp Pro Thr Gln Arg
            20                  25                  30
Gly Gly Gly Gly Gly Gln Arg Gly Ile Val Glu Gln Cys Cys Thr Ser
        35                  40                  45
Ile Cys Ser Leu Tyr Gln Leu Glu Asn Tyr Cys Gly Gly Gly Gly Ala
    50                  55                  60
Gly Gly Gly Gly Asp Cys Pro Lys Cys Pro Ala Pro Glu Met Leu Gly
65                  70                  75                  80
Gly Pro Ser Val Phe Ile Phe Pro Pro Lys Pro Lys Asp Thr Leu Leu
                85                  90                  95
Ile Ala Arg Thr Pro Glu Val Thr Cys Val Val Val Asp Leu Asp Pro
            100                 105                 110
Glu Asp Pro Glu Val Gln Ile Ser Trp Phe Val Asp Gly Lys Gln Met
        115                 120                 125
Gln Thr Ala Lys Thr Gln Pro Arg Glu Glu Gln Phe Ser Gly Thr Tyr
    130                 135                 140
Arg Val Val Ser Val Leu Pro Ile Gly His Gln Asp Trp Leu Lys Gly
145                 150                 155                 160
Lys Gln Phe Thr Cys Lys Val Asn Asn Lys Ala Leu Pro Ser Pro Ile
                165                 170                 175
Glu Arg Thr Ile Ser Lys Ala Arg Gly Gln Ala His Gln Pro Ser Val
            180                 185                 190
Tyr Val Leu Pro Pro Ser Arg Glu Glu Leu Ser Lys Asn Thr Val Ser
        195                 200                 205
Leu Thr Cys Leu Ile Lys Asp Phe Phe Pro Pro Asp Ile Asp Val Glu
    210                 215                 220
Trp Gln Ser Asn Gly Gln Gln Glu Pro Glu Ser Lys Tyr Arg Thr Thr
225                 230                 235                 240
Pro Pro Gln Leu Asp Glu Asp Gly Ser Tyr Phe Leu Tyr Ser Lys Leu
                245                 250                 255
Ser Val Asp Lys Ser Arg Trp Gln Arg Gly Asp Thr Phe Ile Cys Ala
            260                 265                 270
Val Met His Glu Ala Leu His Asn His Tyr Thr Gln Glu Ser Leu Ser
        275                 280                 285
His Ser Pro Gly
    290
```

<210> SEQ ID NO 79
<211> LENGTH: 942
<212> TYPE: DNA
<213> ORGANISM: Artificial Sequence
<220> FEATURE:
<223> OTHER INFORMATION: Fusion Protein DNA

<400> SEQUENCE: 79

```
atggaatgga gctgggtctt tctcttcttc ctgtcagtaa cgactggtgt ccactccttc    60
gtgaaccagc acctgtgcgg ctcccacctg gtggaagctc tggctctcgt gtgcggcgag   120
cggggcttct tctacaccga tcccactggg ggtggcggag aggttctggg tggcggcgga   180
```

```
ggcatcgtgg aacagtgctg cacctccatc tgctccctgt accagctgga aaactactgc    240
ggcggaggtg gtgcaggagg cggtggagac tgccccaagt gccccgctcc cgagatgctg    300
ggcggaccca gcgtgttcat cttccctccc aagcccaagg acacactgct gatcgccagg    360
accccggagt gtacctgcgt ggtggtggac ctggatcccg aagaccccga ggtgcagatc    420
agctggttcg tggatggaaa gcagatgcag accgccaaga cccaaccccg ggaagagcag    480
ttcagcggca cctacagggt ggtgagtgtg ttgcccatcg gccaccagga ctggctgaag    540
gggaagcaat tcacatgcaa ggttaataac aaggccctgc ccagccccat cgagaggacc    600
atcagcaagg ccaggggcca ggcccaccag ccatctgtgt acgtgctgcc cccatctagg    660
gaggaactga gcaagaacac agtcagcctt acttgcctga tcaaggactt cttcccaccg    720
gacatagacg tggagtggca gagtaacggc cagcaggagc ccgagagcaa gtataggacc    780
acaccgcccc aactggacga ggacggaagc tacttcctct acagcaaatt gagcgttgac    840
aaaagcaggt ggcagcgagg cgacaccttc atctgcgccg tgatgcacga ggctttgcat    900
aaccactaca cccaggagag cctgtcccac agccccggat ag                       942
```

```
<210> SEQ ID NO 80
<211> LENGTH: 294
<212> TYPE: PRT
<213> ORGANISM: Artificial Sequence
<220> FEATURE:
<223> OTHER INFORMATION: Fusion Protein

<400> SEQUENCE: 80

Phe Val Asn Gln His Leu Cys Gly Ser His Leu Val Glu Ala Leu Ala
1               5                   10                  15

Leu Val Cys Gly Glu Arg Gly Phe Phe Tyr Thr Asp Pro Thr Gly Gly
            20                  25                  30

Gly Gly Gly Gly Ser Gly Gly Gly Gly Ile Val Glu Gln Cys Cys
        35                  40                  45

Thr Ser Ile Cys Ser Leu Tyr Gln Leu Glu Asn Tyr Cys Gly Gly Gly
    50                  55                  60

Gly Ala Gly Gly Gly Asp Cys Pro Lys Cys Pro Ala Pro Glu Met
65                  70                  75                  80

Leu Gly Gly Pro Ser Val Phe Ile Phe Pro Pro Lys Pro Lys Asp Thr
                85                  90                  95

Leu Leu Ile Ala Arg Thr Pro Glu Val Thr Cys Val Val Val Asp Leu
            100                 105                 110

Asp Pro Glu Asp Pro Glu Val Gln Ile Ser Trp Phe Val Asp Gly Lys
        115                 120                 125

Gln Met Gln Thr Ala Lys Thr Gln Pro Arg Glu Glu Gln Phe Ser Gly
    130                 135                 140

Thr Tyr Arg Val Val Ser Val Leu Pro Ile Gly His Gln Asp Trp Leu
145                 150                 155                 160

Lys Gly Lys Gln Phe Thr Cys Lys Val Asn Asn Lys Ala Leu Pro Ser
                165                 170                 175

Pro Ile Glu Arg Thr Ile Ser Lys Ala Arg Gly Gln Ala His Gln Pro
            180                 185                 190

Ser Val Tyr Val Leu Pro Pro Ser Arg Glu Glu Leu Ser Lys Asn Thr
        195                 200                 205

Val Ser Leu Thr Cys Leu Ile Lys Asp Phe Phe Pro Pro Asp Ile Asp
    210                 215                 220

Val Glu Trp Gln Ser Asn Gly Gln Gln Glu Pro Glu Ser Lys Tyr Arg
```

```
                  225                 230                 235                 240
Thr Thr Pro Pro Gln Leu Asp Glu Asp Gly Ser Tyr Phe Leu Tyr Ser
                      245                 250                 255

Lys Leu Ser Val Asp Lys Ser Arg Trp Gln Arg Gly Asp Thr Phe Ile
                260                 265                 270

Cys Ala Val Met His Glu Ala Leu His Asn His Tyr Thr Gln Glu Ser
            275                 280                 285

Leu Ser His Ser Pro Gly
        290

<210> SEQ ID NO 81
<211> LENGTH: 930
<212> TYPE: DNA
<213> ORGANISM: Artificial Sequence
<220> FEATURE:
<223> OTHER INFORMATION: Fusion Protein DNA

<400> SEQUENCE: 81
atggaatgga gctgggtctt tctcttcttc ctgtcagtaa cgactggtgt ccactccttc      60
gtgaaccagc acctctgcgg cagccacctg gtggaggcct tggccctggt gtgcggcgag     120
aggggcttct tctacaccga tccaggtggc ggtggggag gtggcggagg gatcgtggag      180
cagtgctgca ccagcatctg cagcctgtac caactggaaa actactgcgg cggaggtggt     240
gcaggaggcg gtggagactg ccccaagtgc cccgctcccg agatgctggg cggacccagc     300
gtgttcatct tccctcccaa gcccaaggac acactgctga tcgccaggac cccggaggtg     360
acctgcgtgg tggtggacct ggatcccgaa gaccccgagg tgcagatcag ctggttcgtg     420
gatggaaagc agatgcagac cgccaagacc caaccccggg aagagcagtt cagcggcacc     480
tacagggtgt gagtgtgtt gcccatcggc caccaggact ggctgaaggg gaagcaattc      540
acatgcaagg ttaataacaa ggccctgccc agccccatcg agaggaccat cagcaaggcc     600
aggggccagg cccaccagcc atctgtgtac gtgctgcccc catctaggga ggaactgagc     660
aagaacacag tcagccttac ttgcctgatc aaggacttct tcccaccgga catagacgtg     720
gagtggcaga gtaacggcca gcaggagccc gagagcaagt ataggaccac accgccccaa     780
ctggacgagg acggaagcta cttcctctac agcaaattga gcgttgacaa aagcaggtgg     840
cagcgaggcg acaccttcat ctgcgccgtg atgcacgagg cttttgcataa ccactacacc     900 caggagagcc tgtcccacag ccccggatag                                      930

<210> SEQ ID NO 82
<211> LENGTH: 290
<212> TYPE: PRT
<213> ORGANISM: Artificial Sequence
<220> FEATURE:
<223> OTHER INFORMATION: Fusion Protein

<400> SEQUENCE: 82

Phe Val Asn Gln His Leu Cys Gly Ser His Leu Val Glu Ala Leu Ala
1               5                  10                  15

Leu Val Cys Gly Glu Arg Gly Phe Phe Tyr Thr Asp Pro Gly Gly Gly
                20                  25                  30

Gly Gly Gly Gly Gly Ile Val Glu Gln Cys Cys Thr Ser Ile Cys
            35                  40                  45

Ser Leu Tyr Gln Leu Glu Asn Tyr Cys Gly Gly Gly Ala Gly Gly
        50                  55                  60

Gly Gly Asp Cys Pro Lys Cys Pro Ala Pro Glu Met Leu Gly Gly Pro
```

```
              65                  70                  75                  80
Ser Val Phe Ile Phe Pro Pro Lys Pro Lys Asp Thr Leu Leu Ile Ala
                    85                  90                  95

Arg Thr Pro Glu Val Thr Cys Val Val Val Asp Leu Asp Pro Glu Asp
                100                 105                 110

Pro Glu Val Gln Ile Ser Trp Phe Val Asp Gly Lys Gln Met Gln Thr
                115                 120                 125

Ala Lys Thr Gln Pro Arg Glu Glu Gln Phe Ser Gly Thr Tyr Arg Val
        130                 135                 140

Val Ser Val Leu Pro Ile Gly His Gln Asp Trp Leu Lys Gly Lys Gln
145                 150                 155                 160

Phe Thr Cys Lys Val Asn Asn Lys Ala Leu Pro Ser Pro Ile Glu Arg
                165                 170                 175

Thr Ile Ser Lys Ala Arg Gly Gln Ala His Gln Pro Ser Val Tyr Val
                180                 185                 190

Leu Pro Pro Ser Arg Glu Glu Leu Ser Lys Asn Thr Val Ser Leu Thr
            195                 200                 205

Cys Leu Ile Lys Asp Phe Phe Pro Pro Asp Ile Asp Val Glu Trp Gln
        210                 215                 220

Ser Asn Gly Gln Gln Glu Pro Glu Ser Lys Tyr Arg Thr Thr Pro Pro
225                 230                 235                 240

Gln Leu Asp Glu Asp Gly Ser Tyr Phe Leu Tyr Ser Lys Leu Ser Val
                245                 250                 255

Asp Lys Ser Arg Trp Gln Arg Gly Asp Thr Phe Ile Cys Ala Val Met
                260                 265                 270

His Glu Ala Leu His Asn His Tyr Thr Gln Glu Ser Leu Ser His Ser
        275                 280                 285

Pro Gly
    290

<210> SEQ ID NO 83
<211> LENGTH: 927
<212> TYPE: DNA
<213> ORGANISM: Artificial Sequence
<220> FEATURE:
<223> OTHER INFORMATION: Fusion Protein DNA

<400> SEQUENCE: 83
atggaatgga gctgggtctt tctcttcttc ctgtcagtaa cgactggtgt ccactccttc      60
gtgaaccagc acctctgcgg cagccacctg gtggaggcct tggccctggt gtgcggcgag     120 agggcttct tctacacccc aggtggcggt gggggaggtg gcggagggat cgtggagcag     180
tgctgcacca gcatctgcag cctgtaccaa ctggaaaact actgcggcgg aggtggtgca     240
ggaggcggtg gagactgccc caagtgcccc gctcccgaga tgctgggcgg acccagcgtg     300
ttcatcttcc ctcccaagcc caaggacaca ctgctgatcg ccaggacccc ggaggtgacc     360
tgcgtggtgg tggacctgga tcccgaagac cccgaggtgc agatcagctg gttcgtggat     420
ggaaagcaga tgcagaccgc caagacccaa ccccgggaag agcagttcag cggcacctac     480
agggtggtga gtgtgttgcc catcggccac caggactggc tgaagggaaa gcaattcaca     540
tgcaaggtta ataacaaggc cctgcccagc ccatcgaga ggaccatcag caaggccagg      600
ggccaggccc accagccatc tgtgtacgtg ctgccccat ctaggaggaa actgagcaag      660
aacacagtca gccttacttg cctgatcaag gacttcttcc caccggacat agacgtggag     720
tggcagagta acggccagca ggagcccgag agcaagtata ggaccacacc gccccaactg     780
```
gacgaggacg gaagctactt cctctacagc aaattgagcg ttgacaaaag caggtggcag    840
cgaggcgaca ccttcatctg cgccgtgatg cacgaggctt tgcataacca ctacacccag    900
gagagcctgt cccacagccc cggatag                                        927

<210> SEQ ID NO 84
<211> LENGTH: 289
<212> TYPE: PRT
<213> ORGANISM: Artificial Sequence
<220> FEATURE:
<223> OTHER INFORMATION: Fusion Protein

<400> SEQUENCE: 84

Phe Val Asn Gln His Leu Cys Gly Ser His Leu Val Glu Ala Leu Ala
1               5                   10                  15

Leu Val Cys Gly Glu Arg Gly Phe Phe Tyr Thr Pro Gly Gly Gly Gly
                20                  25                  30

Gly Gly Gly Gly Gly Ile Val Glu Gln Cys Cys Thr Ser Ile Cys Ser
            35                  40                  45

Leu Tyr Gln Leu Glu Asn Tyr Cys Gly Gly Gly Ala Gly Gly Gly
    50                  55                  60

Gly Asp Cys Pro Lys Cys Pro Ala Pro Glu Met Leu Gly Gly Pro Ser
65                  70                  75                  80

Val Phe Ile Phe Pro Pro Lys Pro Lys Asp Thr Leu Leu Ile Ala Arg
                85                  90                  95

Thr Pro Glu Val Thr Cys Val Val Val Asp Leu Asp Pro Glu Asp Pro
            100                 105                 110

Glu Val Gln Ile Ser Trp Phe Val Asp Gly Lys Gln Met Gln Thr Ala
        115                 120                 125

Lys Thr Gln Pro Arg Glu Glu Gln Phe Ser Gly Thr Tyr Arg Val Val
    130                 135                 140

Ser Val Leu Pro Ile Gly His Gln Asp Trp Leu Lys Gly Lys Gln Phe
145                 150                 155                 160

Thr Cys Lys Val Asn Asn Lys Ala Leu Pro Ser Pro Ile Glu Arg Thr
                165                 170                 175

Ile Ser Lys Ala Arg Gly Gln Ala His Gln Pro Ser Val Tyr Val Leu
            180                 185                 190

Pro Pro Ser Arg Glu Glu Leu Ser Lys Asn Thr Val Ser Leu Thr Cys
        195                 200                 205

Leu Ile Lys Asp Phe Phe Pro Pro Asp Ile Asp Val Glu Trp Gln Ser
    210                 215                 220

Asn Gly Gln Gln Glu Pro Glu Ser Lys Tyr Arg Thr Thr Pro Pro Gln
225                 230                 235                 240

Leu Asp Glu Asp Gly Ser Tyr Phe Leu Tyr Ser Lys Leu Ser Val Asp
                245                 250                 255

Lys Ser Arg Trp Gln Arg Gly Asp Thr Phe Ile Cys Ala Val Met His
            260                 265                 270

Glu Ala Leu His Asn His Tyr Thr Gln Glu Ser Leu Ser His Ser Pro
        275                 280                 285

Gly

<210> SEQ ID NO 85
<211> LENGTH: 963
<212> TYPE: DNA
<213> ORGANISM: Artificial Sequence
<220> FEATURE:

<223> OTHER INFORMATION: Fusion Protein DNA

<400> SEQUENCE: 85

```
atggaatgga gctgggtctt tctcttcttc ctgtcagtaa cgactggtgt ccactccttc      60
gtgaaccagc acctgtgcgg ctcccacctg gtggaagctc tggctctcgt gtgcggcgag     120
cggggcttct tctacaccga tcccactgga ggcggtccac gcagaggcat cgtggaacag     180
tgctgcacct ccatctgctc cctgtaccag ctggaaaact actgcggtgg cggaggtggt     240
caaggaggcg gtggacaggg tggaggtggg cagggaggag gcggggagac tgccccaag      300
tgccccgctc ccgagatgct gggcggaccc agcgtgttca tcttccctcc caagcccaag     360
gacacactgc tgatcgccag gaccccggag gtgacctgcg tggtggtgga cctggatccc     420
gaagaccccg aggtgcagat cagctggttc gtggatggaa agcagatgca gaccgccaag     480
acccaacccc gggaagagca gttcagcggc acctacaggg tggtgagtgt gttgcccatc     540
ggccaccagg actggctgaa ggggaagcaa ttcacatgca aggttaataa caaggccctg     600
cccagcccca tcgagaggac catcagcaag gccgggggcc aggcccacca gccatctgtg     660
tacgtgctgc ccccatctag gaggaactg agcaagaaca cagtcagcct tacttgcctg     720
atcaaggact tcttcccacc ggacatagac gtggagtggc agagtaacgg ccagcaggag     780
cccgagagca gtataggac cacaccgccc caactggacg aggacggaag ctacttcctc     840
tacagcaaat tgagcgttga caaaagcagg tggcagcgag cgacaccttt catctgcgcc     900
gtgatgcacg aggctttgca taaccactac acccaggaga gcctgtccca cagccccgga     960
tag                                                                    963
```

<210> SEQ ID NO 86
<211> LENGTH: 301
<212> TYPE: PRT
<213> ORGANISM: Artificial Sequence
<220> FEATURE:
<223> OTHER INFORMATION: Fusion Protein

<400> SEQUENCE: 86

```
Phe Val Asn Gln His Leu Cys Gly Ser His Leu Val Glu Ala Leu Ala
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys Thr Ser Ile Cys Ser
        35                  40                  45

Leu Tyr Gln Leu Glu Asn Tyr Cys Gly Gly Gly Gly Gln Gly Gly
    50                  55                  60

Gly Gly Gln Gly Gly Gly Gly Gln Gly Gly Gly Gly Asp Cys Pro
65                  70                  75                  80

Lys Cys Pro Ala Pro Glu Met Leu Gly Gly Pro Ser Val Phe Ile Phe
                85                  90                  95

Pro Pro Lys Pro Lys Asp Thr Leu Leu Ile Ala Arg Thr Pro Glu Val
            100                 105                 110

Thr Cys Val Val Val Asp Leu Asp Pro Glu Asp Pro Glu Val Gln Ile
        115                 120                 125

Ser Trp Phe Val Asp Gly Lys Gln Met Gln Thr Ala Lys Thr Gln Pro
    130                 135                 140

Arg Glu Glu Gln Phe Ser Gly Thr Tyr Arg Val Val Ser Val Leu Pro
145                 150                 155                 160

Ile Gly His Gln Asp Trp Leu Lys Gly Lys Gln Phe Thr Cys Lys Val
```

|   |   |   | 165 |   |   |   | 170 |   |   |   | 175 |   |
|---|---|---|---|---|---|---|---|---|---|---|---|---|

Asn Asn Lys Ala Leu Pro Ser Pro Ile Glu Arg Thr Ile Ser Lys Ala
            180                 185                 190

Arg Gly Gln Ala His Gln Pro Ser Val Tyr Val Leu Pro Pro Ser Arg
        195                 200                 205

Glu Glu Leu Ser Lys Asn Thr Val Ser Leu Thr Cys Leu Ile Lys Asp
    210                 215                 220

Phe Phe Pro Pro Asp Ile Asp Val Glu Trp Gln Ser Asn Gly Gln Gln
225                 230                 235                 240

Glu Pro Glu Ser Lys Tyr Arg Thr Thr Pro Pro Gln Leu Asp Glu Asp
                245                 250                 255

Gly Ser Tyr Phe Leu Tyr Ser Lys Leu Ser Val Asp Lys Ser Arg Trp
            260                 265                 270

Gln Arg Gly Asp Thr Phe Ile Cys Ala Val Met His Glu Ala Leu His
        275                 280                 285

Asn His Tyr Thr Gln Glu Ser Leu Ser His Ser Pro Gly
    290                 295                 300

<210> SEQ ID NO 87
<211> LENGTH: 927
<212> TYPE: DNA
<213> ORGANISM: Artificial Sequence
<220> FEATURE:
<223> OTHER INFORMATION: Fusion Protein DNA

<400> SEQUENCE: 87

| atggaatgga gctgggtctt tctcttcttc ctgtcagtaa cgactggtgt ccactccttc | 60 |
| gtgaaccagc acctctgcgg cagccacctg gtggaggcct tggccctggt gtgcggcgag | 120 |
| agggcttct tctacacccca gggtggcggt ggggaggtg gcggagggat cgtgagcag | 180 |
| tgctgcacca gcatctgcag cctgtaccaa ctggaaaact actgcggcgg aggtggtgca | 240 |
| ggaggcggtg gagactgccc caagtgcccc gctcccgaga tgctggggcgg acccagcgtg | 300 |
| ttcatcttcc ctcccaagcc caaggacaca ctgctgatcg ccaggaccccc ggaggtgacc | 360 |
| tgcgtggtgg tggacctgga tcccgaagac cccgaggtgc agatcagctg gttcgtggat | 420 |
| ggaaagcaga tgcagaccgc caagacccaa ccccgggaag agcagttcag cggcacctac | 480 |
| agggtggtga gtgtgttgcc catcggccac caggactggc tgaaggggaa gcaattcaca | 540 |
| tgcaaggtta ataacaaggc cctgcccagc ccatcgaga ggaccatcag caaggccagg | 600 |
| ggccaggccc accagccatc tgtgtacgtg ctgcccccat ctaggaggga actgagcaag | 660 |
| aacacagtca gccttacttg cctgatcaag gacttcttcc caccggacat agacgtggag | 720 |
| tggcagagta acggccagca ggagcccgag agcaagtata ggaccacacc gccccaactg | 780 |
| gacgaggacg gaagctactt cctctacagc aaattgagcg ttgacaaaag caggtggcag | 840 |
| cgaggcgaca ccttcatctg cgccgtgatg cacgaggctt tgcataacca ctacacccag | 900 |
| gagagcctgt cccacagccc cggatag | 927 |

<210> SEQ ID NO 88
<211> LENGTH: 289
<212> TYPE: PRT
<213> ORGANISM: Artificial Sequence
<220> FEATURE:
<223> OTHER INFORMATION: Fusion Protein

<400> SEQUENCE: 88

Phe Val Asn Gln His Leu Cys Gly Ser His Leu Val Glu Ala Leu Ala

```
 1               5                   10                  15
Leu Val Cys Gly Glu Arg Gly Phe Phe Tyr Thr Gln Gly Gly Gly
            20                  25                  30
Gly Gly Gly Gly Gly Ile Val Glu Gln Cys Cys Thr Ser Ile Cys Ser
        35                  40                  45
Leu Tyr Gln Leu Glu Asn Tyr Cys Gly Gly Gly Ala Gly Gly Gly
        50                  55                  60
Gly Asp Cys Pro Lys Cys Pro Ala Pro Glu Met Leu Gly Gly Pro Ser
65                  70                  75                  80
Val Phe Ile Phe Pro Pro Lys Pro Lys Asp Thr Leu Leu Ile Ala Arg
                85                  90                  95
Thr Pro Glu Val Thr Cys Val Val Val Asp Leu Asp Pro Glu Asp Pro
                100                 105                 110
Glu Val Gln Ile Ser Trp Phe Val Asp Gly Lys Gln Met Gln Thr Ala
                115                 120                 125
Lys Thr Gln Pro Arg Glu Glu Gln Phe Ser Gly Thr Tyr Arg Val Val
        130                 135                 140
Ser Val Leu Pro Ile Gly His Gln Asp Trp Leu Lys Gly Lys Gln Phe
145                 150                 155                 160
Thr Cys Lys Val Asn Asn Lys Ala Leu Pro Ser Pro Ile Glu Arg Thr
                165                 170                 175
Ile Ser Lys Ala Arg Gly Gln Ala His Gln Pro Ser Val Tyr Val Leu
                180                 185                 190
Pro Pro Ser Arg Glu Glu Leu Ser Lys Asn Thr Val Ser Leu Thr Cys
        195                 200                 205
Leu Ile Lys Asp Phe Phe Pro Pro Asp Ile Asp Val Glu Trp Gln Ser
        210                 215                 220
Asn Gly Gln Gln Glu Pro Glu Ser Lys Tyr Arg Thr Thr Pro Pro Gln
225                 230                 235                 240
Leu Asp Glu Asp Gly Ser Tyr Phe Leu Tyr Ser Lys Leu Ser Val Asp
                245                 250                 255
Lys Ser Arg Trp Gln Arg Gly Asp Thr Phe Ile Cys Ala Val Met His
            260                 265                 270
Glu Ala Leu His Asn His Tyr Thr Gln Glu Ser Leu Ser His Ser Pro
        275                 280                 285
Gly

<210> SEQ ID NO 89
<211> LENGTH: 966
<212> TYPE: DNA
<213> ORGANISM: Artificial Sequence
<220> FEATURE:
<223> OTHER INFORMATION: Fusion Protein DNA

<400> SEQUENCE: 89
atggaatgga gctgggtctt tctcttcttc ctgtcagtaa cgactggtgt ccactccttc      60
gtgaaccagc acctgtgcgg ctcccacctg gtggaagctc tggaactcgt gtgcggcgag     120
cggggcttct ctacacccc taagacagga ggttctggtg gcggcggagg catcgtggaa      180
cagtgctgca cctccacctg ctccctggac cagctggaaa actactgcgg tggcggaggt     240
ggtcaaggag gcggtggaca gggtggaggt gggcaggag gaggcggggg agactgcccc      300
aagtgccccg ctcccgagat gctgggcgga cccagcgtgt tcatcttccc tcccaagccc    360
aaggacacac tgctgatcgc caggaccccg gaggtgacct gcgtggtggt ggacctggat    420
```

-continued

```
cccgaagacc ccgaggtgca gatcagctgg ttcgtggatg gaaagcagat gcagaccgcc   480
aagacccaac cccgggaaga gcagttcaac ggcacctaca gggtggtgag tgtgttgccc   540
atcggccacc aggactggct gaaggggaag caattcacat gcaaggttaa taacaaggcc   600
ctgcccagcc ccatcgagag gaccatcagc aaggccaggg gccaggccca ccagccatct   660
gtgtacgtgc tgcccccatc tagggaggaa ctgagcaaga acacagtcag ccttacttgc   720
ctgatcaagg acttcttccc accggacata gacgtggagt ggcagagtaa cggccagcag   780
gagcccgaga gcaagtatag gaccacaccg ccccaactgg acgaggacgg aagctacttc   840
ctctacagca aattgagcgt tgacaaaagc aggtggcagc gaggcgacac cttcatctgc   900
gccgtgatgc acgaggcttt gcataaccac tacacccagg agagcctgtc ccacagcccc   960
ggatag                                                             966
```

```
<210> SEQ ID NO 90
<211> LENGTH: 302
<212> TYPE: PRT
<213> ORGANISM: Artificial Sequence
<220> FEATURE:
<223> OTHER INFORMATION: Fusion Protein

<400> SEQUENCE: 90

Phe Val Asn Gln His Leu Cys Gly Ser His Leu Val Glu Ala Leu Glu
1               5                   10                  15

Leu Val Cys Gly Glu Arg Gly Phe Phe Tyr Thr Pro Lys Thr Gly Gly
                20                  25                  30

Ser Gly Gly Gly Gly Gly Ile Val Glu Gln Cys Cys Thr Ser Thr Cys
            35                  40                  45

Ser Leu Asp Gln Leu Glu Asn Tyr Cys Gly Gly Gly Gly Gly Gln Gly
        50                  55                  60

Gly Gly Gly Gln Gly Gly Gly Gly Gln Gly Gly Gly Gly Asp Cys
65                  70                  75                  80

Pro Lys Cys Pro Ala Pro Glu Met Leu Gly Gly Pro Ser Val Phe Ile
                85                  90                  95

Phe Pro Pro Lys Pro Lys Asp Thr Leu Leu Ile Ala Arg Thr Pro Glu
                100                 105                 110

Val Thr Cys Val Val Val Asp Leu Asp Pro Glu Asp Pro Glu Val Gln
            115                 120                 125

Ile Ser Trp Phe Val Asp Gly Lys Gln Met Gln Thr Ala Lys Thr Gln
        130                 135                 140

Pro Arg Glu Glu Gln Phe Asn Gly Thr Tyr Arg Val Val Ser Val Leu
145                 150                 155                 160

Pro Ile Gly His Gln Asp Trp Leu Lys Gly Lys Gln Phe Thr Cys Lys
                165                 170                 175

Val Asn Asn Lys Ala Leu Pro Ser Pro Ile Glu Arg Thr Ile Ser Lys
                180                 185                 190

Ala Arg Gly Gln Ala His Gln Pro Ser Val Tyr Val Leu Pro Pro Ser
            195                 200                 205

Arg Glu Glu Leu Ser Lys Asn Thr Val Ser Leu Thr Cys Leu Ile Lys
        210                 215                 220

Asp Phe Phe Pro Pro Asp Ile Asp Val Glu Trp Gln Ser Asn Gly Gln
225                 230                 235                 240

Gln Glu Pro Glu Ser Lys Tyr Arg Thr Thr Pro Pro Gln Leu Asp Glu
                245                 250                 255

Asp Gly Ser Tyr Phe Leu Tyr Ser Lys Leu Ser Val Asp Lys Ser Arg
```

```
                260                 265                 270
Trp Gln Arg Gly Asp Thr Phe Ile Cys Ala Val Met His Glu Ala Leu
            275                 280                 285

His Asn His Tyr Thr Gln Glu Ser Leu Ser His Ser Pro Gly
            290                 295                 300
```

<210> SEQ ID NO 91
<211> LENGTH: 969
<212> TYPE: DNA
<213> ORGANISM: Artificial Sequence
<220> FEATURE:
<223> OTHER INFORMATION: Fusion Protein DNA

<400> SEQUENCE: 91

```
atggaatgga gctgggtctt tctcttcttc ctgtcagtaa cgactggtgt ccactccttc    60
gtgaaccagc acctgtgcgg ctcccacctg gtggaagctc tggaactcgt gtgcggcgag   120
cggggcttcc actacggggg tggcggagga ggttctggtg cggcggagg catcgtggaa    180
cagtgctgca cctccacctg ctccctggac cagctggaaa actactgcaa ccatggcgga   240
ggtggtcaag gaggcggtgg acagggtgga ggtgggcagg gaggaggcgg gggagactgc   300
cccaagtgcc ccgctcccga gatgctgggc ggacccagcg tgttcatctt ccctcccaag   360
cccaaggaca cactgctgat cgccaggacc ccggaggtga cctgcgtggt ggtggacctg   420
gatcccgaag accccgaggt gcagatcagc tggttcgtgg atggaaagca gatgcagacc   480
gccaagaccc aaccccggga agagcagttc aacggcacct acagggtggt gagtgtgttg   540
cccatcggcc accaggactg gctgaagggg aagcaattca catgcaaggt taataacaag   600
gccctgccca gccccatcga gaggaccatc agcaaggcca ggggccaggc ccaccagcca   660
tctgtgtacg tgctgccccc atctagggag gaactgagca gaacacagt cagccttact    720
tgcctgatca aggacttctt cccaccggac atagacgtgg agtggcagag taacggccag   780
caggagcccg agagcaagta taggaccaca ccgccccaac tggacgagga cggaagctac   840
ttcctctaca gcaaattgag cgttgacaaa agcaggtggc agcgaggcga caccttcatc   900
tgcgccgtga tgcacgaggc tttgcataac cactacaccc aggagagcct gtcccacagc   960
cccggatag                                                            969
```

<210> SEQ ID NO 92
<211> LENGTH: 303
<212> TYPE: PRT
<213> ORGANISM: Artificial Sequence
<220> FEATURE:
<223> OTHER INFORMATION: Fusion Protein

<400> SEQUENCE: 92

```
Phe Val Asn Gln His Leu Cys Gly Ser His Leu Val Glu Ala Leu Glu
1               5                   10                  15

Leu Val Cys Gly Glu Arg Gly Phe His Tyr Gly Gly Gly Gly Gly
            20                  25                  30

Ser Gly Gly Gly Gly Gly Ile Val Glu Gln Cys Cys Thr Ser Thr Cys
        35                  40                  45

Ser Leu Asp Gln Leu Glu Asn Tyr Cys Asn His Gly Gly Gly Gly Gln
    50                  55                  60

Gly Gly Gly Gly Gln Gly Gly Gly Gln Gly Gly Gly Gly Asp
65                  70                  75                  80

Cys Pro Lys Cys Pro Ala Pro Glu Met Leu Gly Gly Pro Ser Val Phe
                85                  90                  95
```

Ile Phe Pro Pro Lys Pro Lys Asp Thr Leu Leu Ile Ala Arg Thr Pro
            100                 105                 110

Glu Val Thr Cys Val Val Val Asp Leu Asp Pro Glu Asp Pro Glu Val
        115                 120                 125

Gln Ile Ser Trp Phe Val Asp Gly Lys Gln Met Gln Thr Ala Lys Thr
    130                 135                 140

Gln Pro Arg Glu Glu Gln Phe Asn Gly Thr Tyr Arg Val Val Ser Val
145                 150                 155                 160

Leu Pro Ile Gly His Gln Asp Trp Leu Lys Gly Lys Gln Phe Thr Cys
                165                 170                 175

Lys Val Asn Asn Lys Ala Leu Pro Ser Pro Ile Glu Arg Thr Ile Ser
            180                 185                 190

Lys Ala Arg Gly Gln Ala His Gln Pro Ser Val Tyr Val Leu Pro Pro
        195                 200                 205

Ser Arg Glu Glu Leu Ser Lys Asn Thr Val Ser Leu Thr Cys Leu Ile
    210                 215                 220

Lys Asp Phe Phe Pro Pro Asp Ile Asp Val Glu Trp Gln Ser Asn Gly
225                 230                 235                 240

Gln Gln Glu Pro Glu Ser Lys Tyr Arg Thr Thr Pro Pro Gln Leu Asp
                245                 250                 255

Glu Asp Gly Ser Tyr Phe Leu Tyr Ser Lys Leu Ser Val Asp Lys Ser
            260                 265                 270

Arg Trp Gln Arg Gly Asp Thr Phe Ile Cys Ala Val Met His Glu Ala
        275                 280                 285

Leu His Asn His Tyr Thr Gln Glu Ser Leu Ser His Ser Pro Gly
    290                 295                 300

<210> SEQ ID NO 93
<211> LENGTH: 966
<212> TYPE: DNA
<213> ORGANISM: Artificial Sequence
<220> FEATURE:
<223> OTHER INFORMATION: Fusion Protein DNA

<400> SEQUENCE: 93
atggaatgga gctgggtctt tctcttcttc ctgtcagtaa cgactggtgt ccactccttc      60
gtgaaccagc acctgtgcgg ctcccacctg gtggaagctc tggaactcgt gtgcggcgag     120
cggggcttct tctacggggg tggcggagga ggttctggtg gcggcggagg catcgtggaa     180
cagtgctgca cctccacctg ctccctggac cagctggaaa actactgcgg tggcggaggt     240
ggtcaaggag gcggtggaca gggtggaggt gggcagggag gaggcggggg agactgcccc     300
aagtgccccg ctcccgagat gctgggcgga cccagcgtgt tcatcttccc tccaagccc      360 aaggacacac tgctgatcgc caggaccccg gaggtgacct gcgtggtggt ggacctggat     420
cccgaagacc ccgaggtgca gatcagctgg ttcgtggatg gaaagcagat gcagaccgcc     480
aagacccaac cccgggaaga gcagttcaac ggcacctaca gggtggtgag tgtgttgccc     540
atcggccacc aggactggct gaaggggaag caattcacat gcaaggttaa taacaaggcc     600
ctgcccagcc ccatcgagag gaccatcagc aaggccaggg gccaggccca ccagccatct     660
gtgtacgtgc tgcccccatc tagggaggaa ctgagcaaga acacagtcag ccttacttgc     720
ctgatcaagg acttcttccc accggacata gacgtggagt ggcagagtaa cggccagcag     780
gagcccgaga gcaagtatag gaccacaccg ccccaactgg acgaggacgg aagctacttc     840
ctctacagca aattgagcgt tgacaaaagc aggtggcagc gaggcgacac cttcatctgc     900

```
gccgtgatgc acgaggcttt gcataaccac tacacccagg agagcctgtc ccacagcccc    960
ggatag                                                                966
```

```
<210> SEQ ID NO 94
<211> LENGTH: 302
<212> TYPE: PRT
<213> ORGANISM: Artificial Sequence
<220> FEATURE:
<223> OTHER INFORMATION: Fusion Protein

<400> SEQUENCE: 94
```

```
Phe Val Asn Gln His Leu Cys Gly Ser His Leu Val Glu Ala Leu Glu
1               5                   10                  15

Leu Val Cys Gly Glu Arg Gly Phe Phe Tyr Gly Gly Gly Gly Gly
            20                  25                  30

Ser Gly Gly Gly Gly Ile Val Glu Gln Cys Cys Thr Ser Thr Cys
        35                  40                  45

Ser Leu Asp Gln Leu Glu Asn Tyr Cys Gly Gly Gly Gly Gln Gly
    50                  55                  60

Gly Gly Gln Gly Gly Gly Gly Gln Gly Gly Gly Gly Asp Cys
65                  70                  75                  80

Pro Lys Cys Pro Ala Pro Glu Met Leu Gly Gly Pro Ser Val Phe Ile
                85                  90                  95

Phe Pro Pro Lys Pro Lys Asp Thr Leu Leu Ile Ala Arg Thr Pro Glu
            100                 105                 110

Val Thr Cys Val Val Val Asp Leu Asp Pro Glu Asp Pro Glu Val Gln
        115                 120                 125

Ile Ser Trp Phe Val Asp Gly Lys Gln Met Gln Thr Ala Lys Thr Gln
    130                 135                 140

Pro Arg Glu Glu Gln Phe Asn Gly Thr Tyr Arg Val Val Ser Val Leu
145                 150                 155                 160

Pro Ile Gly His Gln Asp Trp Leu Lys Gly Lys Gln Phe Thr Cys Lys
                165                 170                 175

Val Asn Asn Lys Ala Leu Pro Ser Pro Ile Glu Arg Thr Ile Ser Lys
            180                 185                 190

Ala Arg Gly Gln Ala His Gln Pro Ser Val Tyr Val Leu Pro Pro Ser
        195                 200                 205

Arg Glu Glu Leu Ser Lys Asn Thr Val Ser Leu Thr Cys Leu Ile Lys
    210                 215                 220

Asp Phe Phe Pro Pro Asp Ile Asp Val Glu Trp Gln Ser Asn Gly Gln
225                 230                 235                 240

Gln Glu Pro Glu Ser Lys Tyr Arg Thr Thr Pro Pro Gln Leu Asp Glu
                245                 250                 255

Asp Gly Ser Tyr Phe Leu Tyr Ser Lys Leu Ser Val Asp Lys Ser Arg
            260                 265                 270

Trp Gln Arg Gly Asp Thr Phe Ile Cys Ala Val Met His Glu Ala Leu
        275                 280                 285

His Asn His Tyr Thr Gln Glu Ser Leu Ser His Ser Pro Gly
    290                 295                 300

<210> SEQ ID NO 95
<211> LENGTH: 978
<212> TYPE: DNA
<213> ORGANISM: Artificial Sequence
<220> FEATURE:
<223> OTHER INFORMATION: Fusion Protein DNA
```

<400> SEQUENCE: 95

```
atggaatgga gctgggtctt tctcttcttc ctgtcagtaa cgactggtgt ccactccttc      60
gtgaaccagc acctgtgcgg ctcccacctg gtggaagctc tggaactcgt gtgcggcgag     120
cggggcttcc actacggggg tggcggagga ggttctggtg gcggcggagg catcgtggaa     180
cagtgctgca cctccacctg ctccctggac cagctggaaa actactgcgg tggcggaggt     240
ggtcaaggag gcggtggaca gggtggaggt gggcagggag gaggcggggg acgctgcact     300
gacacccctc catgccctgt gcccgagccc ctgggtggcc cagcgtact gatcttccca      360
ccgaaaccca aggacatcct gaggatcacc cgcaccccgg aggtgacctg cgtggtgctg     420
gacctgggca gggaggaccc cgaagtgcaa atcagctggt tcgtggacgg aaaggaggtg     480
cacaccgcca gacccaatc aagggagcag cagttcaacg gcacctacag ggtggtgagc      540
gtgttgccca tagagcacca ggactggctg accggcaagg agttcaagtg ccgcgtgaac     600
cacattgatc tccccagccc catcgagagg actatctcca aggcccgagg agggcccac      660
aagcccagtg tatacgtgct gccgccctct ccgaaggaac tgagctctag cgacaccgtg     720
agcatcacct gcctgatcaa ggacttctac cctcccgaca tagacgtaga gtggcagagc     780
aacggccagc aggagcccga aggaagcac aggatgaccc caccccaact ggacgaggac      840
ggctcatact ttctttatag caagctgagt gtggacaaga gcaggtggca gcagggcgac     900
cctttcactt gcgccgtaat gcacgagacc ctgcagaatc actacaccga cctgtcactg     960
agccatagcc ccggatag                                                    978
```

<210> SEQ ID NO 96
<211> LENGTH: 306
<212> TYPE: PRT
<213> ORGANISM: Artificial Sequence
<220> FEATURE:
<223> OTHER INFORMATION: Fusion Protein

<400> SEQUENCE: 96

```
Phe Val Asn Gln His Leu Cys Gly Ser His Leu Val Glu Ala Leu Glu
1               5                   10                  15
Leu Val Cys Gly Glu Arg Gly Phe His Tyr Gly Gly Gly Gly Gly Gly
                20                  25                  30
Ser Gly Gly Gly Gly Ile Val Glu Gln Cys Cys Thr Ser Thr Cys
            35                  40                  45
Ser Leu Asp Gln Leu Glu Asn Tyr Cys Gly Gly Gly Gly Gln Gly
        50                  55                  60
Gly Gly Gln Gly Gly Gly Gln Gly Gly Gly Gly Arg Cys
65                  70                  75                  80
Thr Asp Thr Pro Pro Cys Pro Val Pro Glu Pro Leu Gly Gly Pro Ser
                85                  90                  95
Val Leu Ile Phe Pro Pro Lys Pro Lys Asp Ile Leu Arg Ile Thr Arg
            100                 105                 110
Thr Pro Glu Val Thr Cys Val Val Leu Asp Leu Gly Arg Glu Asp Pro
        115                 120                 125
Glu Val Gln Ile Ser Trp Phe Val Asp Gly Lys Glu Val His Thr Ala
    130                 135                 140
Lys Thr Gln Ser Arg Glu Gln Gln Phe Asn Gly Thr Tyr Arg Val Val
145                 150                 155                 160
Ser Val Leu Pro Ile Glu His Gln Asp Trp Leu Thr Gly Lys Glu Phe
                165                 170                 175
```

```
Lys Cys Arg Val Asn His Ile Asp Leu Pro Ser Pro Ile Glu Arg Thr
            180                 185                 190

Ile Ser Lys Ala Arg Gly Arg Ala His Lys Pro Ser Val Tyr Val Leu
        195                 200                 205

Pro Pro Ser Pro Lys Glu Leu Ser Ser Ser Asp Thr Val Ser Ile Thr
210                 215                 220

Cys Leu Ile Lys Asp Phe Tyr Pro Pro Asp Ile Asp Val Glu Trp Gln
225                 230                 235                 240

Ser Asn Gly Gln Gln Glu Pro Glu Arg Lys His Arg Met Thr Pro Pro
                245                 250                 255

Gln Leu Asp Glu Asp Gly Ser Tyr Phe Leu Tyr Ser Lys Leu Ser Val
            260                 265                 270

Asp Lys Ser Arg Trp Gln Gln Gly Asp Pro Phe Thr Cys Ala Val Met
        275                 280                 285

His Glu Thr Leu Gln Asn His Tyr Thr Asp Leu Ser Leu Ser His Ser
            290                 295                 300

Pro Gly
305
```

<210> SEQ ID NO 97
<211> LENGTH: 969
<212> TYPE: DNA
<213> ORGANISM: Artificial Sequence
<220> FEATURE:
<223> OTHER INFORMATION: Fusion Protein DNA

<400> SEQUENCE: 97

```
atggaatgga gctgggtctt tctcttcttc ctgtcagtaa cgactggtgt ccactccttc    60
gtgaaccagc acctgtgcgg ctcccacctg gtggaagctc tggaactcgt gtgcggcgag   120
cggggcttcc actacggggg tggcggagga ggttctggtg gcggcggagg catcgtggaa   180
cagtgctgca cctccacctg ctccctggac cagctggaaa actactgcgg tggcggaggt   240
ggtcaaggag gcggtggaca gggtggaggt gggcagggag gaggcggggg atgcaacaac   300
tgcccgtgtc cggatgcggc cctcctgggc ggaccgagcg tgttcatttt ccctcctaag   360
cccaaggaca ttctggtgac cgccaggacc cccacggtga cctgcgtggt agtagatctc   420
gatcccgaaa acccagaggt gcaaatcagc tggttcgtgg actctaagca agtgcaaacc   480
gccaacacgc aaccccgcga ggaacagagc aacggcacct acagggtggt gagcgtgctg   540
cccatcgggc atcaggactg gctgagcggc aagcagttta atgcaaggt taacaacaag   600
gcactgccca gccccatcga ggagatcatc agcaagaccc cgggacaggc ccaccagccc   660
aacgtgtacg tccttcctcc gagccgcgac gagatgagca gaacaccgt gacgctgacc   720
tgtttggtga aggacttctt cccacccgag atcgacgtgg agtggcaaag caatggccag   780
caggagcccg agagcaaata caggatgacc ccaccccaac tggatgagga tggcagctat   840
ttcctctaca gcaaattgtc cgtggacaaa agcaggtgg agagggcga caccttcatc   900
tgcgccgtca tgcacgaggc ccttcacaat cactacaccc agatcagcct gagccactct   960
cccggatag                                                          969
```

<210> SEQ ID NO 98
<211> LENGTH: 303
<212> TYPE: PRT
<213> ORGANISM: Artificial Sequence
<220> FEATURE:
<223> OTHER INFORMATION: Fusion Protein

<400> SEQUENCE: 98

```
Phe Val Asn Gln His Leu Cys Gly Ser His Leu Val Glu Ala Leu Glu
1               5                   10                  15
Leu Val Cys Gly Glu Arg Gly Phe His Tyr Gly Gly Gly Gly Gly Gly
            20                  25                  30
Ser Gly Gly Gly Gly Ile Val Glu Gln Cys Cys Thr Ser Thr Cys
        35                  40                  45
Ser Leu Asp Gln Leu Glu Asn Tyr Cys Gly Gly Gly Gly Gln Gly
    50                  55                  60
Gly Gly Gln Gly Gly Gly Gly Gln Gly Gly Gly Gly Gly Cys Asn
65                  70                  75                  80
Asn Cys Pro Cys Pro Gly Cys Gly Leu Leu Gly Gly Pro Ser Val Phe
                85                  90                  95
Ile Phe Pro Pro Lys Pro Lys Asp Ile Leu Val Thr Ala Arg Thr Pro
            100                 105                 110
Thr Val Thr Cys Val Val Val Asp Leu Asp Pro Glu Asn Pro Glu Val
            115                 120                 125
Gln Ile Ser Trp Phe Val Asp Ser Lys Gln Val Gln Thr Ala Asn Thr
    130                 135                 140
Gln Pro Arg Glu Glu Gln Ser Asn Gly Thr Tyr Arg Val Val Ser Val
145                 150                 155                 160
Leu Pro Ile Gly His Gln Asp Trp Leu Ser Gly Lys Gln Phe Lys Cys
                165                 170                 175
Lys Val Asn Asn Lys Ala Leu Pro Ser Pro Ile Glu Glu Ile Ile Ser
            180                 185                 190
Lys Thr Pro Gly Gln Ala His Gln Pro Asn Val Tyr Val Leu Pro Pro
        195                 200                 205
Ser Arg Asp Glu Met Ser Lys Asn Thr Val Thr Leu Thr Cys Leu Val
    210                 215                 220
Lys Asp Phe Phe Pro Pro Glu Ile Asp Val Glu Trp Gln Ser Asn Gly
225                 230                 235                 240
Gln Gln Glu Pro Glu Ser Lys Tyr Arg Met Thr Pro Pro Gln Leu Asp
                245                 250                 255
Glu Asp Gly Ser Tyr Phe Leu Tyr Ser Lys Leu Ser Val Asp Lys Ser
            260                 265                 270
Arg Trp Gln Arg Gly Asp Thr Phe Ile Cys Ala Val Met His Glu Ala
        275                 280                 285
Leu His Asn His Tyr Thr Gln Ile Ser Leu Ser His Ser Pro Gly
    290                 295                 300
```

<210> SEQ ID NO 99
<211> LENGTH: 969
<212> TYPE: DNA
<213> ORGANISM: Artificial Sequence
<220> FEATURE:
<223> OTHER INFORMATION: Fusion Protein DNA

<400> SEQUENCE: 99

```
atggaatgga gctgggtctt tctcttcttc ctgtcagtaa cgactggtgt ccactccttc    60
gtgaaccagc acctgtgcgg ctcccacctg gtggaagctc tggaactcgt gtgcggcgag   120
cggggcttcc actacggggg tggcggagga ggttctggtg gcggcggagg catcgtggaa   180
cagtgctgca cctccacctg ctccctggac cagctggaaa actactgcgg tggcggaggt   240
ggtcaaggag gcggtggaca gggtggaggt gggcaggag gaggcggggg atgcatcagc   300
```

-continued

```
ccctgccccg tgccggagag cctgggtggc cctagcgtgt tcatattccc tcccaagccc    360
aaggacatcc tgaggatcac caggaccccc gagatcacct gtgtggtgct ggatcttggc    420
agggaagacc ccgaagtcca gatcagctgg ttcgtggatg gcaaggaggt gcacaccgcc    480
aagacccagc cgagggagca gcagttcaac tccacctaca gggtggtgag cgtgctgcct    540
atcgagcatc aggactggct gaccggcaaa gagttcaagt gcagggtgaa ccacatcggc    600
ctgcccagcc ccatcgagag gaccatcagc aaagccaggg gccaggccca ccagcccagt    660
gtgtacgtgc ttcccctag cccaaaggaa ctgagtagca gcgataccgt gaccctgacc    720
tgcctgatca aggacttttt cccgccagaa atagacgtgg agtggcagag caacggccag    780
ccggagcccg agagcaaata ccacaccacc gcccctcaac tggacgagga cgggagctac    840
ttcctgtata gcaagctgag cgttgacaag agcaggtggc aacagggcga caccttcacc    900
tgcgccgtga tgcacgaagc tctgcaaaac cactacaccg acctgtcact gagccatagc    960
cccggatag                                                             969
```

<210> SEQ ID NO 100
<211> LENGTH: 303
<212> TYPE: PRT
<213> ORGANISM: Artificial Sequence
<220> FEATURE:
<223> OTHER INFORMATION: Fusion Protein

<400> SEQUENCE: 100

```
Phe Val Asn Gln His Leu Cys Gly Ser His Leu Val Glu Ala Leu Glu
1               5                   10                  15

Leu Val Cys Gly Glu Arg Gly Phe His Tyr Gly Gly Gly Gly Gly
            20                  25                  30

Ser Gly Gly Gly Gly Gly Ile Val Glu Gln Cys Cys Thr Ser Thr Cys
        35                  40                  45

Ser Leu Asp Gln Leu Glu Asn Tyr Cys Gly Gly Gly Gly Gln Gly
    50                  55                  60

Gly Gly Gln Gly Gly Gly Gln Gly Gly Gly Gly Cys Ile
65                  70                  75                  80

Ser Pro Cys Pro Val Pro Glu Ser Leu Gly Gly Pro Ser Val Phe Ile
                85                  90                  95

Phe Pro Pro Lys Pro Lys Asp Ile Leu Arg Ile Thr Arg Thr Pro Glu
            100                 105                 110

Ile Thr Cys Val Val Leu Asp Leu Gly Arg Glu Asp Pro Glu Val Gln
        115                 120                 125

Ile Ser Trp Phe Val Asp Gly Lys Glu Val His Thr Ala Lys Thr Gln
    130                 135                 140

Pro Arg Glu Gln Gln Phe Asn Ser Thr Tyr Arg Val Val Ser Val Leu
145                 150                 155                 160

Pro Ile Glu His Gln Asp Trp Leu Thr Gly Lys Glu Phe Lys Cys Arg
                165                 170                 175

Val Asn His Ile Gly Leu Pro Ser Pro Ile Glu Arg Thr Ile Ser Lys
            180                 185                 190

Ala Arg Gly Gln Ala His Gln Pro Ser Val Tyr Val Leu Pro Pro Ser
        195                 200                 205

Pro Lys Glu Leu Ser Ser Ser Asp Thr Val Thr Leu Thr Cys Leu Ile
    210                 215                 220

Lys Asp Phe Phe Pro Pro Glu Ile Asp Val Glu Trp Gln Ser Asn Gly
225                 230                 235                 240
```

Gln Pro Glu Pro Glu Ser Lys Tyr His Thr Thr Ala Pro Gln Leu Asp
            245                 250                 255

Glu Asp Gly Ser Tyr Phe Leu Tyr Ser Lys Leu Ser Val Asp Lys Ser
        260                 265                 270

Arg Trp Gln Gln Gly Asp Thr Phe Thr Cys Ala Val Met His Glu Ala
    275                 280                 285

Leu Gln Asn His Tyr Thr Asp Leu Ser Leu Ser His Ser Pro Gly
290                 295                 300

<210> SEQ ID NO 101
<211> LENGTH: 966
<212> TYPE: DNA
<213> ORGANISM: Artificial Sequence
<220> FEATURE:
<223> OTHER INFORMATION: Fusion Protein DNA

<400> SEQUENCE: 101
atggaatgga gctgggtctt tctcttcttc ctgtcagtaa cgactggtgt ccactccttc      60
gtgaaccagc acctgtgcgg ctcccacctg gtggaagctc tggaactcgt gtgcggcgag     120
cggggcttcc actacggggg tggcggagga ggttctggtg cggcggagg catcgtggaa      180 cagtgctgca cctccacctg ctccctggac cagctggaaa actactgcgg tggcggaggt     240
ggtcaaggag gcggtggaca gggtggaggt gggcagggag gaggcggggg agactgcccc     300
aagtgccccg ctcccgagat gctgggcgga cccagcgtgt tcatcttccc tcccaagccc     360
aaggacacac tgctgatcgc caggaccccg gaggtgacct gcgtggtggt ggccctggat     420
cccgaagacc ccgaggtgca gatcagctgg ttcgtggatg gaaagcagat gcagaccgcc     480
aagacccaac cccgggaaga gcagttcagc ggcacctaca gggtggtgag tgtgttgccc     540
atcggccacc aggactggct gaaggggaag caattcacat gcaaggttaa taacaaggcc     600
ctgcccagcc ccatcgagag gaccatcagc aaggccaggg gccaggccca ccagccatct     660
gtgtacgtgc tgcccccatc tagggaggaa ctgagcaaga cacagtcagc cttacttgc    720 ctgatcaagg acttcttccc accggacata gacgtggagt ggcagagtaa cggccagcag    780 gagccccgaga gcaagtatag gaccacaccg ccccaactgg acgaggacgg aagctacttc    840
ctctacagca aattgagcgt tgacaaaagc aggtggcagc gaggcgacac cttcatctgc    900
gccgtgatgc acgaggcttt gcataaccac tacacccagg agagcctgtc ccacagcccc    960
ggatag                                                              966

<210> SEQ ID NO 102
<211> LENGTH: 302
<212> TYPE: PRT
<213> ORGANISM: Artificial Sequence
<220> FEATURE:
<223> OTHER INFORMATION: Fusion Protein

<400> SEQUENCE: 102

Phe Val Asn Gln His Leu Cys Gly Ser His Leu Val Glu Ala Leu Glu
1               5                   10                  15

Leu Val Cys Gly Glu Arg Gly Phe His Tyr Gly Gly Gly Gly Gly
            20                  25                  30

Ser Gly Gly Gly Gly Ile Val Glu Gln Cys Cys Thr Ser Thr Cys
        35                  40                  45

Ser Leu Asp Gln Leu Glu Asn Tyr Cys Gly Gly Gly Gly Gln Gly
    50                  55                  60

| | | | | | | | | | | | | | | | |
|---|---|---|---|---|---|---|---|---|---|---|---|---|---|---|---|
|Gly|Gly|Gly|Gln|Gly|Gly|Gly|Gln|Gly|Gly|Gly|Asp|Cys|||
|65| | | |70| | | |75| | | |80|||

Pro Lys Cys Pro Ala Pro Glu Met Leu Gly Gly Pro Ser Val Phe Ile
                    85                      90                      95

Phe Pro Pro Lys Pro Lys Asp Thr Leu Leu Ile Ala Arg Thr Pro Glu
            100                      105                      110

Val Thr Cys Val Val Val Ala Leu Asp Pro Glu Asp Pro Glu Val Gln
            115                      120                      125

Ile Ser Trp Phe Val Asp Gly Lys Gln Met Gln Thr Ala Lys Thr Gln
    130                      135                      140

Pro Arg Glu Glu Gln Phe Ser Gly Thr Tyr Arg Val Val Ser Val Leu
145                    150                      155                160

Pro Ile Gly His Gln Asp Trp Leu Lys Gly Lys Gln Phe Thr Cys Lys
            165                      170                      175

Val Asn Asn Lys Ala Leu Pro Ser Pro Ile Glu Arg Thr Ile Ser Lys
            180                      185                      190

Ala Arg Gly Gln Ala His Gln Pro Ser Val Tyr Val Leu Pro Pro Ser
        195                      200                      205

Arg Glu Glu Leu Ser Lys Asn Thr Val Ser Leu Thr Cys Leu Ile Lys
    210                      215                      220

Asp Phe Phe Pro Pro Asp Ile Asp Val Glu Trp Gln Ser Asn Gly Gln
225                    230                      235                240

Gln Glu Pro Glu Ser Lys Tyr Arg Thr Thr Pro Pro Gln Leu Asp Glu
            245                      250                      255

Asp Gly Ser Tyr Phe Leu Tyr Ser Lys Leu Ser Val Asp Lys Ser Arg
        260                      265                      270

Trp Gln Arg Gly Asp Thr Phe Ile Cys Ala Val Met His Glu Ala Leu
    275                      280                      285

His Asn His Tyr Thr Gln Glu Ser Leu Ser His Ser Pro Gly
            290                      295                      300

```
<210> SEQ ID NO 103
<211> LENGTH: 966
<212> TYPE: DNA
<213> ORGANISM: Artificial Sequence
<220> FEATURE:
<223> OTHER INFORMATION: Fusion Protein DNA

<400> SEQUENCE: 103
atggaatgga gctgggtctt tctcttcttc ctgtcagtaa cgactggtgt ccactccttc      60
gtgaaccagc acctgtgcgg ctcccacctg gtggaagctc tggaactcgt gtgcggcgag     120
cggggcttcc actacggggg tgcggagga ggttctggtg cggcggagg catcgtggaa      180 cagtgctgca cctccacctg ctccctggac cagctggaaa actactgcgg tggcggaggt     240
ggtcaaggag gcggtggaca gggtggaggt gggcagggag gaggcggggg agactgcccc     300
aagtgccccg ctcccgagat gctgggcgga cccagcgtgt tcatcttccc tcccaagccc     360
aaggacacac tgctgatcgc caggaccccg gaggtgacct gcgtggtggt ggacctggat     420
cccgaagacc ccgaggtgca gatcagctgg ttcgtggatg gaaagcagat gcagaccgcc     480
aagacccaac ccgggaaga gcagttcagc ggcacctaca gggtggtgag tgtgttgccc     540
atcggccacc aggactggct gaaggggaag caattcacat gcaaggttaa taacaaggcc     600
ctgcccagcc ccatcgagag gaccatcagc aaggccaggg gccaggccca ccagccatct     660
gtgtacgtgc tgcccccatc tagggaggaa ctgagcaaga acacagtcag ccttacttgc     720
```

```
ctgatcaagg acttcttccc accggacata gacgtggagt ggcagagtaa cggccagcag   780
gagcccgaga gcaagtatag gaccacaccg ccccaactgg acgaggacgg aagctacttc   840
ctctacagca aattgagcgt tgacaaaagc aggtggcagc gaggcgacac cttcatctgc   900
gccgtgatgc acgaggcttt gcataaccac tacacccagg agagcctgtc ccacagcccc   960
ggatag                                                              966
```

```
<210> SEQ ID NO 104
<211> LENGTH: 302
<212> TYPE: PRT
<213> ORGANISM: Artificial Sequence
<220> FEATURE:
<223> OTHER INFORMATION: Fusion Protein

<400> SEQUENCE: 104
```

| | | | | | | | | | | | | | | |
|---|---|---|---|---|---|---|---|---|---|---|---|---|---|---|
| Phe | Val | Asn | Gln | His | Leu | Cys | Gly | Ser | His | Leu | Val | Glu | Ala | Leu | Glu |
| 1 | | | | 5 | | | | | 10 | | | | | 15 | |
| Leu | Val | Cys | Gly | Glu | Arg | Gly | Phe | His | Tyr | Gly | Gly | Gly | Gly | Gly |
| | | 20 | | | | | 25 | | | | | 30 | | |
| Ser | Gly | Gly | Gly | Gly | Ile | Val | Glu | Gln | Cys | Cys | Thr | Ser | Thr | Cys |
| | | 35 | | | | | 40 | | | | | 45 | | |
| Ser | Leu | Asp | Gln | Leu | Glu | Asn | Tyr | Cys | Gly | Gly | Gly | Gly | Gln | Gly |
| | 50 | | | | | 55 | | | | | 60 | | | |
| Gly | Gly | Gly | Gln | Gly | Gly | Gly | Gln | Gly | Gly | Gly | Gly | Asp | Cys |
| 65 | | | | | 70 | | | | | 75 | | | | 80 |
| Pro | Lys | Cys | Pro | Ala | Pro | Glu | Met | Leu | Gly | Gly | Pro | Ser | Val | Phe | Ile |
| | | | | 85 | | | | | 90 | | | | | 95 | |
| Phe | Pro | Pro | Lys | Pro | Lys | Asp | Thr | Leu | Leu | Ile | Ala | Arg | Thr | Pro | Glu |
| | | | 100 | | | | | 105 | | | | | 110 | | |
| Val | Thr | Cys | Val | Val | Val | Asp | Leu | Asp | Pro | Glu | Asp | Pro | Glu | Val | Gln |
| | | | 115 | | | | | 120 | | | | | 125 | | |
| Ile | Ser | Trp | Phe | Val | Asp | Gly | Lys | Gln | Met | Gln | Thr | Ala | Lys | Thr | Gln |
| | | 130 | | | | | 135 | | | | | 140 | | | |
| Pro | Arg | Glu | Glu | Gln | Phe | Ser | Gly | Thr | Tyr | Arg | Val | Val | Ser | Val | Leu |
| 145 | | | | | 150 | | | | | 155 | | | | | 160 |
| Pro | Ile | Gly | His | Gln | Asp | Trp | Leu | Lys | Gly | Lys | Gln | Phe | Thr | Cys | Lys |
| | | | | 165 | | | | | 170 | | | | | 175 | |
| Val | Asn | Asn | Lys | Ala | Leu | Pro | Ser | Pro | Ile | Glu | Arg | Thr | Ile | Ser | Lys |
| | | | 180 | | | | | 185 | | | | | 190 | | |
| Ala | Arg | Gly | Gln | Ala | His | Gln | Pro | Ser | Val | Tyr | Val | Leu | Pro | Pro | Ser |
| | | | 195 | | | | | 200 | | | | | 205 | | |
| Arg | Glu | Glu | Leu | Ser | Lys | Asn | Thr | Val | Ser | Leu | Thr | Cys | Leu | Ile | Lys |
| 210 | | | | | 215 | | | | | 220 | | | | | |
| Asp | Phe | Phe | Pro | Pro | Asp | Ile | Asp | Val | Glu | Trp | Gln | Ser | Asn | Gly | Gln |
| 225 | | | | | 230 | | | | | 235 | | | | | 240 |
| Gln | Glu | Pro | Glu | Ser | Lys | Tyr | Arg | Thr | Thr | Pro | Pro | Gln | Leu | Asp | Glu |
| | | | | 245 | | | | | 250 | | | | | 255 | |
| Asp | Gly | Ser | Tyr | Phe | Leu | Tyr | Ser | Lys | Leu | Ser | Val | Asp | Lys | Ser | Arg |
| | | | 260 | | | | | 265 | | | | | 270 | | |
| Trp | Gln | Arg | Gly | Asp | Thr | Phe | Ile | Cys | Ala | Val | Met | His | Glu | Ala | Leu |
| | | 275 | | | | | 280 | | | | | 285 | | | |
| His | Asn | His | Tyr | Thr | Gln | Glu | Ser | Leu | Ser | His | Ser | Pro | Gly |
| | 290 | | | | | 295 | | | | | 300 | | | |

```
<210> SEQ ID NO 105
```

```
<211> LENGTH: 933
<212> TYPE: DNA
<213> ORGANISM: Artificial Sequence
<220> FEATURE:
<223> OTHER INFORMATION: Fusion Protein DNA

<400> SEQUENCE: 105
atggaatgga gctgggtctt tctcttcttc ctgtcagtaa cgactggtgt ccactccttc      60
gtgaaccagc acctgtgcgg ctccgacctg gtggaagctc tgtatctcgt gtgcggcgag     120
cggggcttct tctacaccga tcccactgga ggcggtccac gcagaggcat cgtggaacag     180
tgctgccact ccatctgctc cctgtaccag ctggaaaact actgcaatgg cggaggtggt     240
tcaggaggcg gtggaggtga gggccccaag tgccccgtgc ccgagattcc cggtgccccc     300
agcgtgttca tctttccccc aaaacccaag gacaccctga gcatcagcag gaccccgag     360
gtgacctgcc tggtggtgga cctgggaccc gacgacagca cgtgcagat cacctggttc     420
gtggacaaca ccgagatgca caccgccaag accaggcctc gggaggagca gttcaacagc     480
acctacaggg tggtgagcgt gctgcccatc ctgcaccagg actggctgaa gggcaaggag     540
ttcaagtgca aggtgaacag caagagcctc cccagcgcca tggagaggac catcagcaag     600
gccaagggtc agccccacga gccccaagtg tacgtgcttc ccccgaccca ggaggagttg     660
agcgagaaca agtgagcgt gacctgcctg atcaagggct ccacccctcc cgacatcgcc     720
gtggagtggg agatcaccgg ccagcctgag ccggaaaata actaccagac cacccctcca     780
cagctggaca gcgacggcac ctacttcctt tacagcaggc tgtctgtgga ccgaagccat     840
tggcaaaggg gcaacaccta cacctgcagc gtgagccacg aggctctgca cagccaccac     900
acccagaagt ctctgaccca gagccccgga tag                                  933

<210> SEQ ID NO 106
<211> LENGTH: 291
<212> TYPE: PRT
<213> ORGANISM: Artificial Sequence
<220> FEATURE:
<223> OTHER INFORMATION: Fusion Protein

<400> SEQUENCE: 106

Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn Gly Gly Gly Ser Gly Gly
    50                  55                  60

Gly Gly Gly Glu Gly Pro Lys Cys Pro Val Pro Glu Ile Pro Gly Ala
65                  70                  75                  80

Pro Ser Val Phe Ile Phe Pro Pro Lys Pro Lys Asp Thr Leu Ser Ile
                85                  90                  95

Ser Arg Thr Pro Glu Val Thr Cys Leu Val Val Asp Leu Gly Pro Asp
            100                 105                 110

Asp Ser Asn Val Gln Ile Thr Trp Phe Val Asp Asn Thr Glu Met His
        115                 120                 125

Thr Ala Lys Thr Arg Pro Arg Glu Glu Gln Phe Asn Ser Thr Tyr Arg
    130                 135                 140

Val Val Ser Val Leu Pro Ile Leu His Gln Asp Trp Leu Lys Gly Lys
145                 150                 155                 160
```

Glu Phe Lys Cys Lys Val Asn Ser Lys Ser Leu Pro Ser Ala Met Glu
                165                 170                 175

Arg Thr Ile Ser Lys Ala Lys Gly Gln Pro His Glu Pro Gln Val Tyr
            180                 185                 190

Val Leu Pro Pro Thr Gln Glu Glu Leu Ser Glu Asn Lys Val Ser Val
        195                 200                 205

Thr Cys Leu Ile Lys Gly Phe His Pro Pro Asp Ile Ala Val Glu Trp
    210                 215                 220

Glu Ile Thr Gly Gln Pro Gly Pro Glu Asn Asn Tyr Gln Thr Thr Pro
225                 230                 235                 240

Pro Gln Leu Asp Ser Asp Gly Thr Tyr Phe Leu Tyr Ser Arg Leu Ser
                245                 250                 255

Val Asp Arg Ser His Trp Gln Arg Gly Asn Thr Tyr Thr Cys Ser Val
            260                 265                 270

Ser His Glu Ala Leu His Ser His His Thr Gln Lys Ser Leu Thr Gln
        275                 280                 285

Ser Pro Gly
    290

<210> SEQ ID NO 107
<211> LENGTH: 930
<212> TYPE: DNA
<213> ORGANISM: Artificial Sequence
<220> FEATURE:
<223> OTHER INFORMATION: Fusion Protein DNA

<400> SEQUENCE: 107

| atggaatgga | gctgggtctt | tctcttcttc | ctgtcagtaa | cgactggtgt | ccactccttc | 60 |
| gtgaaccagc | acctgtgcgg | ctccgacctg | gtggaagctc | tggctctcgt | gtgcggcgag | 120 |
| cggggcttct | tctacaccga | tcccactgga | ggcggtccac | gcagaggcat | cgtggaacag | 180 |
| tgctgccact | ccatctgctc | cctgtaccag | ctggaaaaact | actgcaatgg | tggcggagga | 240 |
| tctggcggag | gcggtgactg | ccccaaatgt | cctccgcctg | agatgctggg | tggccctagc | 300 |
| atcttcatct | tcccgcccaa | gcccaaggat | actctgtcca | ttagcaggac | ccccgaggtg | 360 |
| acctgcctgg | tggtggacct | ggggccagac | gactctgacg | tgcagatcac | ctggttcgta | 420 |
| gacaacaccc | aggtttacac | tgccaagacc | agtcccaggg | aggagcagtt | caacagcaca | 480 |
| tacagggtgg | tgagcgttct | gcccatcctg | caccaggact | ggctgaaagg | caaagagttc | 540 |
| aagtgtaagg | tgaacagcaa | gagcctgccc | agcccccattg | aaaggaccat | cagcaaggac | 600 |
| aagggccagc | cgcacgagcc | ccaagtctac | gtgctgcccc | cagcacagga | gagctgagc | 660 |
| aggaacaagg | ttagcgtgac | atgcctgatc | gagggtttct | accccagcga | catcgccgtg | 720 |
| gagtgggaaa | tcaccggcca | acccgagccc | gagaacaact | acaggaccac | tccgccgcaa | 780 |
| ctggacagcg | acgggaccta | cttcttgtat | agcaggctga | gcgtggaccg | gagcaggtgg | 840 |
| cagaggggca | acacctacac | ttgcagcgtg | agccacgagg | ccttgcacag | ccaccacact | 900 |
| cagaagagtc | tgacccagag | cccgggatag | | | | 930 |

<210> SEQ ID NO 108
<211> LENGTH: 290
<212> TYPE: PRT
<213> ORGANISM: Artificial Sequence
<220> FEATURE:
<223> OTHER INFORMATION: Fusion Protein

<400> SEQUENCE: 108

Phe Val Asn Gln His Leu Cys Gly Ser Asp Leu Val Glu Ala Leu Ala
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn Gly Gly Gly Ser Gly Gly
    50                  55                  60

Gly Gly Asp Cys Pro Lys Cys Pro Pro Glu Met Leu Gly Gly Pro
65              70                  75                  80

Ser Ile Phe Ile Phe Pro Pro Lys Pro Lys Asp Thr Leu Ser Ile Ser
                85                  90                  95

Arg Thr Pro Glu Val Thr Cys Leu Val Val Asp Leu Gly Pro Asp Asp
            100                 105                 110

Ser Asp Val Gln Ile Thr Trp Phe Val Asp Asn Thr Gln Val Tyr Thr
            115                 120                 125

Ala Lys Thr Ser Pro Arg Glu Glu Gln Phe Asn Ser Thr Tyr Arg Val
    130                 135                 140

Val Ser Val Leu Pro Ile Leu His Gln Asp Trp Leu Lys Gly Lys Glu
145                 150                 155                 160

Phe Lys Cys Lys Val Asn Ser Lys Ser Leu Pro Ser Pro Ile Glu Arg
                165                 170                 175

Thr Ile Ser Lys Asp Lys Gly Gln Pro His Glu Pro Gln Val Tyr Val
            180                 185                 190

Leu Pro Pro Ala Gln Glu Glu Leu Ser Arg Asn Lys Val Ser Val Thr
        195                 200                 205

Cys Leu Ile Glu Gly Phe Tyr Pro Ser Asp Ile Ala Val Glu Trp Glu
210                 215                 220

Ile Thr Gly Gln Pro Glu Pro Glu Asn Asn Tyr Arg Thr Thr Pro Pro
225                 230                 235                 240

Gln Leu Asp Ser Asp Gly Thr Tyr Phe Leu Tyr Ser Arg Leu Ser Val
                245                 250                 255

Asp Arg Ser Arg Trp Gln Arg Gly Asn Thr Tyr Thr Cys Ser Val Ser
            260                 265                 270

His Glu Ala Leu His Ser His His Thr Gln Lys Ser Leu Thr Gln Ser
        275                 280                 285

Pro Gly
    290

<210> SEQ ID NO 109
<211> LENGTH: 933
<212> TYPE: DNA
<213> ORGANISM: Artificial Sequence
<220> FEATURE:
<223> OTHER INFORMATION: Fusion Protein DNA

<400> SEQUENCE: 109
atggaatgga gctgggtctt tctcttcttc ctgtcagtaa cgactggtgt ccactccttc    60
gtgaaccagc acctgtgcgg ctccgacctg gtggaagctc tggctctcgt gtgcggcgag   120
cggggcttct tctacaccga tcccactgga ggcggtccac gcagaggcat cgtggaacag   180
tgctgccact ccatctgctc cctgtaccag ctggaaaact actgcaatgg cggaggtggt   240
gcaggaggcg gtggaggtga gggccccaag tgccccgtgc ccgagattcc cggtgccccc   300
agcgtgttca tctttccccc aaaacccaag gacaccctga gcatcagcag gacccccgag   360

```
gtgacctgcc tggtggtgga cctgggaccc gacgacagca acgtgcagat cacctggttc    420
gtggacaaca ccgagatgca caccgccaag accaggcctc gggaggagca gttcaacagc    480
acctacaggg tggtgagcgt gctgcccatc ctgcaccagg actggctgaa gggcaaggag    540
ttcaagtgca aggtgaacag caagagcctg cccagcgcca tggagaggac catcagcaag    600
gccaagggtc agccccacga gccccaagtg tacgtgcttc ccccgaccca ggaggagttg    660
agcgagaaca aagtgagcgt gacctgcctg atcaagggct ccaccctcc cgacatcgcc    720 gtggagtggg agatcaccgg ccagcctgag ccggaaaata actaccagac cacccctcca    780
cagctggaca cgacggcac ctacttcctt tacagcaggc tgtctgtgga ccgaagccat    840
tggcaaaggg gcaacaccta cacctgcagc gtgagccacg aggctctgca cagccaccac    900
acccagaagt ctctgaccca gagccccgga tag                                933
```

<210> SEQ ID NO 110
<211> LENGTH: 291
<212> TYPE: PRT
<213> ORGANISM: Artificial Sequence
<220> FEATURE:
<223> OTHER INFORMATION: Fusion Protein

<400> SEQUENCE: 110

```
Phe Val Asn Gln His Leu Cys Gly Ser Asp Leu Val Glu Ala Leu Ala
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn Gly Gly Gly Ala Gly Gly
    50                  55                  60

Gly Gly Gly Glu Gly Pro Lys Cys Pro Val Pro Glu Ile Pro Gly Ala
65                  70                  75                  80

Pro Ser Val Phe Ile Phe Pro Pro Lys Pro Lys Asp Thr Leu Ser Ile
                85                  90                  95

Ser Arg Thr Pro Glu Val Thr Cys Leu Val Val Asp Leu Gly Pro Asp
            100                 105                 110

Asp Ser Asn Val Gln Ile Thr Trp Phe Val Asp Asn Thr Glu Met His
        115                 120                 125

Thr Ala Lys Thr Arg Pro Arg Glu Glu Gln Phe Asn Ser Thr Tyr Arg
    130                 135                 140

Val Val Ser Val Leu Pro Ile Leu His Gln Asp Trp Leu Lys Gly Lys
145                 150                 155                 160

Glu Phe Lys Cys Lys Val Asn Ser Lys Ser Leu Pro Ser Ala Met Glu
                165                 170                 175

Arg Thr Ile Ser Lys Ala Lys Gly Gln Pro His Glu Pro Gln Val Tyr
            180                 185                 190

Val Leu Pro Pro Thr Gln Glu Glu Leu Ser Glu Asn Lys Val Ser Val
        195                 200                 205

Thr Cys Leu Ile Lys Gly Phe His Pro Pro Asp Ile Ala Val Glu Trp
    210                 215                 220

Glu Ile Thr Gly Gln Pro Glu Pro Glu Asn Asn Tyr Gln Thr Thr Pro
225                 230                 235                 240

Pro Gln Leu Asp Ser Asp Gly Thr Tyr Phe Leu Tyr Ser Arg Leu Ser
                245                 250                 255
```

```
Val Asp Arg Ser His Trp Gln Arg Gly Asn Thr Tyr Thr Cys Ser Val
            260                 265                 270

Ser His Glu Ala Leu His Ser His His Thr Gln Lys Ser Leu Thr Gln
        275                 280                 285

Ser Pro Gly
    290
```

```
<210> SEQ ID NO 111
<211> LENGTH: 933
<212> TYPE: DNA
<213> ORGANISM: Artificial Sequence
<220> FEATURE:
<223> OTHER INFORMATION: Fusion Protein DNA

<400> SEQUENCE: 111
atggaatgga gctgggtctt tctcttcttc ctgtcagtaa cgactggtgt ccactccttc       60
gtgaaccagc acctgtgcgg ctccgacctg gtggaagctc tggctctcgt gtgcggcgag      120
cggggcttct ctacaccga tcccactgga ggcggtccac gcagaggcat cgtggaacag      180
tgctgccact ccatctgctc cctgtaccag ctggaaaact actgcaatgg cggaggtggt      240
tcaggaggcg gtggaggtga gggccccaag tgccccgtgc ccgagattcc cggtgccccc      300
agcgtgttca tctttccccc aaaacccaag gacacccctga gcatcagcag gacccccgag      360
gtgacctgcc tggtggtgga cctgggaccc gacgacagca acgtgcagat cacctggttc      420
gtggacaaca ccgagatgca caccgccaag accaggcctc gggaggagca gttcaacagc      480
acctacaggg tggtgagcgt gctgcccatc ctgcaccagg actggctgaa gggcaaggag      540
ttcaagtgca aggtgaacag caagagcctg cccagcgcca tggagaggac catcagcaag      600
gccaagggtc agccccacga gccccaagtg tacgtgcttc ccccgaccca ggaggagttg      660
agcgagaaca aagtgagcgt gacctgcctg atcaagggct ccaccctcc cgacatcgcc      720 gtggagtggg agatcaccgg ccagcctgag ccggaaaata actaccagac cacccctcca      780
cagctggaca gcgacggcac ctacttcctt tacagcaggc tgtctgtgga ccgaagccat      840
tggcaaaggg gcaacaccta cacctgcagc gtgagccacg aggctctgca cagccaccac      900
acccagaagt ctctgaccca gagccccgga tag                                   933
```

```
<210> SEQ ID NO 112
<211> LENGTH: 291
<212> TYPE: PRT
<213> ORGANISM: Artificial Sequence
<220> FEATURE:
<223> OTHER INFORMATION: Fusion Protein

<400> SEQUENCE: 112

Phe Val Asn Gln His Leu Cys Gly Ser Asp Leu Val Glu Ala Leu Ala
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn Gly Gly Gly Gly Ser Gly Gly
    50                  55                  60

Gly Gly Gly Glu Gly Pro Lys Cys Pro Val Pro Glu Ile Pro Gly Ala
65                  70                  75                  80

Pro Ser Val Phe Ile Phe Pro Pro Lys Pro Lys Asp Thr Leu Ser Ile
                85                  90                  95
```

Ser Arg Thr Pro Glu Val Thr Cys Leu Val Val Asp Leu Gly Pro Asp
            100                 105                 110

Asp Ser Asn Val Gln Ile Thr Trp Phe Val Asp Asn Thr Glu Met His
        115                 120                 125

Thr Ala Lys Thr Arg Pro Arg Glu Glu Gln Phe Asn Ser Thr Tyr Arg
    130                 135                 140

Val Val Ser Val Leu Pro Ile Leu His Gln Asp Trp Leu Lys Gly Lys
145                 150                 155                 160

Glu Phe Lys Cys Lys Val Asn Ser Lys Ser Leu Pro Ser Ala Met Glu
                165                 170                 175

Arg Thr Ile Ser Lys Ala Lys Gly Gln Pro His Glu Pro Gln Val Tyr
            180                 185                 190

Val Leu Pro Pro Thr Gln Glu Glu Leu Ser Glu Asn Lys Val Ser Val
        195                 200                 205

Thr Cys Leu Ile Lys Gly Phe His Pro Pro Asp Ile Ala Val Glu Trp
    210                 215                 220

Glu Ile Thr Gly Gln Pro Glu Pro Glu Asn Asn Tyr Gln Thr Thr Pro
225                 230                 235                 240

Pro Gln Leu Asp Ser Asp Gly Thr Tyr Phe Leu Tyr Ser Arg Leu Ser
                245                 250                 255

Val Asp Arg Ser His Trp Gln Arg Gly Asn Thr Tyr Thr Cys Ser Val
            260                 265                 270

Ser His Glu Ala Leu His Ser His His Thr Gln Lys Ser Leu Thr Gln
        275                 280                 285

Ser Pro Gly
    290

<210> SEQ ID NO 113
<211> LENGTH: 930
<212> TYPE: DNA
<213> ORGANISM: Artificial Sequence
<220> FEATURE:
<223> OTHER INFORMATION: Fusion Protein DNA

<400> SEQUENCE: 113

| | | |
|---|---|---|
| atggaatgga gctgggtctt tctcttcttc ctgtcagtaa cgactggtgt ccactccttc | 60 |
| gtgaaccagc acctgtgcgg ctcccacctg gtggaagctc tggctctcgt gtgcggcgag | 120 |
| cggggcttct tctacaccga tcccgcagga ggcggtccac gcagaggcat cgtggaacag | 180 |
| tgctgcgcat ccgtttgctc cctgtaccag ctggaacact actgcggcgg aggtggtgca | 240 |
| ggaggcggtg gaggtgaggg ccccaagtgc cccgtgcccg agattcccgg tgcccccagc | 300 |
| gtgttcatct ttccccccaaa acccaaggac accctgagca tcagcaggac ccccgaggtg | 360 |
| acctgcctgg tggtggacct gggacccgac gacagcaacg tgcagatcac ctggttcgtg | 420 |
| gacaacaccg agatgcacac cgccaagacc aggcctcggg aggagcagtt caacagcacc | 480 |
| tacagggtgg tgagcgtgct gcccatcctg caccaggact ggctgaaggg caaggagttc | 540 |
| aagtgcaagg tgaacagcaa gagcctgccc agcgccatgg agaggaccat cagcaaggcc | 600 |
| aagggtcagc cccacgagcc ccaagtgtac gtgcttcccc cgacccagga ggagttgagc | 660 |
| gagaacaaag tgagcgtgac ctgcctgatc aagggcttcc accctcccga catcgccgtg | 720 |
| gagtgggaga tcaccggcca gcctgagccg gaaaataact accagaccac ccctccacag | 780 |
| ctggacagcg acggcaccta cttcctttac agcaggctgt ctgtggaccg aagccattgg | 840 |
| caaaggggca cacctacac ctgcagcgtg agccacgagg ctctgcacag ccaccacacc | 900 | cagaagtctc tgacccagag ccccggatag                      930

<210> SEQ ID NO 114
<211> LENGTH: 289
<212> TYPE: PRT
<213> ORGANISM: Artificial Sequence
<220> FEATURE:
<223> OTHER INFORMATION: Fusion Protein

<400> SEQUENCE: 114

```
Phe Val Asn Gln His Leu Cys Gly Ser His Leu Val Glu Ala Leu Ala
1               5                   10                  15

Leu Val Cys Gly Glu Arg Gly Phe Phe Tyr Thr Asp Pro Ala Gly Gly
            20                  25                  30

Gly Pro Arg Arg Gly Ile Val Glu Gln Cys Cys Ala Ser Val Cys Ser
        35                  40                  45

Leu Tyr Gln Leu Glu His Tyr Cys Gly Gly Gly Ala Gly Gly Gly
    50                  55                  60

Gly Gly Glu Gly Pro Lys Cys Pro Val Pro Glu Ile Pro Gly Ala Pro
65              70                  75                  80

Ser Val Phe Ile Phe Pro Pro Lys Pro Lys Asp Thr Leu Ser Ile Ser
                85                  90                  95

Arg Thr Pro Glu Val Thr Cys Leu Val Val Asp Leu Gly Pro Asp Asp
            100                 105                 110

Ser Asn Val Gln Ile Thr Trp Phe Val Asp Asn Thr Glu Met His Thr
        115                 120                 125

Ala Lys Thr Arg Pro Arg Glu Glu Gln Phe Asn Ser Thr Tyr Arg Val
    130                 135                 140

Val Ser Val Leu Pro Ile Leu His Gln Asp Trp Leu Lys Gly Lys Glu
145                 150                 155                 160

Phe Lys Cys Lys Val Asn Ser Lys Ser Leu Pro Ser Ala Met Glu Arg
                165                 170                 175

Thr Ile Ser Lys Ala Lys Gly Gln Pro His Glu Pro Gln Val Tyr Val
            180                 185                 190

Leu Pro Pro Thr Gln Glu Glu Leu Ser Glu Asn Lys Val Ser Val Thr
        195                 200                 205

Cys Leu Ile Lys Gly Phe His Pro Pro Asp Ile Ala Val Glu Trp Glu
    210                 215                 220

Ile Thr Gly Gln Pro Glu Pro Glu Asn Asn Tyr Gln Thr Thr Pro Pro
225                 230                 235                 240

Gln Leu Asp Ser Asp Gly Thr Tyr Phe Leu Tyr Ser Arg Leu Ser Val
                245                 250                 255

Asp Arg Ser His Trp Gln Arg Gly Asn Thr Tyr Thr Cys Ser Val Ser
            260                 265                 270

His Glu Ala Leu His Ser His His Thr Gln Lys Ser Leu Thr Gln Ser
        275                 280                 285

Pro
```

<210> SEQ ID NO 115
<211> LENGTH: 930
<212> TYPE: DNA
<213> ORGANISM: Artificial Sequence
<220> FEATURE:
<223> OTHER INFORMATION: Fusion Protein DNA

<400> SEQUENCE: 115
atggaatgga gctgggtctt tctcttcttc ctgtcagtaa cgactggtgt ccactccttc   60

```
gtgaaccagc acctgtgcgg ctcccacctg gtggaagctc tggctctcgt gtgcggcgag    120
cggggcttct tctacaccga tcccgcagga ggcggtccac gcagaggcat cgtggaacag    180
tgctgcgcat ccgtttgctc cctgtaccag ctggaacact actgcggcgg aggtggtgca    240
ggaggcggtg gaggtgaggg ccccaagtgc cccgtgcccg agattccgg tgcccccagc     300 gtgttcatct tccccccaaa acccaaggac accctgagca tcagcaggac ccccgaggtg    360
acctgcctgg tggtggacct gggacccgac gacagcaacg tgcagatcac ctggttcgtg    420
gacaacaccg agatgcacac cgccaagacc aggcctcggg aggagcagtt cagcagcacc    480
tacagggtgg tgagcgtgct gcccatcctg caccaggact ggctgaaggg caaggagttc    540
aagtgcaagg tgaacagcaa gagcctgccc agcgccatgg agaggaccat cagcaaggcc    600
aagggtcagc ccacgagcc ccaagtgtac gtgcttcccc cgacccagga ggagttgagc     660
gagaacaaag tgagcgtgac ctgcctgatc aagggcttcc accctcccga catcgccgtg    720
gagtgggaga tcaccggcca gcctgagccg gaaaataact accagaccac ccctccacag    780
ctggacagcg acggcaccta cttccttta agcaggctgt ctgtggaccg aagccattgg     840
caaaggggca cacctacac ctgcagcgtg agccacgagg ctctgcacag ccaccacacc      900
cagaagtctc tgacccagag ccccggatag                                      930
```

<210> SEQ ID NO 116
<211> LENGTH: 290
<212> TYPE: PRT
<213> ORGANISM: Artificial Sequence
<220> FEATURE:
<223> OTHER INFORMATION: Fusion Protein

<400> SEQUENCE: 116

```
Phe Val Asn Gln His Leu Cys Gly Ser His Leu Val Glu Ala Leu Ala
1               5                   10                  15

Leu Val Cys Gly Glu Arg Gly Phe Phe Tyr Thr Asp Pro Ala Gly Gly
            20                  25                  30

Gly Pro Arg Arg Gly Ile Val Glu Gln Cys Cys Ala Ser Val Cys Ser
        35                  40                  45

Leu Tyr Gln Leu Glu His Tyr Cys Gly Gly Gly Ala Gly Gly Gly
    50                  55                  60

Gly Gly Glu Gly Pro Lys Cys Pro Val Pro Glu Ile Pro Gly Ala Pro
65                  70                  75                  80

Ser Val Phe Ile Phe Pro Pro Lys Pro Lys Asp Thr Leu Ser Ile Ser
                85                  90                  95

Arg Thr Pro Glu Val Thr Cys Leu Val Val Asp Leu Gly Pro Asp Asp
            100                 105                 110

Ser Asn Val Gln Ile Thr Trp Phe Val Asp Asn Thr Glu Met His Thr
        115                 120                 125

Ala Lys Thr Arg Pro Arg Glu Glu Gln Phe Ser Ser Thr Tyr Arg Val
    130                 135                 140

Val Ser Val Leu Pro Ile Leu His Gln Asp Trp Leu Lys Gly Lys Glu
145                 150                 155                 160

Phe Lys Cys Lys Val Asn Ser Lys Ser Leu Pro Ser Ala Met Glu Arg
                165                 170                 175

Thr Ile Ser Lys Ala Lys Gly Gln Pro His Glu Pro Gln Val Tyr Val
            180                 185                 190

Leu Pro Pro Thr Gln Glu Glu Leu Ser Glu Asn Lys Val Ser Val Thr
        195                 200                 205
```

```
Cys Leu Ile Lys Gly Phe His Pro Pro Asp Ile Ala Val Glu Trp Glu
        210                 215                 220
Ile Thr Gly Gln Pro Glu Pro Glu Asn Asn Tyr Gln Thr Thr Pro Pro
225                 230                 235                 240
Gln Leu Asp Ser Asp Gly Thr Tyr Phe Leu Tyr Ser Arg Leu Ser Val
                245                 250                 255
Asp Arg Ser His Trp Gln Arg Gly Asn Thr Tyr Thr Cys Ser Val Ser
            260                 265                 270
His Glu Ala Leu His Ser His His Thr Gln Lys Ser Leu Thr Gln Ser
        275                 280                 285
Pro Gly
    290
```

<210> SEQ ID NO 117
<211> LENGTH: 927
<212> TYPE: DNA
<213> ORGANISM: Artificial Sequence
<220> FEATURE:
<223> OTHER INFORMATION: Fusion Protein DNA

<400> SEQUENCE: 117

```
atggaatgga gctgggtctt tctcttcttc ctgtcagtaa cgactggtgt ccactccttc     60
gtgaaccagc acctgtgcgg aagccacctg gtggaggcct tggccctggt gtgcggcgag    120
aggggcttct tctacaccga ccccgctggt ggcggaccta ggaggggcat cgtggagcag    180
tgctgcgcca gcgtgtgcag cctgtaccag ttggaacact actgcggagg tggcggagcc    240
ggaggcgggg gagactgccc caaatgtcct ccgcctgaga tgctgggtgg ccctagcatc    300
ttcatcttcc cgcccaagcc caaggatact ctgtccatta gcaggacccc cgaggtgacc    360
tgcctggtgg tggcactggg gccagacgac tctgacgtgc agatcacctg gttcgtagac    420
aacacccagg tttacactgc caagaccagt cccagggagg agcagttcag cagcacatac    480
agggtggtga gcgttctgcc catcctgcac caggactggc tgaaaggcaa agagttcaag    540
tgtaaggtga acagcaagag cctgcccagc cccattgaaa ggaccatcag caaggacaag    600
ggccagccgc acgagcccca agtctacgtg ctgcccccag cacaggaaga gctgagcagg    660
aacaaggtta gcgtgacatg cctgatcgag ggtttctacc ccagcgacat cgccgtggag    720
tgggaaatca ccggccaacc cgagcccgag aacaactaca ggaccactcc gccgcaactg    780
gacagcgacg ggacctactt cttgtatagc aggctgagcg tggaccggag caggtggcag    840
aggggcaaca cctacacttg cagcgtgagc acgaggcct tgcacagcca ccacactcag    900
aagagtctga cccagagccc gggatag                                       927
```

<210> SEQ ID NO 118
<211> LENGTH: 289
<212> TYPE: PRT
<213> ORGANISM: Artificial Sequence
<220> FEATURE:
<223> OTHER INFORMATION: Fusion Protein

<400> SEQUENCE: 118

```
Phe Val Asn Gln His Leu Cys Gly Ser His Leu Val Glu Ala Leu Ala
1               5                  10                  15
Leu Val Cys Gly Glu Arg Gly Phe Phe Tyr Thr Asp Pro Ala Gly Gly
            20                  25                  30
Gly Pro Arg Arg Gly Ile Val Glu Gln Cys Cys Ala Ser Val Cys Ser
        35                  40                  45
```

```
Leu Tyr Gln Leu Glu His Tyr Cys Gly Gly Gly Ala Gly Gly Gly
        50                  55                  60

Gly Asp Cys Pro Lys Cys Pro Pro Glu Met Leu Gly Gly Pro Ser
 65                  70                  75                  80

Ile Phe Ile Phe Pro Lys Pro Lys Asp Thr Leu Ser Ile Ser Arg
                 85                  90                  95

Thr Pro Glu Val Thr Cys Leu Val Ala Leu Gly Pro Asp Asp Ser
            100                 105                 110

Asp Val Gln Ile Thr Trp Phe Val Asp Asn Thr Gln Val Tyr Thr Ala
            115                 120                 125

Lys Thr Ser Pro Arg Glu Glu Gln Phe Ser Ser Thr Tyr Arg Val Val
        130                 135                 140

Ser Val Leu Pro Ile Leu His Gln Asp Trp Leu Lys Gly Lys Glu Phe
145                 150                 155                 160

Lys Cys Lys Val Asn Ser Lys Ser Leu Pro Ser Pro Ile Glu Arg Thr
                165                 170                 175

Ile Ser Lys Asp Lys Gly Gln Pro His Glu Pro Gln Val Tyr Val Leu
            180                 185                 190

Pro Pro Ala Gln Glu Glu Leu Ser Arg Asn Lys Val Ser Val Thr Cys
        195                 200                 205

Leu Ile Glu Gly Phe Tyr Pro Ser Asp Ile Ala Val Glu Trp Glu Ile
210                 215                 220

Thr Gly Gln Pro Glu Pro Glu Asn Asn Tyr Arg Thr Thr Pro Pro Gln
225                 230                 235                 240

Leu Asp Ser Asp Gly Thr Tyr Phe Leu Tyr Ser Arg Leu Ser Val Asp
                245                 250                 255

Arg Ser Arg Trp Gln Arg Gly Asn Thr Tyr Thr Cys Ser Val Ser His
            260                 265                 270

Glu Ala Leu His Ser His His Thr Gln Lys Ser Leu Thr Gln Ser Pro
        275                 280                 285

Gly

<210> SEQ ID NO 119
<211> LENGTH: 168
<212> TYPE: DNA
<213> ORGANISM: Artificial Sequence
<220> FEATURE:
<223> OTHER INFORMATION: Ins Polypeptide DNA

<400> SEQUENCE: 119
ttcgtgaacc agcacctgtg cggaagccac ctggtggagg ccttggccct ggtgtgcggc      60
gagaggggct tcttctacac cgaccccgct ggtggcggac ctaggagggg catcgtggag     120
cagtgctgcg ccagcgtgtg cagcctgtac cagttggaac actactgc                  168

<210> SEQ ID NO 120
<211> LENGTH: 56
<212> TYPE: PRT
<213> ORGANISM: Artificial Sequence
<220> FEATURE:
<223> OTHER INFORMATION: Ins Polypeptide

<400> SEQUENCE: 120

Phe Val Asn Gln His Leu Cys Gly Ser His Leu Val Glu Ala Leu Ala
1               5                   10                  15

Leu Val Cys Gly Glu Arg Gly Phe Phe Tyr Thr Asp Pro Ala Gly Gly
            20                  25                  30
```

Gly Pro Arg Arg Gly Ile Val Glu Gln Cys Cys Ala Ser Val Cys Ser
            35                  40                  45

Leu Tyr Gln Leu Glu His Tyr Cys
            50                  55

<210> SEQ ID NO 121
<211> LENGTH: 969
<212> TYPE: DNA
<213> ORGANISM: Artificial Sequence
<220> FEATURE:
<223> OTHER INFORMATION: Fusion Protein DNA

<400> SEQUENCE: 121
atggaatgga gctgggtctt tctcttcttc ctgtcagtaa cgactggtgt ccactccttc      60
gtgaaccagc acctgtgcgg ctcccacctg gtggaagctc tggaactcgt gtgcggcgag     120
cggggcttcc actacggggg tggcggagga ggttctggtg gcggcggagg catcgtggaa     180
cagtgctgca cctccacctg ctccctggac cagctggaaa actactgcgg tggcggaggt     240
ggtcaaggag gcggtggaca gggtggaggt gggcagggag gaggcggggg aggtgagggc     300
cccaagtgcc ccgtgcccga gattccggt gcccccagcg tgttcatctt ccccccaaaa      360
cccaaggaca ccctgagcat cagcaggacc cccgaggtga cctgcctggt ggtggacctg     420
ggacccgacg acagcaacgt gcagatcacc tggttcgtgg acaacaccga gatgcacacc     480
gccaagacca ggcctcggga ggagcagttc aacagcacct acagggtggt gagcgtgctg     540
cccatcctgc accaggactg gctgaagggc aaggagttca gtgcaaggt gaacagcaag      600
agcctgccca cgcccatgga ggaccatc agcaaggcca agggtcagcc ccacgagccc       660
caagtgtacg tgcttccccc gacccaggag gagttgagcg agaacaaagt gagcgtgacc     720
tgcctgatca agggcttcca ccctcccgac atcgccgtgg agtgggagat caccggccag     780
cctgagccgg aaaataacta ccagaccacc cctccacagc tggacagcga cggcacctac     840
ttcctttaca gcaggctgtc tgtggaccga agccattggc aaagggcaa cacctacacc      900
tgcagcgtga gccacgaggc tctgcacagc caccacaccc agaagtctct gacccagagc     960
cccggatag                                                             969

<210> SEQ ID NO 122
<211> LENGTH: 303
<212> TYPE: PRT
<213> ORGANISM: Artificial Sequence
<220> FEATURE:
<223> OTHER INFORMATION: Fusion Protein

<400> SEQUENCE: 122

Phe Val Asn Gln His Leu Cys Gly Ser His Leu Val Glu Ala Leu Glu
1               5                   10                  15

Leu Val Cys Gly Glu Arg Gly Phe His Tyr Gly Gly Gly Gly Gly
            20                  25                  30

Ser Gly Gly Gly Gly Gly Ile Val Glu Gln Cys Cys Thr Ser Thr Cys
            35                  40                  45

Ser Leu Asp Gln Leu Glu Asn Tyr Cys Gly Gly Gly Gly Gln Gly
            50                  55                  60

Gly Gly Gly Gln Gly Gly Gly Gln Gly Gly Gly Gly Gly Glu
65                  70                  75                  80

Gly Pro Lys Cys Pro Val Pro Glu Ile Pro Gly Ala Pro Ser Val Phe
                85                  90                  95

```
Ile Phe Pro Pro Lys Pro Lys Asp Thr Leu Ser Ile Ser Arg Thr Pro
            100                 105                 110

Glu Val Thr Cys Leu Val Val Asp Leu Gly Pro Asp Asp Ser Asn Val
        115                 120                 125

Gln Ile Thr Trp Phe Val Asp Asn Thr Glu Met His Thr Ala Lys Thr
    130                 135                 140

Arg Pro Arg Glu Glu Gln Phe Asn Ser Thr Tyr Arg Val Val Ser Val
145                 150                 155                 160

Leu Pro Ile Leu His Gln Asp Trp Leu Lys Gly Lys Glu Phe Lys Cys
                165                 170                 175

Lys Val Asn Ser Lys Ser Leu Pro Ser Ala Met Glu Arg Thr Ile Ser
            180                 185                 190

Lys Ala Lys Gly Gln Pro His Glu Pro Gln Val Tyr Val Leu Pro Pro
        195                 200                 205

Thr Gln Glu Glu Leu Ser Glu Asn Lys Val Ser Val Thr Cys Leu Ile
    210                 215                 220

Lys Gly Phe His Pro Pro Asp Ile Ala Val Glu Trp Glu Ile Thr Gly
225                 230                 235                 240

Gln Pro Glu Pro Glu Asn Asn Tyr Gln Thr Thr Pro Pro Gln Leu Asp
                245                 250                 255

Ser Asp Gly Thr Tyr Phe Leu Tyr Ser Arg Leu Ser Val Asp Arg Ser
            260                 265                 270

His Trp Gln Arg Gly Asn Thr Tyr Thr Cys Ser Val Ser His Glu Ala
        275                 280                 285

Leu His Ser His His Thr Gln Lys Ser Leu Thr Gln Ser Pro Gly
    290                 295                 300

<210> SEQ ID NO 123
<211> LENGTH: 966
<212> TYPE: DNA
<213> ORGANISM: Artificial Sequence
<220> FEATURE:
<223> OTHER INFORMATION: Fusion Protein DNA

<400> SEQUENCE: 123
atggaatgga gctgggtctt tctcttcttc ctgtcagtaa cgactggtgt ccactccttc      60
gtgaaccagc acctgtgcgg ctcccacctg gtggaagctc tggaactcgt gtgcggcgag     120
cggggcttcc actacggggg tggcggagga ggttctggtg gcggcggagg catcgtggaa     180
cagtgctgca cctccacctg ctccctggac cagctggaaa actactgcgg tggcggaggt     240
ggtcaaggag gcgtggacac gggtggaggt gggcagggag gaggcggggg agactgcccc     300
aaatgtcctc cgcctgagat gctgggtggc cctagcatct tcatcttccc gcccaagccc     360
aaggatactc tgtccattag caggaccccc gaggtgacct gcctggtggt ggacctgggg     420
ccagacgact ctgacgtgca gatcacctgg ttcgtagaca acacccaggt ttacactgcc     480
aagaccagtc caggggagga gcagttcagc agcacataca gggtggtgag cgttctgccc     540
atcctgcacc aggactggct gaaaggcaaa gagttcaagt gtaaggtgaa cagcaagagc     600
ctgcccagcc ccattgaaag gaccatcagc aaggacaagg ccagccgcacgagccccaa      660 gtctacgtgc tgccccagc acaggaagag ctgagcagga caaggttag cgtgacatgc     720 ctgatcgagg gtttctaccc cagcgacatc gccgtggagt gggaaatcac cggccaaccc     780
gagcccgaga caactacag gaccactccg ccgcaactgg acagcgacgg gacctacttc     840 tgtatagca ggctgagcgt ggaccggagc aggtggcaga ggggcaacac ctacacttgc     900
```

```
agcgtgagcc acgaggcctt gcacagccac cacactcaga agagtctgac ccagagcccg    960
ggatag                                                               966
```

<210> SEQ ID NO 124
<211> LENGTH: 302
<212> TYPE: PRT
<213> ORGANISM: Artificial Sequence
<220> FEATURE:
<223> OTHER INFORMATION: Fusion Protein

<400> SEQUENCE: 124

```
Phe Val Asn Gln His Leu Cys Gly Ser His Leu Val Glu Ala Leu Glu
1               5                   10                  15

Leu Val Cys Gly Glu Arg Gly Phe His Tyr Gly Gly Gly Gly Gly Gly
            20                  25                  30

Ser Gly Gly Gly Gly Gly Ile Val Glu Gln Cys Cys Thr Ser Thr Cys
        35                  40                  45

Ser Leu Asp Gln Leu Glu Asn Tyr Cys Gly Gly Gly Gly Gln Gly Gly
    50                  55                  60

Gly Gly Gln Gly Gly Gly Gln Gly Gly Gly Gly Asp Cys
65                  70                  75                  80

Pro Lys Cys Pro Pro Pro Glu Met Leu Gly Gly Pro Ser Ile Phe Ile
                85                  90                  95

Phe Pro Pro Lys Pro Lys Asp Thr Leu Ser Ile Ser Arg Thr Pro Glu
            100                 105                 110

Val Thr Cys Leu Val Val Asp Leu Gly Pro Asp Asp Ser Asp Val Gln
        115                 120                 125

Ile Thr Trp Phe Val Asp Asn Thr Gln Val Tyr Thr Ala Lys Thr Ser
    130                 135                 140

Pro Arg Glu Glu Gln Phe Ser Ser Thr Tyr Arg Val Val Ser Val Leu
145                 150                 155                 160

Pro Ile Leu His Gln Asp Trp Leu Lys Gly Lys Glu Phe Lys Cys Lys
                165                 170                 175

Val Asn Ser Lys Ser Leu Pro Ser Pro Ile Glu Arg Thr Ile Ser Lys
            180                 185                 190

Asp Lys Gly Gln Pro His Glu Pro Gln Val Tyr Val Leu Pro Pro Ala
        195                 200                 205

Gln Glu Glu Leu Ser Arg Asn Lys Val Ser Val Thr Cys Leu Ile Glu
    210                 215                 220

Gly Phe Tyr Pro Ser Asp Ile Ala Val Glu Trp Glu Ile Thr Gly Gln
225                 230                 235                 240

Pro Glu Pro Glu Asn Asn Tyr Arg Thr Thr Pro Pro Gln Leu Asp Ser
                245                 250                 255

Asp Gly Thr Tyr Phe Leu Tyr Ser Arg Leu Ser Val Asp Arg Ser Arg
            260                 265                 270

Trp Gln Arg Gly Asn Thr Tyr Thr Cys Ser Val Ser His Glu Ala Leu
        275                 280                 285

His Ser His His Thr Gln Lys Ser Leu Thr Gln Ser Pro Gly
    290                 295                 300
```

<210> SEQ ID NO 125
<211> LENGTH: 57
<212> TYPE: PRT
<213> ORGANISM: Artificial Sequence
<220> FEATURE:
<223> OTHER INFORMATION: Ins Polypeptide -continued

```
<400> SEQUENCE: 125

Phe Val Asn Gln His Leu Cys Gly Ser His Leu Val Glu Ala Leu Ala
1               5                   10                  15

Leu Val Cys Gly Glu Arg Gly Phe Phe Tyr Thr Asp Pro Thr Gly Gly
                20                  25                  30

Gly Pro Arg Arg Gly Ile Val Glu Gln Cys Cys Thr Ser Ile Cys Ser
            35                  40                  45

Leu Tyr Gln Leu Glu Asn Tyr Cys Asn
        50                  55

<210> SEQ ID NO 126
<211> LENGTH: 10
<212> TYPE: PRT
<213> ORGANISM: Artificial Sequence
<220> FEATURE:
<223> OTHER INFORMATION: Linker

<400> SEQUENCE: 126

Gly Gly Gly Gly Gly Ala Gly Gly Gly Gly
1               5                   10

<210> SEQ ID NO 127
<211> LENGTH: 19
<212> TYPE: PRT
<213> ORGANISM: Artificial Sequence
<220> FEATURE:
<223> OTHER INFORMATION: Linker

<400> SEQUENCE: 127

Gly Gly Gly Gly Ser Gly Gly Gly Ser Gly Gly Gly Ser Gly
1               5                   10                  15

Gly Gly Gly

<210> SEQ ID NO 128
<211> LENGTH: 19
<212> TYPE: PRT
<213> ORGANISM: Artificial Sequence
<220> FEATURE:
<223> OTHER INFORMATION: Linker

<400> SEQUENCE: 128

Gly Gly Gly Gly Lys Gly Gly Gly Lys Gly Gly Gly Lys Gly
1               5                   10                  15

Gly Gly Gly

<210> SEQ ID NO 129
<211> LENGTH: 21
<212> TYPE: PRT
<213> ORGANISM: Artificial Sequence
<220> FEATURE:
<223> OTHER INFORMATION: Linker

<400> SEQUENCE: 129

Gly Gly Gly Gly Gly Ala Gly Gly Gly Ala Gly Gly Gly Ala
1               5                   10                  15

Gly Gly Gly Gly Gly
            20

<210> SEQ ID NO 130
<211> LENGTH: 21
<212> TYPE: PRT
<213> ORGANISM: Artificial Sequence
<220> FEATURE:
```

```
<223> OTHER INFORMATION: Linker

<400> SEQUENCE: 130

Ser Gly Gly Gly Gly Gln Gly Gly Gly Gly Gln Gly Gly Gly Gly Gln
1               5                   10                  15

Gly Gly Gly Gly Gly
            20

<210> SEQ ID NO 131
<211> LENGTH: 21
<212> TYPE: PRT
<213> ORGANISM: Artificial Sequence
<220> FEATURE:
<223> OTHER INFORMATION: Linker

<400> SEQUENCE: 131

His Gly Gly Gly Gly Gln Gly Gly Gly Gly Gln Gly Gly Gly Gly Gln
1               5                   10                  15

Gly Gly Gly Gly Gly
            20

<210> SEQ ID NO 132
<211> LENGTH: 22
<212> TYPE: PRT
<213> ORGANISM: Artificial Sequence
<220> FEATURE:
<223> OTHER INFORMATION: Linker

<400> SEQUENCE: 132

Pro Gly Gly Gly Gly Gln Gly Gly Gly Gly Gln Gly Gly Gly Gly
1               5                   10                  15

Gln Gly Gly Gly Gly Gly
            20

<210> SEQ ID NO 133
<211> LENGTH: 11
<212> TYPE: PRT
<213> ORGANISM: Artificial Sequence
<220> FEATURE:
<223> OTHER INFORMATION: C-Chain

<400> SEQUENCE: 133

Gly Gly Gly Gly Gly Gly Ser Gly Gly Gly Gly
1               5                   10
```